(12) United States Patent
Esfandyarpour et al.

(10) Patent No.: US 10,125,393 B2
(45) Date of Patent: Nov. 13, 2018

(54) SYSTEMS AND METHODS FOR BIOLOGICAL ANALYSIS AND COMPUTATION

(71) Applicant: GENAPSYS, INC., Redwood City, CA (US)

(72) Inventors: Hesaam Esfandyarpour, Redwood City, CA (US); Meysam R. Barmi, Menlo Park, CA (US); Kosar B. Parizi, Redwood City, CA (US); Saurabh Paliwal, Mountain View, CA (US); Amirhossein Samakar, Fremont, CA (US); Seth Stern, Palo Alto, CA (US)

(73) Assignee: GENAPSYS, INC., Redwood City, CA (US)

( * ) Notice: Subject to any disclaimer, the term of this patent is extended or adjusted under 35 U.S.C. 154(b) by 49 days.

(21) Appl. No.: 15/028,899

(22) PCT Filed: Dec. 10, 2014

(86) PCT No.: PCT/US2014/069624
§ 371 (c)(1),
(2) Date: Apr. 12, 2016

(87) PCT Pub. No.: WO2015/089238
PCT Pub. Date: Jun. 18, 2015

(65) Prior Publication Data
US 2016/0273032 A1     Sep. 22, 2016

Related U.S. Application Data

(60) Provisional application No. 61/914,659, filed on Dec. 11, 2013, provisional application No. 61/914,937, (Continued)

(51) Int. Cl.
*B01L 3/00* (2006.01)
*C12Q 1/6874* (2018.01)
(Continued)

(52) U.S. Cl.
CPC ........ *C12Q 1/6874* (2013.01); *B01L 3/50273* (2013.01); *B01L 3/502715* (2013.01);
(Continued)

(58) Field of Classification Search
None
See application file for complete search history.

(56) References Cited

U.S. PATENT DOCUMENTS 2,014,761 A  9/1935 Faust
4,072,576 A  2/1978 Arwin et al.
(Continued)

FOREIGN PATENT DOCUMENTS

CN  1337580 A  2/2002
CN  101120098 A  2/2008
(Continued)

OTHER PUBLICATIONS

Co-pending U.S. Appl. No. 15/655,616, filed Jul. 20, 2017.
(Continued)

*Primary Examiner* — Xiaoyun R Xu
(74) *Attorney, Agent, or Firm* — Wilson Sonsini Goodrich & Rosati

(57) ABSTRACT

Provided herein are devices and methods suitable for sequencing, detecting, amplifying, analyzing, and performing sample preparation procedures for nucleic acids and other molecules. In some cases, the devices and methods provided herein are used for computation.

17 Claims, 105 Drawing Sheets

Specification includes a Sequence Listing.

Related U.S. Application Data filed on Dec. 11, 2013, provisional application No. 61/914,830, filed on Dec. 11, 2013, provisional application No. 61/914,787, filed on Dec. 11, 2013, provisional application No. 61/914,902, filed on Dec. 11, 2013, provisional application No. 61/914,826, filed on Dec. 11, 2013, provisional application No. 61/915,276, filed on Dec. 12, 2013, provisional application No. 61/915,438, filed on Dec. 12, 2013, provisional application No. 61/940,343, filed on Feb. 14, 2014, provisional application No. 62/047,583, filed on Sep. 8, 2014.

(51) Int. Cl.
*G06F 19/20* (2011.01)
*C12Q 1/6825* (2018.01)
*B01L 7/00* (2006.01)
*G01N 33/66* (2006.01)
*G01N 33/68* (2006.01)

(52) U.S. Cl.
CPC ........ *B01L 3/502761* (2013.01); *G06F 19/20* (2013.01); *B01L 3/502784* (2013.01); *B01L 7/525* (2013.01); *B01L 2200/04* (2013.01); *B01L 2200/0605* (2013.01); *B01L 2200/0647* (2013.01); *B01L 2200/142* (2013.01); *B01L 2200/16* (2013.01); *B01L 2300/02* (2013.01); *B01L 2300/023* (2013.01); *B01L 2300/0627* (2013.01); *B01L 2300/0636* (2013.01); *B01L 2300/088* (2013.01); *B01L 2300/0819* (2013.01); *B01L 2300/0848* (2013.01); *B01L 2300/161* (2013.01); *B01L 2300/1822* (2013.01); *B01L 2400/043* (2013.01); *B01L 2400/0415* (2013.01); *B01L 2400/0427* (2013.01); *B01L 2400/0481* (2013.01); *C12Q 1/6825* (2013.01); *G01N 33/66* (2013.01); *G01N 33/68* (2013.01)

(56) References Cited

U.S. PATENT DOCUMENTS

| | | |
|---|---|---|
| 5,344,545 A | 9/1994 | Tsukada et al. |
| 5,602,042 A | 2/1997 | Farber |
| 5,612,181 A | 3/1997 | Fourmentin-Guilbert |
| 5,795,782 A | 8/1998 | Church et al. |
| 5,834,197 A | 11/1998 | Parton |
| 6,046,097 A | 4/2000 | Hsieh et al. |
| 6,087,095 A | 7/2000 | Rosenthal et al. |
| 6,210,891 B1 | 4/2001 | Nyren et al. |
| 6,327,410 B1 | 12/2001 | Walt et al. |
| 6,632,655 B1 | 10/2003 | Mehta et al. |
| 6,833,246 B2 | 12/2004 | Balasubramanian |
| 6,953,958 B2 | 10/2005 | Baxter et al. |
| 7,081,192 B1 | 7/2006 | Wang et al. |
| 7,223,540 B2 | 5/2007 | Pourmand et al. |
| 7,242,241 B2 | 7/2007 | Toumazou et al. |
| 7,270,981 B2 | 9/2007 | Armes et al. |
| 7,282,370 B2 | 10/2007 | Bridgham et al. |
| 7,291,496 B2 | 11/2007 | Holm-Kennedy |
| 7,312,085 B2 | 12/2007 | Chou et al. |
| 7,317,216 B2 | 1/2008 | Holm-Kennedy |
| 7,323,305 B2 | 1/2008 | Leamon et al. |
| 7,361,466 B2 | 4/2008 | Korlach et al. |
| 7,399,590 B2 | 7/2008 | Piepenburg et al. |
| 7,435,561 B2 | 10/2008 | Piepenburg et al. |
| 7,485,428 B2 | 2/2009 | Armes et al. |
| 7,615,382 B2 | 11/2009 | Wang et al. |
| 7,645,596 B2 | 1/2010 | Williams et al. |
| 7,649,358 B2 | 1/2010 | Toumazou et al. |
| 7,666,598 B2 | 2/2010 | Piepenburg et al. |
| 7,682,837 B2 | 3/2010 | Jain et al. |
| 7,686,929 B2 | 3/2010 | Toumazou et al. |
| 7,692,219 B1 | 4/2010 | Holm-Kennedy |
| 7,695,907 B2 | 4/2010 | Miyahara et al. |
| 7,763,427 B2 | 7/2010 | Piepenburg et al. |
| 7,824,890 B2 | 11/2010 | Hoser et al. |
| 7,875,440 B2 | 1/2011 | Williams et al. |
| 7,888,013 B2 | 2/2011 | Miyahara et al. |
| 7,932,034 B2 | 4/2011 | Esfandyarpour et al. |
| 7,948,015 B2 | 5/2011 | Rothberg et al. |
| 8,030,000 B2 | 10/2011 | Piepenburg et al. |
| 8,062,848 B2 | 11/2011 | Goldstein et al. |
| 8,062,850 B2 | 11/2011 | Piepenburg et al. |
| 8,071,308 B2 | 12/2011 | Piepenburg et al. |
| 8,114,591 B2 | 2/2012 | Toumazou et al. |
| 8,128,796 B2 | 3/2012 | Ishige et al. |
| 8,129,118 B2 | 3/2012 | Weindel et al. |
| 8,137,569 B2 | 3/2012 | Harnack et al. |
| 8,152,991 B2 | 4/2012 | Briman et al. |
| 8,154,093 B2 | 4/2012 | Bradley et al. |
| 8,173,401 B2 | 5/2012 | Chang et al. |
| 8,179,296 B2 | 5/2012 | Kelly et al. |
| 8,257,925 B2 | 9/2012 | Brown et al. |
| 8,301,394 B2 | 10/2012 | Chen et al. |
| 8,426,134 B2 | 4/2013 | Piepenburg et al. |
| 8,460,875 B2 | 6/2013 | Armes et al. |
| 8,518,670 B2 | 8/2013 | Goldstein et al. |
| 8,574,846 B2 | 11/2013 | Piepenburg et al. |
| 8,580,507 B2 | 11/2013 | Piepenburg et al. |
| 8,585,973 B2 | 11/2013 | Esfandyarpour |
| 8,637,253 B2 | 1/2014 | Piepenburg et al. |
| 8,673,560 B2 | 3/2014 | Leamon et al. |
| 8,969,002 B2 | 3/2015 | Esfandyarpour et al. |
| 9,150,915 B2 | 10/2015 | Esfandyarpour et al. |
| 9,184,099 B2 | 11/2015 | Baghbani-Parizi et al. |
| 9,187,783 B2 | 11/2015 | Esfandyarpour et al. |
| 9,274,077 B2 | 3/2016 | Esfandyarpour et al. |
| 9,399,217 B2 | 7/2016 | Esfandyarpour et al. |
| 2002/0132245 A1 | 9/2002 | Boles et al. |
| 2002/0148739 A2 | 10/2002 | Liamos et al. |
| 2003/0078314 A1 | 4/2003 | Johnson et al. |
| 2003/0209432 A1 | 11/2003 | Choong et al. |
| 2004/0014201 A1 | 1/2004 | Kim et al. |
| 2004/0033492 A1 | 2/2004 | Chen |
| 2004/0197793 A1 | 10/2004 | Hassibi et al. |
| 2005/0009022 A1 | 1/2005 | Weiner et al. |
| 2005/0019784 A1 | 1/2005 | Su et al. |
| 2005/0032076 A1 | 2/2005 | Williams et al. |
| 2005/0123937 A1 | 6/2005 | Thorp et al. |
| 2005/0129526 A1 | 6/2005 | Dukhin et al. |
| 2006/0008824 A1 | 1/2006 | Ronaghi et al. |
| 2006/0105373 A1 | 5/2006 | Pourmand et al. |
| 2006/0222569 A1 | 10/2006 | Barten et al. |
| 2007/0132043 A1 | 6/2007 | Bradley et al. |
| 2007/0184463 A1 | 8/2007 | Molho et al. |
| 2007/0275375 A1 | 11/2007 | Van et al. |
| 2008/0009420 A1 | 1/2008 | Schroth et al. |
| 2008/0032295 A1 | 2/2008 | Toumazou et al. |
| 2008/0161200 A1 | 7/2008 | Yu et al. |
| 2008/0166727 A1 | 7/2008 | Esfandyarpour et al. |
| 2008/0171325 A1 | 7/2008 | Brown et al. |
| 2008/0176817 A1 | 7/2008 | Zhou et al. |
| 2008/0187915 A1 | 8/2008 | Polonsky et al. |
| 2008/0241841 A1 | 10/2008 | Murakawa et al. |
| 2008/0286762 A1 | 11/2008 | Miyahara et al. |
| 2008/0302732 A1 | 12/2008 | Soh et al. |
| 2008/0318243 A1 | 12/2008 | Haga et al. |
| 2009/0005259 A1 | 1/2009 | Drmanac |
| 2009/0026082 A1 | 1/2009 | Rothberg et al. |
| 2009/0029385 A1 | 1/2009 | Christians et al. |
| 2009/0032401 A1 | 2/2009 | Ronaghi et al. |
| 2009/0048124 A1 | 2/2009 | Leamon et al. |
| 2009/0127589 A1 | 5/2009 | Rothberg et al. |
| 2009/0166221 A1 | 7/2009 | Ishige et al. |
| 2009/0170716 A1 | 7/2009 | Su et al. |
| 2009/0170724 A1 | 7/2009 | Balasubramanian et al. |
| 2009/0181385 A1 | 7/2009 | McKernan et al. |
| 2009/0191594 A1 | 7/2009 | Ohashi |
| 2010/0000881 A1 | 1/2010 | Franzen et al. |
| 2010/0035252 A1 | 2/2010 | Rothberg et al. |

(56) References Cited

U.S. PATENT DOCUMENTS

| | | |
|---|---|---|
| 2010/0072080 A1 | 3/2010 | Karhanek et al. |
| 2010/0078325 A1 | 4/2010 | Oliver |
| 2010/0112588 A1 | 5/2010 | Farinas et al. |
| 2010/0137143 A1 | 6/2010 | Rothberg et al. |
| 2010/0137413 A1 | 6/2010 | Cummins et al. |
| 2010/0151479 A1 | 6/2010 | Toumazou et al. |
| 2010/0159461 A1 | 6/2010 | Toumazou et al. |
| 2010/0163414 A1 | 7/2010 | Gillies et al. |
| 2010/0167938 A1 | 7/2010 | Su et al. |
| 2010/0188073 A1 | 7/2010 | Rothberg et al. |
| 2010/0197507 A1 | 8/2010 | Rothberg et al. |
| 2010/0209922 A1 | 8/2010 | Williams et al. |
| 2010/0255595 A1 | 10/2010 | Toumazou et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2010/0317531 A1 | 12/2010 | Balasubramanian et al. |
| 2010/0330570 A1 | 12/2010 | Vander et al. |
| 2011/0039266 A1 | 2/2011 | Williams et al. |
| 2011/0117026 A1 | 5/2011 | Tseng et al. |
| 2011/0118139 A1 | 5/2011 | Mehta et al. |
| 2011/0123991 A1 | 5/2011 | Hoser |
| 2011/0159481 A1 | 6/2011 | Liu et al. |
| 2011/0171655 A1 | 7/2011 | Esfandyarpour et al. |
| 2011/0177498 A1 | 7/2011 | Clarke et al. |
| 2011/0183321 A1 | 7/2011 | Williams et al. |
| 2011/0195253 A1 | 8/2011 | Hinz et al. |
| 2011/0195459 A1 | 8/2011 | Hinz et al. |
| 2011/0201057 A1 | 8/2011 | Carr et al. |
| 2011/0201506 A1 | 8/2011 | Hinz et al. |
| 2011/0217697 A1 | 9/2011 | Rothberg et al. |
| 2011/0230375 A1 | 9/2011 | Rothberg et al. |
| 2011/0241081 A1 | 10/2011 | Rothberg et al. |
| 2011/0247933 A1 | 10/2011 | Rothberg et al. |
| 2011/0248319 A1 | 10/2011 | Rothberg et al. |
| 2011/0248320 A1 | 10/2011 | Rothberg et al. |
| 2011/0259745 A1 | 10/2011 | Dehlinger et al. |
| 2011/0263463 A1 | 10/2011 | Rothberg et al. |
| 2011/0287432 A1 | 11/2011 | Wong et al. |
| 2011/0287945 A1 | 11/2011 | Rothberg et al. |
| 2011/0294115 A1 | 12/2011 | Williams et al. |
| 2011/0311979 A1 | 12/2011 | Brown et al. |
| 2012/0013392 A1 | 1/2012 | Rothberg et al. |
| 2012/0021918 A1 | 1/2012 | Bashir et al. |
| 2012/0034607 A1 | 2/2012 | Rothberg et al. |
| 2012/0037961 A1 | 2/2012 | Rothberg et al. |
| 2012/0040844 A1 | 2/2012 | Rothberg et al. |
| 2012/0045844 A1 | 2/2012 | Rothberg et al. |
| 2012/0055811 A1 | 3/2012 | Rothberg et al. |
| 2012/0055813 A1 | 3/2012 | Rothberg et al. |
| 2012/0061255 A1 | 3/2012 | Rothberg et al. |
| 2012/0061256 A1 | 3/2012 | Rothberg et al. |
| 2012/0061733 A1 | 3/2012 | Rothberg et al. |
| 2012/0065093 A1 | 3/2012 | Rothberg et al. |
| 2012/0071363 A1 | 3/2012 | Rothberg et al. |
| 2012/0085660 A1 | 4/2012 | Rothberg et al. |
| 2012/0088682 A1 | 4/2012 | Rothberg et al. |
| 2012/0094871 A1 | 4/2012 | Hinz et al. |
| 2012/0129173 A1 | 5/2012 | Piepenburg et al. |
| 2012/0129703 A1 | 5/2012 | Rothberg et al. |
| 2012/0129728 A1 | 5/2012 | Rothberg et al. |
| 2012/0129732 A1 | 5/2012 | Rothberg et al. |
| 2012/0135870 A1 | 5/2012 | Rothberg et al. |
| 2012/0135893 A1 | 5/2012 | Drmanac et al. |
| 2012/0138460 A1 | 6/2012 | Baghbani-Parizi et al. |
| 2012/0156728 A1 | 6/2012 | Li et al. |
| 2012/0157322 A1 | 6/2012 | Myllykangas et al. |
| 2012/0173159 A1 | 7/2012 | Davey et al. |
| 2012/0175252 A1 | 7/2012 | Toumazou et al. |
| 2012/0222496 A1 | 9/2012 | Mamigonians |
| 2012/0258456 A1 | 10/2012 | Armes et al. |
| 2012/0258499 A1 | 10/2012 | Piepenburg et al. |
| 2012/0264617 A1 | 10/2012 | Pettit |
| 2012/0295819 A1 | 11/2012 | Leamon et al. |
| 2012/0302454 A1 | 11/2012 | Esfandyarpour |
| 2012/0322113 A1 | 12/2012 | Erlander et al. |
| 2013/0005613 A1 | 1/2013 | Leamon et al. |
| 2013/0023011 A1 | 1/2013 | Leamon et al. |
| 2013/0059290 A1 | 3/2013 | Armes |
| 2013/0059762 A1 | 3/2013 | Leamon et al. |
| 2013/0090860 A1 | 4/2013 | Sikora et al. |
| 2013/0096013 A1 | 4/2013 | Esfandyarpour et al. |
| 2013/0109577 A1 | 5/2013 | Korlach et al. |
| 2013/0183211 A1 | 7/2013 | Senftleber |
| 2013/0203634 A1 | 8/2013 | Jovanovich et al. |
| 2013/0225421 A1 | 8/2013 | Li et al. |
| 2013/0231254 A1 | 9/2013 | Kawashima et al. |
| 2013/0281307 A1 | 10/2013 | Li et al. |
| 2014/0034497 A1 | 2/2014 | Davis et al. |
| 2014/0045701 A1 | 2/2014 | Esfandyarpour et al. |
| 2014/0057339 A1 | 2/2014 | Esfandyarpour et al. |
| 2014/0073531 A1 | 3/2014 | Esfandyarpour |
| 2014/0099674 A1 | 4/2014 | Piepenburg et al. |
| 2014/0106338 A1 | 4/2014 | Fischer et al. |
| 2014/0235457 A1 | 8/2014 | Esfandyarpour et al. |
| 2014/0272952 A1 | 9/2014 | May et al. |
| 2014/0329699 A1 | 11/2014 | Esfandyarpour |
| 2015/0148264 A1 | 5/2015 | Esfandyarpour et al. |
| 2015/0344943 A1 | 12/2015 | Oberstrass |
| 2015/0368707 A1 | 12/2015 | Esfandyarpour et al. |
| 2015/0376692 A1 | 12/2015 | Esfandyarpour et al. |
| 2016/0076097 A1 | 3/2016 | Esfandyarpour et al. |
| 2016/0077049 A1 | 3/2016 | Baghbani-Parizi et al. |
| 2016/0340721 A1 | 11/2016 | Esfandyarpour |
| 2017/0073750 A1 | 3/2017 | Esfandyarpour et al. |

FOREIGN PATENT DOCUMENTS

| | | |
|---|---|---|
| CN | 101848757 A | 9/2010 |
| CN | 102980922 A | 3/2013 |
| EP | 0676623 A2 | 10/1995 |
| EP | 1499738 B1 | 7/2008 |
| EP | 1992706 A2 | 11/2008 |
| EP | 2290096 A2 | 3/2011 |
| EP | 2336361 A2 | 6/2011 |
| EP | 2428588 A2 | 3/2012 |
| EP | 2287341 B1 | 2/2013 |
| EP | 1759012 B1 | 5/2013 |
| EP | 2660336 A1 | 11/2013 |
| JP | 2006512583 A | 4/2006 |
| JP | 2008525822 A | 7/2008 |
| JP | 2010513869 A | 4/2010 |
| JP | 2010517040 A | 5/2010 |
| JP | 2010517041 A | 5/2010 |
| JP | 2010518401 A | 5/2010 |
| WO | WO-0118246 A1 | 3/2001 |
| WO | WO-0137958 A2 | 5/2001 |
| WO | WO-0142508 A2 | 6/2001 |
| WO | WO-0227909 A2 | 4/2002 |
| WO | WO-02061146 A1 | 8/2002 |
| WO | WO-2004027024 A2 | 4/2004 |
| WO | WO-2005008450 A2 | 1/2005 |
| WO | WO-2005108612 A2 | 11/2005 |
| WO | WO-2005121363 A2 | 12/2005 |
| WO | WO-2006050346 A2 | 5/2006 |
| WO | WO-2007030505 A1 | 3/2007 |
| WO | WO-2007041619 A2 | 4/2007 |
| WO | WO-2007098049 A2 | 8/2007 |
| WO | WO-2008076406 A2 | 6/2008 |
| WO | WO-2009012112 A1 | 1/2009 |
| WO | WO-2009052348 A2 | 4/2009 |
| WO | WO-2009074926 A1 | 6/2009 |
| WO | WO-2009122159 A2 | 10/2009 |
| WO | WO-2009150467 A1 | 12/2009 |
| WO | WO-2010008480 A2 | 1/2010 |
| WO | WO-2010026488 A2 | 3/2010 |
| WO | WO-2010037085 A1 | 4/2010 |
| WO | WO-2010041231 A2 | 4/2010 |
| WO | WO-2010047804 A1 | 4/2010 |
| WO | WO-2010075188 A2 | 7/2010 |
| WO | WO-2010138187 A1 | 12/2010 |
| WO | WO-2010141940 A1 | 12/2010 |

(56) References Cited

FOREIGN PATENT DOCUMENTS

| WO | WO-2011106556 A2 | 9/2011 |
|---|---|---|
| WO | WO-2012047889 A2 | 4/2012 |
| WO | WO-2012166742 A2 | 12/2012 |
| WO | WO-2013082619 A1 | 6/2013 |
| WO | WO-2013119765 A1 | 8/2013 |
| WO | WO-2013188582 A1 | 12/2013 |
| WO | WO-2014012107 A2 | 1/2014 |
| WO | WO-2014043143 A1 | 3/2014 |
| WO | WO-2014152625 A1 | 9/2014 |
| WO | WO-2015089238 A1 | 6/2015 |
| WO | WO-2015138696 A1 | 9/2015 |
| WO | WO-2015161054 | 10/2015 |

OTHER PUBLICATIONS

Notice of Allowance dated May 12, 2017 for U.S. Appl. No. 14/653,230.
Notice of Allowance dated Jul. 6, 2017 for U.S. Appl. No. 14/653,230.
Notice of Allowance dated Jul. 10, 2017 for U.S. Appl. No. 14/688,764.
Notice of Allowance dated Jul. 20, 2017 for U.S. Appl. No. 14/688,764.
Notice of Allowance dated Jul. 31, 2017 for U.S. Appl. No. 14/119,859.
Office Action dated Feb. 14, 2017 for U.S. Appl. No. 14/653,230.
Office Action dated Apr. 5, 2017 for U.S. Appl. No. 14/859,725.
Office Action dated Apr. 24, 2017 for U.S. Appl. No. 14/119,859.
Co-pending U.S. Appl. No. 15/726,193, filed Oct. 5, 2017.
Co-pending U.S. Appl. No. 15/726,217, filed Oct. 5, 2017.
European Search Report dated Oct. 11, 2017 for European Patent Application No. EP14869402.9.
Notice of Allowance dated Sep. 8, 2017 for U.S. Appl. No. 14/653,230.
Office Action dated Sep. 1, 2017 for U.S. Appl. No. 14/361,902.
Office Action dated Oct. 23, 2017 for U.S. Appl. No. 14/859,725.
Peng et al. Interdigitated Array Electrodes with Magnetic Function as a Particle-Based Biosensor. Sensors, 2007 IEEE. pp. 1097-1100.
Rothberg, et al. An integrated semiconductor device enabling non-optical genome sequencing. Nature. Jul. 20, 2011; 475(7356); pp. 348-52. With Supplementary Information, 25 pages.
Saias et al. Design, modeling and characterization of microfluidic architectures for high flow rate, small footprint microfluidic systems. Lab Chip. Mar. 7, 2011;11(5):822-32.
Tamayol et al. Laminar Flow in Microchannels With Noncircular Cross Section. J. Fluids Eng 132(11), 111201 (Nov 3, 2010) (9 pages).
Brouns, et al. Small CRISPR RNAs guide antiviral defense in prokaryotes. Science. Aug. 15, 2008;321(5891):960-4.
Cagnin, et al. Overview of electrochemical DNA biosensors: new approaches to detect the expression of life. Sensors (Basel). 2009;9(4):3122-48. doi: 10.3390/s90403122. Epub Apr. 24, 2009.
Carte, et al. Cas6 is an endoribonuclease that generates guide RNAs for invader defense in prokaryotes. Genes Dev. Dec. 15, 2008;22(24):3489-96.
Cho, et al. Bis-aptazyme sensors for hepatitis C virus replicase and helicase without blank signal. Nucleic Acids Res. Nov. 27, 2005;33(20):e177.
Co-pending U.S. Appl. No. 15/183,406, filed Jun. 15, 2016.
Daniels, et al. Label-Free Impedance Biosensors: Opportunities and Challenges. Electroanalysis. May 16, 2007;19(12):1239-1257.
Daniels, et al. Simultaneous Measurement of Nonlinearity and Electrochemical Impedance for Protein Sensing Using Two-Tone Excitation. 30th Annual International IEEE EMBS Conference. Vancouver, British Columbia, Canada, Aug. 20-24, 2008. 5753-5756.
Didion, et al. Invaders: Recognition of Double-Stranded DNA by Using Duplexes Modified with Interstrand Zippers of 2'-O-(Pyren-1-yl)methyl-ribonucleotides. Chembiochem. Sep. 2, 2013;14(13):1534-1538. doi: 10.1002/cbic.201300414. Epub 2013 Aug. 23, 2013.

Dimov, et al. Stand-alone self-powered integrated microfluidic blood analysis system (SIMBAS). Lab Chip. Mar. 7, 2011;11(5):845-50.
Edman, et al. Electric field directed nucleic acid hybridization on microchips. Nucleic Acids Res. Dec. 15, 1997; 25(24): 4907-14.
Ellington, et al. In vitro selection of RNA molecules that bind specific ligands. Nature. Aug. 30, 1990;346(6287):818-22.
Esfandyarpour, et al. 3D modeling of impedance spectroscopy for protein detection in nanoneedle biosensors. Proceedings of the COMSOL Conference 2007, Boston.
Esfandyarpour, et al. A Novel Nanoneedle Biosensor for DNA Sequencing (abstract). Dec. 31, 2008. Available at http://www.nsti.org/Nanotech2008/showabstract.html?absno=1522.
European search report and search opinion dated Jan. 5, 2015 for EP Application No. 12792216.9.
European search report and search opinion dated Mar. 12, 2014 for EP Application No. 11831452.5.
European search report and search opinion dated Jul. 13, 2015 for EP Application No. 12852490.7.
Finn, et al. Efficient incorporation of positively charged 2',3'-dideoxynucleoside-5'-triphosphates by DNA polymerases and their application in 'direct-load' DNA sequencing. Nucleic Acids Res. Aug. 15, 2003;31(16):4769-78.
Gardeniers, et al. Silicon micromachined hollow microneedles for transdermal liquid transport. Journal of Microelectromechanical Systems. 2003;12(6):855-862.
Haurwitz, et al. Sequence- and structure-specific RNA processing by a CRISPR endonuclease. Science. Sep. 10, 2010;329(5997):1355-8.
Hollis, et al. Structure of the gene 2.5 protein, a single-stranded DNA binding protein encoded by bacteriophage T7. Proc Natl Acad Sci U S A. Aug. 14, 2001;98(17):9557-62. Epub Jul. 31, 2001.
International search report and written opinion dated Feb. 26, 2013 for PCT/US2012/039880.
International search report and written opinion dated Mar. 19, 2013 for PCT/US2012/067645.
International search report and written opinion dated Apr. 13, 2012 for PCT/US2011/054769.
International search report and written opinion dated Aug. 21, 2014 for PCT Application No. PCT/US2014/027544.
International search report and written opinion dated Oct. 26, 2015 for PCT/US2015/026135.
Javanmard, et al. A microfluidic platform for electrical detection of DNA hybridization. Sens Actuators B Chem. May 20, 2011;154(1):22-27. Epub Mar. 30, 2010.
Kaushik, et al. Lack of pain associated with microfabricated microneedles. Anesth Analg. Feb. 2001;92(2):502-4.
Kim, et al. Replication of DNA microarrays prepared by in situ oligonucleotide polymerization and mechanical transfer. Anal Chem. Oct. 1, 2007;79(19):7267-74.
Kitano, et al. Molecular structure of RNA polymerase and its complex with DNA. J Biochem. Jan. 1969;65(1):1-16.
Kunin, et al. Evolutionary conservation of sequence and secondary structures in CRISPR repeats. Genome Biol. 2007;8(4):R61.
Kurosaki, et al. Rapid and simple detection of Ebola virus by reverse transcription-loop-mediated isothermal amplification. J Virol Methods. Apr. 2007;141(1):78-83.
Lee, et al. Ion-sensitive field-effect transistor for biological sensing. Sensors (Basel). 2009;9(9):7111-31. doi: 10.3390/s90907111. Epub Sep. 7, 2009.
Lin, et al. Replication of DNA microarrays from zip code masters. J Am Chem Soc. Mar. 15, 2006;128(10):3268-72.
Liu, et al. Immobilization of DNA onto poly(dimethylsiloxane) surfaces and application to a microelectrochemical enzyme-amplified DNA hybridization assay. Langmuir. Jul. 6, 2004;20(14):5905-10.
Makarova, et al. A putative RNA-interference-based immune system in prokaryotes: computational analysis of the predicted enzymatic machinery, functional analogies with eukaryotic RNAi, and hypothetical mechanisms of action. Biol Direct. Mar. 16, 2006;1:7.
Manickam, et al. A CMOS Electrochemical Impedance Spectroscopy (EIS) Biosensor Array. IEEE Trans Biomed Circuits Syst. Dec. 2010;4(6):379-90. doi: 10.1109/TBCAS.2010.2081669.

(56) References Cited

OTHER PUBLICATIONS

Margulies, et al. Genome sequencing in microfabricated high-density picolitre reactors. Nature. Sep. 15, 2005;437(7057):376-80. Epub Jul. 31, 2005.
Notice of allowance dated Mar. 28, 2016 for U.S. Appl. No. 13/481,858.
Notice of allowance dated May 19, 2016 for U.S. Appl. No. 13/481,858.
Notice of allowance dated Jun. 3, 2015 for U.S. Appl. No. 14/596,111.
Notice of allowance dated Jul. 1, 2015 for U.S. Appl. No. 13/824,129.
Notice of allowance dated Jul. 13, 2015 for U.S. Appl. No. 14/596,111.
Notice of allowance dated Aug. 25, 2015 for U.S. Appl. No. 14/596,111.
Notice of allowance dated Sep. 1, 2015 for U.S. Appl. No. 14/596,111.
Notice of allowance dated Nov. 21, 2014 for U.S. Appl. No. 13/632,513.
Notice of allowance dated Dec. 3, 2015 for U.S. Appl. No. 13/838,816.
Notice of allowance dated Dec. 15, 2015 for U.S. Appl. No. 13/838,816.
Notomi, et al. Loop-mediated isothermal amplification of DNA. Nucl Acids Res. Jun. 15, 2000; 28(12):E63.
Office action dated Jan. 28, 2014 for U.S. Appl. No. 13/838,816.
Office action dated Jan. 29, 2014 for U.S. Appl. No. 13/481,858.
Office action dated Jan. 30, 2015 for U.S. Appl. No. 13/481,858.
Office action dated Apr. 6, 2016 for U.S. Appl. No. 14/835,070.
Office action dated Apr. 9, 2015 for U.S. Appl. No. 14/596,111.
Office action dated May 1, 2015 for U.S. Appl. No. 13/824,129.
Office action dated Jul. 18, 2013 for U.S. Appl. No. 13/481,858.
Office action dated Jul. 23, 2014 for U.S. Appl. No. 13/824,129.
Office action dated Jul. 25, 2014 for U.S. Appl. No. 13/481,858.
Office action dated Sep. 2, 2014 for U.S. Appl. No. 13/632,513.
Office action dated Oct. 7, 2015 for U.S. Appl. No. 13/838,816.
Office action dated Nov. 5, 2013 for U.S. Appl. No. 13/632,513.
Office action dated Dec. 17, 2015 for U.S. Appl. No. 13/481,858.
Office action dated Dec. 17, 2015 for U.S. Appl. No. 14/835,070.
Office action dated Dec. 19, 2014 for U.S. Appl. No. 13/838,816.
Piepenburg, et al. DNA detection using recombination proteins. PLoS Biol. Jul. 2006;4(7):e204.
Ren, et al. Rapid and sensitive detection of hepatitis B virus 1762T/1764A double mutation from hepatocellular carcinomas using LNA-mediated PCR clamping and hybridization probes. Journal of Virological Methods. 2009; 158:24-29.
Sabounchi, et al. Sample concentration and impedance detection on a microfluidic polymer chip. Biomed Microdevices. Oct. 2008;10(5):661-70. doi: 10.1007/s10544-008-9177-4.
Senapati, et al. A nonamembrane-based nucleic acid sensing platform for portable diagnostics. Topics in Current Chemistry. Apr. 27, 2011; 304:153-169.
Sivamani, et al. Microneedles and transdermal applications. Expert Opin Drug Deliv. Jan. 2007;4(1):19-25.
Sosnowski, et al. Rapid determination of single base mismatch mutations in DNA hybrids by direct electric field control. Proc Natl Acad Sci U S A. Feb. 18, 1997; 94(4): 1119-1123.
Terns, et al. CRISPR-based adaptive immune systems. Curr Opin Microbiol. Jun. 2011;14(3):321-7.
Van, Der Oost et al. CRISPR-based adaptive and heritable immunity in prokaryotes. Trends Biochem Sci. Aug. 2009;34(8):401-7.
Voelkerding, et al. Next generation sequencing: from basic research to diagnostics. Clin. Chem. 2009; 55(4):641-658.
Wang, et al. Interaction of the Cas6 riboendonuclease with CRISPR RNAs: recognition and cleavage. Structure. Feb. 9, 2011;19(2):257-64.
Zhang, et al. Dielectrophoresis for manipulation of micro/nano particles in microfluidic systems. Anal Bioanal Chem. Jan. 2010;396: 401-20.
Andreotti, et al. Immunoassay of infectious agents. Biotechniques. Oct. 2003;35(4):850-9.
Bell, et al. Detection of Bacillus anthracis DNA by LightCycler PCR. J Clin Microbiol. Aug. 2002;40(8):2897-902.
Boo, et al. Electrochemical nanoneedle biosensor based on multiwall carbon nanotube. Anal Chem. Jan. 15, 2006;78(2):617-20.
Esfandyarpour, et al. 3D Modeling of Impedance Spectroscopy for Protein Detection in Nanoneedle Biosensors. Proceedings of the International COMSOL Conference 2007, Boston, MA, USA, pp. 169-173 (Oct. 4-6, 2007).
Esfandyarpour, et al. Geometrical Optimization of Pyrophosphate Concentration in Thermosequencing Platform for DNA Sequencing. Proceedings of the COMSOL Conf. 2007, Boston.
Gao, et al. Silicon nanowire arrays for label-free detection of DNA. Anal Chem. May 1, 2007;79(9):3291-7. Epub Apr. 4, 2007.
Guiducci, et al. A Biosensor for Direct Detection of DNA Sequences Based on Capacitance Measurements. ESSDERC 2002, pp. 479-482.
Javanmard, et al. Electrical Detection of Proteins and DNA Using Bioactivated Microfluidic Channels: Theoretical and Experimental Considerations. J Vac Sci Technol B Microelectron Nanometer Struct Process Meas Phenom. Nov. 2009;27(6):3099-3103.
Office Action dated Mar. 4, 2016 for U.S. Appl. No. 14/081,358.
Office Action dated Oct. 5, 2015 for U.S. Appl. No. 14/081,358.
Patolsky, et al. Electrical detection of single viruses. Proc Natl Acad Sci U S A. Sep. 28, 2004;101(39):14017-22. Epub Sep. 13, 2004.
Patolsky, et al. Fabrication of silicon nanowire devices for ultrasensitive, label-free, real-time detection of biological and chemical species. Nat Protoc. 2006;1(4):1711-24.
Roosen-Runge, et al. Protein diffusion in crowded electrolyte solutions. Biochim Biophys Acta. Jan. 2010;1804(1):68-75. doi: 10.1016/j.bbapap.2009.07.003. Epub Jul. 17, 2009.
Safir, et al. Fabrication of an insulated probe on a self-assembled metallic nanowire for electrochemical probing in cells. IEEE 2006, pp. 898-900.
Yazdanpanah, et al. Selective self-assembly at room temperature of individual freestanding Ag2Ga alloy nanoneedles. J. Appl. Phys. 98, pp. 073510-7 (2005).
Zheng, et al. Multiplexed electrical detection of cancer markers with nanowire sensor arrays. Nat Biotechnol. Oct. 2005;23(10):1294-301. Epub Sep. 18, 2005.
European Search Report dated Nov. 14, 2017 for European Patent Application No. EP15779780.4.
International Search Report and Written Opinion dated Nov. 16, 2017 for International PCT Patent Application No. PCT/US2017/43159.
Notice of Allowance dated Dec. 8, 2017 for U.S. Appl. No. 14/119,859.
Smolina et al. End invasion of peptide nucleic acids (PNAs) with mixed-base composition into linear DNA duplexes. Nucleic Acids Research. vol. 33. No. 11. pp. e146-e146. Sep. 25, 2005.
U.S. Appl. No. 15/230,048 Notice of Allowance dated Apr. 5, 2018.
Zanoli et al. Isothermal Amplification Methods for the Detection of Nucleic Acids in Microfluidic Devices. Biosensors. vol. 3. No. 1. pp. 18-43. Dec. 27, 2012.
Co-pending U.S. Appl. No. 16/007,829, filed Jun. 13, 2018.
Co-pending U.S. Appl. No. 16/007,969, filed Jun. 13, 2018.
U.S. Appl. No. 15/183,406 Office Action dated Jun. 21, 2018.

SYSTEMS AND METHODS FOR BIOLOGICAL ANALYSIS AND COMPUTATION

CROSS-REFERENCE

This application is a national stage entry of International Application No. PCT/US2014/069624, filed Dec. 10, 2014, which application claims the benefit of U.S. Provisional Patent Application No. 61/914,937, filed Dec. 11, 2013, U.S. Provisional Patent Application No. 61/914,830, filed Dec. 11, 2013, U.S. Provisional Patent Application No. 61/915,276, filed Dec. 12, 2013, U.S. Provisional Patent Application No. 61/915,438, filed Dec. 12, 2013, U.S. Provisional Patent Application No. 61/914,659, filed Dec. 11, 2013, U.S. Provisional Patent Application No. 61/914,826, filed Dec. 11, 2013, U.S. Provisional Patent Application No. 61/914,902, filed Dec. 11, 2013, U.S. Provisional Patent Application No. 61/914,787, filed Dec. 11, 2013, U.S. Provisional Patent Application No. 61/940,343, filed Feb. 14, 2014, and U.S. Provisional Patent Application No. 62/047,583, filed Sep. 8, 2014, each of which applications is incorporated herein by reference in its entirety and for all purposes.

SEQUENCE LISTING

The instant application contains a Sequence Listing which has been filed electronically in ASCII format and is hereby incorporated by reference in its entirety. The ASCII copy, created on Nov. 17, 2016, is named 42808-715_831_SL.txt and is 910 bytes in size.

BACKGROUND

The goal to elucidate the entire human genome has created interest in technologies for rapid nucleic acid (e.g., DNA) sequencing, both for small and large scale applications. Important parameters are sequencing speed, length of sequence that can be read during a single sequencing run, and amount of nucleic acid template required to generate sequencing information. Large scale genome projects are currently too expensive to realistically be carried out for a large number of subjects (e.g., patients). Furthermore, as knowledge of the genetic basis for human diseases increases, there will be an ever-increasing need for accurate, high-throughput DNA sequencing that is affordable for clinical applications. Practical methods for determining the base pair sequences of single molecules of nucleic acids, preferably with high speed and long read lengths, may provide measurement capability.

Nucleic acid sequencing is a process that can be used to provide sequence information for a nucleic acid sample. Such sequence information may be helpful in diagnosing and/or treating a subject with a condition. For example, the nucleic acid sequence of a subject may be used to identify, diagnose and potentially develop treatments for genetic diseases. As another example, research into pathogens may lead to treatment for contagious diseases. Unfortunately, though, existing sequencing technology of the status quo is expensive and may not provide sequence information within a time period and/or at an accuracy that may be sufficient to diagnose and/or treat a subject with a condition.

Computer data storage is a technology that has computer components and recording media used to retain data electronically. The most commonly used data storage technologies are semiconductor, magnetic, and optical. Data may be stored in data storage media, which data in a data storage device.

A modern digital computer represents data using the binary numeral system. Text, numbers, pictures, audio, and nearly any other form of information can be converted into a string of bits, or binary digits, each of which has a value of 1 or 0. The most common unit of storage is the byte, equal to 8 bits. A piece of information can be handled by any computer or device whose storage space is large enough to accommodate the binary representation of the piece of information, or simply data.

Data may be electronically encoded by assigning a bit pattern to each character, digit, or multimedia object. Many standards exist for encoding (e.g., character encodings like ASCII, image encodings like JPEG, video encodings like MPEG-4).

DNA computing is a form of computing that uses DNA, biochemistry and molecular biology to store data, access data and/or perform computations. One of potential advantage of DNA computing is that, similar to parallel computing, it can try many different possibilities at once owing to having many different molecules of DNA.

SUMMARY

Recognized herein is the need for improved devices and methods for performing computation with, sequencing, amplifying, analyzing, and/or performing sample preparation procedures for nucleic acids and other biomolecules.

An aspect of the disclosure provides a device comprising a well-less sensing array with a plurality of sensors in a housing. At least a subset of the plurality of sensors can be individually addressable and each sensor of the plurality can be adapted to directly measure an electronic signature associated with a biological species in solution. The housing can have a footprint that is less than or equal to about 250,000 $mm^2$ and the device can have a weight that is less than or equal to about 10 pounds.

In some embodiments, the device can further comprise a fluid flow path in fluid communication with the sensing array. The fluid flow path can be in communication with a repository comprising one or more reagents for nucleic acid sequencing. In some embodiments, the fluid flow path can provide beads to the sensing array in an emulsion. In some embodiments, the biological species can be a nucleic acid such as, for example, a circular nucleic acid.

In some embodiments, the footprint can be less than or equal to about 100,000 $mm^2$. In some embodiments, the footprint can be greater than or equal to about 500 $mm^2$. In some embodiments, the weight can be less than or equal to about 5 pounds. In some embodiments, the weight can be greater than or equal to about 0.1 pounds. In some embodiments, the sensing array can provide a single-pass bead loading fill factor of at least about 50%. In some embodiments, the sensing array can provide a nucleic acid sequencing read length of at least about 20 base pairs (bp) with a non-linearity of less than or equal to about 10 bases. In some embodiments, the read length may be for a nucleic acid homopolymer.

In some embodiments, the sensing array may be part of a chip that is removable from the housing. The chip can be a single-use chip and can be disposable. In some embodiments, the sensing array may be substantially planar. In some embodiments, the sensing array can provide a nucleic acid sequencing throughput of at least about 100 base pairs (bp) in a time period that is less than or equal to about 2 days.

The nucleic acid sequencing can be, for example, targeted sequencing and/or whole genome sequencing.

In some embodiments, the device can further comprise a computer processor coupled to the sensing array. The computer processor can be programmed to receive signals from the sensing array that are indicative of a direct electrical signature of the species. In some embodiments, the sensing array may be adapted for nucleic acid sequencing, proton detection, protein detection, or pathogen detection. In some embodiments, the sensing array may be adapted for nucleic acid amplification. In some embodiments, the device can be transportable by a user.

In some embodiments, the electronic signature can be an impedance or a change in impedance. The impedance or change in impedance can be associated with a bead adjacent to the sensor, an electrode of the sensor and/or a species in a fluid adjacent to the sensor. In some embodiments, the electronic signature can be a charge or a change in charge. The charge or change in charge can be associated with a bead adjacent to the sensor, an electrode of the sensor and/or a species in a fluid adjacent to the sensor. In some embodiments, a system may comprise a device.

An additional aspect of the disclosure provides a method for biological detection. The method can comprise providing a device comprising a sensing array with a plurality of sensors in a housing. At least a subset of the plurality of sensors can be individually addressable and each sensor of the plurality can be adapted to directly measure an electronic signature associated with a biological species in solution. The housing can have a footprint that is less than or equal to about 250,000 mm² and the device can have a weight that is less than or equal to about 10 pounds. Moreover, the method can further comprise directing a solution comprising the biological species to the sensing array and directly measuring an electronic signature associated with the biological species using the sensor.

In some embodiments, the device may further comprise a fluid flow path in fluid communication with the sensing array. The fluid flow path can be in communication with a repository comprising one or more reagents for nucleic acid sequencing and/or can provide beads to the sensing array in an emulsion. In some embodiments, all or substantially all of the plurality of sensors may be individually addressable. In some embodiments, the biological species may be a nucleic acid such as, for example, a circular nucleic acid.

In some embodiments, the footprint may be less than or equal to about 100,000 mm². In some embodiments, the footprint may be greater than or equal to about 500 mm². In some embodiments, the weight may be less than or equal to about 5 pounds. In some embodiments, the weight may be greater than or equal to about 0.1 pounds. In some embodiments, the sensing array can provide a single-pass bead loading fill factor of at least about 50%. In some embodiments, the sensing array can provide a nucleic acid sequencing read length of at least about 20 base pairs (bp) with a non-linearity of less than or equal to about 10 bases. In some embodiments, the read length may be for a nucleic acid homopolymer.

In some embodiments, the sensing array may be part of a chip that is removable from the housing. The chip can be a single-use chip and/or can be disposable. In some embodiments, the sensing array may be substantially planar. In some embodiments, the sensing array provides a nucleic acid sequencing throughput of at least about 100 base pairs (bp) in a time period that is less than or equal to about 2 days. In some embodiments, the nucleic acid sequencing may be targeted sequencing and/or whole genome sequencing.

In some embodiments, the device may further comprise a computer processor coupled to the sensing array. The computer processor can be programmed to receive signals from the sensing array that are indicative of a direct electrical signature of the species. In some embodiments, the sensing array can be adapted for nucleic acid sequencing, proton detection, protein detection, or pathogen detection. In some embodiments, the sensing array may be adapted for nucleic acid amplification and/or fluid enrichment. In some embodiments, the device may be transportable by a user.

In some embodiments, the electronic signature may be an impedance or a change in impedance. The impedance or change in impedance may be associated with a bead adjacent to the sensor, an electrode of the sensor or a species in a fluid adjacent to the sensor. In some embodiments, the electronic signature may be a charge or a change in charge. The charge or change in charge may be associated with a bead adjacent to the sensor, an electrode of the sensor or a species in a fluid adjacent to the sensor.

An additional aspect of the disclosure provides a method for data storage. The method can comprise receiving bits encoding at least one computer-executable directive for storing data and, using a computer processor, generating a nucleic acid sequence that encodes the data. The nucleic acid sequence can comprise nucleic acid subunits that correspond to the bits. Moreover, the method can further comprise using an array of individually addressable nucleic acid synthesis sites, generating a nucleic acid molecule having the nucleic acid sequence at a first site of the array at the exclusion of generating an additional nucleic acid molecule having the nucleic acid sequence at a second site of the array.

In some embodiments, the bits can encode a plurality of computer-executable directives. In some embodiments, the data can be stored in computer memory. In some embodiments, the nucleic acid subunits can be selected from at least two distinct subunits. A subset of the at least two distinct subunits can correspond to a 1 or 0. In some embodiments, an individual site of the nucleic acid synthesis sites may comprise a pair of electrodes.

In some embodiments, generating a nucleic acid molecule having the nucleic acid at a first site of the array at the exclusion of generating an additional nucleic acid molecule having the nucleic acid sequence at a second site the array can comprise alternately and sequentially directing to the first site nucleic acid subunits or precursors thereof that are selected based on the nucleic acid sequence. In some embodiments, the method can further comprise excluding from the second site the nucleic subunits or precursors thereof that are alternately and sequentially directed to the first site. In some embodiments, the method can further comprise attracting a given nucleic acid subunit or precursor thereof to the first site or not repelling the given nucleic acid subunit or precursor thereof from the first site. In some embodiments, the method can further comprise repelling the given nucleic acid subunit or precursor thereof from the second site or not attracting the given nucleic acid subunit or precursor thereof to the second site.

In some embodiments, the given nucleic acid subunit or precursor thereof can be attracted to the first site and/or repelled from the second site using an electric field generated at each of the first and second sites. In some embodiments, the electric field can be generated by one or more electrodes at the first and second sites. In some embodiments, the given nucleic acid subunit or precursor thereof can be attracted to the first site and/or repelled from the second site using a magnetic field generated at each of the first and second sites. In some embodiments, the magnetic field may be generated by one or more magnetic elements at the first and second sites. In some embodiments, the given nucleic acid subunit or precursor thereof may be attached to a magnetic bead.

In some embodiments, the nucleic acid subunits or precursors can be alternately and sequentially directed to the first site via fluid flow. The fluid flow may be fluid flow in at least one microfluidic channel. In some embodiments, the method can further comprise removing the nucleic acid molecule from the array after the nucleic acid molecule is generated. In some embodiments, the nucleic acid molecule may be generated at more than one site of the array. In some embodiments, the nucleic acid molecule may be generated at only one site of the array. In some embodiments, a plurality of the nucleic acid molecules is generated at the first site. In some embodiments, the nucleic acid molecule may be generated in the absence of a nucleic acid template.

In some embodiments, the nucleic acid molecule can be generated on a reaction surface at the first site. The reaction surface may be, for example, a particle or surface of a well at the first site. In some embodiments, the nucleic acid molecule can be generated on the reaction surface via covalent coupling of a nucleic acid subunit or precursor thereof of the nucleic acid molecule to the reaction surface. In some embodiments, the nucleic acid molecule can be generated on the reaction surface via coupling of a nucleic acid subunit or precursor thereof of the nucleic acid molecule to a linker coupled to the reaction surface. In some embodiments, the nucleic acid molecule can be generated on the reaction surface via non-covalent coupling of a nucleic acid subunit or precursor thereof of the nucleic acid molecule to the reaction surface. The non-covalent coupling can be, for example, a binding interaction between members of a binding pair.

In some embodiments, the array may be substantially planar. In some embodiments, the first site can further comprise a sensor capable of detecting signals indicative of an impedance change, a charge change, a change in pH, or a change in temperature associated with the generating of the nucleic acid molecule. In some embodiments, the sensor may comprise a pair of electrodes. In some embodiments, the sensor may be electrically coupled to the Debye layer of a surface of the sensor, a surface of the nucleic acid molecule, or a reaction surface coupled to the nucleic acid molecule. In some embodiments, the method can further comprise removing a given nucleic acid subunit or precursor thereof of the nucleic acid molecule from the first site if the sensor detects that the given nucleic acid subunit or precursor thereof of the nucleic acid molecule is incorrectly incorporated to the nucleic acid molecule during the generating.

An additional aspect of the disclosure provides a method for accessing data. The method can comprise providing an array of individually addressable sites, where a given site of the array has a nucleic acid molecule with a sequence of nucleic acid subunits that corresponds to bits encoding at least one computer-executable directive for storing data. The method can further comprise, at the given site, identifying the sequence of nucleic acid subunits by measuring an impedance, conductance and/or charge associated with the nucleic acid molecule. The method can further comprise, using a computer processor, identifying the bits from the sequence of nucleic acid subunits, and generating the data from the bits.

In some embodiments, an additional site of the array may not have an additional nucleic acid molecule with the sequence of nucleic acid subunits. In some embodiments, an additional site of the array may have an additional nucleic acid molecule with the sequence of nucleic acid subunits. In some embodiments, the identifying can comprise sequencing the nucleic acid molecule. In some embodiments, the sequencing can comprise performing a nucleic acid extension reaction using a primer that hybridizes to the nucleic acid molecule. In some embodiments, the impedance, conductance and/or charge associated with the nucleic acid molecule can be indicative of nucleotide incorporation events during the nucleic acid extension reaction.

In some embodiments, the identifying may comprise hybridizing an oligonucleotide that comprises a sequence at least partially complementary to the sequence of nucleic acid subunits to the nucleic acid molecule. In some embodiments, the impedance, conductance and/or charge associated with the nucleic acid molecule may be indicative of the hybridizing the oligonucleotide to the nucleic acid molecule.

In some embodiments, the sequence of nucleic acid subunits that is identified may be stored in computer memory. In some embodiments, the method may further comprise storing the data in computer memory. In some embodiments, the nucleic acid subunits may comprise at least two distinct subunits. A subset of the at least two distinct subunits can correspond to a 1 or 0. In some embodiments, the given site may comprise a plurality of the nucleic acid molecules.

In some embodiments, the method can further comprise assembling generated data into a larger piece of data. In some embodiments, the nucleic acid molecule may comprise a primer binding sequence. In some embodiments, the primer binding sequence can function as a searchable index.

In some embodiments, a sensor at the given site can detect signals indicative of the impedance, conductance and/or charge during the measuring. In some embodiments, the sensor can comprise a pair of electrodes. In some embodiments, the sensor may be electrically coupled to the Debye layer of a surface of the sensor, the nucleic acid molecule, or a surface coupled to the nucleic acid molecule.

In some embodiments, the nucleic acid molecule may be coupled to a surface at the given site. The surface may be, for example, a particle or a surface of a well at the site. In some embodiments, the surface may be removable from the site. In some embodiments, the nucleic acid molecule may be coupled to the surface via hybridization with another nucleic acid molecule coupled to the surface. In some embodiments, the nucleic acid molecule may be coupled to the surface via a covalent bond. In some embodiments, the nucleic acid molecule may be coupled to the surface via a non-covalent interaction.

An additional aspect of the disclosure provides a system for data storage. The system can comprise an array of individually addressable nucleic acid synthesis sites, where an individual synthesis site of the array synthesizes a nucleic acid molecule from individual nucleic acid subunits or precursors thereof. The system can also include a computer processor. The computer processor can receive bits encoding at least one computer-executable directive for storing data and can generate a nucleic acid sequence that encodes the data. The nucleic acid sequence can comprise nucleic acid subunits that correspond to the bits. The computer processor can also transmit electrical signals to the array to generate a nucleic acid molecule having the nucleic acid sequence at a first site of the array at the exclusion of generating an additional nucleic acid molecule having the nucleic acid sequence at a second site of the array.

In some embodiments, the system can further comprise computer memory that stores the data and/or the nucleic acid sequence. In some embodiments, the individual nucleic acid subunits can be selected from at least two distinct subunits. A subset of the at least two distinct subunits can correspond to a 1 or 0. In some embodiments, the individual synthesis site may comprise a pair of electrodes.

In some embodiments, the computer processor can transmit electrical signals to the array to alternately and sequentially direct the individual nucleic acid subunits or precursors thereof to the individual synthesis site based on the nucleic acid sequence. In some embodiments, the computer processor can transmit electrical signals to the array that exclude the individual nucleic subunits or precursors from an additional individual synthesis site of the array. In some embodiments, the individual synthesis site can be configured to attract a given nucleic acid subunit or precursor thereof to the individual synthesis site or not repel the given nucleic acid subunit or precursor thereof from the individual synthesis site. In some embodiments, an additional individual synthesis site of the array can be configured to repel the given nucleic acid subunit or precursor thereof from the additional individual synthesis site or not attract the given nucleic acid subunit or precursor thereof to the additional individual synthesis site.

In some embodiments, the individual synthesis site can attract the given nucleic acid subunit or precursor thereof and/or an additional individual synthesis site of the array can repel the given nucleic acid subunit or precursor thereof by generating an electric field. In some embodiments, the system can further comprise one or more electrodes at the individual synthesis site and/or the additional individual synthesis site that generate the electric field.

In some embodiments, the individual synthesis site can attract the given nucleic acid subunit or precursor thereof and/or an additional individual site of the array repels the given nucleic acid subunit or precursor thereof by generating a magnetic field. In some embodiments, the system can further comprise one or more magnetic elements at the individual synthesis site and/or the additional individual synthesis site that generate the magnetic field.

In some embodiments, the system can further comprise a fluid flow apparatus that can alternately and sequentially direct the individual nucleic acid subunits or precursors to the individual synthesis site. In some embodiments, the fluid flow apparatus can comprise at least one microfluidic channel.

In some embodiments, the system may further comprise a reaction surface at the individual synthesis site on which the nucleic acid molecule can be synthesized. The reaction surface can be, for example, a particle or a surface of a well at the individual synthesis site. In some embodiments, the reaction surface may be removable from the individual synthesis site. In some embodiments, the reaction surface may be magnetically immobilized at the individual synthesis site. In some embodiments, the array may be substantially planar.

In some embodiments, the individual synthesis site may comprise a sensor capable of detecting signals indicative of an impedance change, a charge change, a change in pH, or a change in temperature associated with one or more nucleic acid molecules at the individual synthesis site. In some embodiments, the sensor may comprise a pair of electrodes. In some embodiments, during sensing, the sensor may be electrically coupled to the Debye layer of a surface of the sensor, a surface of the one or more nucleic acid molecules, or a reaction surface coupled to the one or more nucleic acid molecules.

An additional aspect of the disclosure provides a system for accessing data. The system may comprise an array of individually addressable sites. An individual site of the array can have a nucleic acid molecule with a sequence of nucleic acid subunits that corresponds to bits encoding at least one computer-executable directive for storing data. The system can further comprise a sensor at the given site that measures signals indicative of an impedance, conductance and/or charge associated with the nucleic acid molecule and a computer processor coupled to the sensor. The computer process can identify the sequence of nucleic acid subunits from signals received from the sensor; identify the bits from the sequence of nucleic acid subunits; generate the data from the bits; and store the data in a memory location.

In some embodiments, an additional individual site of the array may not have an additional nucleic acid molecule with the sequence of nucleic acid subunits. In some embodiments, an additional individual site of the array may have an additional nucleic acid molecule with the sequence of nucleic acid subunits. In some embodiments, the sensor can measure signals indicative of nucleotide incorporation events during a nucleic acid extension reaction associated with the nucleic acid molecule. In some embodiments, the sensor can measure signals indicative of one or more hybridization events associated with the nucleic acid molecule.

In some embodiments, the memory location or an additional memory location can store the sequence of nucleic acid subunits identified by the computer processor. In some embodiments, the nucleic acid subunits may comprise at least two distinct subunits. A subset of the at least two distinct subunits can correspond to a 1 or 0. In some embodiments, the individual site may comprise a plurality of nucleic acid molecules comprising the sequence of nucleic acid subunits. In some embodiments, the computer processor can assemble the data into a larger piece of data.

In some embodiments, the nucleic acid molecule may comprise a primer binding sequence. In some embodiments, the primer binding sequence can be configured to function as a searchable index. In some embodiments, the sensor may comprise a pair of electrodes. In some embodiments, during sensing, the sensor may be electrically coupled to the Debye layer of a surface of the sensor, the nucleic acid molecule, or a surface coupled to the nucleic acid molecule.

In some embodiments, the nucleic acid molecule may be coupled to a surface at the individual site. The surface may be, for example, a particle or a surface of a well at the individual site. It some embodiments, the surface may be removable from the individual site. In some embodiments, the nucleic acid molecule may be coupled to the surface via hybridization with another nucleic acid molecule coupled to the surface. In some embodiments, the nucleic acid molecule may be coupled to the surface via a covalent bond. In some embodiments, the nucleic acid molecule may be coupled to the surface via a non-covalent interaction.

An additional aspect of the disclosure provides a method for managing a database of polynucleotides. The method can comprise assigning a higher level metadata to each polynucleotide in the database of polynucleotides. The higher level metadata can be based on a first unique segment for each polynucleotide. The method can also include assigning a lower level metadata to polynucleotides in the database of polynucleotides that have a common higher level metadata. The lower level metadata can be based on a second unique segment of the polynucleotides that have a common higher level metadata.

An additional aspect of the disclosure provides a system. The system can comprise a chamber and an input funnel.

The chamber can comprise a first surface having a width (W) and a length (L); a second surface parallel to the first surface; and a space between the first surface and the second surface having a height (H). The space between the first and second surfaces can be configured to direct fluid flow and H can be less than about 3 millimeters (mm). The input funnel can have a wide end in fluid communication with the space between the first surface and the second surface. In addition, the input funnel can have a narrow end medial to the wide end and in fluid communication with the wide end. The wide end can have a first thickness ($t_0$) at its mid-point, a second thickness ($t_1$) at its edges, and a height (h) between the wide end to the narrow end. In some embodiments, ($t_0$) may be less than ($t_1$).

In some embodiments, the system can further comprise an output funnel having a wide end in fluid communication with the space between the first surface and the second surface. The output funnel can also include a narrow end in fluid communication with the wide end. The wide end can have a third thickness ($t_2$) at its mid-point and a fourth thickness ($t_3$) at its edges, and a height ($h_2$) between the wide end and the narrow end.

In some embodiments, the device can be configured to direct fluid flow through the narrow end of the input funnel, through the space between the first surface and the second surface, and out of the narrow end of the output funnel. In some embodiments, the input funnel may be oriented perpendicularly to the first surface and the second surface. In some embodiments, the space may be configured to direct fluid flow such that the fluid flow has a Reynolds number of less than about 2100. In some embodiments, the space may be configured to direct fluid flow such that the linear flow rate of the fluid flow at any two points within the space varies by at most about 20%. In some embodiments, the space may be configured to direct fluid flow such that the volumetric flow rate of the fluid flow at any two points within the space varies by at most about 20%.

In some embodiments, (H) may be less than about 100 micrometers. In some embodiments, (h) may be about 10 mm. In some embodiments, the ratio of ($t_0$)/($t_1$) may be less than about 0.95. In some embodiments, (H) can be about 100 μm, ($t_1$) can be about 500 μm, ($t_0$) can be about 300 μm and (h) can be about 2 mm. In some embodiments, the chamber can comprise walls and the walls can be curved. In some embodiments, a distance from the first surface to the second surface may be greater proximate to the center of the chamber than at the edges of the chamber. In some embodiments, the ratio of a distance from the first surface to the second surface at a point proximate to the center of the chamber to a distance from the first surface to the second surface at a point proximate to the edge of the chamber may be less than about 0.8. In some embodiments, the ratio of a distance from the first surface to the second surface proximate to the center of the chamber to ($t_0$) or ($t_1$) may be less than about 0.8. In some embodiments, at least one of (W) or (L) can be at least about 1 mm.

An additional aspect of the disclosure provides a system. The system can comprise a hydrophobic substrate comprising an array of hydrophilic regions; a plurality of sensors, with at least one sensor located within or adjacent to each of the hydrophilic regions; and a magnetic array. At least one magnet of the magnetic array can be located within, or adjacent to each of the hydrophilic regions. The sensors can be used for detecting a chemical reaction.

In some embodiments, the hydrophobic substrate can be created by depositing one or more layers of alkylsilane, silicone, teflon, fluoroalkylsilane, hydrophobic phosphonates, hydrophobic carboxylates, hydrophobic polycarboxylates, hydrophobic polythiols or any combination thereof on a surface of a substrate. In some embodiments, the hydrophilic regions may comprise silicon oxide, silanes, PEGylated silanes, proteins, dextrans, polysaccharides, hydrophilic polymers, polyphosponic acids, polyacrylic acids, zwitterionic polymers or any combination thereof. In some embodiments, the hydrophilic regions may be ozonized. In some embodiments, the hydrophilic regions may be patterned by a photoresist. In some embodiments, the hydrophilic regions may comprise gold or platinum.

In some embodiments, the sensors may comprise electrodes. In some embodiments, there may be at least one electrode per hydrophilic region. In some embodiments, the system may further comprise a module for generating droplets of reagents for the chemical reaction. Such a module, for example, may generate droplets comprising magnetic beads. In some embodiments, the module for generating droplets may comprise a single static spray nozzle, a single movable spray nozzle, a static array of spray nozzles, a movable array of spray nozzles, an original printer head, or a modified printer head. In some embodiments, the hydrophobic substrate may be configured to transport the droplets to the hydrophilic regions. In some embodiments, the array of hydrophilic regions may comprise an array of wells. An individual well of the array of wells can comprise a hydrophilic region.

An additional aspect of the disclosure provides a method. The method can comprise providing a chamber comprising an array of sensors and magnets associated with the sensors. The array can comprise hydrophobic and hydrophilic regions and the sensors and magnets can be located within or adjacent to the hydrophilic regions. The method can further comprise flowing a plurality of magnetic particles over the array, such that the particles are immobilized by the magnets to provide immobilized particles. The method can further comprise flowing a solution containing reagents over the immobilized particles and generating droplets of the reagents adjacent to the hydrophilic regions by introducing an immiscible fluid into the chamber. The method can further comprise detecting a species in each droplet using the sensors.

In some embodiments, the immiscible fluid may be air or oil. In some embodiments, the method may further comprise using a Peltier device to control a temperature of the chamber and/or array. In some embodiments, the droplet can have a volume of at least about 10 picoliters (pL). In some embodiments, droplets can be placed in a corner of the chamber with a heat source proximate to the droplets. In some embodiments, the droplets may be isolated from each other. In some embodiments, the droplets can be generated by flowing in the solution containing reagents from a first inlet and flowing in the immiscible fluid from a second inlet. In some embodiments, flowing the reagents over the particles, generating droplets of the reagents and detecting a species in the droplets using the sensors may be repeated for one or more cycles.

In some embodiments, the reagents may comprise DNA and repeated flows of solutions comprising DNA and immiscible fluids may increase the fraction of array locations having DNA. In some embodiments, the reagents may comprise nucleotides and repeated flows of nucleotides can result in sequencing of a DNA template at each array location. In some embodiments, after droplet generation, the method may further comprise performing a reaction (e.g., nucleic acid amplification, nucleic acid sequencing) within each droplet. In some embodiments, the method may further comprise detecting the reaction in each droplet using one or more of the sensors. In some embodiments, the droplets may be transportable by electrowetting (EW) or by electrowetting on dielectric (EWOD).

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. Systems and methods for biological analysis that can be combined with the present disclosure to yield additional embodiments of the present disclosure are described in PCT Patent Application No. PCT/US2011/054769, PCT Patent Application No. PCT/US2012/039880, PCT Patent Application No. PCT/US2012/067645, PCT Patent Application No. PCT/US2014/027544, and U.S. patent application Ser. No. 13/481,858, each of which is incorporated herein by reference in its entirety.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

DETAILED DESCRIPTION

Figure 1:
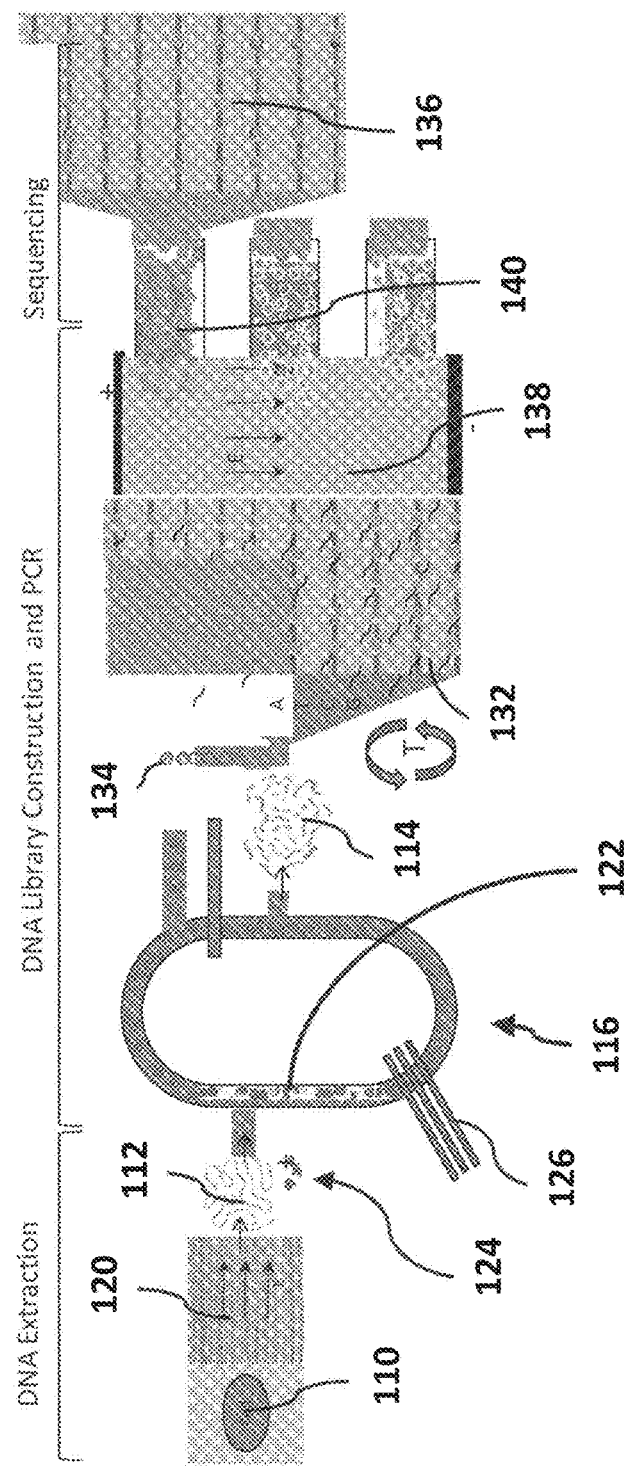
FIG. 1 is a schematic of an integrated sequencing platform.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "adjacent to," as used herein, generally means next to, in proximity to, or in sensing or electronic vicinity (or proximity) of. For example, a first object adjacent to a second object can be in contact with the second object, or may not be in contact with the second object but may be in proximity to the second object. In some examples, a first object adjacent to a second object is within about 0 micrometers ("microns"), 0.001 microns, 0.01 microns, 0.1 microns, 0.2 microns, 0.3 microns, 0.4 microns, 0.5 microns, 1 micron, 2 microns, 3 microns, 4 microns, 5 microns, 10 microns, or 100 microns of the second object.

The present disclosure provides a system that can employ the use of nucleic acid molecules for data storage. The system can include a solid state substrate with locations on the substrate for containing biological and/or chemical matter. The locations on the substrate may be referred to as "pixels" and each individual pixel is arranged such that the substrate has an array of pixels.

The term "nucleic acid," as used herein, generally refers to a molecule comprising one or more nucleic acid subunits. A nucleic acid may include one or more subunits selected from adenosine (A), cytosine (C), guanine (G), thymine (T) and uracil (U), or variants thereof. A nucleotide can include A, C, G, T or U, or variants thereof. A nucleotide can include any subunit that can be incorporated into a growing nucleic acid strand. Such subunit can be an A, C, G, T, or U, or any other subunit that is specific to one or more complementary A, C, G or U, or complementary to a purine (i.e., A or G, or variant thereof) or a pyrimidine (i.e., C, T or U, or variant thereof). In some examples, a nucleic acid is deoxyribonucleic acid (DNA), ribonucleic acid (RNA), or derivatives or variants thereof. A nucleic acid may be single-stranded or double stranded. In some cases, a nucleic acid molecule is circular.

The terms "nucleic acid molecule," "nucleic acid sequence," "nucleic acid fragment," "oligonucleotide" and "polynucleotide," as used herein, generally refer to a polymeric form of nucleotides that may have various lengths, either deoxyribonucleotides (DNA) or ribonucleotides (RNA), or analogs thereof. An oligonucleotide is typically composed of a specific sequence of four nucleotide bases: adenine (A); cytosine (C); guanine (G); and thymine (T) (uracil (U) for thymine (T) when the polynucleotide is RNA). Thus, the term "oligonucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Oligonucleotides may include one or more non-standard nucleotide(s), nucleotide analog(s) and/or modified nucleotides.

Examples of modified nucleotides include, but are not limited to diaminopurine, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxy succinimide esters (NHS). Alternatives to standard DNA base pairs or RNA base pairs in the oligonucleotides of the present disclosure can provide higher density in bits per cubic mm, higher safety (resistant to accidental or purposeful synthesis of natural toxins), easier discrimination in photo- programmed polymerases, or lower secondary structure. Such alternative base pairs compatible with natural and mutant polymerases for de novo and/or amplification synthesis are described in Betz K, Malyshev D A, Lavergne T, Welte W, Diederichs K, Dwyer T J, Ordoukhanian P, Romesberg F E, Marx A (2012).

The term "polymerase," as used herein, generally refers to any enzyme capable of catalyzing a polymerization reaction. Examples of polymerases include, without limitation, a nucleic acid polymerase. A polymerase can be a polymerization enzyme. In some cases, a transcriptase or a ligase is used (i.e., enzymes which catalyze the formation of a bond).

Integrated Sequencing Platforms

An integrated sequencing platform may include a nucleic acid (e.g., DNA) extraction system, a library construction system, an amplification system, an enrichment system, and a sequencing system. In some embodiments the systems may be separate and/or in modular format. In some embodiments, the integrated sequencing platform can include one, two, three, four, or all five of these systems. In some cases, the systems can be integrated within a single microfluidic device and/or a single array (e.g., a re-usable array). An example of such an integrated platform is depicted in FIG. 1. Additional examples of such integrated sequencing platforms can be found in PCT Patent Application No. PCT/US2011/054769, PCT Patent Application No. PCT/US2012/039880, PCT Patent Application No. PCT/US2012/067645, PCT Patent Application No. PCT/US2014/027544, and U.S. patent application Ser. No. 13/481,858, each of which is incorporated herein by reference in its entirety.

An integrated system may comprise a library construction system (e.g., nucleic acid library construction system), which may include a fragmentation and/or size selection element. An example of a library construction system is shown in FIG. 1. As shown in FIG. 1, a library construction system may include a nucleic acid (e.g., DNA) fragmentation and size selection element 116. The fragmentation and size selection element 116 can be configured to produce double-stranded nucleic acid fragments, which may or may not have blunted ends, via the elements and methods described below. The fragmentation and size selection element 116 can include one or more microfluidic channels 122 within which nucleic acid may be disposed along with a set of fragmentation beads 124. Nucleic acid 112 collected in a nucleic acid (e.g., DNA) extraction system (shown for example in FIG. 1) can be conveyed or "injected" into the nucleic acid (e.g., DNA) fragmentation and size selection element 116 by any suitable method (e.g., pressurized injection, electrophoretic movement, gravity feed, heat-induced movement, ultrasonic movement and/or the like). Similarly, fragmentation beads 124 can be conveyed into the nucleic acid (e.g., DNA) fragmentation element and size selection element 116 by any suitable method.

The fragmentation element and/or size selection element 116 may include a pump 126 to produce movement of a fluid (e.g., a fluid comprising nucleic acid (e.g., DNA) and fragmentation beads 124) within a microfluidic channel 122. The pump 126 can be, for example, a peristaltic pump. In some embodiments, the pump 126 can include one or more microfluidic elements in fluid communication with the microfluidic channel 122, and may have a flexible side-wall that, when deformed, produces a flow within the microfluidic channel 122. In other embodiments, however, any other suitable mechanism can be used as an alternative or in addition to produce movement fluid within the microfluidic channel 122, with non-limiting examples, that include selective heating and cooling of the fluid, pneumatic pressurization of the microfluidic channel, electrophoretic motion, or the like.

The fragmentation beads 124 can be constructed from any material suitable for separating, cutting and/or otherwise dividing a nucleic acid (e.g., DNA) into nucleic acid fragments (e.g., DNA fragments). In some embodiments, the fragmentation beads 124 can be constructed from glass, polydimethylsiloxane (PDMS), ceramic or the like. Moreover, the fragmentation beads 124 can have any suitable size and/or geometry such that the fragmentation element produces fragments having the desired characteristics (e.g., length, strand characteristics, or the like). For example, in some embodiments, the fragmentation beads 124 can be substantially spherical and can have a diameter of 50 µm or less. In other embodiments, the fragmentation beads can have a diameter of 500 nm or less, or any diameter between 50 µm and 500 nm.

Moreover, the size and/or geometry of the microfluidic channel 122 (e.g., cross-sectional shape, aspect ratio or the like) can be selected such that the movement of the nucleic acid (e.g., DNA) within the microfluidic channel 122 and contact of the nucleic acid with the fragmentation beads 124 fragments (e.g., via shearing) the nucleic acid as desired. In some embodiments, the microfluidic channel 122 may be in the range of 1 to 500 µm in hydraulic diameter (i.e., the cross-sectional area of the microfluidic channel 122 can be substantially rectangular, thus the size can be represented as a hydraulic diameter). In other embodiments, the hydraulic diameter of the microfluidic channel 122 can be in the range of 10 to 200 µm. In yet other embodiments, the hydraulic diameter of the microfluidic channel 122 can be in the range of 500 nm or less. In other embodiments, the microfluidic channel 122 can have any suitable shape, such as semi-circular, oval, tapered or the like. In some embodiments enzymatic polishing of sheared nucleic acid (e.g., DNA) ends can be done such that the ends are blunt ends.

In other embodiments, an enzymatic solution can be conveyed into the microfluidic channel 122 to, at least partially, produce enzymatic fragmentation of nucleic acid (e.g., DNA).

In some embodiments, nucleic acid (e.g., deoxyribonucleic acid (DNA)) amplification and sequencing may be performed sequentially within the same system. In such cases, sample nucleic acid may be associated with a plurality of carriers, such as, for example, beads or other types of particles. In some cases, the carriers may be magnetic carriers, such as, for example, magnetic beads or paramagnetic beads. In some cases, the magnetic carriers can be entered into an array (e.g., a substantially planar array comprising a substantially planar substrate) of magnetic features such that the magnetic carriers are held in place by a localized magnetic field at each position (e.g., pixel) of the array. In some embodiments, carriers (including magnetic carriers) can be held in place at each position of an array (e.g., a substantially planar array) by electrostatic force via one or more electrodes due to the charge of the carrier or the associated nucleic acid. In other embodiments, the carriers can be held in place at each position of the array by physical trenches or wells. In some embodiments, the carriers can be held in place at each position of the array by interaction of a species bound to the carrier with a species bound to the array (e.g., hybridization of oligonucleotides or via ligand-capture moiety pairs). Upon immobilization of the carriers to an array, amplification of the associated nucleic acid and sequencing of the amplified nucleic acid can be completed sequentially or simultaneously.

In some embodiments, carriers may be first entered into an array (e.g., via flow through microfluidic channels associated with the array) and captured by the array. After carrier capture, sample nucleic acid may be contacted with the array (e.g., via flow through microfluidic channels associated with the array) and subsequently captured by the carriers. Capture may occur, for example, via nucleic acids associated with the carriers and capable of hybridizing with the sample nucleic acid. Such nucleic acids may also be used as primers for amplification reactions described elsewhere herein. In some embodiments, nucleic acid to be amplified and/or sequenced is associated with carriers prior to their capture by an array.

Alternatively, a surface of the array (e.g., sensor surface, array substrate surface, etc.) may comprise elements suitable for capturing sample nucleic acid, including nucleic acids capable of hybridizing with the sample nucleic acid. Such nucleic acids may also be capable of serving as primers for amplification reactions described elsewhere herein. Such a configuration may be suitable for amplifying and sequencing a nucleic acid in the absence of a carrier.

In some embodiments, the sample nucleic acid may be provided to an array at extremely dilute concentrations in order to obtain a desired ratio of molecules of sample nucleic acid to carrier. For example, ratios of one molecule of nucleic acid for one carrier (e.g., bead), one molecule of nucleic acid for two carriers, one molecule of nucleic acid for three carriers, one molecule of nucleic acid for five beads, or less, etc. may be desired.

During amplification reactions, one or more electrodes at a sensor position of the array may be used for concentration of reagents useful for nucleic acid amplification, forming a "virtual well" associated with a carrier, sensor, or substrate at the array position via an electric field. Virtual wells can permit amplification of nucleic acids at a sensor position without cross-contamination of reactants with those of other sensors of the array. In certain embodiments, amplification within a virtual well can generate a clonal population of nucleic acid associated with a carrier, sensor surface, or substrate associated with the virtual well.

Nucleic acid amplification may be performed in multiple cycles if desired. Once a first round of amplification is completed after contacting an array with sample nucleic acid, an array may be washed in order to remove any unbound amplicons and other reagents in solution. Following washing, a second round of amplification may be completed, by contacting the array with sample nucleic acid and subjecting captured sample nucleic acid to appropriate conditions. Where clonal populations are generated, the sample may bind only to sites (e.g., carriers, sensor surfaces, etc.) not already comprising amplicons, as sites with amplicons from first round of amplification may be fully loaded amplicons. The process may be repeated for any number of amplification cycles until capture sites are exhausted. Utilizing multiple rounds of amplification may help eliminate double Poisson distribution problems and help ensure that each sensor site is associated with only nucleic acid sequence, such as a clonal population of amplicons attached to a carrier. Moreover, multiple rounds of amplification may also help maximize the use of an array, as each round of amplification can better ensure that all of the pixels of the array of occupied with amplicons for sequencing.

Moreover, during sequencing reactions, one or more of the same electrodes and/or different electrodes may be used to detect a reaction of interest, such as nucleotide incorporation. In some cases, sensing may be completed using a NanoNeedle and/or NanoBridge sensor, or other electrical or optical sensors suitable for detection. A NanoBridge sensor may function as a pH or charge sensor, as described in U.S. Published Patent Application No. US 2012/0138460, titled "BIOSENSOR DEVICES, SYSTEMS AND METHODS THEREFOR", which is incorporated herein by reference in its entirety. A sensor (e.g., NanoNeedle sensor) may function as a charge, conductivity and/or impedance sensor, as described in PCT Patent Application No. PCT/US2011/054769, PCT Patent Application No. PCT/US2012/039880, PCT Patent Application No. PCT/US2012/067645, PCT Patent Application No. PCT/US2014/027544, and U.S. patent application Ser. No. 13/481,858, each of which is incorporated herein by reference in its entirety. In some embodiments, a sequencing reaction of interest may be DNA sequencing.

The detection may be based on at least one of local pH change, local impedance change, local heat detection, local capacitance change, local charge concentration (or change thereof), and local conductivity change. In some embodiments, detection may be based on a local conductivity change, local impedance change, local capacitance change, local charge concentration (or change thereof) of a carrier, a nucleic acid, or other analyte associated with the carrier and/or a sensor. Such measurements may be made by directly detecting (or detecting signals that are indicative of) a local pH change, local impedance change, local heat detection, local capacitance change, local charge concentration (or change thereof), and local conductivity change, such as local conductivity change of a carrier, a nucleic acid (or other analyte) associated with the carrier and/or a sensor. In some cases, detection occurs within the Debye length (e.g., Debye layer) of (i) a carrier, (ii) a nucleic acid associated with a carrier or sensor, and/or (iii) a sensor. Such a sensor configuration is described, for example, in PCT Patent Application No. PCT/US2011/054769, PCT Patent Application No. PCT/US2012/039880, PCT Patent Application No. PCT/US2012/067645, PCT Patent Application No. PCT/US2014/027544, and U.S. patent application Ser. No. 13/481,858, each of which is incorporated herein by reference in its entirety.

Following the completion of sequencing, carriers/nucleic acids may be dissociated from the array, the carriers and array optionally separated from bound species and washed, and either or both of the carriers and array subsequently re-used for another round of amplification and/or sequencing. Dissociation of a carrier from the array may be completed, for example, by removal/reversal of a magnetic and/or electric field used to hold the carrier in place. In addition or as an alternative, fluid flow and/or other type of field (e.g., external magnetic field, external electric field) capable of exerting forces sufficient for overcoming magnetic and/or electrostatic forces used to hold a carrier in place may also be used to dissociate the carrier from an array. Where nucleic acids are directly associated with the array, in the absence of a carrier, the array may be treated with appropriate reagents or energy (e.g., enzymatic reagents, chemical reagents, thermal energy, etc.) to remove bound nucleic acids from the array. In some cases, though, it may be desirable to remove a carrier or nucleic acid from an array prior to amplification and/or sequencing. Such removal can be achieved in analogous fashion as described herein.

In some embodiments, a combined amplification and sequencing system may comprise a magnetic array that can trap a magnetic bead or particle by magnetic force at a plurality of the array positions. In some cases, a magnetic bead may be a paramagnetic bead. Each of the array positions may also comprise electrodes capable of producing electric fields and/or functioning as sensors. Each magnetic bead or particle can comprise a nucleic acid (e.g., DNA) segment that may be clonally amplified, for example, with the aid of electric fields generated by one or more of the electrodes at each array position.

In some embodiments, a combined amplification and sequencing system may comprise an array of electrodes that can trap a magnetic bead or particle by electrostatic force at a plurality of the array positions. In some cases, a magnetic bead may be a paramagnetic bead. One or more of the same electrodes or different electrodes at each of the array positions may also be capable of producing electric fields and/or functioning as sensors. Each magnetic bead or particle can comprise a nucleic acid (e.g., DNA) segment that may be clonally amplified, for example, with the aid of electric fields generated by one or more of the electrodes at each array position.

An example of a combined amplification and sequencing system and use of the example system is depicted in FIG. 2. As shown in FIG. 2A, the system 200 may include an array on a substrate 201 that can comprise sensors (e.g., nanosensors) 205 sometimes in communication with microfluidic channels defined within the platform. Sensors 205 may be associated with substrate 201, and substrate 201 may also be associated with magnetic 210 and electrode 205 and 207 elements. Magnetic beads may be positioned over the sensors 205 by magnetic 210 or electrode 205 and 207 elements. The magnetic elements may form localized magnetic fields and the electrode elements may form localized electric fields in order to position a carrier at each sensor 205 of the array. Moreover, the magnetic and/or electric fields may create an area of confinement for carriers at each position of the array.

Figure 2A:
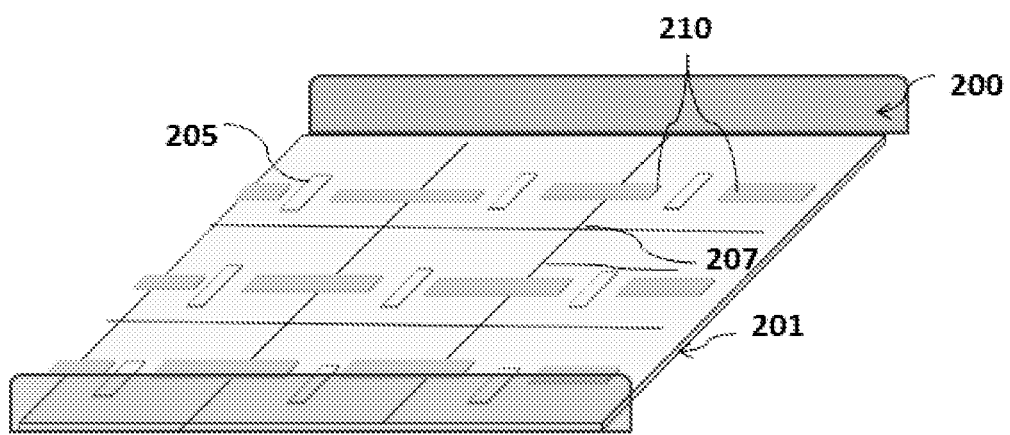
FIG. 2A shows a schematic of an example sensor array.
Figure 2B:
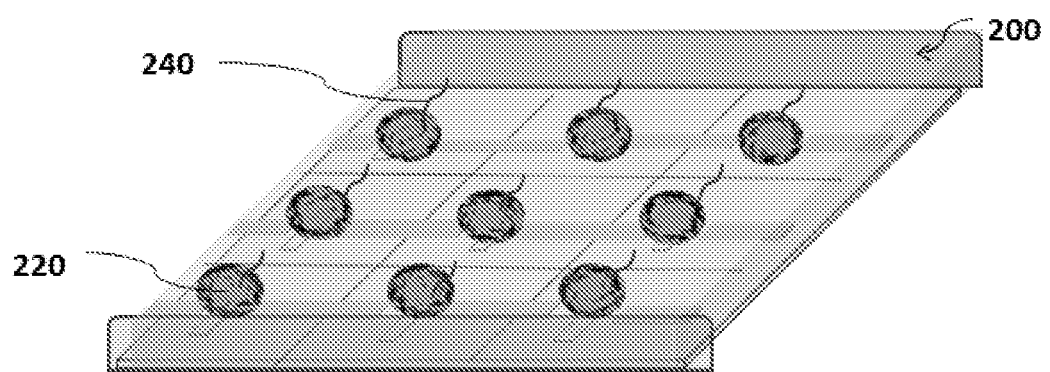
FIG. 2B shows a schematic of an example sensor array with carriers immobilized to the array.

As shown in FIG. 2B, a sample comprising DNA 240 (e.g., DNA fragments) may be conveyed into the system 200. As can be appreciated, DNA 240 is shown as an example and could be any suitable type of nucleic acid, including types of nucleic acids described elsewhere herein. In some cases, introduction of the DNA 240 may be via microfluidic channels associated with the array. As shown, the array may be configured with pre-localized magnetic beads 220 and the magnetic beads may be associated with primers capable of hybridizing with DNA 240, such that DNA 240 is captured by and becomes associated with the beads 220. The magnetic beads 220 may be positioned on the array via the magnetic elements 210 and/or electrode 205 and 207 elements. Alternatively or in addition, primers may be attached, bound, or associated with a sensor at a position of the array and used to trap DNA 240 at the sensor.

Figure 2C:
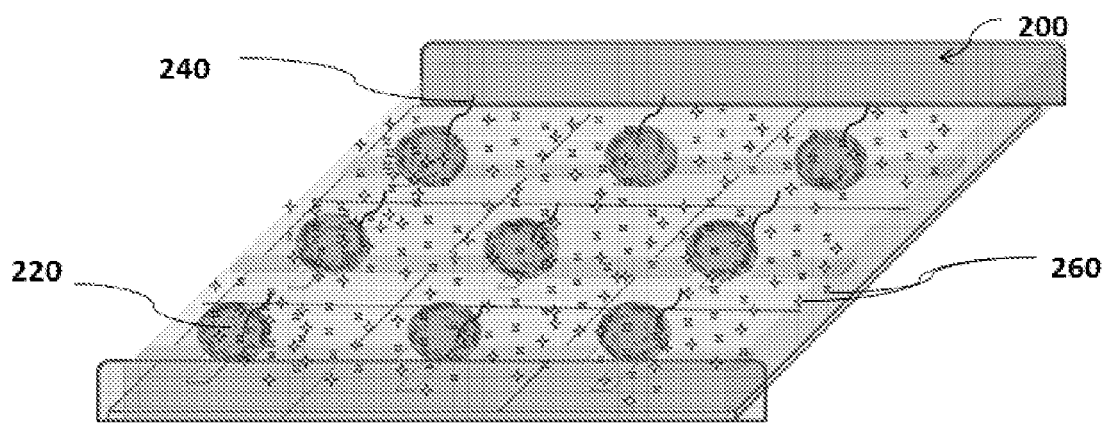
FIG. 2C shows a schematic of an example sensor array with carriers immobilized to the array and in contact with reagents suitable for nucleic acid amplification.

As shown in FIG. 2C, reagents 260 (e.g., polymerase, deoxyribonucleotides (dNTPs), and additional primers) may be simultaneously, previously, or subsequently introduced to the array. In some cases, introduction of the reagents 260 may be via flow through microfluidic channels associated with the array, such that the reagents 260 are contacted with the magnetic beads 220 via flow. Via magnetic and/or electrostatic forces from the appropriate array elements, the magnetic beads 220 can be maintained in the desired position as reagents 260 make contact with the magnetic beads 220 via flow.

Figure 2D:
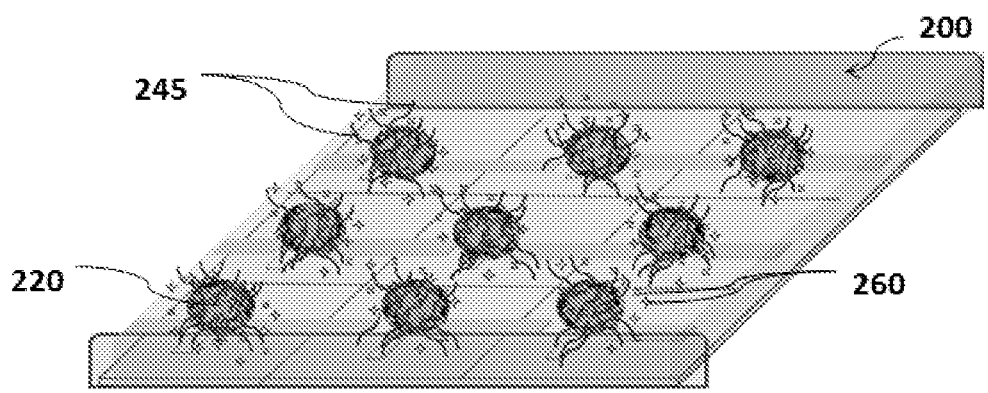
FIG. 2D shows a schematic of an example sensor array where nucleic acid amplification occurs at each array pixel.

As shown in FIG. 2D, the DNA 240 associated with magnetic beads 220 can be clonally amplified to produce amplified DNA 245 and 255 on the surface of the magnetic beads 220. Clonal amplification may be completed using any suitable method including a polymerase chain reaction (PCR), a primer extension reaction, isothermal amplification, or other techniques.

Figure 2E:
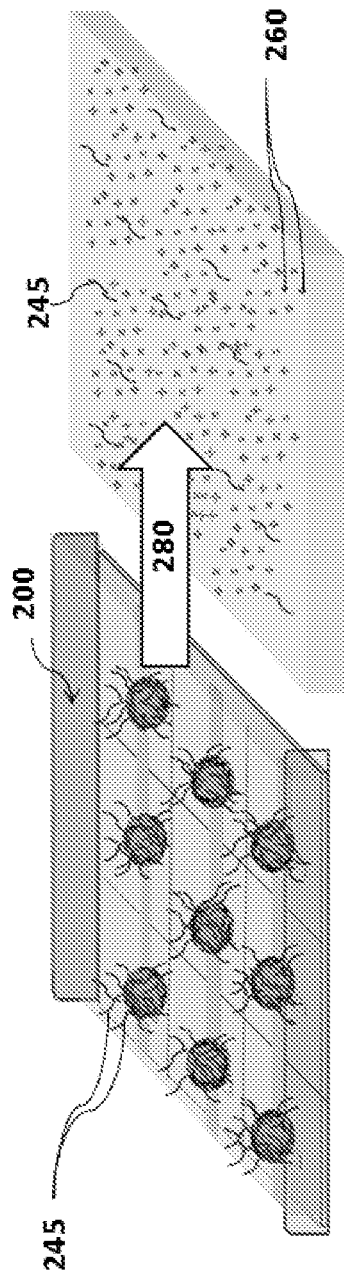
FIG. 2E shows a schematic example of removing reagents from an example sensor array.

As shown in FIG. 2E, the magnetic beads 220 in the array may be washed 280, removing unbound amplicons 245 and reagents 260 in solution following amplification of DNA 240. The result can be magnetic beads 220 comprising clonal sets of amplified DNA 255 associated with array positions. Washing 280 may be completed by any suitable method, such as, for example, washing with a buffer solution at a flow rate sufficient to remove the unbound amplicons 245 and reagents 260 in solution, but insufficient to detach the magnetic beads 220 from their respective positions on the array.

Figure 2F:
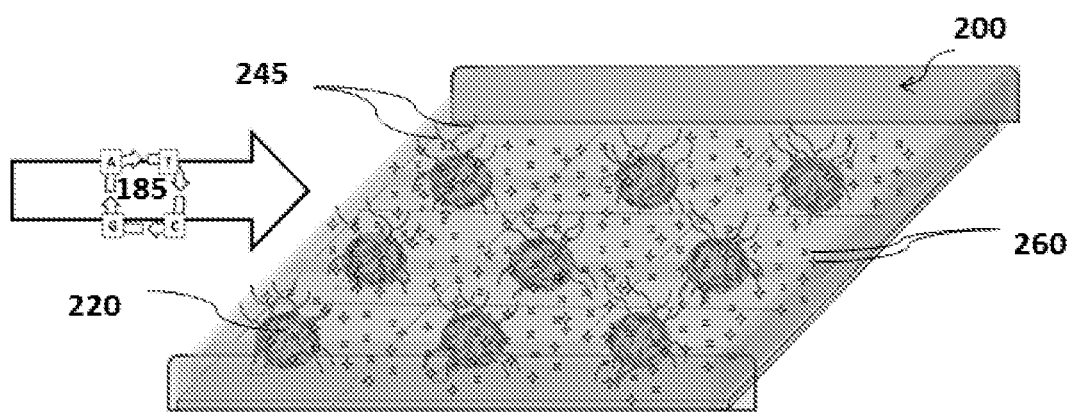
FIG. 2F shows a schematic of an example sensor array where nucleic acids are sequenced at each pixel of the array.

As shown in FIG. 2F, another aliquot of reagents 260 (e.g., polymerase, primers, etc.) and sequential cycles of individual dNTPs 285 may then be contacted (e.g., via flow) with the sensor array, permitting incorporation of the dNTPs into the amplified DNA 255 of magnetic beads 220. dNTPs may be introduced in individual cycles, (e.g., cycle 1=A, cycle 2=T, etc.). where there may be a wash step with buffer in between each cycle to help reduce the chance of contamination from unincorporated nucleotides. Polymerase used for the sequencing reaction, may be the same type of polymerase that is used for the amplification reaction, or may be a different type of polymerase, and can be introduced prior to or with introduction of the dNTPs. Detection of the incorporated dNTPs during each cycle can be used to sequence the amplified DNA 255, and, thus, the original sample DNA 240. Detection may occur, for example, via one or both of electrodes 205 and 207. In some cases, electrodes 205 and 207 can detect nucleotide incorporation events by measuring local impedance changes of the magnetic beads 220 and/or the amplified DNA (or other nucleic acid) 255 associated with the magnetic beads 220. Such measurement can be made, for example, by directly measuring local impedance change or measuring a signal that is indicative of local impedance change. In some cases, detection of impedance occurs within the Debye length (e.g., Debye layer) of the magnetic beads 220 and/or the amplified DNA 255 associated with the magnetic beads 220. Nucleotide incorporation events may also be measured by directly measuring a local charge change or local conductivity change or a signal that is indicative of one or more of these as described elsewhere herein. Detection of charge change or conductivity change can occur within the Debye length (e.g., Debye layer) of the magnetic beads 220 and/or amplified DNA 255 associated with the magnetic beads 220.

Additional examples of combined amplification and sequencing systems, for example, may be found in PCT Patent Application No. PCT/US2011/054769, PCT Patent Application No. PCT/US2012/039880, PCT Patent Application No. PCT/US2012/067645, PCT Patent Application No. PCT/US2014/027544, and U.S. patent application Ser. No. 13/481,858, which are incorporated herein by reference in their entireties.

In some embodiments, after amplification of sample nucleic acid onto carriers, but before sequencing, the carriers subjected to amplification conditions may be sorted in an enrichment system, such as, for example, an electrophoretic sorter, where sorting is achieved via electrophoretic force applied to carriers. The electrophoretic sorter may be part of a system used to conduct amplification and sequencing, or it may be part of a different system. In the electrophoretic sorter, null carriers (e.g., carriers without amplicons), as well as carriers subject to incomplete amplification or those comprising overly short amplicons, can be sorted from carriers comprising the desired amplicons. Additional examples of enrichment systems and electrophoretic sorters are described in PCT Patent Application No. PCT/US2011/054769, PCT Patent Application No. PCT/US2012/039880, PCT Patent Application No. PCT/US2012/067645, PCT Patent Application No. PCT/US2014/027544, and U.S. patent application Ser. No. 13/481,858, which are incorporated herein by reference in their entireties.

An electrophoretic sorter may comprise channels capable of accepting sorted carriers. Carriers (e.g., beads) with appropriate amounts of amplified product and with amplicons of adequate length may have sufficient charge to be pulled off to an outlet channel. Where the electrophoretic sorter is a separate system, such carriers can be collected from the outlet channel and provided back into the amplification/sequencing system for sequencing, where the steps of introducing reagents and detecting nucleotide incorporation events may occur as described above.

Carriers (e.g., beads) without appropriate amounts of amplified product and/or without amplicons of adequate length may flow through the electrophoretic sorter and, instead, be directed into a waste channel. The carriers may be collected from the waste channel and may be reused for another cycle of amplification or other purpose upon appropriate cleaning to remove any undesirable species. For example, carriers may be washed with a bleaching agent, such as hydrogen peroxide, to help ensure that no contaminants remain on the carriers so that they may be reused.

The arrays and methods described herein can be used for a variety of applications and detection of different biological or biochemical moieties in addition to nucleic acids, such as antibody-antigen detection, protein detection, cell analysis, drug-discovery or screening, ligand, small molecules or other types of analysis. Moreover, the devices and methods described herein are not limited to DNA applications, and may be used for reactions and analysis of interest for RNA, protein detection, small molecules, etc. or other biomolecules.

In addition to sequencing reactions and/or nucleotide incorporation events, arrays and associated sensors may also be useful in sensing other biomolecules (e.g., oligonucleotides, proteins, small molecules, peptides, etc.) and/or reactions of interest using any of the methods and devices described herein, including directly measuring local impedance change, local charge change or local change in conductivity or measuring a signal that is indicative of local impedance change, local charge change or local change in conductivity.

In some embodiments, a sensor may detect a nucleic acid hybridization reaction. For example, a carrier (e.g., a bead) may be linked to a nucleic acid and hybridization of the nucleic acid with another nucleic acid (e.g., a primer or oligonucleotide probe) may be detected. In some embodiments, a sensor may detect a protein-protein interaction. For example, a carrier (e.g., a bead) may be coupled to a protein species (e.g., antibody, antibody fragment, peptide, etc.) capable of binding with an additional protein (e.g., a ligand). Binding of the additional protein to the protein species coupled to the carrier may be detected. Binding of small molecules to species linked to carriers may also be detected. In some cases, a plurality of detection methods may be employed to detect a biomolecule or a biological reaction of interest. Non-limiting examples of additional detection methods include an enzyme-linked immunosorbent assay (ELISA), detection of a tag (e.g., optical dyes, fluorescent dyes), detection of a released or generated species during a biological reaction of interest, etc.

A sensor (e.g., an individual sensor) described herein may be independently addressable. An independently addressable sensor as used herein, can refer to an individual sensor in an array whose response can be independently detected from the responses of other sensors in the array. An independently addressable sensor can also refer to an individual sensor in an array that can be controlled independently from other sensors in the array.

In some embodiments, the nucleic acids are not on carriers (e.g., beads). The nucleic acid can be immobilized directly onto a surface, such as a chip and/or sensor surface. For example, in order to integrate detection on-chip, various types of biomolecules may be patterned on-chip. Methods described herein may be used to covalently immobilize nucleic acids (e.g., DNA) directly onto a microchannel surface, a configuration which may be useful, for example, for an enzyme-linked DNA hybridization assay. In some embodiments, DNA or other nucleic acids can be directly attached to PDMS (polydimethylsiloxane) microfluidic channels, and the use of these PDMS-immobilized capture probes can be used for further immobilization of proteins. Such an approach may be used with other approaches for controlling surface properties of PDMS and the use of surface modifications for immobilization of DNA, RNA, and proteins, such as those described in D. Liu, R. K. Perdue, L. Sun, R. M. Crooks, Langmuir 20, 5905, which is entirely incorporated herein by reference.

In some embodiments, the immobilization of nucleic acid (e.g., DNA) onto a PDMS surface may involve a plurality of steps which can include: plasma-induced oxidation of the PDMS surface, functionalization of the oxidized surface with a silane coupling agent bearing a distal thiol group (mercaptopropylsilane, MPS), and subsequent reaction of the thiol groups with acrylamide-modified DNA. The silanization step can be carried out using a vapor-phase reaction method. The plasma-treated PDMS may be exposed to acid (e.g., HCl) vapor before the MPS vapor, as the acid can act as a catalyst that increases the rate of MPS immobilization on the PDMS surface. Subsequent exposure of the PDMS-linked DNA to its biotinylated complement can provide a platform for immobilization of a protein (e.g., alkaline phosphatase (AP)). PDMS immobilization of species can be compatible with a variety of species, including those described herein. In some cases, PDMS immobilization can provide for immobilizing any suitable oligonucleotide or streptavidin-modified protein onto a PDMS surface.

Devices for Biological Detection

The methods and systems described herein can be performed in a device. The device can perform any one or more of the operations of a method, including but not limited to nucleic acid extraction, fragmentation, library preparation, immobilization (e.g., on a carrier), amplification, confinement, bead enrichment, sequencing, or data analysis and communication.

Figure 3:
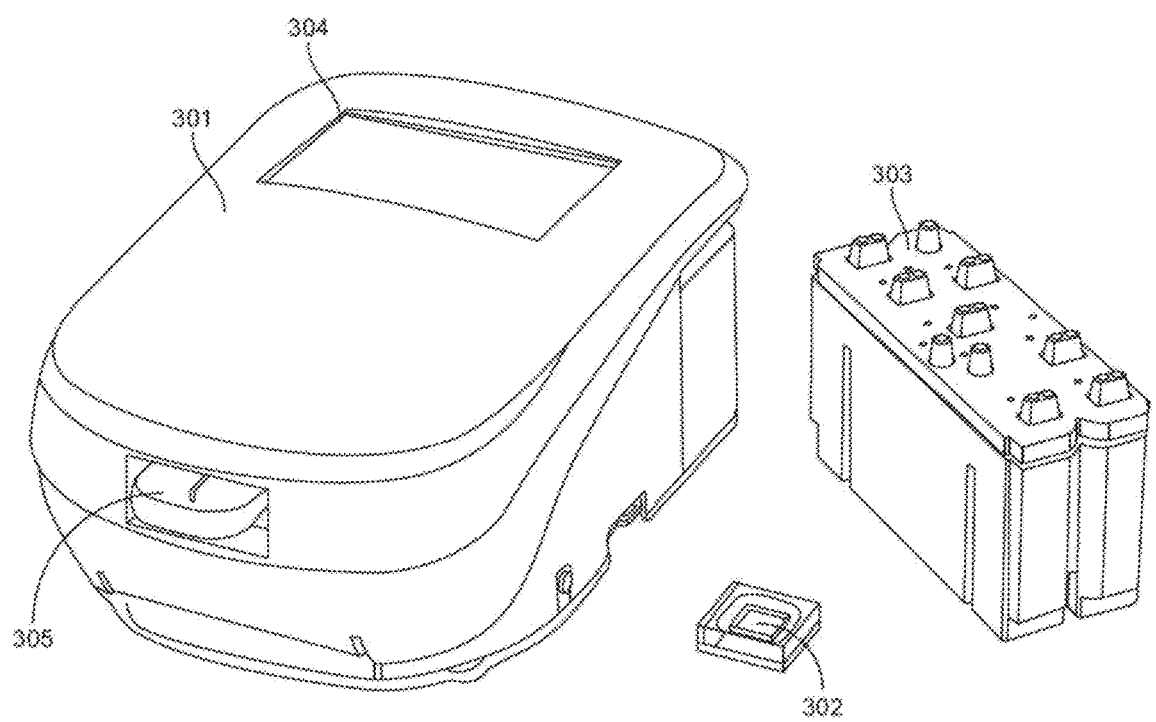
FIG. 3 shows a biological detection device comprising a housing, a removable chip and a removable reagent reservoir.

FIG. 3 shows a biological detection device 301, a removable chip 302 with an array of sensors, and a reagent reservoir 303 that can be inserted into and removed from the biological detection device 301. In some examples, the reagent reservoir 303 includes primers, nucleotides and polymerase enzymes for nucleic acid sequencing.

The biological detection device 301 can include a screen 304 that can include a user interface, such as a graphical user interface. The screen 304 can enable a user to operate the device 301, such as for nucleic acid sequencing.

The biological detection device 301 can include a port 305 that is configured to accept the removable chip 302. In some examples, upon insertion of the removable chip 302 into the device 301, nucleic acid sequencing can be performed using the array of sensors of the chip 302 and the reagents in the reagent reservoir 303.

An aspect of the present disclosure provides a sensing device comprising a sensing array with a plurality of sensors in a housing, where at least a subset of the plurality of sensors is individually addressable, where each sensor of the plurality is adapted to directly measure an electronic signature associated with a biological species in solution, where the housing has a footprint that is less than or equal to about 250,000 mm$^2$, and where the device has a weight that is less than or equal to about 200 pounds, 175 pounds, 150 pounds, 125 pounds, 100 pounds, 75 pounds, 50 pounds, 25 pounds, 10 pounds or less. In some embodiments, the sensing device does not include wells. As an alternative, the sensing device can include wells. The sensing array can be removable from the housing.

In an embodiment, the device further can comprise a fluid flow path in fluid communication with the sensing array. The fluid flow path can be in communication with a repository comprising one or more reagents for nucleic acid sequencing. In some cases, the fluid flow path can provide beads to the sensing array in an emulsion or, alternatively, without an emulsion.

In some situations, at least some, all or substantially all of the plurality of sensors can be individually addressable. For instance, each sensor of the array can be addressed (e.g., read) separately from other sensors in the array. Each sensor can have one or more electrodes for measuring the electronic signature. Examples of electrodes and electrode configurations that may be employed for use with sensors of the present disclosure are provided in PCT Patent Application No. PCT/US2011/054769, PCT Patent Application No. PCT/US2012/039880, PCT Patent Application No. PCT/US2012/067645, PCT Patent Application No. PCT/US2014/027544, and U.S. patent application Ser. No. 13/481,858, each of which applications is entirely incorporated herein by reference for all purposes.

In some embodiments, the biological species can be molecular species such as biomolecule, with non-limiting examples that include nucleic acids, polypeptides, proteins, carbohydrates and fatty acids. In some examples, the biological species is a nucleic acid, including any type of nucleic acid described elsewhere herein. In some embodiments, the nucleic acid can be single stranded or double stranded. In some examples, the nucleic acid is circular.

The device can have a footprint that is less than or equal to about 200,000 mm$^2$, 150,000 mm$^2$, 100,000 mm$^2$, 50,000 mm$^2$, 10,000 mm$^2$, 5,000 mm$^2$, or 1,000 mm$^2$. In some cases, the footprint is greater than or equal to about 50 mm$^2$, 100 mm$^2$, 200 mm$^2$, 300 mm$^2$, 400 mm$^2$, or 500 mm$^2$. The device can have a footprint that is less than that of a personal computer (PC), such as a laptop or tablet PC.

The weight of the device can be less than or equal to about 9 pounds, 8 pounds, 7 pounds, 6 pounds, 5 pounds, 4 pounds, 3 pounds, 2 pounds, 1 pounds, or 0.5 pounds. In some cases, the weight of the device is greater than or equal to about 0.1 pounds, 0.2 pounds, 0.3 pounds, 0.4 pounds, 0.5 pounds, 0.6 pounds, 0.7 pounds, 0.8 pounds, 0.9 pounds, 1 pound, 2 pounds, 3 pounds, 4 pounds, 5 pounds, 6 pounds, 7 pounds, 8 pounds or 9 pounds.

In some embodiments, the sensing array can provide a single-pass bead loading fill factor of at least about 50%, 60%, 70%, 80%, 90%, 95%, 96%, 97%, 98%, 99%, or 99.9% (i.e., the fill factor is the percentage of the array having a bead). In some embodiments, the sensing array can provide a nucleic acid sequencing read length of at least about 20 base pairs (bp), 25 bp, 30 bp, 31 bp, 32 bp, 33 bp, 34 bp, 35 bp, 40 bp, 50 bp, 100 bp, 500 bp, 1000 bp, 5000 bp, 10,000 bp, or 100,000 by with a non-linearity of less than or equal to about 10 bases, 5 bases, 4 bases, 3 bases, 2 bases, 1 base, or 0.5 bases. The read length can be for a nucleic acid homopolymer (e.g., all A, C, T or G). FIG. 2 is an example plot of change in signal (mV, y-axis) versus nucleic acid bases added (x-axis) during a nucleic acid sequencing reaction. The data shows a homopolymer read length of about 33 base pairs The sensing array can be part of a chip that is removable from the housing. The chip can be a single-use chip or multi-use chip. The chip can be disposable (e.g., formed of an environmentally friendly material) and/or can be reusable. The sensing array can be substantially planar.

The sensing array can provide a nucleic acid sequencing throughput of at least about 100 base pairs (bp), 500 bp, 1000 bp, 20,000 bp, or 100,000 bp, in a time period that is less than or equal to about 2 days, 1 day, 12 hours, 6 hours, 3 hours, 2 hours, 1 hour, 45 minutes, 30 minutes, 15 minutes, 10 minutes, or 5 minutes. In some cases, a sensing array can be used to perform targeted sequencing and/or whole genome sequencing.

In some situations, the device further comprises a computer processor (or other electronic logic) coupled to the sensing array. The computer processor can be programmed to receive signals from the sensing array that are indicative of a direct electrical signature of the species.

In some cases, the sensing array is adapted for nucleic acid sequencing, proton detection, protein detection, or pathogen detection. The sensing array can be adapted for nucleic acid amplification and/or fluid enrichment.

The device can be portable such that it can be readily transported by a user or a machine. For example, the machine may be transportable on a vehicle. In some examples, the vehicle is an automobile, motorcycle, scooter, helicopter, airplane, truck, military vehicle, spacecraft, or robot.

The measured electronic signature can be an impedance or a change in impedance associated with (i) a bead adjacent to the sensor, (ii) an electrode of the sensor or (iii) a species in a fluid adjacent to the sensor. As an alternative or in addition to, the electronic signature can be a charge or a change in charge associated with (i) a bead or other type of particle adjacent to the sensor, (ii) an electrode of the sensor or (iii) a species in a fluid adjacent to the sensor. As an alternative or in addition to, the electronic signature can be a conductivity or a change in conductivity associated with (i) a bead or other type of particle adjacent to the sensor, (ii) an electrode of the sensor or (iii) a species in a fluid adjacent to the sensor. Various details for measuring an electronic signature can be as described in PCT Patent Application No. PCT/US2011/054769, PCT Patent Application No. PCT/US2012/039880, PCT Patent Application No. PCT/US2012/067645, PCT Patent Application No. PCT/US2014/027544, and U.S. patent application Ser. No. 13/481,858, each of which applications is entirely incorporated herein by reference for all purposes.

In some cases, the device is part of a system for biological detection. The system can include a single device of multiple devices. Each device can be for the same biological detection or different biological detection. The devices can be in communication with each other through any suitable type of connectivity, including, for example, wireless connectivity.

Another aspect of the present disclosure provides a method for biological detection, comprising providing a sensing device comprising a sensing array with a plurality of sensors in a housing, where at least a subset of the plurality of sensors is individually addressable, where each sensor of the plurality is adapted to directly measure an electronic signature associated with a biological species in solution, where the housing has a footprint that is less than or equal to about 250,000 $mm^2$, 200,000 $mm^2$, 150,000 $mm^2$, 100,000 $mm^2$, 50,000 $mm^2$, 10,000 $mm^2$, 5,000 $mm^2$, or 1,000 $mm^2$ and where the device has a weight that is less than or equal to about 200 pounds, 175 pounds, 150 pounds, 125 pounds, 100 pounds, 75 pounds, 50 pounds, 25 pounds or 10 pounds. Next, a solution comprising the biological species can be directed to the sensing array. The solution can be directed using a fluid flow system comprising, for example, one or more pumps and/or flow actuators. In some embodiments, an electronic signature associated with the biological species can be directly measured using the sensor, as described elsewhere herein. The sensing device can be as described above or elsewhere herein.

In some cases, the sensing device can be provided on a vehicle. The vehicle can be an automobile, motorcycle, scooter, helicopter, airplane, truck, military vehicle, spacecraft, or robot. The vehicle can be moved from a first location to a second location that can be different than the first location. In some situations, while the vehicle is moving from the first location to the second location, (i) the solution is directed to the sensing array and (ii) an electronic signature associated with the biological species is directly measured using the sensor.

The device can be transportable by a user. In some situations, while the user is moving from a first location to a second location, (i) the solution is directed to the sensing array and (ii) an electronic signature associated with the biological species is directly measured using the sensor.

Control Systems

Figure 5:
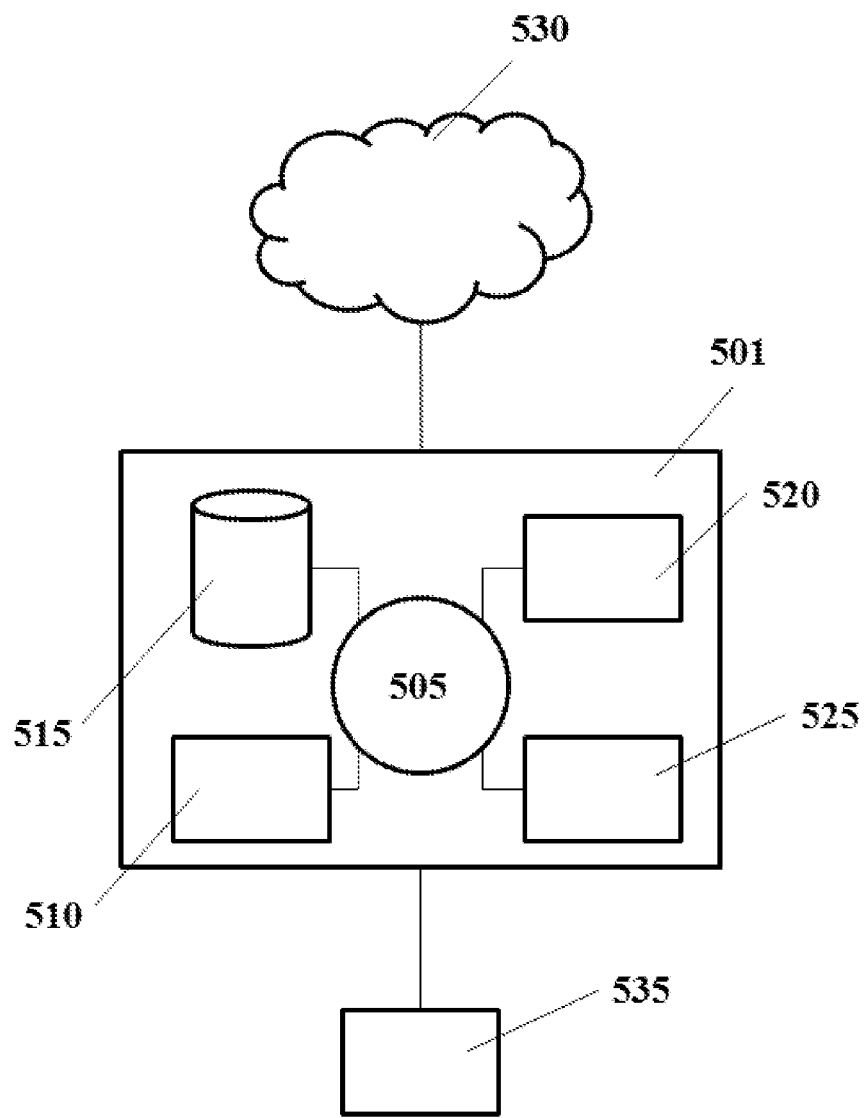
FIG. 5 shows a computer system that is programmed or otherwise configured to control or implement devices, systems and methods of the present disclosure.

The present disclosure provides computer control systems that are programmed to implement methods of the disclosure. FIG. 5 shows a computer system 501 that is programmed or otherwise configured for biological detection. The computer system 501 can regulate various aspects of sensing devices, systems and methods of the present disclosure, such as, for example, methods for biological detection. In some embodiments, the computer system 501 can receive signals from a sensor and determine a change in local impedance, local charge and/or local conductivity as described elsewhere herein.

Figure 4:
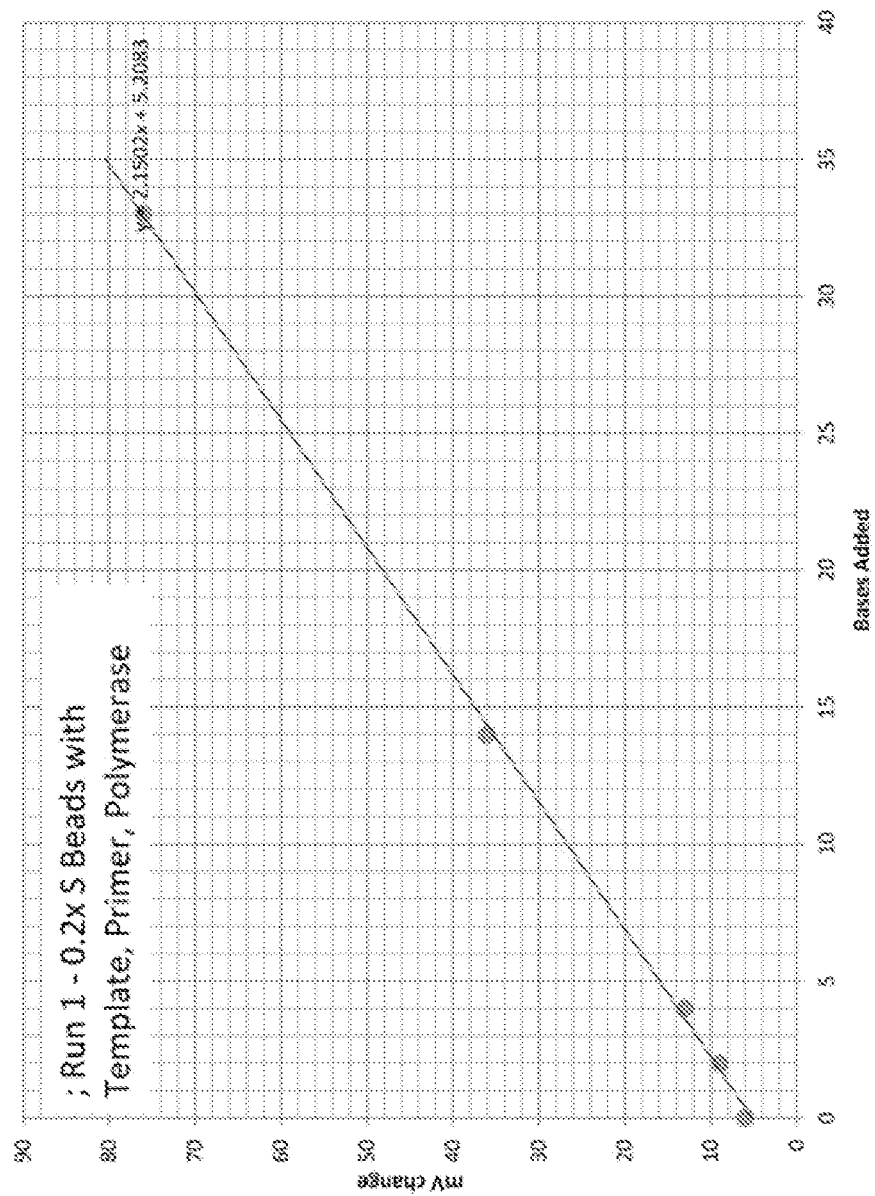
FIG. 4 is a plot of change in signal (mV, y-axis) versus nucleic acid bases added (x-axis) during a nucleic acid sequencing reaction. The data shows a homopolymer read length of about 33 base pairs.

For example, FIG. 4 is an example plot of change in signal (mV, y-axis) versus nucleic acid bases added (x-axis) during a nucleic acid sequencing reaction. The data shows a homopolymer read length of about 33 base pairs.

The computer system 501 can be part of or separate from a device or system for biological detection. In some examples, the system 501 is integrated with a device or system for biological detection, such as a nucleic acid sequencing device. For example, the system 501 can be included in a housing that also contains a sensing array, which can be provided via a removable chip.

The computer system 501 includes a central processing unit (CPU, also "processor" and "computer processor" herein) 505, which can be a single core or multi core processor, or a plurality of processors for parallel processing. The computer system 501 also includes memory or memory location 510 (e.g., random-access memory, read-only memory, flash memory), electronic storage unit 515 (e.g., hard disk), communication interface 520 (e.g., network adapter) for communicating with one or more other systems, and peripheral devices 525, such as cache, other memory, data storage and/or electronic display adapters. The memory 510, storage unit 515, interface 520 and peripheral devices 525 are in communication with the CPU 505 through a communication bus (solid lines), such as a motherboard. The storage unit 515 can be a data storage unit (or data repository) for storing data. The computer system 501 can be operatively coupled to a computer network ("network") 530 with the aid of the communication interface 520. The network 530 can be the Internet, an internet and/or extranet, or an intranet and/or extranet that is in communication with the Internet. The network 530 in some cases is a telecommunication and/or data network. The network 530 can include one or more computer servers, which can enable distributed computing, such as cloud computing. The network 530, in some cases with the aid of the computer system 501, can implement a peer-to-peer network, which may enable devices coupled to the computer system 501 to behave as a client or a server.

The CPU 505 can execute a sequence of machine-readable instructions, which can be embodied in a program or software. The instructions may be stored in a memory location, such as the memory 510. Examples of operations performed by the CPU 505 can include fetch, decode, execute, and writeback.

The storage unit 515 can store files, such as drivers, libraries and saved programs. The storage unit 515 can store user data, e.g., user preferences and user programs. The computer system 501 in some cases can include one or more additional data storage units that are external to the computer system 501, such as located on a remote server that is in communication with the computer system 501 through an intranet or the Internet.

The computer system 501 can communicate with one or more remote computer systems through the network 530. For instance, the computer system 501 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 501 via the network 530.

Methods as described herein can be implemented by way of machine (e.g., computer processor) executable code stored on an electronic storage location of the computer system 501, such as, for example, on the memory 510 or electronic storage unit 515. The machine executable or machine readable code can be provided in the form of software. During use, the code can be executed by the processor 505. In some cases, the code can be retrieved from the storage unit 515 and stored on the memory 510 for ready access by the processor 505. In some situations, the electronic storage unit 515 can be precluded, and machine-executable instructions are stored on memory 510.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 501 can include or be in communication with an electronic display 535 that comprises a user interface (UI) for providing, for example, an output or readout of a sensing device of system coupled to the computer system 501. Such readout can include a nucleic acid sequencing readout, such as a sequence of nucleic acid bases that comprise a given nucleic acid sample. Examples of UI's include, without limitation, a graphical user interface (GUI) and web-based user interface. The electronic display 535 can be a computer monitor, or a capacitive or resistive touchscreen.

Devices, methods and systems of the present disclosure can be combined with or modified by other devices, systems and/or methods, such as, for example, those described in PCT Patent Application No. PCT/US2011/054769, PCT Patent Application No. PCT/US2012/039880, PCT Patent Application No. PCT/US2012/067645, PCT Patent Application No. PCT/US2014/027544, and U.S. patent application Ser. No. 13/481,858, each of which applications is entirely incorporated herein by reference for all purposes. These applications provide example devices and methods for directly measuring an electronic signature associated with a biological species in solution, such as impedance or charge measurement, and for making biological measurements for use in, for example, nucleic acid sequencing, including targeted sequencing and whole genome sequencing.

Devices, systems and methods of the present disclosure may be used for various types of measurements, such as pathogen detection, protein detection and nucleic acid sequencing, including measuring a nucleic acid sequence and single-nucleotide polymorphism (SNP) detection. Such methods may be used by a subject, a healthcare provide to diagnose and/or treat the subject, or in forensics analysis.

Systems and Methods for Computation

While there are systems and methods presently available to store information electronically, recognized herein are various issues with such methods. Current systems and methods may not be capable of meeting the ever growing need for increased storage. As digital information continues to accumulate, higher density and longer-term storage solutions may be necessary, and current methods for storing information may not be capable of meeting the demand for higher density and longer-term storage.

Recognized herein is the need for improved methods and systems of storing data, accessing data and/or performing computations. Nucleic acid based data storage is an alternative to current systems and methods presently available to store data electronically. Deoxyribonucleic acid (DNA) computing is a form of computing that uses DNA, biochemistry and molecular biology to store data, access data and/or perform computations. One potential advantage of DNA computing is that, similar to parallel computing, it can try many different possibilities at once owing to having many different molecules of DNA. In some embodiments, the devices and methods of the present disclosure have individually addressable arrays that can be used to perform computation using nucleic acid molecules.

The present disclosure provides devices, systems and methods that employ the use of nucleic acid molecules, such as deoxyribonucleic acid (DNA), ribonucleic acid (RNA), or variants thereof, for data storage and computing. The systems and methods described herein have an array of sites referred to as pixels at which DNA can be synthesized, degraded, sequenced, attached, detached and/or hybridized. The pixels can be independently addressed, that is, each site can perform any one of DNA synthesis, degradation, sequencing, attachment, detachment and/or hybridization irrespective of such actions being performed at any other site of the array. In some cases, an electrical field can be formed around each pixel to attract molecules to or repel molecules from the vicinity of the pixel as described in PCT Patent Application Serial No. PCT/US2014/027544, which is incorporated herein by reference in its entirety. The present disclosure provides systems and methods for DNA based computing that can be performed by the independent actions of an array of a large number of pixels (e.g., at least about 100, 1000, 10000, 50000, 100000, 500000, 1000000, 5000000, or 10000000 pixels).

Individually Addressable Arrays

Figure 6A:
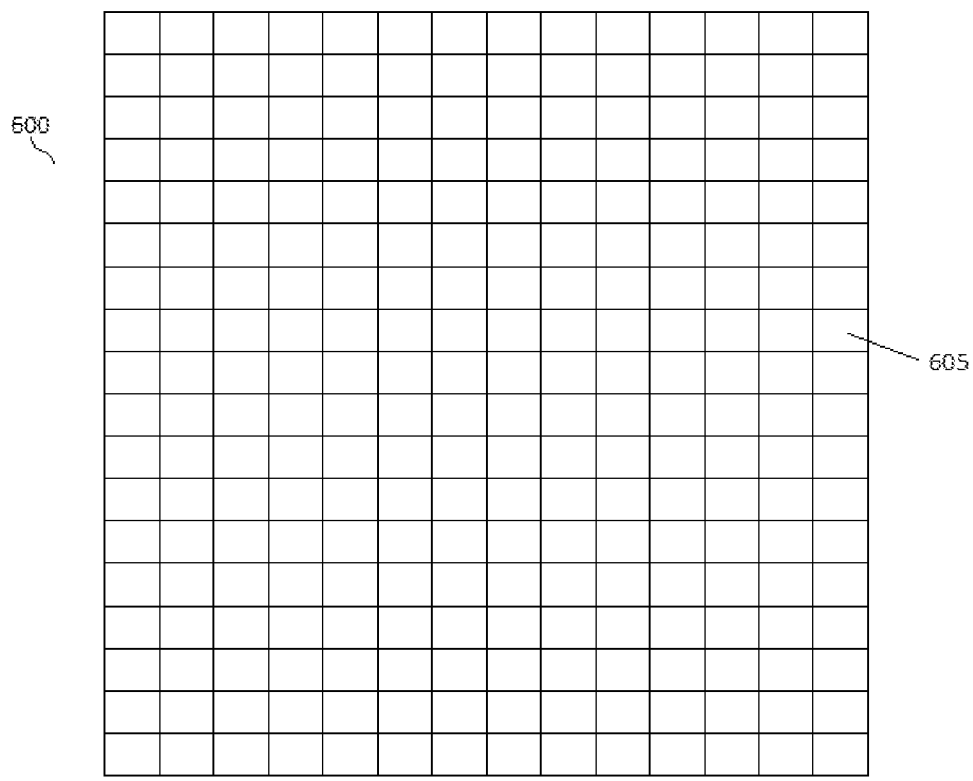
FIG. 6A shows an array of individually addressable pixels.

In an aspect of the present disclosure, as shown in the example system of FIG. 6A, the system can include an array of pixels 600 where each pixel 605 is individually addressable.

Figure 6B:
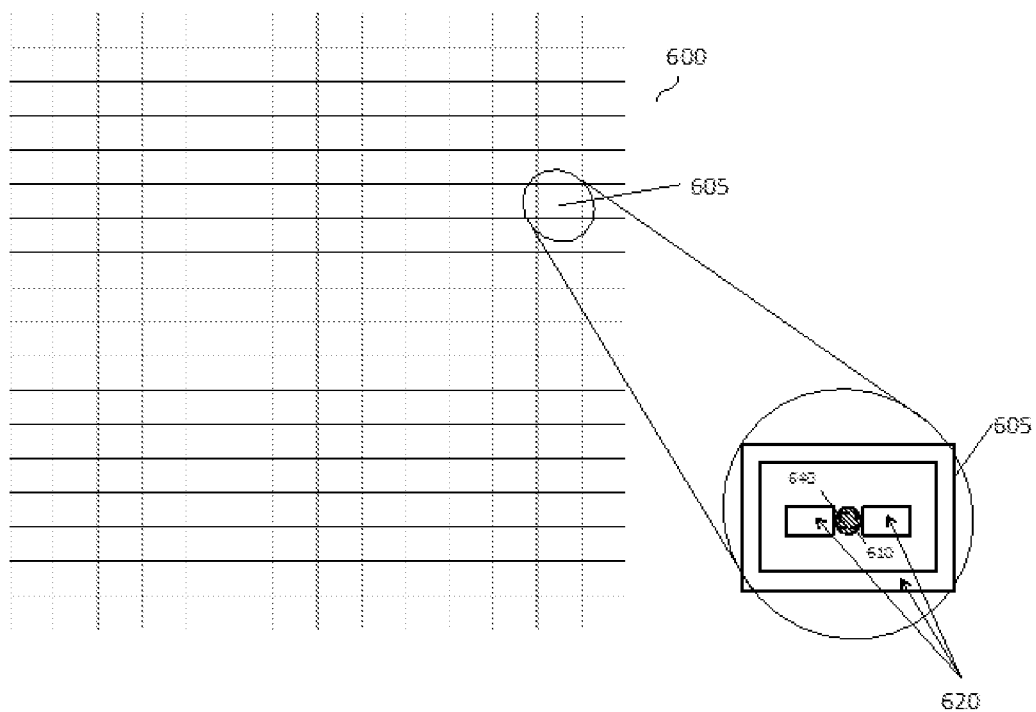
FIG. 6B shows a close up view of a pixel of FIG. 6A.

FIG. 6B shows a close up view of one of the pixels 605 of FIG. 6A. The components associated with each pixel 605 may include detection sensor components, such as electrodes 620 for the detection of reactions of interest and/or detection of the state of biological/chemical matter, and dedicated voltage delivery components for enabling electrical control of each pixel via the application of a voltage function. The pixels may also contain magnets 640 (shown by dashed lines) for binding magnetic particles 610 (located above magnets 640), wells etched into the substrate (not shown), binding sites for binding biological and/or chemical targets, etc. The content of each pixel 605 will depend on the contemplated use for the system.

In some embodiments, the system has individually addressable pixels where the data readout associated with each pixel may be accessed. As reactions of interest occur in each pixel, the data associated with each individual pixel may be accessed. For example, in the case of DNA sequencing, the data associated with the detection of a nucleotide incorporation event may be accessed for the individual pixel where the incorporation event is occurring. This access may occur in real-time and there may be data readout for the particular pixel of interest as the reaction is happening and as the data is being generated. In other embodiments, the data may be accessed sometime after the data has been generated and sometime after the reaction of interest has occurred.

Figure 6C:
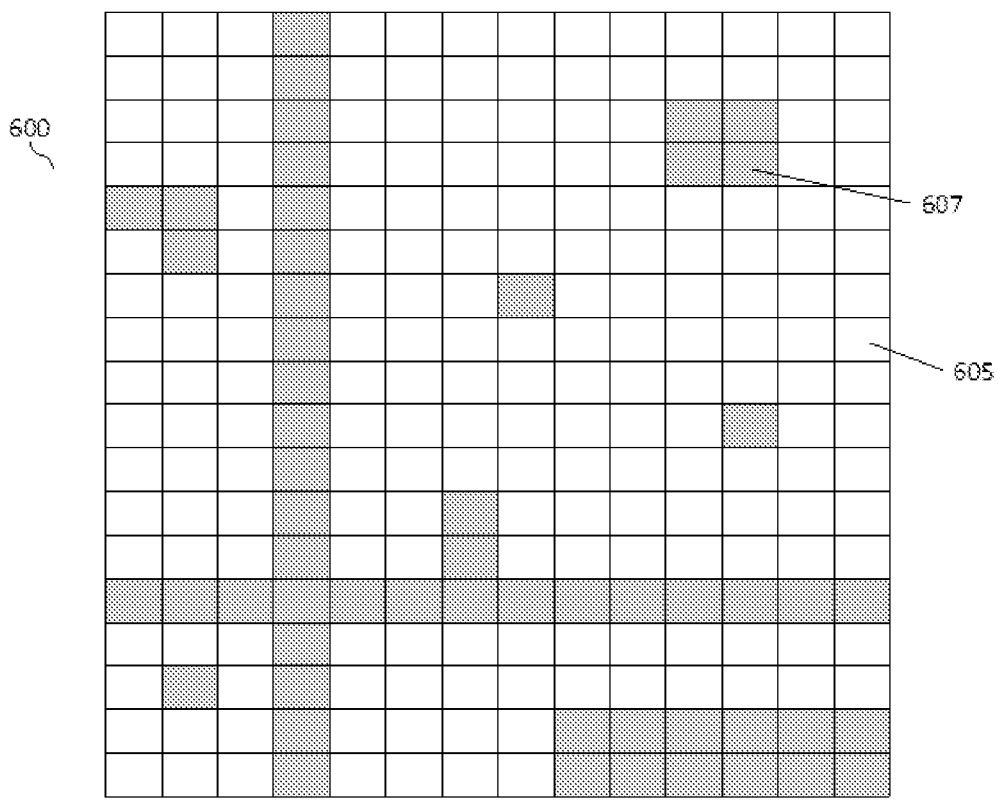
FIG. 6C shows a sorting function via individually addressable pixels.

In other embodiments, individually addressable pixels can contain a dedicated voltage delivery component where biological and/or chemical matter of interest can be manipulated via the application of a voltage function to the individual pixel. The voltage function can be applied by a computer processor or circuit that is programmed or otherwise configured to apply a voltage function or a plurality of voltage functions. The voltage function may be an alternating current (AC) or direct current (DC) voltage function. For example, if the pixel includes electrodes the voltage function may be applied to the electrodes in order to establish an electric field. Biological matter, such as nucleotides, proteins, DNA, RNA, etc. can be attracted or repelled depending on the properties of the electric field. In some embodiments, the electric field can act as a "gate" for each pixel, either confining biological and/or chemical matter in the pixel or facilitating the removal of the matter either by charge repulsion and/or diffusion in solution. As shown in FIG. 6C, this can allow for the selective retention or removal of the contents of certain pixels 605 based on the contents of individual pixels 605. For example, in the case of nucleic acid (e.g., DNA) amplification on magnetic beads, there may be null pixels 607 (shown in the figure as grey pixels) where amplification has not occurred and the magnetic beads associated with the null pixels 607 can be removed by magnetic repulsion through an electromagnet in the pixel, by charge repulsion via the "electric gate," or a combination of both methods. This function may be considered a "sorting" function where the individually addressable pixels can selectively remove beads and thus "sort" through very large numbers of beads and samples.

The type of voltage function and its properties can depend on the particular reaction of interest as well as the type of biological and/or chemical matter. For example, a different voltage function may be used during nucleic acid (e.g., DNA) amplification versus nucleic acid (e.g., DNA) sequencing.

In some embodiments, the system may be used in conjunction with carrier particles, such as beads. In an embodiment, the beads may be magnetic and may bind to one or more magnets associated with individual pixels. In other embodiments, the system may not use carrier particles, but may bind biological and/or chemical targets of interest to each pixel in an alternate configuration. For example, the targets may be bound through a biotin-streptavidin bond, or contained in wells in the substrate.

In some embodiments of the system, there may be combined amplification and sequencing systems and methods on the same chip.

Systems and Methods for Accessing Data

An aspect of the present disclosure provides a method for accessing data. The method can comprise providing an array of individually addressable sites, where a given site of the array has a nucleic acid molecule with a sequence of nucleic acid subunits that corresponds to bits encoding at least one computer-executable directive for storing data. The method can include, at the given site, identifying the sequence of nucleic acid subunits by measuring an impedance, ,conductance, or charge (or change thereof) associated with the nucleic acid molecule, an environment adjacent or in proximity to the nucleic acid molecule, or a bead (or particle) coupled to the nucleic acid molecule. The method can use a computer processor to identify the bits from the sequence of nucleic acid subunits and generate the data from the bits.

In such a method, according to some embodiments, there may be a substrate having a plurality of locations, or pixels, for containing biological matter. The biological matter can for instance be a nucleic acid (e.g., DNA) or a variant thereof. Nucleic acid (e.g., DNA) can be delivered to specific pixels on the substrate of a single chip and these pixels can also be referred to as "nano-reactors."

Figure 7:
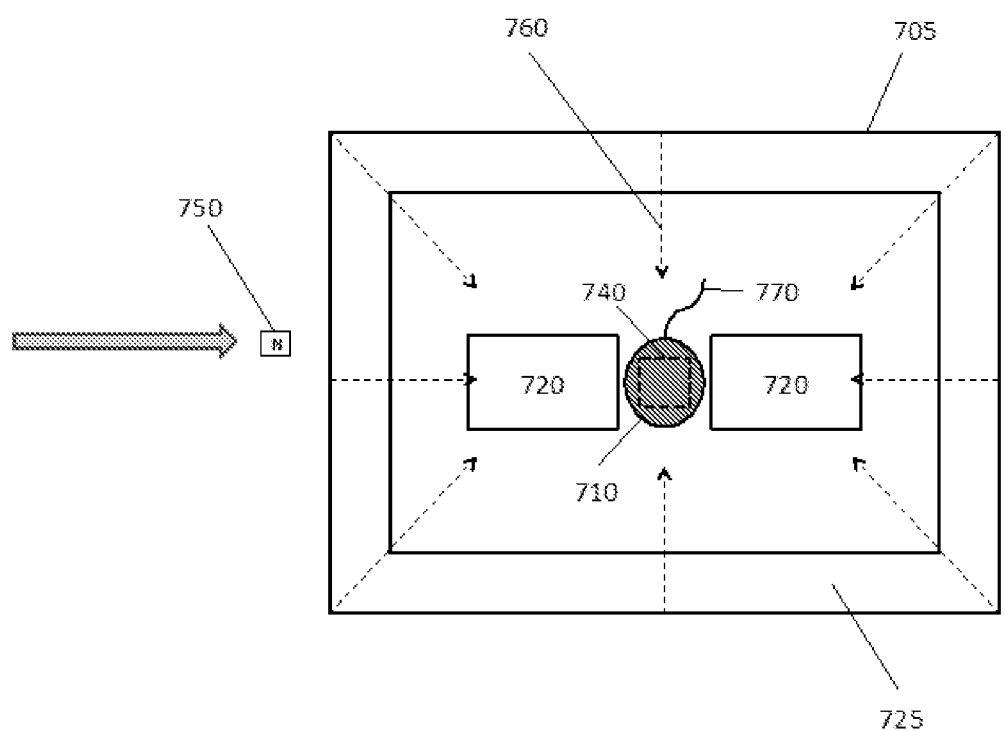
FIG. 7 shows an electric "gate" associated with a pixel.

FIG. 7 shows an exemplary embodiment of polynucleotide sequencing based on selective containment of nucleotides 750 and detection of a hybridization event by detector sensors, in this embodiment "inner detection electrodes" 720. A pixel 705 may contain inner detection electrodes 720, a magnet 740 (shown by dashed lines), a magnetic bead 710 (located above magnet 740), nucleic acid (e.g., DNA) 715, and outer electrodes 725. The outer electrodes 725 may generate an electric field 760 in order to contain one or more nucleotides 750 of interest within the pixel 705. This electric field 760 can act as an "electric gate" and either contain or repel moieties in the system. The inner detection electrodes 720 can detect the state of hybridization and whether or not an incorporation event has occurred in a template nucleic acid (e.g., DNA) strand 770. If the incorrect nucleotide has been introduced into the pixel 705 and there is no incorporation, the electric gate can reverse the electric field to repel the nucleotide or nucleotides in the pixel 705. Then next cycle of nucleotides can then be introduced and the process can be repeated until the entire length of the template nucleic acid (e.g., DNA) 770 is sequenced. There can be a single nucleic acid type or more than one type according to a particular application.

Another aspect of the present disclosure provides a system for accessing data. The system can comprise an array of individually addressable sites, where an individual site of the array has a nucleic acid molecule with a sequence of nucleic acid subunits that corresponds to bits encoding at least one computer-executable directive for storing data. The system can include a sensor at the given site that measures signals indicative of an impedance, conductance and/or charge (or change thereof) associated with the nucleic acid molecule and a computer processor coupled to the sensor. The computer processor can identify the sequence of nucleic acid subunits from signals received from the sensor, identifies the bits from the sequence of nucleic acid subunits, generate the data from the bits, and store the data in a memory location.

In some cases, an additional site of the array does not have an additional nucleic acid molecule with the sequence of nucleic acid subunits. In some cases, an additional site of the array can have an additional nucleic acid molecule with the sequence of nucleic acid subunits.

Identifying the nucleic acid sequence of the nucleic acid subunits can comprise sequencing the nucleic acid molecule. In some cases, the sequencing comprises performing a nucleic acid extension reaction using a primer that hybridizes to the nucleic acid molecule. The impedance, conductance and/or charge (or change thereof) associated with the nucleic acid molecule, environment in proximity to the nucleic acid molecule, and/or bead (or particle) coupled to the nucleic acid molecule can be indicative of nucleotide incorporation events during the nucleic acid extension reaction.

Identifying the nucleic acid sequence of the nucleic acid subunits can comprise hybridizing an oligonucleotide that comprises a sequence at least partially complementary to the sequence of nucleic acid subunits to the nucleic acid molecule. In some embodiments, the impedance, conductance and/or charge (or change thereof) associated with the nucleic acid molecule, environment in proximity to the nucleic acid molecule, and/or bead (or particle) coupled to the nucleic acid molecule is indicative of the hybridizing the oligonucleotide to the nucleic acid molecule.

The sequence of nucleic acid subunits can be stored in computer memory. In some cases, the method further comprises storing the data in computer memory.

In some embodiments, the nucleic acid subunits can comprise at least two distinct subunits, where a subset of the at least two distinct subunits corresponds to a 1 or 0. In some cases, a given site comprises a plurality of the nucleic acid molecules. The method can further comprise assembling generated data into a larger piece of data.

In some instances, the nucleic acid molecule can comprise a primer binding sequence. The primer binding sequence can function as a searchable index.

In some cases, a sensor at the given site can detect signals indicative of the impedance conductance and/or charge (or change thereof) during the measuring. In some embodiments, the sensor can comprise a pair of electrodes. The sensor can be electrically coupled to the Debye layer of a surface of the sensor, the nucleic acid molecule, or a surface (e.g., bead) coupled to the nucleic acid molecule. For examples, if the sensor includes at least 1, 2, 3, 4, 5, 6, 7, 8, 9, or 10 electrodes, at least some, most or all of the electrodes can be in a Debye layer of the nucleic acid molecule, a Debye layer of the environment in proximity to the nucleic acid molecule, and/or a Debye layer or a bead (or particle) coupled to the nucleic acid molecule during sensing. In some cases, the nucleic acid molecule can be coupled to a surface at the given site. The surface can be, without limitation, a particle or a surface of a well at the site. In some cases, the surface can be removable from the site. In some cases, the nucleic acid molecule can be coupled to the surface via hybridization with another nucleic acid molecule coupled to the surface. In some embodiments, the nucleic acid molecule can be coupled to the surface via a covalent bond. The nucleic acid molecule can be coupled to the surface via a non-covalent interaction.

In some cases, the sensor can measure signals indicative of nucleotide incorporation events during a nucleic acid extension reaction associated with the nucleic acid molecule. The sensor can measure signals indicative of one or more hybridization events associated with the nucleic acid molecule. In some embodiments, the memory location or an additional memory location can store the sequence of nucleic acid subunits identified by the computer processor.

In an embodiment, a route for delivering a nucleic acid (e.g., DNA) sample may be via magnetic beads that can be secured in place using a local magnetic field. In other embodiments, there may be no beads or particles, but nucleic acid (e.g., DNA) may be bound within the pixel in an alternate configuration. For example, the nucleic acid (e.g., DNA) may be bound through a biotin-streptavidin bond, or contained in wells in the substrate.

In some embodiments, amplification of nucleic acid (e.g., DNA) on a bead in a pixel can be achieved via an amplification process. A bead may be covered in primers and a first single stranded nucleic acid template may bind to a first primer. The first single stranded nucleic acid template may be formed into double stranded nucleic acid by the addition of nucleotides and reagents. These nucleotides and reagents may be directed into a pixel by local voltages. Once the double stranded nucleic acid template is formed, a strand of the double stranded nucleic acid can be separated through heating and may be contained in the same pixel by local voltages, preventing diffusion into a neighboring pixel and potential cross-contamination of different nucleic acid samples. This single strand may then hybridize to another primer on the same bead and the amplification process may begin again. This process can be repeated until all the primers on the bead are occupied by amplified nucleic acid. The flow of separated single strand nucleic acid, nucleotides, and reagents can be influenced by local voltages applied at each nano-rector.

In some embodiments, there may be more than one type of template nucleic acid on the same bead.

In an alternative embodiment, a strand of double stranded template nucleic acid may be separated via heating and can be directed by local voltages to land on a different bead in another pixel where it can hybridize to another primer. This process can be repeated and the flow of separated single strand nucleic acid can be influenced by local voltages applied at each pixel.

In some embodiments, the amplification reaction may be assisted by directing moieties such as polymerases and nucleotides to targeted specific nano-reactors or beads. The dedicated voltage delivery system can be used to control the flow of these moieties into specific pixels. A dedicated sensor system, such as an array of electrodes, can be used in some embodiments to sense the state of amplification. For instance, once the population of a specific type of strand grows above a certain limit, the corresponding growth in the electrical signal can be monitored in order to determine which pixels have the most amplification or which beads are null beads with no amplification.

In some embodiments, the sensor data can be used to identify pixels with the desired amplicons. The voltage delivery system which delivers dedicated voltages to individually addressable pixels may be used to retain the amplified nucleic acid and repel or release the non-amplified or suspect nucleic acid population, for instance by releasing a bead or the nucleic acid itself from select pixels.

In a further embodiment, after amplification is complete, the voltage delivery system may be used to release some or all of the contents of each pixel and the system may wash the amplicons, reagents, nucleotides, and beads to an outlet or sorting system.

In another embodiment, after amplification is complete, nucleic acid (e.g., DNA) sequencing may commence in pixels with amplified nucleic acid. The system can allow for both amplification and sequencing on the same pixel array. Nucleotides and other sequencing reagents may be flowed into the array and the electric gate can be used to contain them in individual pixels. The detector components in the pixel, such as, for example, electrodes, can be used to detect incorporation events. For example, a known (or predetermined) nucleotide base or precursor can be pulsed and brought into contact with a single stranded nucleic acid molecule having a primer and polymerization enzyme coupled thereto. If the base is incorporated during a primer extension reaction, the impedance, conductance and or charge of the nucleic acid molecule, environment in proximity to the nucleic acid molecule, and/or bead (or particle) coupled to the nucleic acid molecule is changed, which change is detectable by individual pixel and is indicative of an incorporation event. In some embodiments, the cyclical addition and removal of nucleotides can allow for sequencing by synthesis on the system. The sequencing may occur in pixels that are filled with amplicons, allowing for a stronger signal and better sequencing results. When sequencing has been completed, the voltage delivery system may be used to remove the contents of target pixels, allowing for a reusable array.

Amplification and sequencing methods described herein can be useful for a number of forms of biological matter, such as for example proteins, peptides, nucleic acids (DNA, RNA and cDNA), etc. In all cases, the dedicated sensor system data may be used to selectively contain certain biological matter in target pixels and release biological matter and/or carrier particles from other pixels.

In some embodiments, different voltage functions can be used for combined nucleic acid (e.g., DNA) amplification and subsequent nucleic acid sequencing on the same substrate. For instance, a first voltage function is used to contain amplified nucleic acid and a second voltage function is used to repel or release non-amplified nucleic acid.

In other embodiments, during the sequencing of a polynucleotide on a plurality of locations on the substrate, individual voltages can be used to control and confine the reaction and reaction byproducts at each location. In some embodiments, this is possible by using a dedicated sensor at each location to sense the state of hybridization.

In some embodiments, a dedicated moieties delivery scheme may be used for phase detection and rephasing. The state of hybridization at each location can be measured. If measurements indicate that a threshold of out-of-phase sequences are present at certain locations, nucleotides or nucleotide segments may be delivered to the certain locations to bring the out-of-phase sequences back into phase.

In some embodiments, competitive reactions including delivery of nucleotide bases or nucleotide derivative to specific locations can be used for rephasing.

In some embodiments, repair proteins can be delivered to out-of-phase locations using a dedicated voltage delivery system. Since these moieties have electric charge, they can be repelled from the in-phase locations and attracted to out-of-phase locations by properly modulating the voltage based on the sensing data from each location.

In some embodiments, based on sensing data, an ideal base position in a sequencing process can be identified. Once ideal base positions are identified, nucleotides can be incorporated to rephase polynucleotides that lag by two bases, and then nucleotides can be incorporated to rephase polynucleotides that lag by one base. Alternatively multiple-base combinations can be used for rephasing.

In some embodiments, more than one type of polynucleotide can be sequenced. The dedicated individual sensing data can be used to examine and differentiate polynucleotide sequences on different locations. The voltage delivery system can then be used to individually select and deliver moieties to different locations. The sensing system, in return, can measure the incorporation of further nucleotides or other segments, onto each location. This can be used as a feedback loop for planning delivery of certain moieties like nucleotides to each location separately. In this manner, a parallel sequencing of different types of polynucleotides can be performed on the same substrate.

In some embodiments, the reaction of interest that is detected by the dedicated detection sensor can be a nucleotide hybridization reaction for polynucleotide sequencing. In some embodiments, primers may be confined in the pixels. In an embodiment, a primer can be bound to a magnetic bead in a pixel. Single stranded template nucleic acid (e.g., DNA) may be flowed into the system such that there is on average one nucleic acid per pixel. The voltage of each pixel may be selectively controlled such that only a nucleotide of interest may be contained within the pixel via an "electric gate" formed by the voltage associated with the pixel. In some examples, this may be generated by associated electrodes. The determination of whether or not to allow a particular nucleotide to enter an individual pixel may depend on whether or not the nucleotide is the next complementary base pair in the desired sequence.

Systems and Methods for Storing Data

An aspect of the present disclosure provides a method for data storage. The method can comprise receiving bits encoding at least one computer-executable directive for storing data. The method can use a computer processor to generate a nucleic acid sequence that encodes the data, where the nucleic acid sequence comprises nucleic acid subunits that correspond to the bits. The method can include using an array of individually addressable nucleic acid synthesis sites to generate a nucleic acid molecule having the nucleic acid sequence at a first site of the array at the exclusion of generating an additional nucleic acid molecule having the nucleic acid sequence at a second site of the array.

In some embodiments, the system may also have the capability to allow for the synthesis of nucleic acid (e.g., DNA), or allow for "nucleic acid writing." In some embodiments, the user may wish to create a particular nucleic acid sequence and/or slight variations of a known nucleic acid sequence. In some embodiments, a single stranded template nucleic acid with a known sequence may be located inside an individual pixel. The single stranded template nucleic acid may be held in a location in the pixel by a primer, a chemical bond, or a bead (e.g., magnetically attractable bead). In other embodiments, there may be a plurality of primers in various locations in the pixels and they can be confined by the use of dedicated voltage delivery to each pixel.

In further embodiments, there may be a template nucleotide or the template nucleic acid may be partially or fully double stranded and synthesis may occur by chemical methods, such as for example ligation.

The electrical gating capabilities of the individually addressable pixels may be used to selectively allow or prevent the entry of nucleotides into a pixel. The determination of whether or not to allow nucleotides to enter an individual pixel may depend on whether or not the nucleotide is the next complementary base pair in the desired sequence. Correct incorporation can be determined by the measurement of nucleotide hybridization in each pixel. A correct base pair addition will register as an electrical signal and can be detected by a detection sensor component, such as for example an electrode. In some embodiments, this electrical signal may be a change in impedance or charge. In other embodiments, this electric signal may be a change in conductivity.

In some embodiments, in order to avoid or minimize incorrect incorporation of homopolymers (e.g., adding an incorrect string of AAAA nucleotides to the sequence instead of only one "A" simply because there are many "A" nucleotides in the pixel at the time), enzymes used in nucleotide incorporation reactions can be engineered such that they can only add one nucleotide at a time. This can be achieved by, for example, adding a terminator to nucleotides. In other embodiments, nucleic acid (e.g., DNA) synthesis can also be achieved by using synthetic nucleic acid and ligase methods.

Another aspect of the present disclosure provides a system for data storage. The system can comprise an array of individually addressable nucleic acid synthesis sites, where an individual synthesis site of the array synthesizes a nucleic acid molecule from individual nucleic acid subunits or precursors thereof. The system can include a computer processor that receives bits encoding at least one computer-executable directive for storing data; generates a nucleic acid sequence that encodes the data, where the nucleic acid sequence comprises nucleic acid subunits that correspond to the bits; and transmits electrical signals to the array to generate a nucleic acid molecule having the nucleic acid sequence at a first site of the array at the exclusion of generating an additional nucleic acid molecule having the nucleic acid sequence at a second site of the array.

In some embodiments, the bits can encode a plurality of computer-executable directives. The data can be stored in computer memory. In some cases, the nucleic acid sequence can be stored in computer memory. In some instances, the nucleic acid subunits can be selected from at least two distinct subunits, where a subset of the at least two distinct subunits corresponds to a 1 or 0.

In some cases, an individual site of the nucleic acid synthesis sites can comprise a pair of electrodes. The method can comprise alternately and sequentially directing to the first site nucleic acid subunits or precursors thereof that are selected based on the nucleic acid sequence.

In some cases, the method can further comprise excluding from the second site the nucleic subunits or precursors thereof that are alternately and sequentially directed to the first site. In some instances, the method can further comprise attracting a given nucleic acid subunit or precursor thereof to the first site or not repelling the given nucleic acid subunit or precursor thereof from the first site. In some cases, the method can further comprise repelling the given nucleic acid subunit or precursor thereof from the second site or not attracting the given nucleic acid subunit or precursor thereof to the second site. The given nucleic acid subunit or precursor thereof can be attracted to the first site and/or repelled from the second site using an electric field generated at each of the first and second sites. The electric field can be generated by one or more electrodes at the first and second sites. In some cases, the given nucleic acid subunit or precursor thereof can be attracted to the first site and/or repelled from the second site using a magnetic field generated at each of the first and second sites. The magnetic field can be generated by one or more magnetic elements at the first and second sites.

The given nucleic acid subunit or precursor thereof can be attached to a magnetic bead.

In some embodiments, the nucleic acid subunits or precursors can be alternately and sequentially directed to the first site via fluid flow. The fluid flow can be fluid flow in at least one microfluidic channel.

The method can further comprise removing the nucleic acid molecule from the array.

In some cases, the nucleic acid molecule can be generated at more than one site of the array. In some embodiments, the nucleic acid molecule can be generated at only one site of the array. In some instances, a plurality of the nucleic acid molecules can be generated at the first site.

The nucleic acid molecule can be generated in the absence of a nucleic acid template.

In some cases, the nucleic acid molecule can be generated on a reaction surface at the first site. The reaction surface can be a particle or a surface of a well at the first site.

In some cases, the nucleic acid molecule can be generated on the reaction surface via covalent coupling of a nucleic acid subunit or precursor thereof of the nucleic acid molecule to the reaction surface. In some instances, the nucleic acid molecule can be generated on the reaction surface via coupling of a nucleic acid subunit or precursor thereof of the nucleic acid molecule to a linker coupled to the reaction surface. The linker can comprise a nucleic acid.

In some instances, the nucleic acid molecule can be generated on the reaction surface via non-covalent coupling of a nucleic acid subunit or precursor thereof of the nucleic acid molecule to the reaction surface. The non-covalent coupling can be a binding interaction between members of a binding pair.

In some cases, the array can be substantially planar (e.g., deviates from a plane by no more than 0.1%, 0.5%, 1%, 5%, or 10% of the longest dimension of the array at any one point of the plane).

In some cases, the first site can further comprise a sensor capable of detecting signals indicative of an impedance change, a charge change, a change in conductivity, a change in pH, or a change in temperature associated with the generating of the nucleic acid molecule. The sensor can comprise a pair of electrodes. The sensor can be electrically coupled to the Debye layer of a surface of the sensor, a surface of the nucleic acid molecule, or a reaction surface coupled to the nucleic acid molecule.

In some embodiments, the method can further comprise removing a given nucleic acid subunit or precursor thereof of the nucleic acid molecule from the first site if the sensor detects that the given nucleic acid subunit or precursor thereof of the nucleic acid molecule is incorrectly incorporated to the nucleic acid molecule during the generating.

In some cases, the computer processor can transmit electrical signals to the array to alternately and sequentially direct the individual nucleic acid subunits or precursors thereof to the individual synthesis site based on the nucleic acid sequence. The computer processor can transmit electrical signals to the array that exclude the individual nucleic acid subunits or precursors from an additional individual synthesis site of the array.

In some cases, the system can further comprise one or more magnetic elements at the individual synthesis site and/or the additional individual synthesis site that generates the magnetic field.

The system can further comprise a fluid flow apparatus that alternately and sequentially directs the individual nucleic acid subunits or precursors to the individual synthesis site. The fluid flow apparatus can comprise at least one microfluidic channel.

The individual synthesis site can comprise a sensor capable of detecting signals indicative of an impedance change, a charge change, a change in pH, or a change in temperature associated with one or more nucleic acid molecules at the individual synthesis site. During sensing, the sensor can be electrically coupled to the Debye layer of a surface of the sensor, a surface of the one or more nucleic acid molecules, or a reaction surface coupled to the one or more nucleic acid molecules.

Computational Modules

The basic operations of nucleic acid (e.g., DNA) synthesis, degradation, sequencing, attachment, detachment and/or hybridization can be combined to create any number of computational modules. A computational module can involve any combination of storing, writing and manipulating a nucleic acid molecule (e.g., DNA) according to a programmed algorithm.

Examples of indexing storing, writing and manipulating nucleic acid molecules using "folders" and "meta-data" are provided herein.

Primer Indexing: In some embodiments, a system may be searchable via primer indexing. A fully or partially single stranded nucleic acid (e.g., DNA) sequence of interest may be linked to a known primer sequence. If there are a variety of different types of nucleic acid sequences of interest, each sample may have its own specific primer sequence.

Figure 8A:
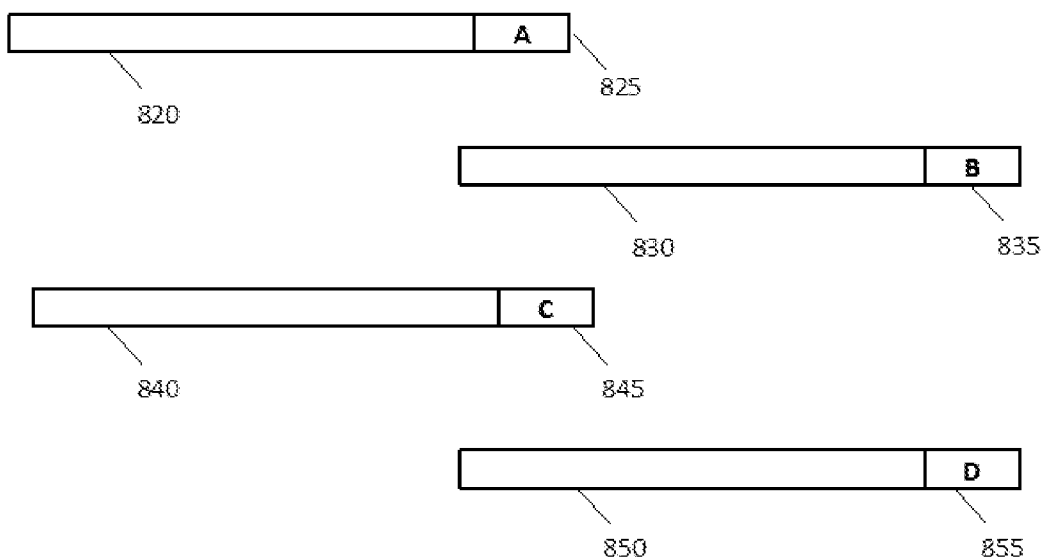
FIG. 8A shows primer labels and associated DNA for DNA indexing.

For example, as shown in FIG. 8A, single stranded nucleic acid (e.g., DNA) may be in the system from four different sample sources: nucleic acid from sample A 820, nucleic acid from sample B 830, nucleic acid from sample C 840, and nucleic acid from sample D 850. The nucleic acid from each sample may be indexed with its own primer such that nucleic acid from sample A is linked to primer A 825, nucleic acid from sample B is linked to primer B 835, nucleic acid from sample C is linked to primer C 845, nucleic acid from sample D is linked to primer D 855, etc. These unique primers can function as an "index" for a particular "folder." That is, the primer is the "label" for naming the "folder" in order to keep track of which nucleic acid came from which source. Although in this example the biological compound of interest is nucleic acid, this method may be applied to different compounds such as proteins, peptides, carbohydrates, etc. and the label may be a known primer or another biological molecule.

Searchable Indexing: A system may allow for methods of "searching" a primer index in order to identify the location or locations of biological material from a target sample. Examples outlined below are shown with beads associated with nucleic acid molecules, but direct attachment of nucleic acid molecules to surfaces or other methods may also be used.

Figure 8B:
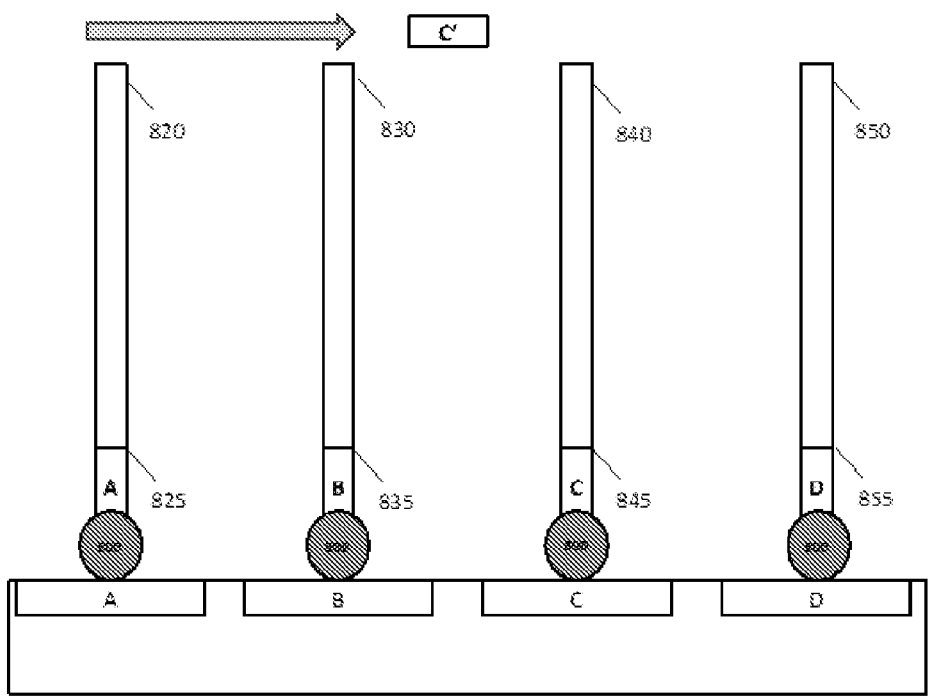
FIG. 8B shows a DNA molecule with primer labels bound to beads for DNA indexing and the injection of C', a complimentary sequence to Primer C.
Figure 8C:
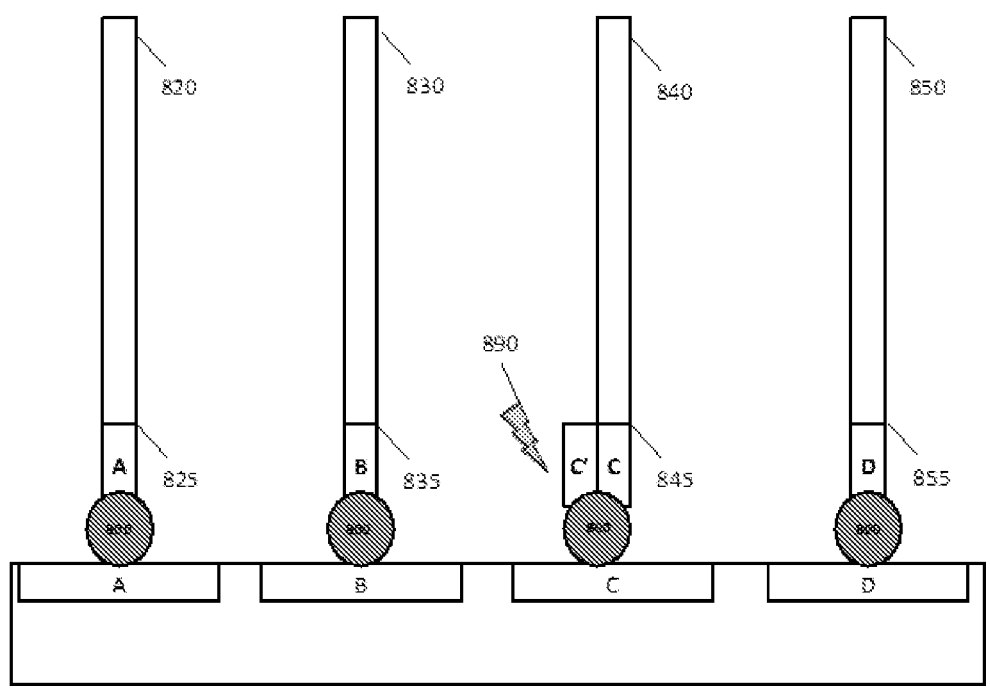
FIG. 8C shows the detection of a DNA of interest via hybridization of a complimentary primer.

FIG. 8B illustrates an embodiment of the present system where nucleic acid (e.g., DNA) is bound to a bead 800 labeled with primer A 825, primer B 835, primer C 845, and primer D 855 according to the sample of origin—nucleic acid from sample A 820, nucleic acid from sample B 830, nucleic acid from sample C 840, and nucleic acid from sample D 850. Each nucleic acid is located in one pixel and each pixel includes a detection sensor component for sensing a nucleic acid hybridization event. Pixel A corresponds to nucleic acid from sample A 820, Pixel B corresponds to nucleic acid from sample B 830, Pixel C corresponds to nucleic acid from sample C 840, and Pixel D corresponds to nucleic acid from sample D 850. In this embodiment, the search to be performed is for the nucleic acid from sample C. The compliment of primer C 845, complimentary fragment C', can be flowed into the system. When complimentary fragment C' binds to primer C 845, the detection sensor component in pixel C can sense an incorporation event 890 and the individually addressable pixels of the system will generate a readout. This readout can indicate that an incorporation event 890 has occurred at pixel C and that the nucleic acid from sample C 845 is located in that pixel.

This search method may allow searching tens, hundreds, thousands, or millions of pixels and can yield the location or locations of biological components of interest based on the binding of a complementary label. Although in this example the biological compound of interest is nucleic acid, this method may be applied to different compounds such as proteins, peptides, carbohydrates etc. and the label may be a known primer or another biological molecule.

Figure 9A:
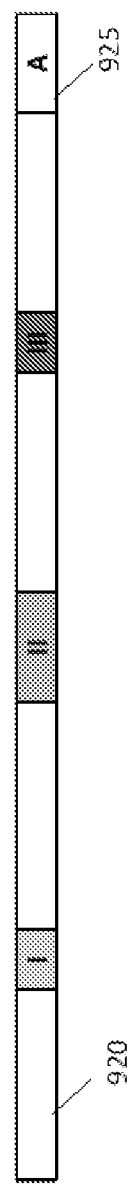
FIG. 9A shows sequences I, II, and III used for sub-indexing.

Sub-Indexing: In a further embodiment, the system may have searchable "sub-folders" in addition to the primers that act as "folders." Examples outlined below are shown with beads associated with nucleic acid molecules, but direct attachment of nucleic acid molecules to surfaces or other methods may also be used FIG. 9A shows a nucleic acid (e.g., DNA) fragment from sample A 920 that is labeled with primer A 925. While labeling with primer A 925 allows for the nucleic acid to be found using the search methods outlined above, in certain situations it may be desirable to search for a specific sequence within the nucleic acid. In some embodiments, short known sequences can be incorporated into the nucleic acid to act as "sub-folders".

For example, sequence I, sequence II, and sequence III can be incorporated into nucleic acid shown in FIG. 9A, at desired locations. Sequence I may be proximate to a location that codes for protein of interest I, Sequence II may be proximate to a location that codes for protein of interest II, and Sequence III may be proximate to a location that codes for protein of interest III.

Figure 9B:
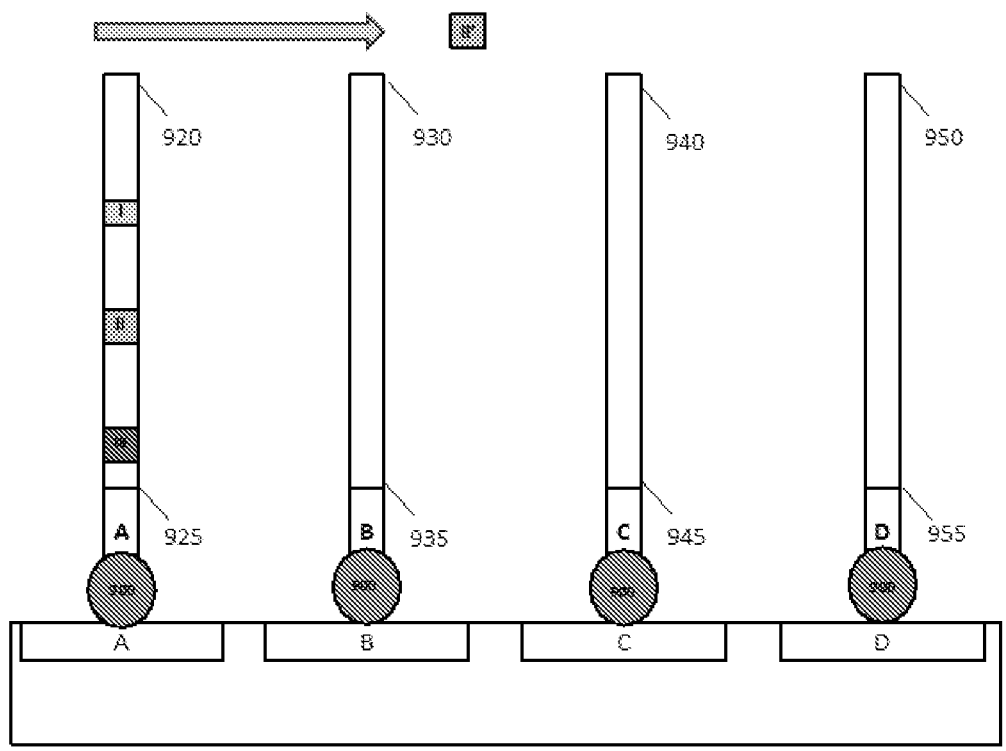
FIG. 9B shows a DNA molecule with sub-index sequences I, II, and III with primer labels bound to beads for DNA sub-indexing and the injection of a complimentary sequence to sequence II (II').
Figure 9C:
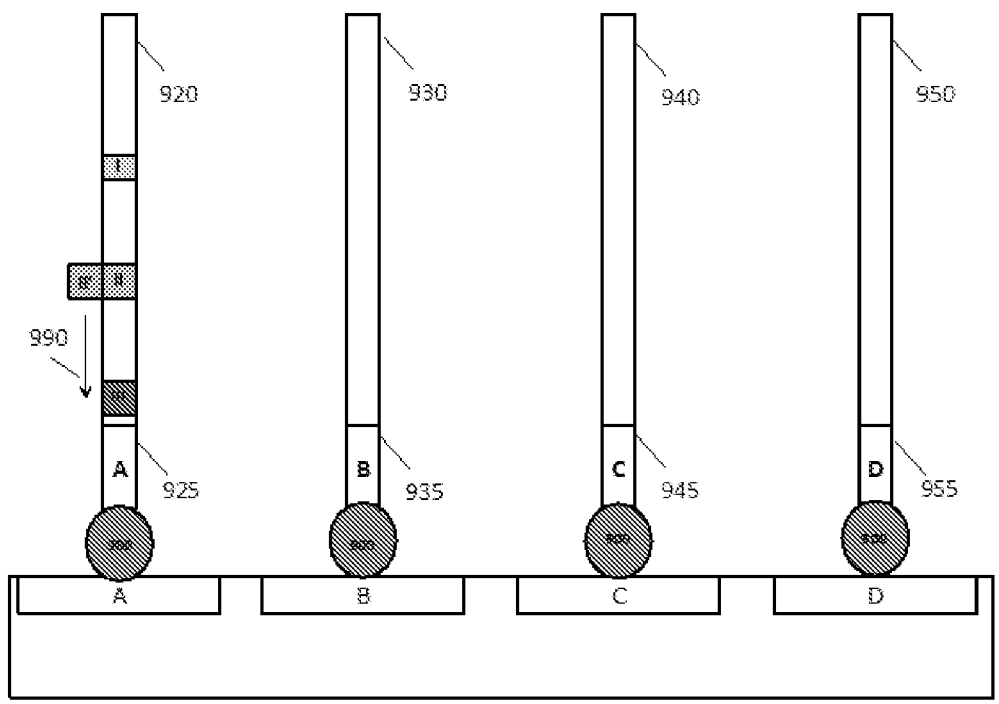
FIG. 9C shows the detection and DNA "reading" associated with a sequence sub-index and the portion of interest of the DNA.

In an embodiment shown in FIG. 9B, the complement of sequence I, sequence II, and sequence III may be injected in an array where each nucleic acid (e.g., DNA) from each of four samples may be bound to a bead 900. A pixel A corresponds to a nucleic acid from sample A 920, a Pixel B corresponds to a nucleic acid from sample B 930, a pixel C corresponds to a nucleic acid from sample C 940, and a pixel D corresponds to a nucleic acid from sample D 950. If, for example, the sequence of interest is located around sequence II, then complimentary sequence II' may be flowed into the system and act as a primer. When complimentary sequence II' binds to sequence II, it can become a primer and then nucleotides may be cycled into the pixel. In this manner, the section of interest may be "read" through sequencing by synthesis 990 as a correct incorporation event can generate a measurable electrical signal that can be detected by the detection sensors. In some embodiments, the sequences I, II, and III can also have "stop" sequences coded such that, for the example above, once all the nucleotides have been incorporated from sequence II up to sequence III, the "stop" coding portion of sequence III will stop the nucleotide incorporation.

In other embodiments, the nucleic acid sequences, such as sequences I, II, and III can be designed such that they occur every "X" number of bases in a sequence. For example, the sub-index sequences I, II, III, etc. can be integrated into the sequence every 100, 200, 300, 500, 1000, etc. bases. In this manner, when "reading" a section of interest, the nucleotide injection can be stopped after the appropriate number of sequences since it is known how many bases separate the sub-index sequences. For example, the number of bases between sequences I, II, and III can be 300 bases and thus if the section of interest is only between sequences II and III, then the "reading" can be stopped after 300 nucleotides have been incorporated.

In some embodiments, the system may be used to store information, similar to a hard drive in a traditional computer. Nucleotides (e.g., A, T, C, and G) and various combinations of these in different lengths (e.g., ACTA, GCA, TTATAC, etc.) can be used to "code" for information. In this manner, virtually any type of information can be "stored" within the nucleic acid.

In a further embodiment, a nucleic acid can be considered to have four "bits" (e.g., the nucleotide bases A, T, C, G), versus a traditional computer transistor that only has two bits (the binary 0 and 1). Furthermore, nucleic acid molecules can be three-dimensional (3D) and have directionality on the z-axis, where the distance between each layer is about 3 angstroms or less. These properties of nucleic acids can allow for very dense storage.

The combinations available for coding may be any combination of the bases of a nucleic acid in either single stranded or double stranded formation. In some embodiments, at least about 1, 2, 3, 4, 5, 10, 20, 50, 100, 1000, or 10000, etc. nucleotides comprising bases can be used to code for a specific piece of information.

In some embodiments, DNA or other polynucleotides can be stored and managed in a database. In other embodiments, there may be metadata assigned to each polynucleotide where the metadata is based on a known unique segment for each nucleotide. In other embodiments, there may be a search scheme implemented to search this database. A search scheme may include preparing a portion of the polynucleotide for hybridization and hybridizing a complementary segment to the known unique segment in the nucleotide and measuring the resulting hybridization. In some embodiments, there may be a higher level metadata assigned to each polynucleotide. This higher level metadata may be based on a first unique segment for each polynucleotide and then a lower level metadata may be assigned where there is a common higher level metadata. The lower level metadata may be based on another unique segment different than the first unique segment.

Figure 10A:
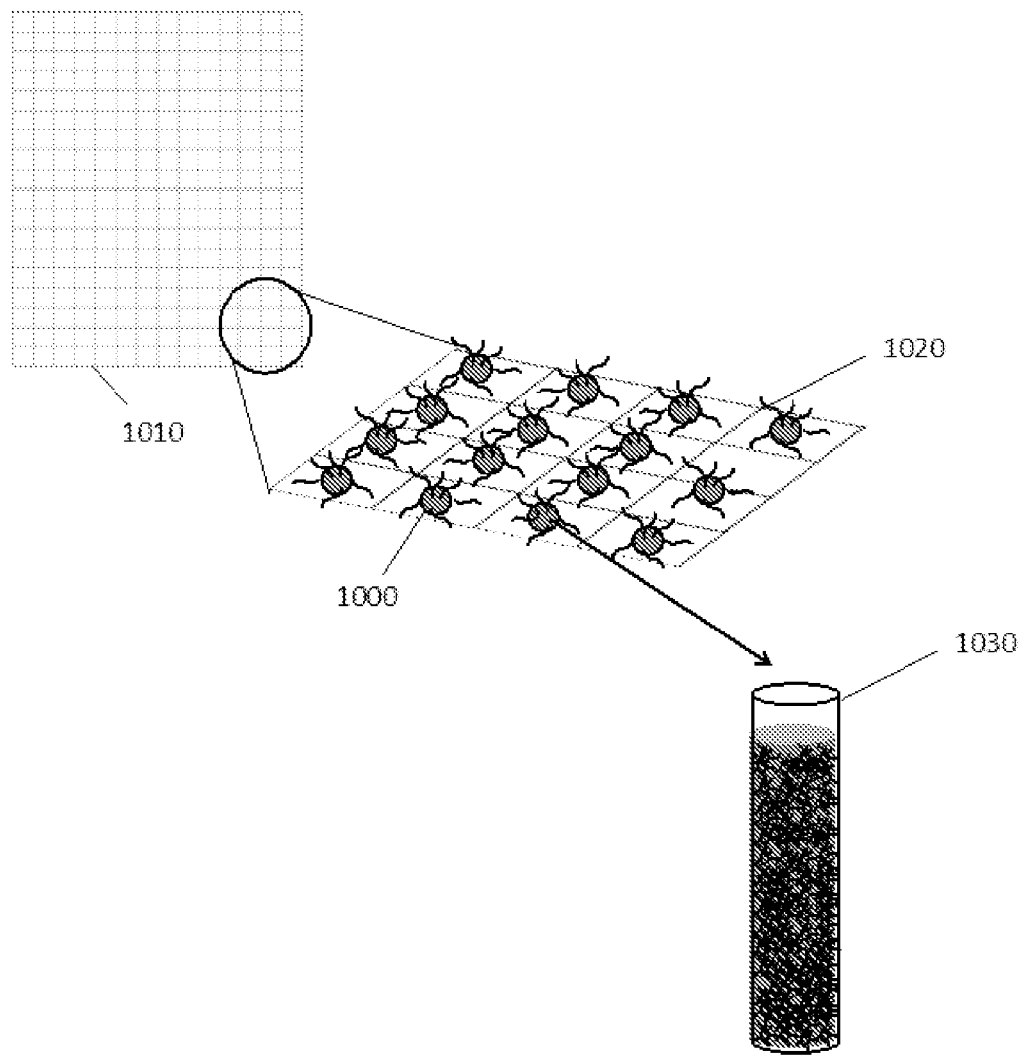
FIG. 10A shows DNA from an array being stored in a tube.
Figure 10B:
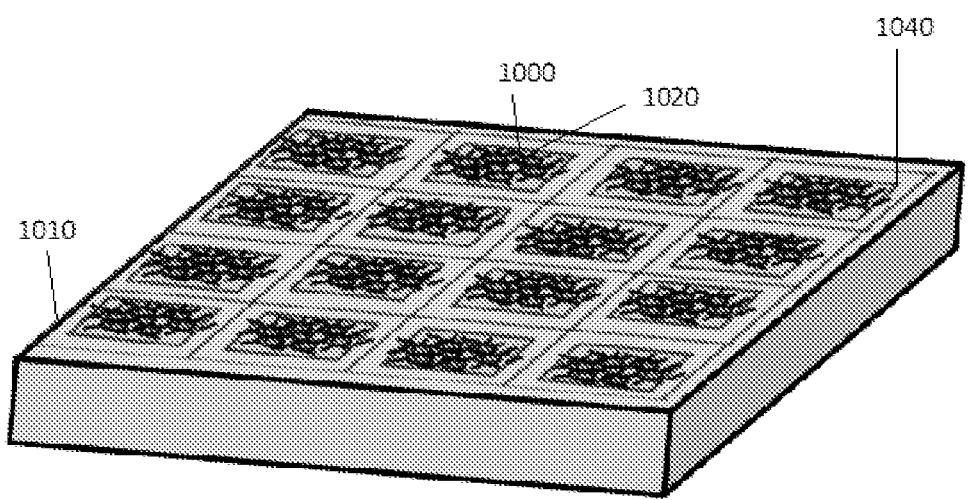
FIG. 10B shows DNA from an array being stored in an array of wells.
Figure 10C:
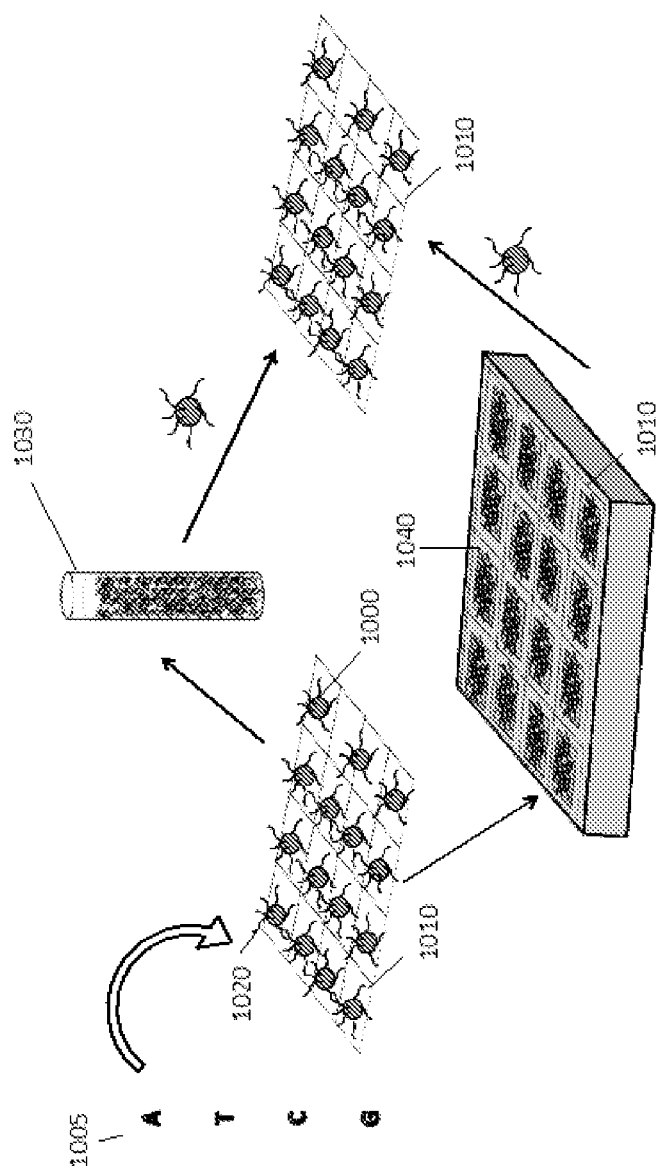
FIG. 10C shows an overview of a DNA writing, DNA storage, and DNA reading system.

FIGS. 10A-10C shows another example of nucleic acid (e.g., DNA) computing using the individually addressable arrays as described herein. FIG. 10A shows, in an embodiment, that nucleic acid 1020 associated with beads 1000 from an array 1010 of pixels may be stored in a tube 1030. FIG. 10B shows, in another embodiment, that nucleic acid 1020 associated with beads 1000 may be stored in an array 1010 with wells 1040.

FIG. 10C shows, in an embodiment, an overview of a system where there may be nucleic acid "writing" via injection of nucleotides 1005. The nucleic acid 1020 may be written on beads 1000 and the beads 1000 are bound to an array 1010. Then, the information in the nucleic acid 1020 may be stored via, for example, an array 1010 of wells 1040 and/or a tube 1030. Finally, when a user desires to access the stored data, the beads 1000 with associated nucleic acid 1020 stored in the test tube 1030 and/or array of wells 1040, the nucleic acid and associated beads may be reintroduced onto an array 1010 such that nucleic acid "reading" may occur by, for example, sequencing by synthesis or another method. The cycle of nucleic acid writing, nucleic acid storage, and nucleic acid reading may be repeated. The nucleic acid molecule can be synthesized chemically and/or enzymatically. The individual nucleotides can be introduced to the site of synthesis in the order in which they are to be linked in the polynucleotide.

Code for Translating Nucleic Acid Sequence to Numerical Data

The present disclosure provides an example of a code for translating a nucleic acid (e.g., DNA) sequence to numerical data. For example, the following values from 1-10 can be mapped to the following nucleotides and/or nucleotide sequences as shown in Table 1:

TABLE 1

| Nucleotide | Number |
| --- | --- |
| T | 1 |
| G | 2 |
| C | 3 |
| TC | 4 |
| GC | 5 |
| CC | 6 |
| CTC | 7 |
| CGC | 8 |
| CCC | 9 |
| TTT | 0 |
| A | Break |

The "break", which corresponds to nucleotide A, indicates the end of the nucleotide code for a number and the beginning of a new number. Thus, for example, if the number of interest is: 471029402748350, then the corresponding nucleic acid sequence is as follows (the bolded "A" has been added for emphasis for ease of visual separation of the numbers):

(SEQ ID NO: 1)
TCACTCATATTTAGACCCATCATTTAGACTCATCACGCACAGCATTTA.

One or more coded nucleic acids of interest may be stored in the pixels. The exemplary embodiment describes a system where nucleotides and their combinations correspond to digits 0-9 and a break. In other embodiments, all types of data may be stored in any variety of nucleotide combinations. In some embodiments, RNA, amino acids in proteins, and other biological compounds can be used to store various types of data.

Devices, systems and methods of the present disclosure may be combined with and/or modified by other devices, systems, and methods, such as those described in WO2014014991, which is entirely incorporated herein by reference.

Biological Applications

The features of the system, namely individual control of each pixel or group of pixels of the array, enable a broad range of applications. In some embodiments, the system may be used for a variety of purposes such as polynucleotide hybridization arrays, drug screening, drug detection, detection of cells, protein assays, and the like. These or other purposes can involve nucleic acid sequencing and/or nucleic acid synthesis, but that is not required.

As described herein, the systems and methods can have an array of sites referred to as pixels. These pixels can be individually addressed such that reagents and/or reaction products can be delivered to or from any individual pixel by manipulating the electrical field surrounding the pixel. Each pixel can be coupled with a detection circuit and have instructions sent to it and/or data collected from it on an individual basis. In some cases, the data can include the impedance or resistance of the material located at the pixel.

The systems and methods described herein can be used to measure gene expression levels at the RNA or protein level. For example, mRNA can be isolated from one or more populations of cells and reverse-transcribed to cDNA with reverse transcriptase. Each of the pixels of the array can have a different single stranded DNA sequence that is complimentary to a cDNA sequence such that the array has a binding partner for all of the open reading frames of the cellular genome. The amount of cDNA hybridizing at each of the pixel locations can be measured to determine the expression level of the gene corresponding to that pixel. In some cases, the expression level is relative to a reference population of cells (e.g., a population of cells that have not been subjected to a drug).

The systems and methods described herein can be used in a drug screen. For example, a plurality of cells, such as cancer cells can be dispersed amongst the pixels of the array. Each of the pixels can comprise a mini-reactor that each has a different candidate drug. In some cases, only a small portion of the candidate drugs have the desired effect upon the cells, so it may be impractical to screen them using conventional routes. In this case, the volumes adjacent to each pixel are small and $10^5$, $10^6$, $10^7$, $10^8$, $10^9$, $10^{10}$, or more candidate drugs can be screened in parallel. Each of the pixels can be monitored for growth of the cells, death of the cells, or production of a metabolite by the cells for example. Promising candidate drugs can be released from their pixel and identified using mass spectrometry for example.

Another aspect of the present disclosure provides a system comprising a substrate having a plurality of locations for containing biological matter (e.g., cells, proteins, nucleic acids, or antibodies), each location having a detection sensor component for detecting a state of the biological matter and a dedicated voltage delivery component and being addressable via applying a voltage function to individually manipulate the biological matter based on the state of the biological material.

The system can be adapted to selectively contain certain biological matter with a first state and release biological matter with a second state. The first state can be a cell having an antibody bound to it and the second state can be a cell not having an antibody bound to it. In another example, the first state can be a cell producing a metabolite and the second state can be a cell not producing a metabolite.

In some embodiments, different voltage functions can be used for combined (e.g., DNA) amplification and subsequent nucleic acid (e.g., DNA) sequencing on the same solid state substrate. In some cases, a first voltage function can be used to contain amplified nucleic acid (e.g., DNA) and a second voltage function can be used to repel or release non-amplified nucleic acid.

Another aspect of the present disclosure provides a method comprising performing amplification and producing a clonal population of a polynucleotide on a plurality of locations on a substrate using dedicated voltage delivery to each location to control and confine the reaction and reaction byproducts at each location, using a dedicated sensor at each location to sense the state of amplification, and performing polynucleotide sequencing on the clonal population based on the sensed state of amplification.

The method can further comprise sensing at each location if polynucleotide has undergone proper amplification, using the dedicated voltage delivery to retain correct copies of the polynucleotide and to release or expel incorrect copies of the polynucleotide. The dedicated voltage delivery can be used to convey moieties to each location during sequencing. The moieties can include at least one of nucleotide, polymerase, and nucleotide segment.

Another aspect of the present disclosure provides a method comprising confining a plurality of cells (e.g., prokaryotic or eukaryotic) in specific locations, each location having a dedicated detection sensor for detecting a state of a cell at the location and a dedicated voltage delivery component, further measuring the state of each cell via its dedicated detection sensor and using a dedicated voltage function based on the state of the cell to deliver certain moieties to specific cells.

Another aspect of the present disclosure provides a method comprising confining a plurality of cells in specific locations, each location having a dedicated detection sensor for detecting a state of a cell at the location and a dedicate voltage delivery component, further measuring the state of each cell via its dedicated detection sensor and using a dedicated voltage function based on the state of the cell to remove the contents of target cells.

Another aspect of the present disclosure provides a method for polynucleotide sequencing comprising confining a plurality of primers and hybridizing a nucleotide onto the primer in specific locations, each location having a detection sensor for detecting a state of hybridization at that location and a dedicate voltage delivery component, and individually controlling the voltage of each location for selectively hybridizing nucleotides on each location.

Another aspect of the present disclosure provides a method for nucleic acid (e.g., DNA) synthesis by nucleotide hybridization, the method comprising placing a plurality of primers on a plurality of specific locations on a substrate, confining the primers with dedicated voltage delivery to each of the plurality locations, measuring a status of nucleotide hybridization in each location, and selectively delivering nucleotides to specific locations based on the status.

Another aspect of the present disclosure provides a method for managing in a database of polynucleotides, the method comprising assigning metadata to each polynucleotide, the metadata being based on a known unique segment for each nucleotide.

The method can further comprise implementing a search scheme to the database of polynucleotide, the search scheme comprising preparing a portion of the polynucleotide for hybridization, and attempting hybridizing a complementary segment to the known unique segment in the nucleotide, and measuring the hybridization.

Another aspect of the present disclosure provides a method for managing a database of polynucleotides, the method comprising assigning a higher level metadata to each polynucleotide, the higher level metadata being based on a first unique segment for each polynucleotide, further assigning a lower level metadata to polynucleotides that have a common higher level metadata, the lower level metadata being based on a second unique segment.

In an embodiment, each location, or pixel, may have a dedicated detection sensor, one or more electrodes, for detecting the state of a cell of interest in the pixel. This state may be monitored after the introduction of reagents that produce a detectable reaction when in contact with the cell of interest. This detectable reaction of interest may be monitored via a change in a dedicated voltage function. The dedicated voltage function may also be used to deliver or contain moieties of interest to specific cells within a pixel. In some embodiments, the dedicated voltage function may be changed such that the contents of a pixel are released and removed from the system.

In some cases, biological cells may be used instead of beads in the system. The cells may be grown in each pixel, with each pixel having a single cell or more than one cell. Each cell may have a nucleic acid (e.g., DNA) of interest inserted in it prior to or after introduction into the system. In some embodiments, a drug or compound of interest may be injected into the chamber with cells and the state of the cell may be measured.

In some instances, the array may be used for detection of proteins. Various tags may be attached to various antigens and then the antigens may be introduced into the chamber. When a particular antigen attached to a protein of interest, the tag may be used to detect which antigen out of the group attached. In some embodiments, if the tag cannot be attached to the antigen itself, the tag may be attached to a secondary antibody. Detection of the tag may be electrical (e.g., electrostatic or electrochemical) using a detection sensor, optical, etc.

Chip Packaging

The devices, systems and methods described herein can use a microfluidic platform that utilizes integrated circuit components and semiconductor devices. In traditional semiconductor packaging, heat is typically removed from the top of the silicon chip, that is, the side away from the Printed Circuit Board (PCB). Typically less than 10% of the heat is removed downward into the PCB.

In the case of the microfluidic integrated circuit (IC) packages, heat may not be easily removed from a surface because of the presence of a fluidic chamber or flow cell. For example, a flow cell can be directly in the heat transfer path, between transistor junctions and any topside heat sink. Furthermore, the flow cell can be made of glass or plastic, which can be poor conductors of heat. The flow cell can also have chambers containing liquids and/or gas that can boil and be prevented from performing their function. Also, flow in a flow cell can be temperature dependent.

Recognized herein is the need for improved systems for microfluidic IC packages. In these cases, a semiconductor package comprising a PCB can be modified in order to efficiently remove heat through the backside (i.e., the bottom of the chip attached to the PCB).

In an aspect, the present disclosure provides systems for optimizing heat flow such that it is directed away from integrated circuit components in a microfluidic semiconductor device. In an aspect, the disclosure provides a microfluidic semiconductor packaging system for establishing an efficient heat path. The system can comprise (a) a package substrate; (b) a microfluidic chip mounted onto the package substrate; (c) a microfluidic flow cell proximate to the microfluidic chip and attached to the package substrate; (d) a printed circuit board proximate to the package substrate, where the printed circuit board has a cut-out; and (e) a heat sink where at least a portion of the heat sink is placed through the cut-out of the printed circuit board such that a heat flow path is established from the microfluidic chip down to the heat sink.

In some cases, the microfluidic chip may be mounted onto the package substrate by one or more clamps. A clamp may secure the microfluidic chip to the substrate by applying pressure to the microfluidic chip such that it applies pressure to and contacts the package substrate. Such a configuration may be useful in modulating thermal contact resistance between the microfluidic chip and the package substrate. In some cases, one or more clamps may aid in minimizing the variation of pressure exerted on the microfluidic chip in its contact with the package substrate. Minimizing such pressure may be useful in minimizing the variability in thermal contact resistance between the microfluidic chip and the package substrate. In some embodiments, one or more clamps may be exert a pressure on a microfluidic chip such that the pressure exerted by the microfluidic device on the package substrate across the microfluidic device's contact with the package substrate varies by no more than 50%, 45%, 40%, 35%, 30%, 25%, 20%, 19%, 18%, 17%, 16%, 15%, 14%, 13%, 12%, 11%, 10%, 9%, 8%, 7%, 6%, 5%, 4%, 3%, 2%, or 1%.

In some cases, the system further comprises fins attached to the heat sink for the efficient transfer of heat. In some instances, the heat sink is electrically isolated from the substrate package by at least one of anodizing and chromate conversion of the heat sink. In some embodiments, the heat sink is composed at least in part of aluminum nitride. The system can further comprise a heat slug proximate to the package substrate. In some embodiments, the system can further comprise a Peltier device or other similar device that can aid in temperature control inside the system.

For example, in an aspect, the present disclosure provides a system for achieving heat flow from the silicon chip to a die attach pad within the semiconductor package. This system can include metal-filled vias in a tight pitch array and also power/ground planes directly below the chip shadow to spread the heat laterally from chip hot spots.

The substrate can be made of any material used in semiconductor packaging, such as for example, alumina, aluminum nitride, and beryllium oxide. In order to achieve more effective thermal conductance through the semiconductor package, the vias can be filled with metal. Any suitable metal can be selected, such as for example, gold or copper. The metal-filled vias can provide a high thermal conductivity path through the substrate material.

The bottom layer of the package can have a metal heat spreader in addition to any electrical contacts required by the design. The die can be connected to the die paddle by a high thermal conductivity die attach adhesive. Any suitable metal can be used for the metal heat spreader. The high thermal conductivity die attach adhesive can include glue adhesive or any other type of adhesive suitable for this function.

In another aspect, the package substrate can contain a "heat slug", which is a flat metal square built into the substrate. The slug can be the same thickness as the substrate and can be placed directly below the center of the silicon die. The slug can be made of copper or another thermally conductive metal.

In another aspect, the PCB to which the package is mounted can have a cut-out to allow a metal-to-metal contact between the last layer of the package and a metal heat sink that is pushed through the PCB. Electrical routing on the PCB including power and ground can be routed clear of this cut out area to avoid exposed metal. The cut out can be placed directly beneath the die area of the package, such that there is a vertical connection from the back of the silicon chip through the package, forming a connection to a heat sink without intervening PCB material.

Figure 11A:
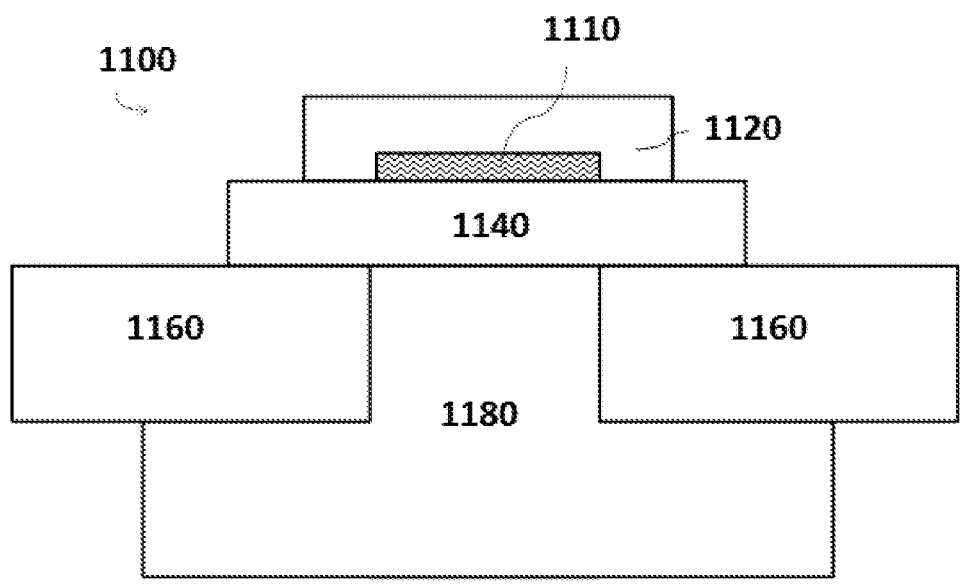
FIG. 11A shows one embodiment of a microfluidic semiconductor package.
Figure 11B:
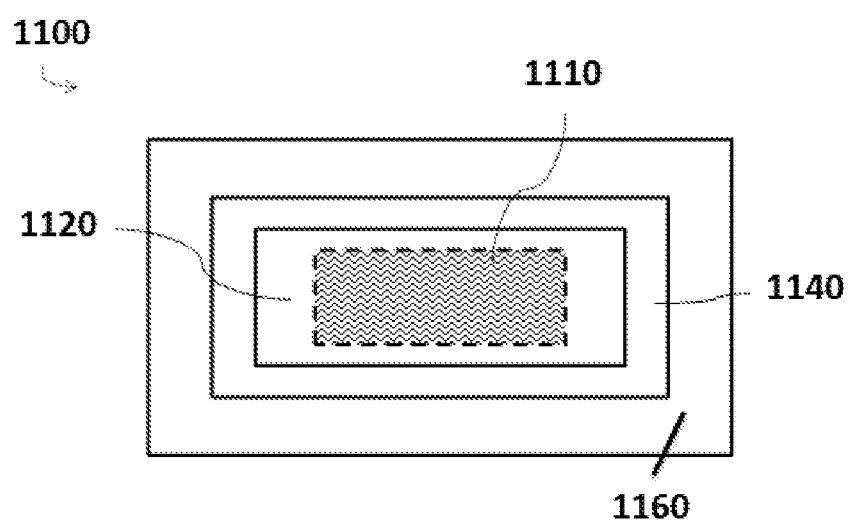
FIG. 11B shows a top view of the embodiment of FIG. 11A of a microfluidic semiconductor package.
Figure 11C:
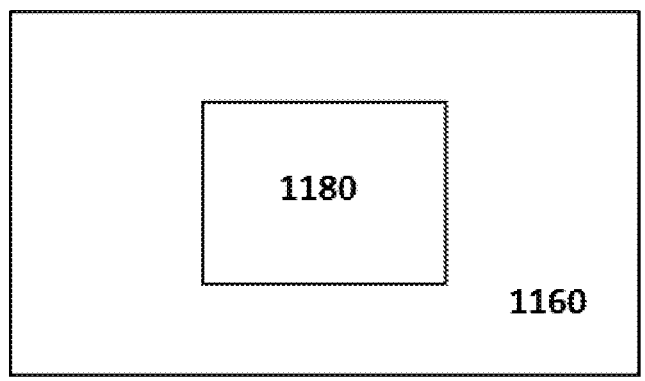
FIG. 11C shows a top view of a cut-out printed circuit board and associated heat sink in the embodiment of FIG. 11A.

FIG. 11A illustrates one embodiment of a microfluidic semiconductor package 1100. Microfluidic chip 1110 is covered by a microfluidic flow cell 1120. Both microfluidic chip 1110 and microfluidic flow cell 1120 are supported by a package substrate 1140. The package substrate 1140 is mounted onto a printed circuit board 1160. The printed circuit board 1160 has a cut-out to allow the metal heat 1180 to contact the package substrate 1140. FIG. 11B shows a top view of microfluidic semiconductor package 1100. The dashed lines in the figure indicate that the microfluidic flow cell 1120 covers microfluidic chip 1100. FIG. 11C shows a top view of just the printed circuit board 1160 with the heat sink 1180 underneath in order to illustrate the cut-out in the printed circuit board 1160.

In yet another aspect, it may be desirable for the contact between the heat sink and the back of the package to be made efficiently. Heat transfer efficiency can be improved by including solder, thermal grease, thermal adhesive, and/or by maintaining pressure between the heat sink and the back of the package with the aid of one or more clamps as described elsewhere herein.

In another aspect, air gaps that may act as thermal insulation are reduced or eliminated by having the heat sink and the back of the package flat and/or flush to each other.

Figure 11D:
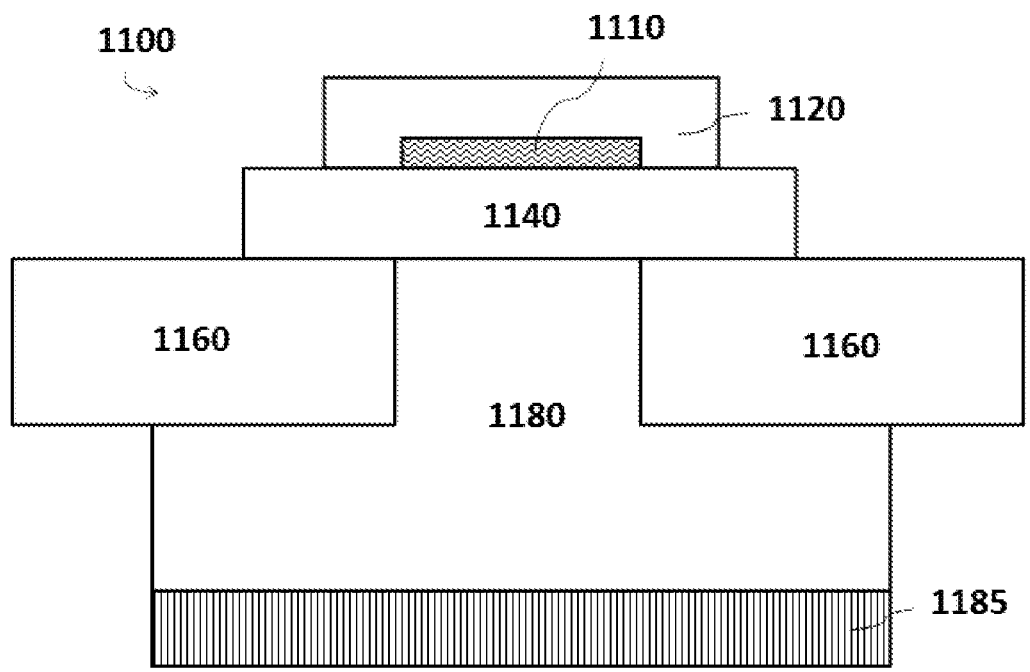
FIG. 11D shows another embodiment of a microfluidic semiconductor package with a heat sink that includes fins.

In another aspect, the heat sink (or Peltier or heat pipe or other heat transfer device) can be configured to efficiently transfer heat from the package to the air for convective heat transfer. The heat sink can have a portion with fins in order to increase the surface area for a more efficiently transfer of heat. FIG. 11D shows the microfluidic semiconductor package 1100 of FIG. 11A with a heat sink 1180 including fins 1185. In a further embodiment, the air can be driven at high velocity across the heat sink by fans to increase heat transfer efficiency. In some embodiments, a thermometer may be embedded inside the heat sink to measure its temperature. A temperature control board can receive such temperature measurements from the thermometer and can be used to control the chip temperature. The temperature control board can control the chip temperature such that its temperature is maintained at a desired set point with accuracy of about +/−5° C., +/−4° C., +/−3° C., +/−2° C., +/−1° C., +/−0.9° C., +/−0.8° C., +/−0.7° C., +/−0.6° C., +/−0.5° C., +/−0.4° C., +/−0.3° C., +/−0.2° C., +/−0.1° C., +/−0.05° C., +/−0.01° C. +/−0.005° C., +/−0.001° C., or less. In some embodiments, such temperature control can be useful in controlling chip temperature in the ranges of 10° C. to 100° C., 10° C. to 75° C., 10° C. to 50° C., or 10° C. to 30° C.

In another aspect, the heat sink can be electrically isolated from the package. This can be accomplished by anodization or chromate conversion of the heat sink. Alternatively, an electrically insulative but thermally conductive material can be used to construct the heat sink, such as for example, aluminum nitride.

In another aspect, the use of heat pipe or other two-phase cooling system can be used instead of a copper block or Peltier device to remove heat from the back side of the chip. In one embodiment, the heat pipe can be attached to the back of the chip package. The heat pipe can remove the heat from the back of the device (e.g., where the liquid can be condensed and heat can be transferred to a heat sink). A heat pipe is a closed tube or other shape that has a "hot end" and a "cold end". At the hot end, a suitable liquid (preferably an inert, low boiling point, non-corrosive, high heat capacity liquid) boils when the hot end is placed in contact with the device that is to be cooled. At the cold end, the vapors can be condensed, and transfer the heat from the latent heat of condensation to a heat sink, radiator, or other cooling device. Gravity can then transfer the liquid back from the cold end to the hot end of the heat pipe. In order to use gravity, the cool end of the heat pipe can be at the same level as, or above the hot end.

In another aspect, the cooling technique can include a heat pipe and spray cooling. This two-phase cooling technique can involve spraying coolant in a fine aerosol mist onto the back side of the chip package (where it may evaporate). This can take place in a closed chamber to prevent any liquid from escaping. The liquid can be an inert fluoro-hydrocarbon or other material that has a boiling point at or near the temperature that is required to be maintained on the backside of the chip. The latent heat of condensation can be absorbed by the vapor and pumped away to a condenser where the heat can be transferred to a heat sink. The cooled liquid may then be returned to the chamber via a pump or compressor.

Reagent Handling and Fluidic Systems

Recognized herein is the need for improved systems and methods for inputting biological/chemical reagents into a microfluidic system as well as storing these compounds.

The present disclosure provides systems and methods for the storage of biological/chemical compounds as well as delivery into a microfluidic system. These systems can be removable and/or reusable.

The present disclosure provides integration of a reagent input device with a microfluidic flow cell for the analysis of biological and chemical reactions of interest. In some embodiments, such a configuration includes various inputs, which can include inputs for dNTPs (e.g., for sequencing reactions), and may also contain buffers, salts, enzymes (e.g., polymerase or phosphatase) or any other moieties (e.g., as required for incorporation of nucleotides). In some embodiments, inputs for various buffers, wash reagents, or polymerase containing buffers can be included. These fluids may also contain salts and any other moieties for polymerization, for stripping coatings from the flow cell, or for re-coating the flow cell.

In an aspect, the present disclosure provides an apparatus comprising: (a) a cartridge that holds a plurality of reagent bags, where each reagent bag has an inner chamber and an outlet, where the inner chamber is filled with a fluid; (b) a valve connected to each reagent bag which regulates the outlet of the bag; and (c) a plurality of needles connected to the valves and reagent bags, where each needle is in contact with a seal proximate to the outlet of the bag and each needle is at least partially in the inner chamber of the bags for connecting the reagent bags with a manifold of a microfluidic device.

In some embodiments, the reagent bags are held by a support inside the cartridge.

The apparatus can further comprise an air inlet tube for modulating pressure inside the cartridge. In some cases, the reagent bags are shaped to be at least one of rectangular, folded at the top with a flat bottom, triangular, and oval.

The seal can comprise a bottom layer, a middle layer, and a top layer. The middle layer can be formed in a washer shape with a cut out portion in order to prevent leakage of the fluid. The apparatus can further comprise an additional outer layer associated with the cartridge for collecting waste.

In another aspect, the present disclosure provides an apparatus comprising a flexible container that has an inner chamber and an outlet, where the inner chamber is filled with a fluid and a valve regulates the outlet of the container, the flexible container being used to deliver fluid to a channel connected to the outlet via pressure applied to the container. The apparatus can further comprise a balloon located inside the flexible container that may be inflated and deflated for mixing the fluid in the container.

Figure 12:
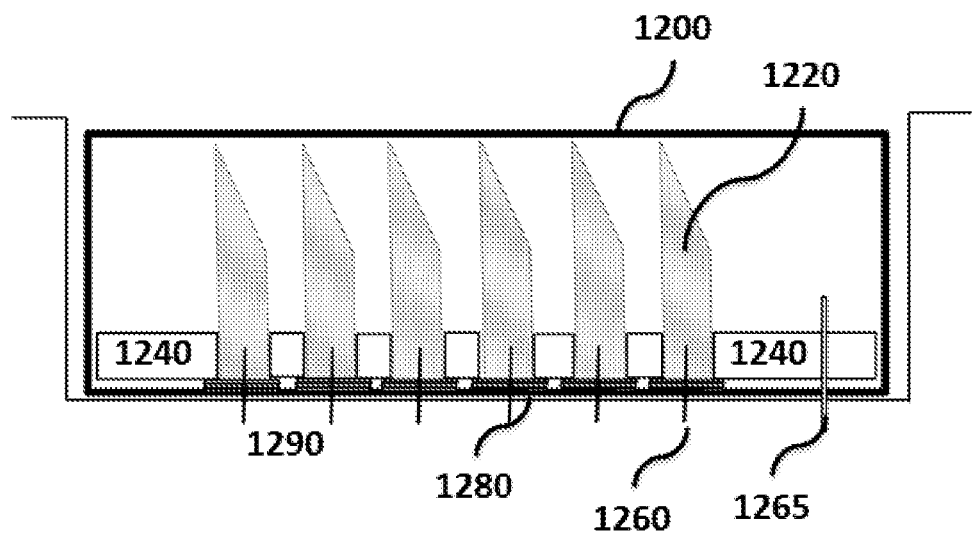
FIG. 12 shows a diagram of an exemplary reagent input device including a cartridge that houses reagent bags.

In one embodiment, as shown by a side view in FIG. 12, the reagent input device can have a cartridge 1200 which holds multiple bags filled with reagents, illustrated as reagent bags 1220. The cartridge 1200 may be connected to the flow cell via needles 1260 that make contact with the reagents as well as the valving system, or manifold 1290, of the flow cell. In one embodiment the cartridge 1200 houses reagent bags 1220 that may be held by a support 1240 where the support 1240 allows for a needle 1260 to pierce the bag through a seal 1280. The needle 1260 makes a fluidic connection between the reagents in reagent bags 1220 and the manifold 1290. In some embodiments, there may be an air inlet tube 1265.

In some embodiments, the pressure in the cartridge 1200 is larger than the pressure inside the manifold 1290, and this pressure can be modulated in order to control the flow of reagents from reagent bags 1220 into the microfluidic channels of manifold 1290. FIG. 12 shows, in an exemplary embodiment, six reagent bags 1220 which may correspond to the nucleotides A, T, C, and G or other suitable nucleotides as well as buffer solutions 1 and 2 used for nucleic acid (e.g., DNA) sequencing. In other embodiments, there may be 1, 2, 5, 10, 50, 100, etc. reagent bags for any type of experiment or procedure of interest.

The reagent bags 1220 may be folded at the top (as shown) with a flat bottom, or they may be rectangular, oval, triangular, or any other shape. The bags may be made of a polymer, plastic, paper, metal, etc. or any other material. Likewise, the support 1240 may be rectangular with cut-outs to hold the reagent bags. In the embodiment shown in FIG. 12, the perimeter of the cut-out is equal to the circumference of the reagent bags in order to help ensure a good fit and to help hold the bags upright. In other embodiments, the support 1240 may have any other shape and mechanism to help hold the reagent bags in place. In a further embodiment, the reagent bags may be configured or shaped such that there is no need for a support.

Figure 13A:
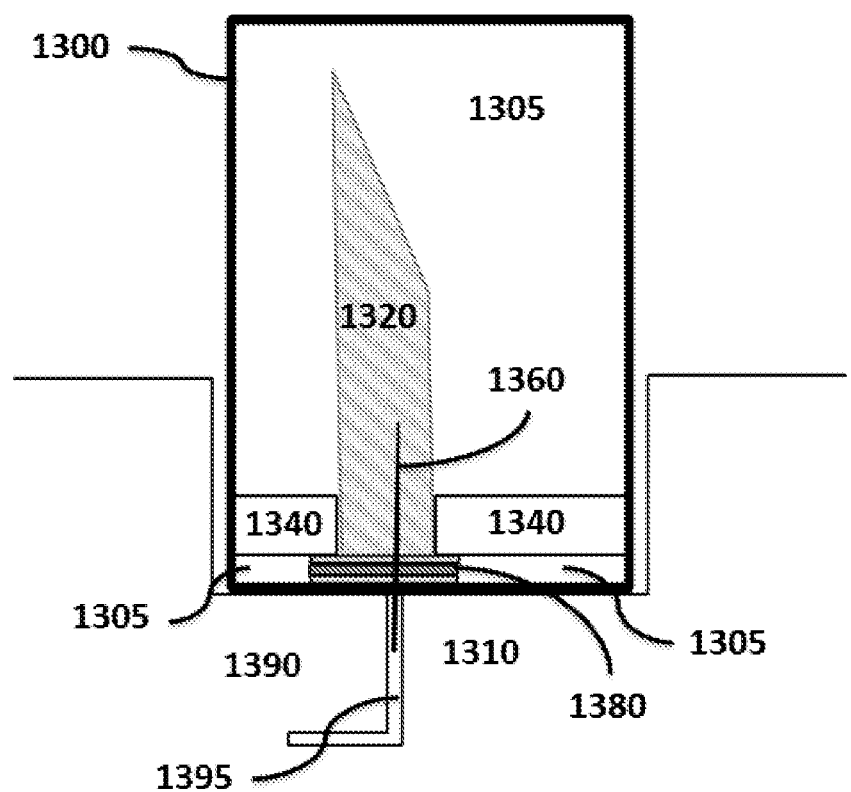
FIG. 13A shows a diagram of a close-up side view of the exemplary reagent input device of FIG. 12.

FIG. 13A shows, in another embodiment, a close-up side view of the reagent input device with just one reagent bag (to better illustrate one embodiment of the construction of the device—a device can include more than one reagent bag). In this embodiment, cartridge 1300 holds reagent bag 1300 which is held by support 1340. The needle 1360 is in fluidic contact with the reagent bag 1320 and seal 1380 forms and airtight/watertight interface between reagent back 1300 and manifold 1390. The needle 1360 serves as the conduit between reagent bag 1320 and a microfluidic channel 1395 of the manifold. The flow of reagents into the manifold may be controlled by valves in the manifold (not shown). In some embodiments, the cartridge pressure 1305 may be higher than the manifold pressure 1310.

Figure 13B:
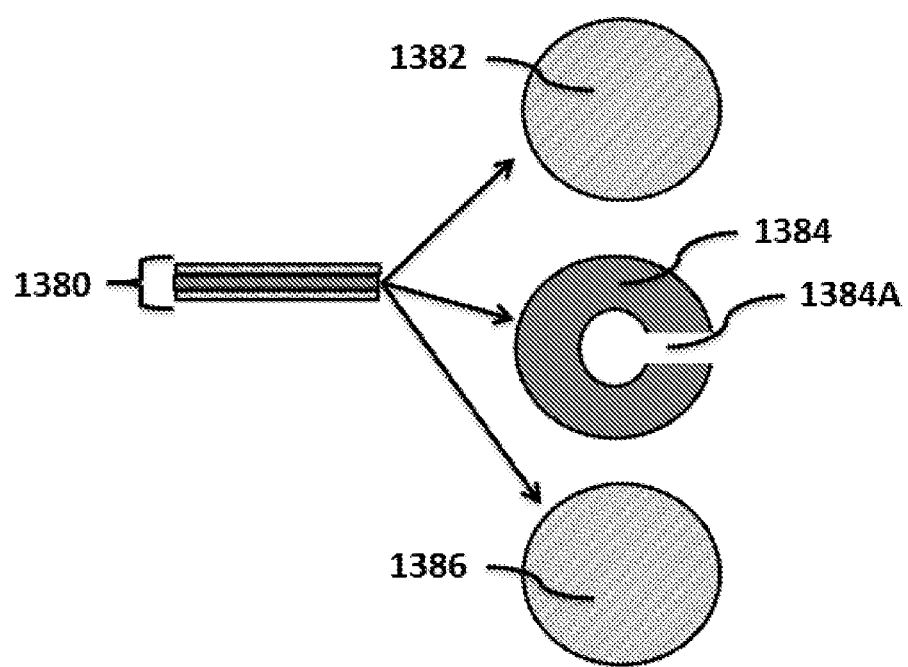
FIG. 13B illustrates a close-up, expanded view of one embodiment of a seal contained in the reagent input device.

FIG. 13B shows a close up, expanded view of seal 1380 in one embodiment. The top layer 1382 and the bottom layer 1386 are shown in this embodiment to be circular and may be comprised of any material such as for example rubber, plastic, glass, etc. The middle layer 1384 is shown to be formed in a washer shape with a portion 1384A that is cut out in order to help ensure that if there is any leakage, it will be air not fluid.

In a further embodiment, there may be a hard element, such as a hard plastic material, incorporated into the bag so that the needle does not pierce the bag as it becomes empty. Depending on the use of a support structure and how the bag collapses as it empties, there may or may not be a need for a hard element to protect the bag from the needle. In a further embodiment, the bag may be made of a material that cannot be pierced by the needle.

Although FIG. 13B shows the layers of the seal to be circular, they may be any other shape such as for example rectangular, oval, triangular, etc. The seal may only have one layer, or it may have two, three, five, ten, etc. or any other number of layers.

The pressure inside the cartridge and outside of the cartridge may be less than 1, 1, 2, 5, 10, etc. atm so long as there is a difference in pressure such that the input of the reagents may be controlled and leakage of air/fluid may be minimized or eliminated.

Figure 14:
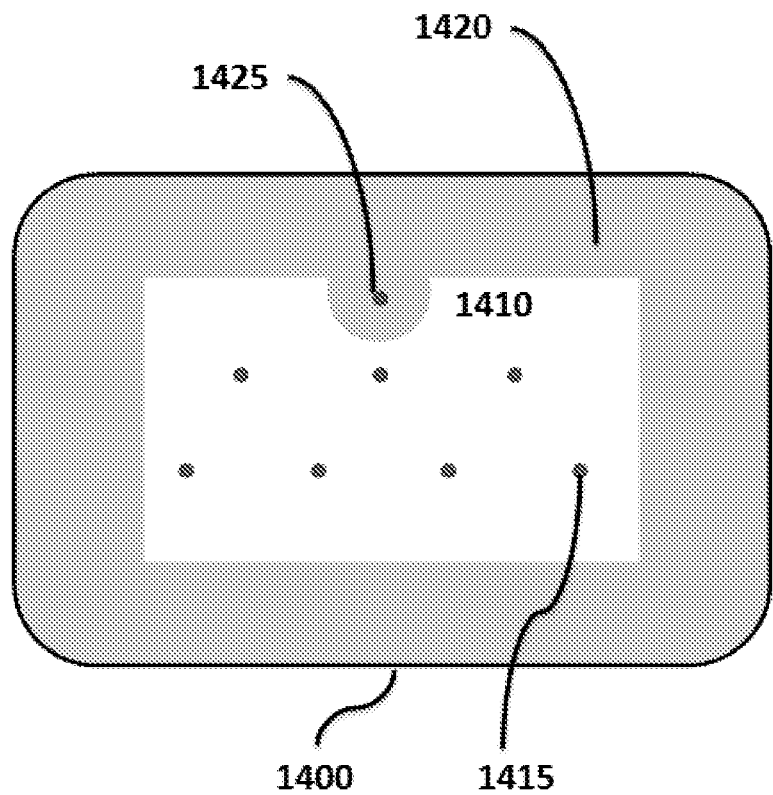
FIG. 14 shows a top view of a reagent input cartridge with a double chamber configuration.

FIG. 14 shows, in another embodiment, a top view of the cartridge 1400, but with a double chamber configuration. The inner chamber 1410 holds the reagent bags and has inlets 1415 for the needles and optionally for the air tube. The outer chamber 1420 may be used to collect waste from the manifold and has a waste inlet 1425. As can be seen from this top view, the reagent bags are placed according to the position of the inlets 1415 and they may be arranged in a staggered configuration (shown), in a linear configuration, in a circular configuration, or any other type of configuration. In a further embodiment, the cartridge may have a single chamber with a waste inlet such that the waste empties directly into the same chamber that houses the reagent bags.

In some embodiments, the reagent input device and cartridge may be fabricated such that they are "tamper proof". The device may be sealed off such that the reagent bags cannot be easily accessed. In one embodiment, for example, the cartridge may be welded shut.

Figure 15:
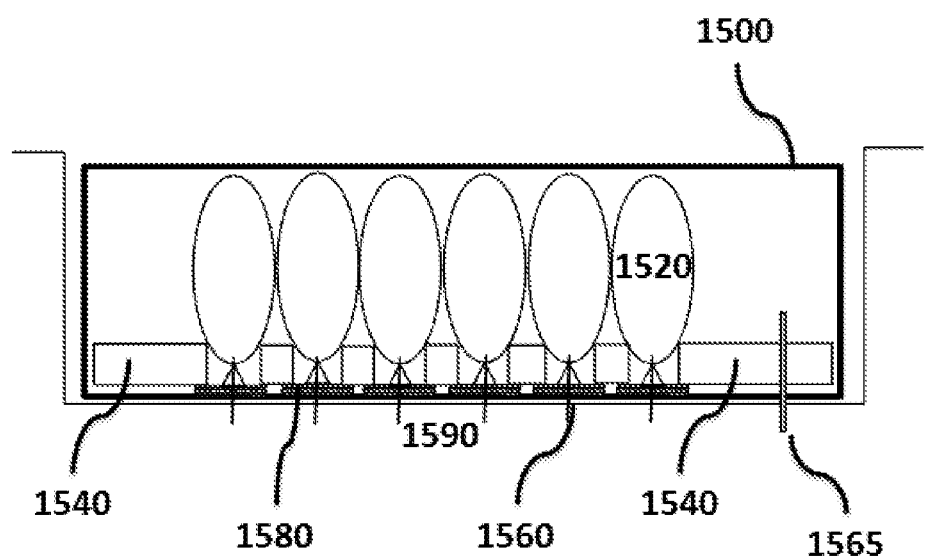
FIG. 15 shows a diagram of an exemplary reagent input device with a cartridge that houses flexible reagent containers.
Figure 16:
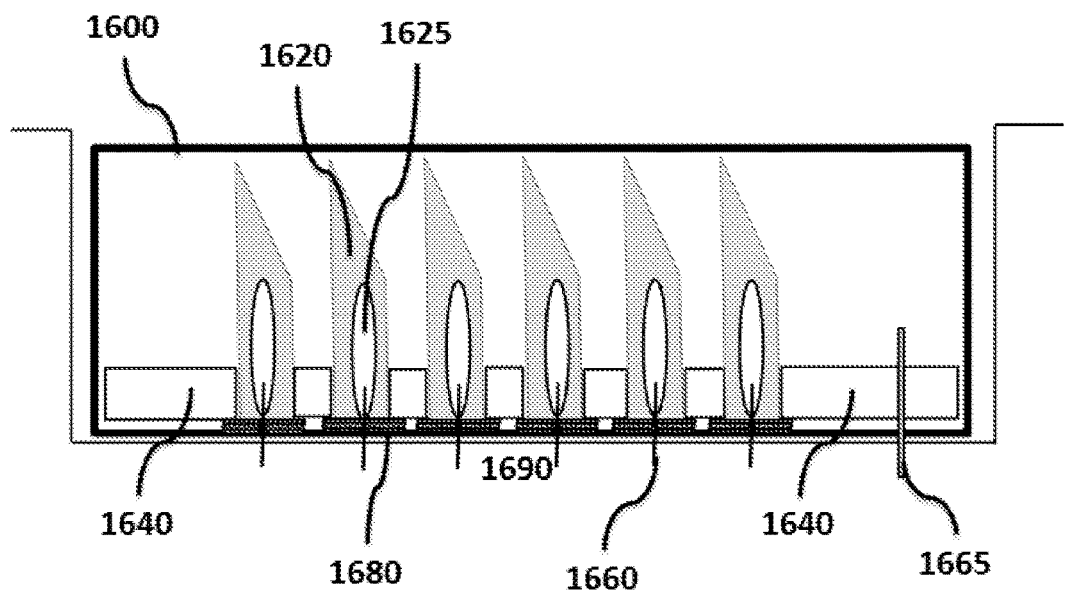
FIG. 16 shows a diagram of an exemplary reagent input device with a cartridge that houses flexible reagent containers or reagent bags where each container and/or bag contains a balloon for mixing reagents.

In another embodiment, as shown in FIG. 15, the reagent input device may have flexible reagent containers, such as for example balloons 1520, instead of or in addition to the reagent bags that are housed inside a cartridge 1500. The liquid may enter the reagent balloon 1520 and fill it up such that the balloon is under pressure. The reagent balloon may be made of a variety of materials, depending on the needs of the system and the type of regent used. Some sample materials that may be used include rubber, polyurethane, silicone, etc. or another material.

Then, the balloon may be sealed by any method known to those skilled in the art, such as for example a valve or another type of mechanism for controlling flow.

When the seal is opened at the appropriate time, the liquid will flow out of the balloon 1520 and into the manifold 1590 due to the pressurized environment inside the balloon 1520. The balloon 1520 may be in fluid contact with the manifold 1590 by any method known to those skilled in the art. In some embodiments, the balloon may be connected to a tube that leads into the manifold of the system.

In another embodiment, as shown in FIG. 15 a balloon 1535 may be located inside reagent bags 1520 or another reagent container. The balloon 1535 may be used to mix reagents 1520 inside the reagent bags 1520 such that there are no or minimal bubbles formed inside the liquid due to the mixing. The balloon 1535 may be inflated and deflated by, for example, attaching the balloon 1535 to an air tube 1565 that is connected to a manifold 1590. Air may rush in and out of the balloon 1535 during the desired time, such that the balloon 1535 is inflated and deflated at a set frequency. This inflation and deflation of the balloon 1535 will cause the reagents 1520 inside the bag 1520 to mix.

In yet another embodiment, a reagent container may contain a flat surface on a moveable mechanism, such as for example on washers. The flat surface may be pushed either up or down, such that the liquid is pushed out when the flat surface is pushed down.

In some embodiments, the apparatuses described here can hold fluids and/or gases. The apparatuses may hold reagents such as nucleotides, buffers, polymerase, water, air, etc. or other reagents known to those skilled in the art. In some embodiments, the reagents may be reagents used for DNA sequencing and/or DNA amplification.

Figure 17:
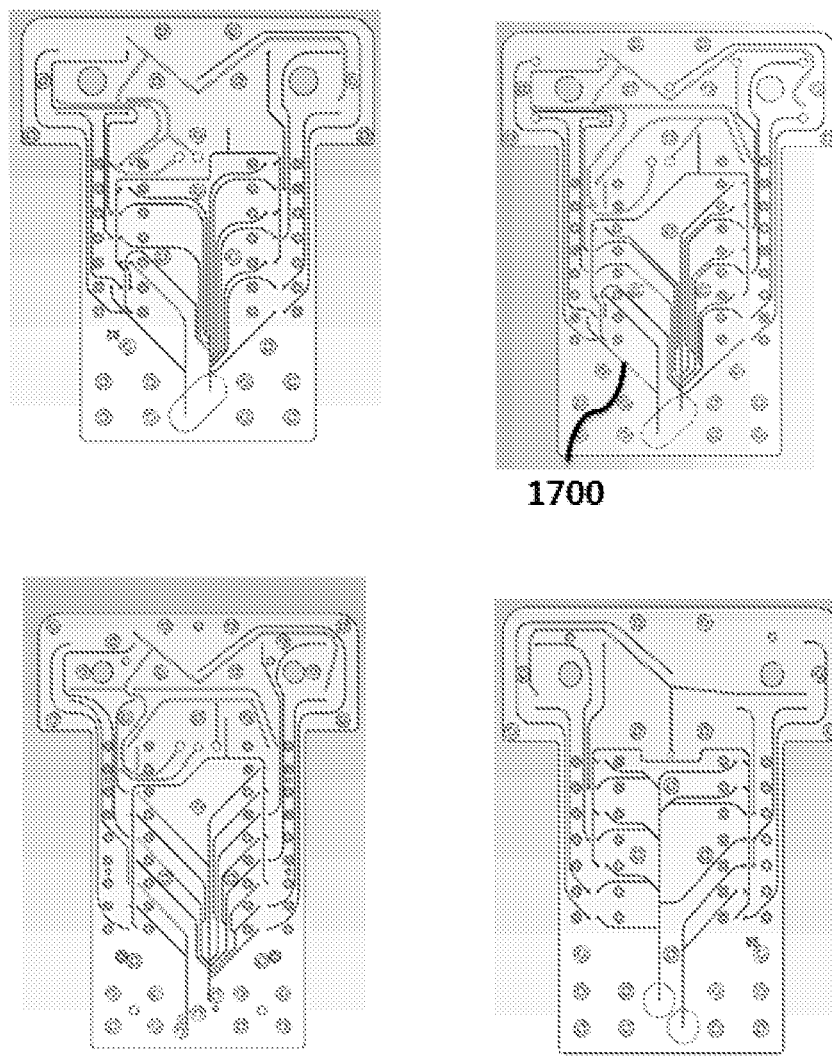
FIG. 17 shows four different embodiments of a manifold design for transporting reagents and other moieties through a microfluidic device.
Figure 18:
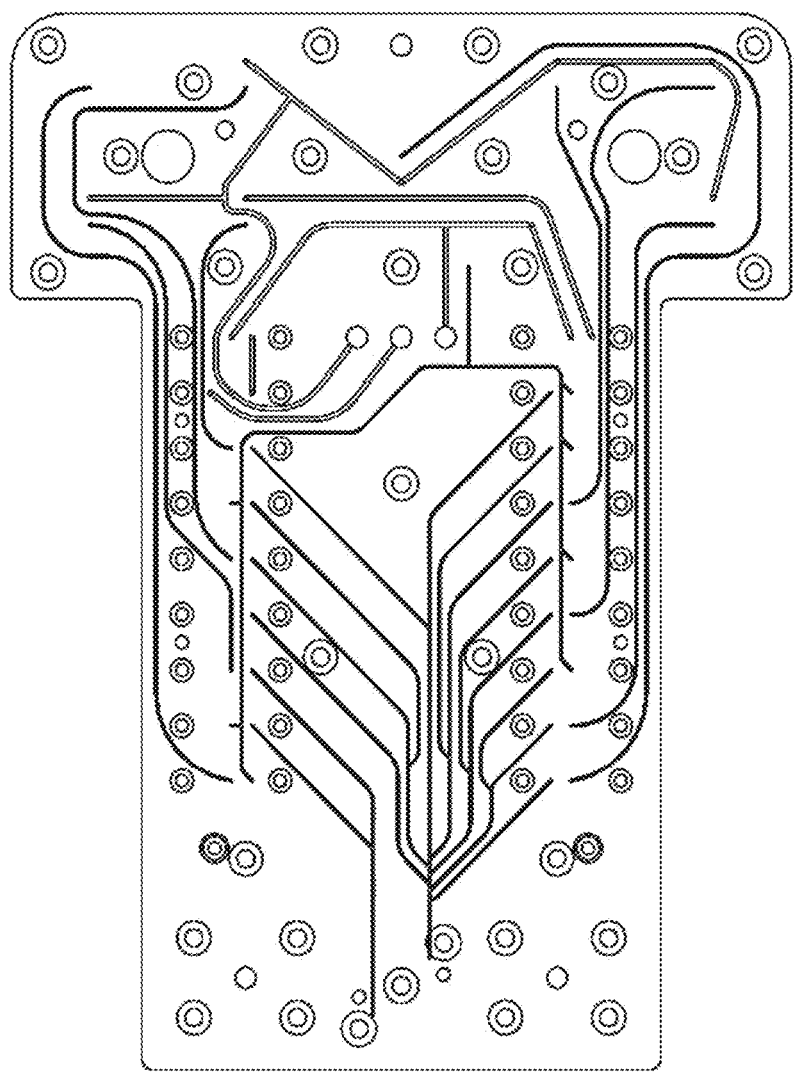
FIG. 18 shows a photograph of one embodiment of a manifold.
Figure 19:
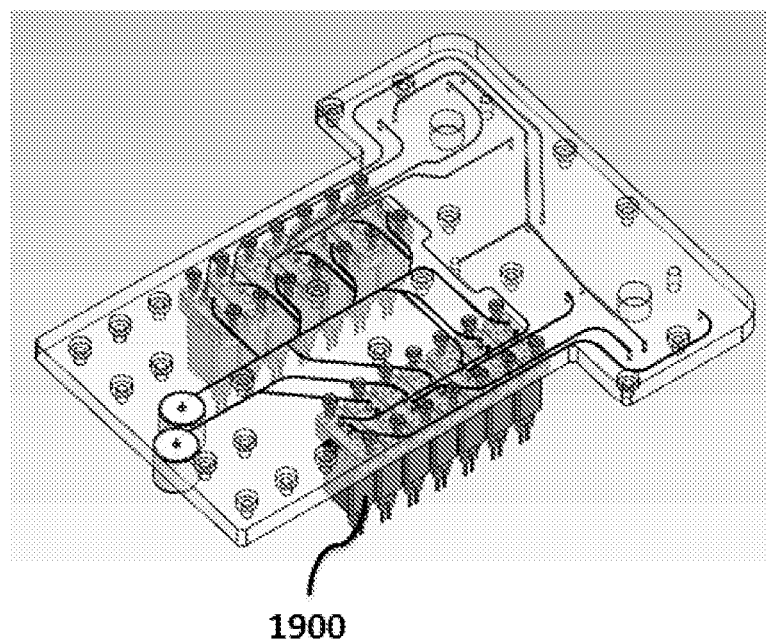
FIG. 19 shows one embodiment of a manifold design with associated valves.
Figure 20:
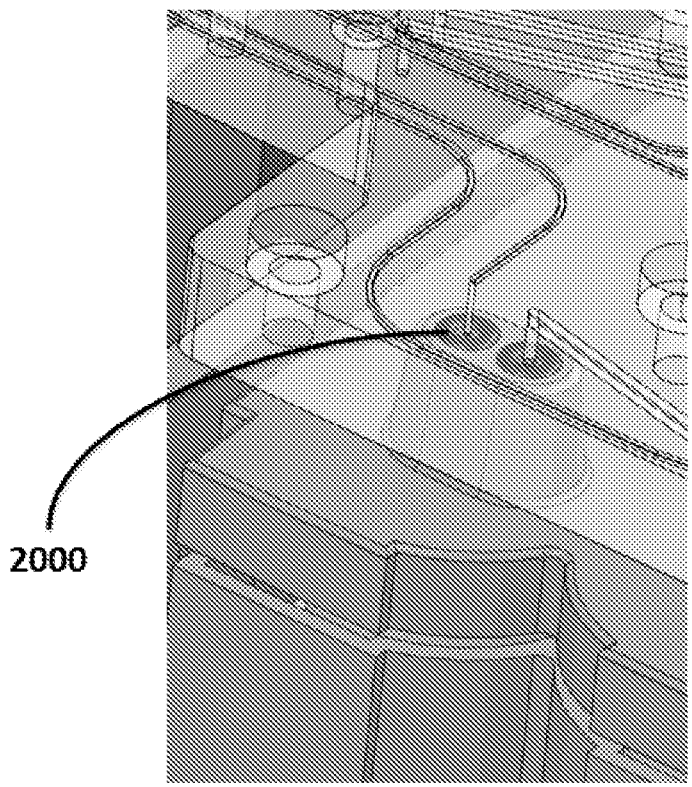
FIG. 20 shows one embodiment of a tubeless system where there is a direct connection between a manifold and a cartridge by use of o-rings.

In another aspect, the device does not use fluids in a bag. The fluid can be stored in a cartridge that is connected to the chip by a fluidic manifold. The fluidic manifold does not have any hoses or pipes in some cases. The manifold can be designed such that the system does not form gas bubbles (e.g., air) when operated. In some cases, the system is operated for at least about 1 minute, at least about 20 minutes, at least about 1 hour, at least about 5 hours, or at least about 10 hours without forming a bubble. FIG. 17 shows four different embodiments of a manifold design for transporting reagents and other moieties through a microfluidic device. The lines interior to the device are fluidic flow paths 1700. FIG. 18 shows a photograph of one embodiment of a manifold. Valves can be in contact with the fluidic flow paths and the openings thereto on the manifold. FIG. 19 shows one embodiment of a manifold design with associated valves 1900. The valves can be fluidically connected to the manifold in any suitable way. For example, FIG. 20 shows one embodiment of a tubeless system where there is a direct connection between a manifold and a cartridge by use of o-rings 2000.

The manifold can be washed. In one embodiment, a software script is used to wash a manifold of a microfluidic device between nucleotide injection and buffer cycles (e.g., in order to prevent contamination with respect to the reaction of interest, such as for example nucleic acid (e.g., DNA) sequencing). The script below shows how a "barrier" wash cycle can be initiated between nucleotide and buffer injections during a sequencing run:

```
;subscript that creates diffusive barrier|
;before purging the next fluidic line|
;Use B2 to keep chip pressurized between steps|
:Barrier|
Valve Preset:No Liquid Flow|0.25
Valve Preset:Prime B2|0.25
Valve Preset:Wash B2 BW S|0.50
Valve Preset:Wash B2 S and M|0.25
Valve Preset:Wash B2 B1 M|0.50
Valve Preset:Backflow B2 and B1 Nuc|1.00
Valve Preset:Backflow B2 Nuc|3.00
Valve Preset:Backflow Nuc and B2 Nuc|0.50
Valve Preset:Backflow B2 Nuc|2.00
Valve Preset:Wash B2 M|0.50
Valve Preset:Prime B2|0.25
Valve Preset:No Liquid Flow|0.25
|
|
;subscript that creates diffusive barrier|
;before purging the next fluidic line|
;Use B2 to keep chip pressurized between steps|
:shortBarrier|
Valve Preset:Wash B2 S|0.25
Valve Preset:Wash B2 S and M|0.25
Valve Preset:Backflow B2 G|0.50
Valve Preset:Wash B2 B1 M|0.50
```

Figure 21A:
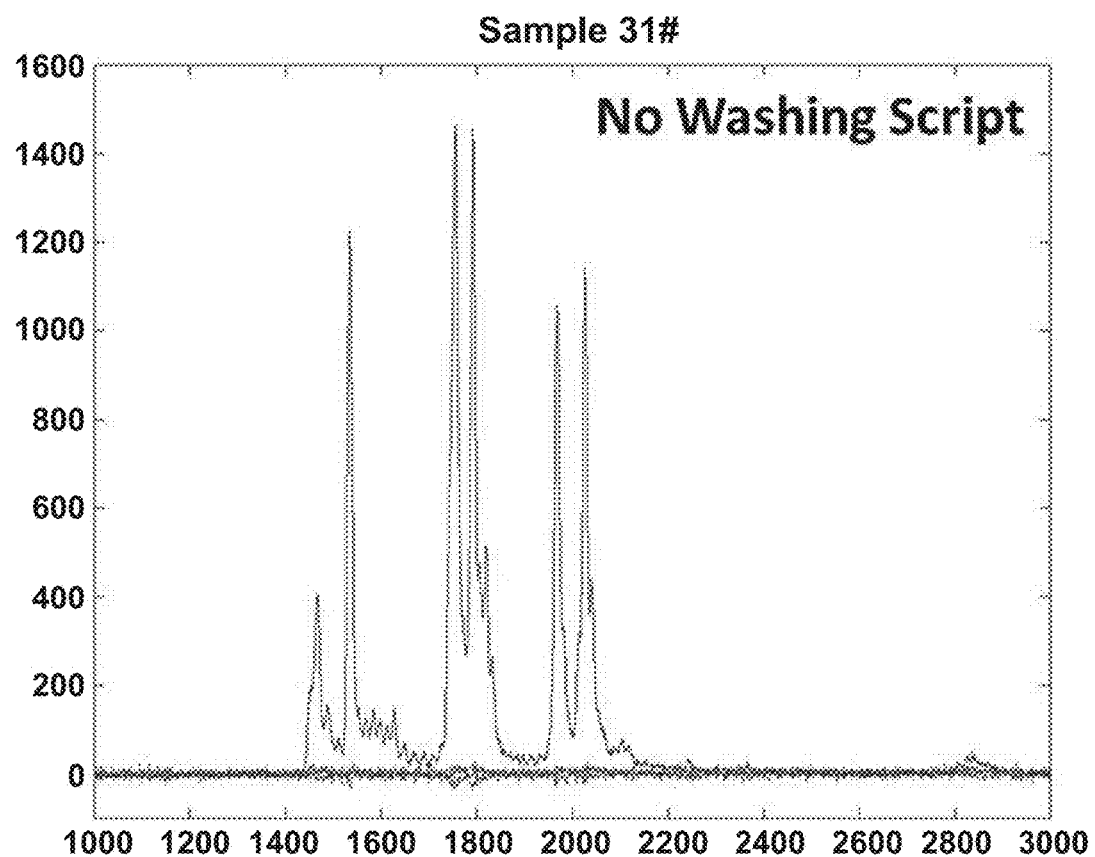
FIG. 21A shows an example of sequencing data acquired from a run without a washing script.
Figure 21B:
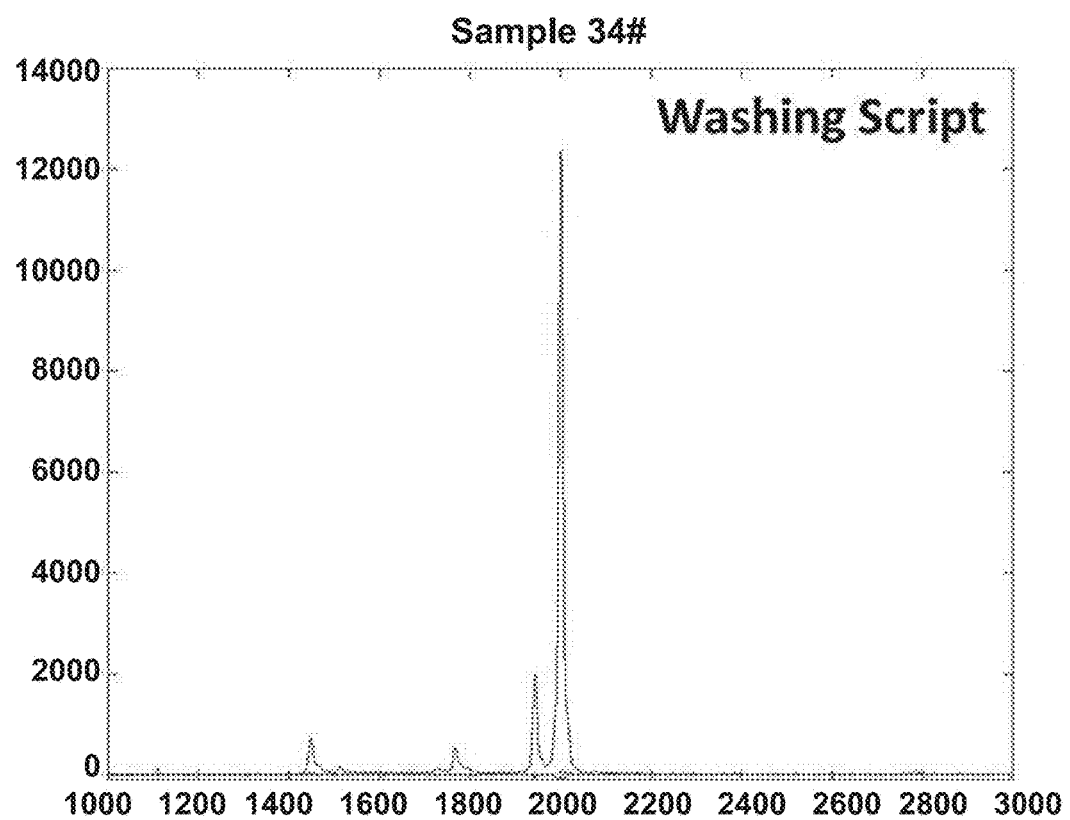
FIG. 21B shows an example of sequencing data acquired from a run with a washing script.

An example of the results of a washing of the manifold can be seen by comparing the sequencing data of FIG. 21A and FIG. 21B. There are relatively more peaks visible without the washing script (FIG. 21A) than with the washing script (FIG. 21B).

Fluidic Connectors

The methods and devices described herein may be used to sequence a nucleic acid. Such devices may utilize microfluidic platforms for DNA sequencing or other associated testing of biological matter. These systems can avoid contamination when transferring fluid from a reagent package into the system manifold via a connector system. This system can achieve substantially contamination-free fluid transfer between devices (e.g., less than about 1%, less than about 0.5%, less than about 0.1%, less than about 0.05%, or less than about 0.01% contamination).

Recognized herein is the need for improved connector systems for clean and effective fluid transfer. The present disclosure provides a push-to-connect connector system for providing fluid (liquid or gas) transfer between fluidic components.

In one embodiment, a push-to-connect connector system can be used in conjunction with fluidic cartridges that may house reagents for use in an associated device. This device may be, for example, a DNA sequencing device and the push-to-connect connector system can allow for the connection and transfer of biological reagents used in DNA sequencing. Some exemplary biological reagents may include nucleotides, buffers, and blood.

In some aspects, the present disclosure addresses the need for a low-cost, leak-proof, multiple channel, quick-connect, quick-disconnect and substantially contamination-free fluid flow connector that transfers fluid between two fluidic components. This connector may allow for a connection to disposable cartridges that can house, for example, biological reagents. By adding a simple latch mechanism, the system may also be used as an inline connector to connect two flexible or rigid pipes. It also can be used to connect two fluidic devices directly to each other. The connector assembly allows not only a substantially leak-proof structure, but also a way of delivering fluid such that there can be a lower risk of contamination into the system from unwanted exposure to contaminants from outside sources, such as air pollutants.

Moreover, the female side of the system can include plastic and rubber injection-moldable parts that can be manufactured at a low cost. The system may be connected and/or disconnected by a simple push/pull action and as a result it can be used to connect multiple fluid channels at the same time. The female connector can be designed in such a way that it may include a removable seal to be taken off before the first insertion. In some embodiments, the female connector may be disposable.

In an aspect, provided herein is a push-to-connect connector system for fluid transfer comprising: (a) a female connector comprising a hollow cavity and multi-layer seals within a top portion of the cavity, the multi-layer seals having a pin receiving channel; (b) a male connector comprising a fluid transfer pin having first and second ends, a pin inlet channel extending between the first and second ends, and at least one fluidic transfer inlet proximate to the first end, the fluid transfer pin being moveable from a first position, where the pin is positioned in the interior of the male connector, to a second position, where the pin extends between the male connector and the female connector and into the pin receiving channel; (c) a cover sleeve proximate to the male connector, the cover sleeve being axially displaceable such that it moves from a first position where it is flush with the first end of the fluid transfer pin, to a second position where the cover sleeve is located around the male connector, the cover sleeve and the pin being coupled to move the pin from the first position to the second position;

and (d) a fluid cartridge connected to the female connector such that there is fluid contact when the pin is in the second position. In some embodiments, the connector system further comprises at least two push-to-connect connector assemblies.

In some cases, the female connector further comprises a removable protective cover. The female connector can be disposable.

Figure 22:
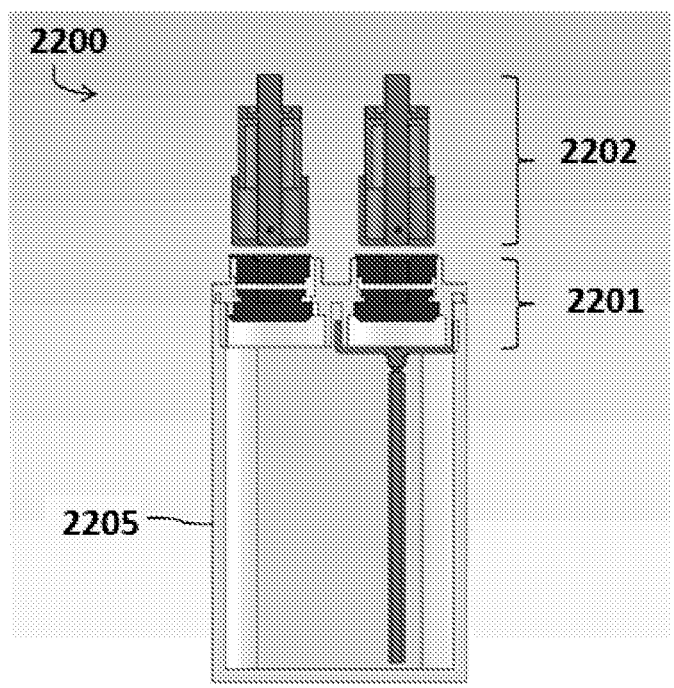
FIG. 22 shows an exemplary embodiment of a push-to-connect connector system for fluid (or gas) transfer.

As shown in FIG. 22, in some embodiments, the push-to-connect connector system 2200 may include two sub-assemblies: a female connector 2201 and a male connector 2202. The male connector 2202 may be configured to be mounted onto the female connector 2201. In some embodiments, the female connector 2201 may be integrated with a fluid cartridge 2205 and the male connector 2202 can be screwed into an associated device, product, fluidic manifold, etc.

Figure 23A:
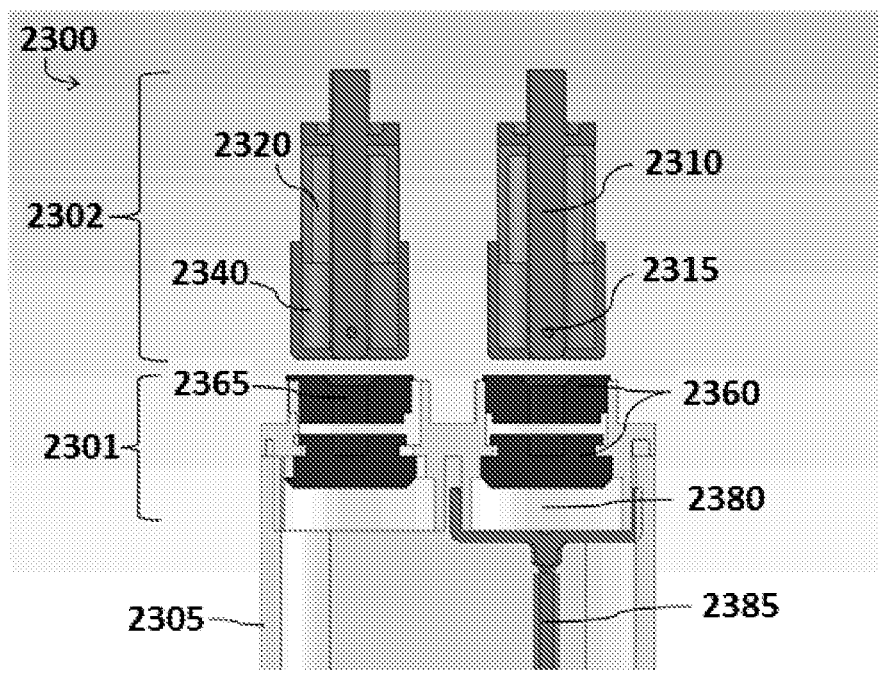
FIG. 23A shows a more detailed view of the push-to-connect connector system of FIG. 22.

In one aspect, as shown in FIG. 23A, the push-to-connect connector system 2300 may include a fluid cartridge 2305, a male connector 2302 which comprises a fluidic transfer pin 2310 with associated fluidic transfer inlets 2315, a spring holder 2320, and a cover sleeve 2340. The cover sleeve 2340 can protect the sides of fluidic transfer pin 2310 from potential contaminants. In some embodiments, there may be a spring (not shown) inside the spring holder 2320 to ensure that the cover sleeve 2340 covers the fluidic transfer pin 2310. In another embodiment, the female connector 2301 may include a multi-layer flexible seal 2360 with an associated pin receiving channel 2365, and a receiving chamber 2380. The female connector may be proximate to outlet channel 2385 which may lead to the fluidic reservoir of a cartridge 2305. The fluid transfer pin 2310, receiving chamber 2380, and other components of push-to-connect connector system 2300 can be made of a wide variety of materials known to those skilled in the art. For example, the components may be made of metal and/or plastic. Examples of potential materials include brass, stainless steel, and polycarbonate. In some embodiments, the multi-layer flexible seal 2360 can be made of rubber and/or o-rings.

Figure 23B:
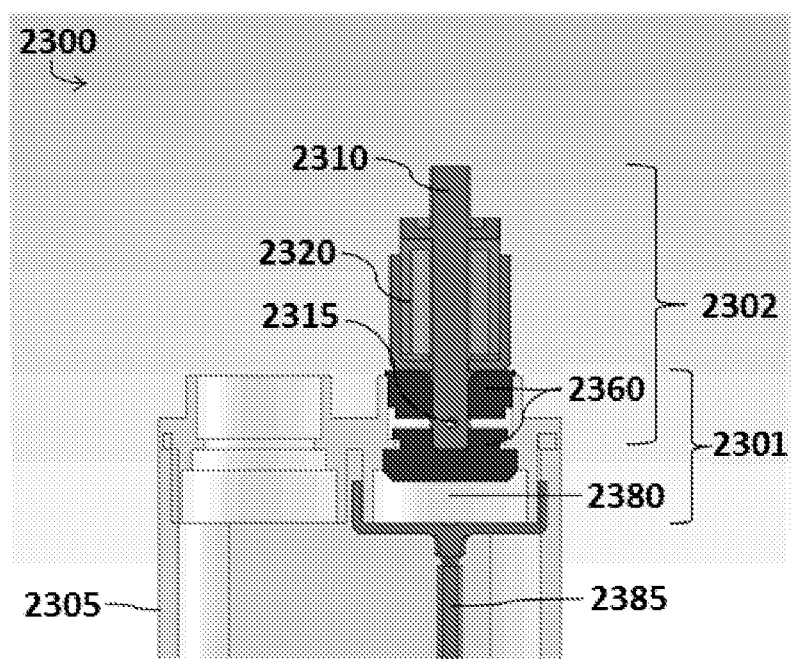
FIG. 23B shows one step in the process of using the exemplary push-to-connect connector system of FIG. 22.

In another aspect, as shown in FIG. 23B, the male connector 2302 may be aligned with the female connector 2301. Then, the male connector 2302 can be placed in physical contact with the female connector 2301. If the female connector 2301 is disposable, it may have a peel-off cover to protect it from potential contamination before use. A force may be applied along the axis of the fluidic transfer pin 2310 such that fluidic transfer pin 2310 is driven through the multi-layer flexible seal 2360 and inside the receiving channel 2365, thereby displacing cover sleeve 2340 in an upward direction. At this stage the flat face of fluidic transfer pin 2310 is fully covered by one portion of multi-layer flexible seal 2360 in order to help avoid potential contamination.

Figure 23C:
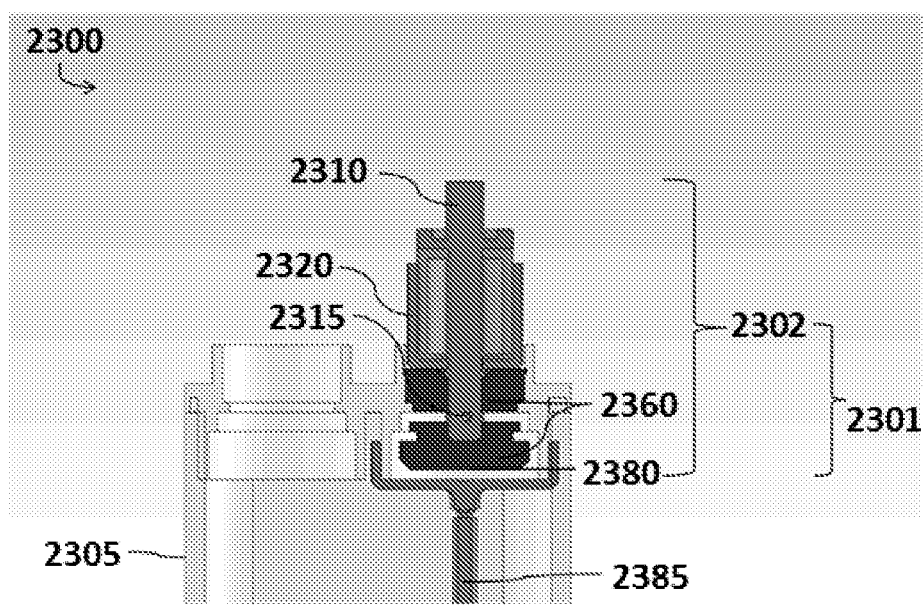
FIG. 23C shows another step in the process of using the exemplary push-to-connect connector system of FIG. 22 such that the fluid (or gas) is transferred.

In a further aspect, as shown in FIG. 23C, a force may be further applied to the push-to-connect connector system 2300 such that a portion of the multi-layer flexible seal 2360 enters the receiving chamber 2380. At this stage, the fluidic transfer pin 2310 may be in fluidic contact with the outlet channel 2385. Thus, the fluid from the fluid cartridge 2305 can pass through outlet channel 2385 and into fluid transfer inlets 2315. The fluid may then pass through a pin inlet channel (not shown) along the axis of fluidic transfer pin 2310 and then reach the associated device (not shown) in fluidic contact with male connector 2302.

Figure 23D:
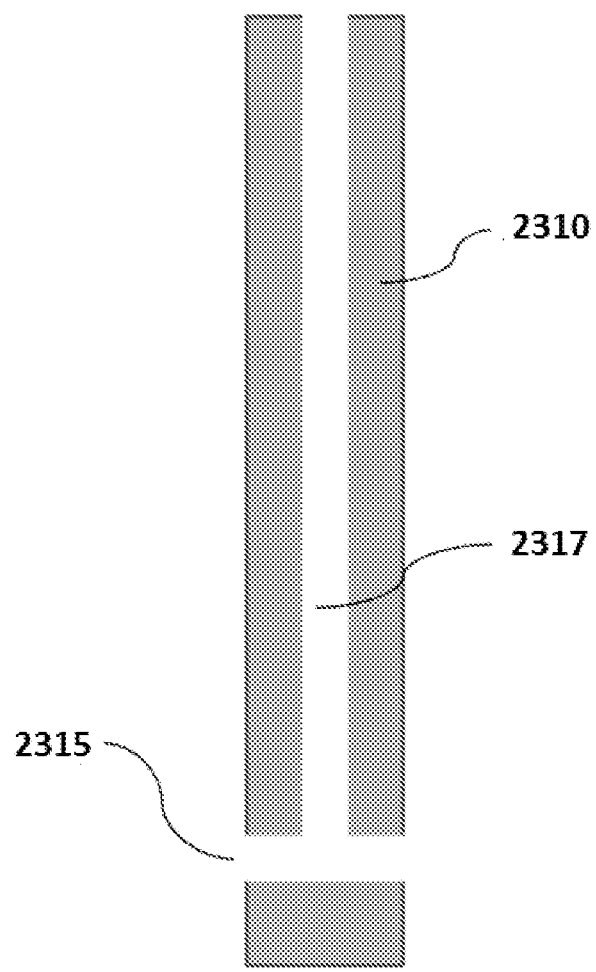
FIG. 23D shows one embodiment of a cross section of a fluid transfer pin.

FIG. 23D illustrates, in one embodiment, a cross section of fluid transfer pin 2310, including a pin inlet channel 2317 for the transfer of fluid from fluid transfer inlet 2315 to an associated device (not shown).

Figure 24A:
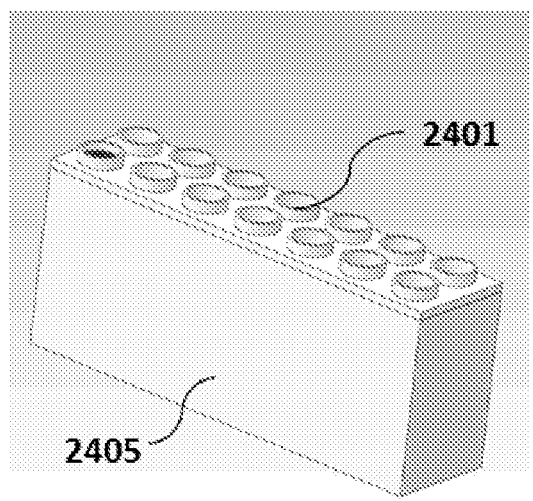
FIG. 24A shows on embodiment of a fluid cartridge integrated with female connectors.

FIG. 24A shows, in one embodiment, a fluid cartridge 2405 integrated with female connectors 2401.

Figure 24B:
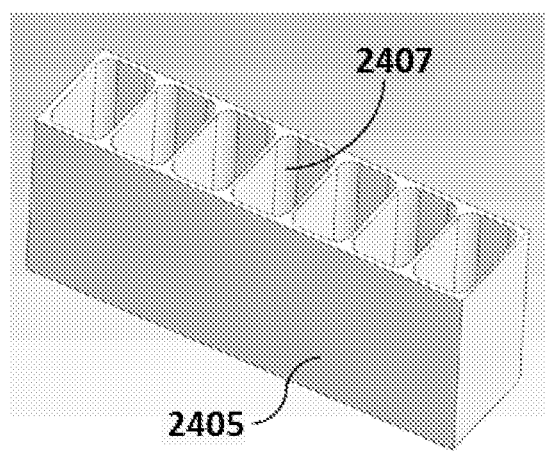
FIG. 24B shows an embodiment of reservoirs located in a fluid cartridge.

FIG. 24B shows, in another embodiment, the reservoirs 2407 that can be located inside the fluid cartridge 2405. In some embodiments, there may be two push-to-connect connector assemblies (not shown) for each reservoir 2407: one connector assembly may function as an inlet port for pressurized gas and the second connector assembly can be the outlet port for liquid. In some embodiments, when the pressurized gas is applied and passed through the first connector system, the pressurized gas can drive the liquid out of cartridge 2407, through the second push-to-connect connector system, and into an associated device. One embodiment of this type of configuration is shown in FIG. 22 where there are two push-to-connect connectors (each with one female connector 2201 and one male connector 2202) associated with one fluid cartridge 2205.

Lids for Microfluidic Systems

Recognized herein is the need for improved devices and lids that prevent leakage of fluids from microfluidic devices. In an aspect, the present disclosure provides lid devices for microfluidic systems to minimize or eliminate leakage of fluid.

When designing a microfluidic semiconductor device, one consideration can be the design of a lid for the system. The lid can contain the fluid within the chamber, protect the semiconductor device surface, maintain a uniform flow rate across the semiconductor device surface, and allow users to visually inspect its operation while in use.

The lid may be made out of a variety of materials. Some examples include polycarbonate, glass and/or acrylic materials. The lid may be entirely made out of one material, two materials, or a variety of materials. The selection of the material or materials may depend on the specifications of the system as well as its intended purpose. For example, a lid may block Ultra-Violet light at a certain wavelength, may be biocompatible, and may be optically clear and/or withstand certain types of chemical treatments.

In addition to the composition of the lid, the shape and attachment methods with respect to the lid may also be considered when designing the system. Microfluidic semi-conductor devices may include liquid(s) contained therein. If the lid is not properly designed and/or attached to the system, the liquid may leak out of the microfluidic chamber and damage other portions of the semiconductor device.

In an aspect, the present disclosure provides a device for covering a microfluidic semiconductor device. The device can comprise a lid, where the lid comprises a substantially planar top portion, a first prong and a second prong, where the first and second prongs support the lid on a substrate and define a microfluidic chamber. The device can comprise a plurality of beads where the first and second prongs are proximate to, and exert pressure on, the beads for fluidically sealing the microfluidic chamber and where the beads are in contact with the substrate. In some cases, the lid comprises at least one of polycarbonate, glass, and acrylic.

In another aspect, the present disclosure provides a device for covering a microfluidic semiconductor device. The device can comprise a lid, where the lid comprises a substantially planar top portion, a first prong and a second prong, where the first and second prongs support the lid on a substrate and define a microfluidic chamber. The device can further comprise a tapered portion on the lid or substrate contacting the lid where the tapered portions are proximate to the prongs for holding an adhesive in order to fluidically seal the microfluidic chamber. The adhesive can hold the prongs to the substrate. The lid can comprise at least one of polycarbonate, glass, and acrylic. In some cases, the device can have a groove within the substrate into which a gasket may be inserted.

Figure 25:
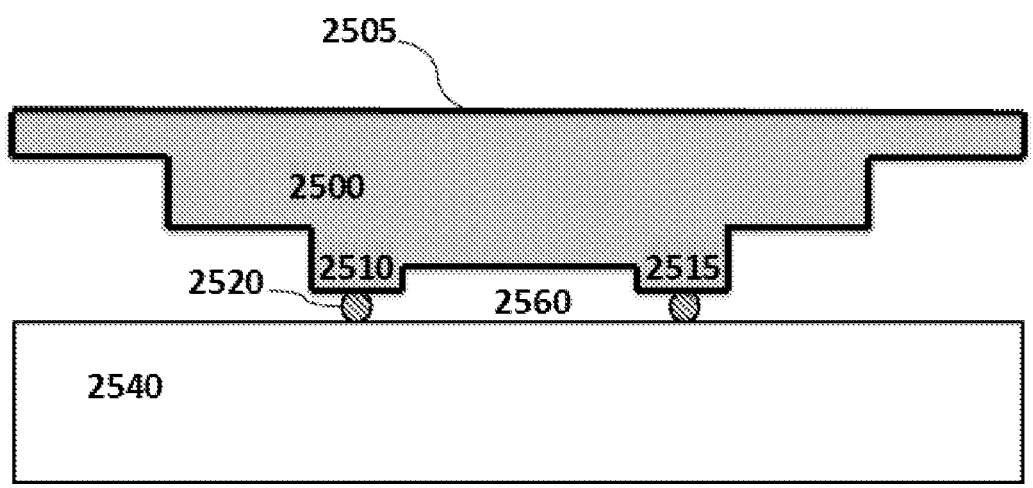
FIG. 25 shows an example of a lid device for a microfluidic system.

In one embodiment, as shown in FIG. 25, a lid 2500 with a substantially planar top portion 2505 rests on a base 2540 with beads 2520 inside and the pressure of a first prong 2510 and a second prong 2515 on the beads 2520 seals the microfluidic chamber 2560 of the device, to the height of the beads 2520, from the rest of the system. The beads 2520 rest on base 2540. The beads can be glass or any other rigid material.

Figure 26:
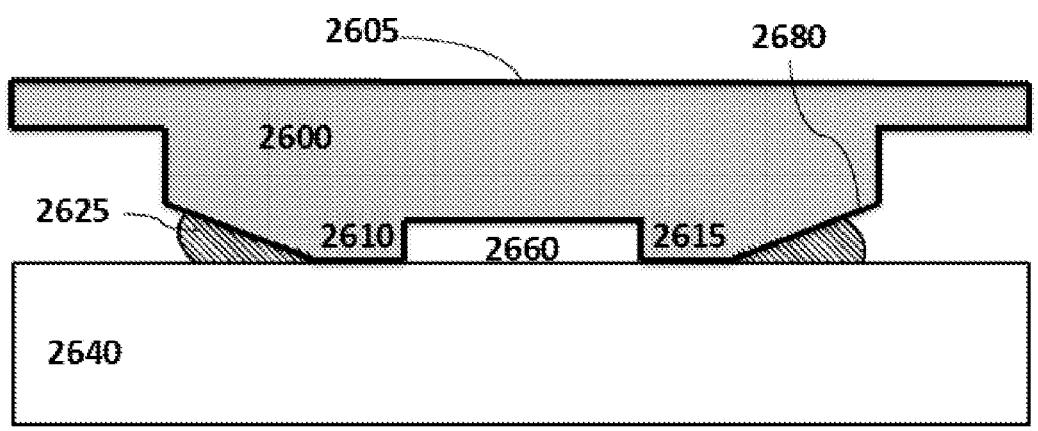
FIG. 26 shows another example of a lid device for a microfluidic system.

In another embodiment, as shown in FIG. 26, a lid 2600 with a substantially planar top portion 2605 is attached directly to a base 2640 via a first prong 2610 and a second prong 2615 using an adhesive 2625. In some embodiments, the adhesive 2625 may be an epoxy that is either heat or UV cured. The width of the adhesive may be about 10 micrometers (μm), about 20 μm, about 50 μm, about 75 μm, about 100 μm, about 200 μm, about 500 μm, or more. The height of the adhesive can be about 10 μm, about 20 μm, about 50 μm, about 75 μm, about 100 μm, about 200 μm, about 500 μm, or more.

In some embodiments, the sides of the lid 2600 may be tapered 2680 such that the adhesive 2625 is pushed away from the microfluidic chamber 2660. This creates a region that is filled with adhesive 2625 in order to prevent leakage, yet this region is not within the microfluidic chamber 2660 itself. In this manner, the height of the microfluidic chamber 2660 is set by a first prong 2610 and a second prong 2615 of the lid 2600 and not by the adhesive 2625 itself. Furthermore, this allows for wider tolerances on the placement, width and height of the adhesive 2625 since the adhesive 2625 does not need to rest on the prongs and it does not set the chamber height.

In another embodiment, the lid may have a groove within the substrate that is in contact with the semiconductor device surface so that a gasket can be inserted. This gasket can act as the main seal to prevent the fluid from leaking out and the adhesive may be used to hold the lid and gasket in place. This can allow for a more constant distance between the semiconductor device surface and the lid as well as a more uniform seal.

Control of Microfluidic Systems

Recognized herein is the need for improved systems and methods for controlling microfluidic devices in an efficient and cost effective manner. The present disclosure provides systems and methods for controlling microfluidic devices and their associated biological samples, carrier particles, reagents, and other moieties.

In an aspect, the present disclosure provides a system comprising a substantially planar nano-sensor array where the array can comprise electrodes for generating gas bubbles for controlling the movement of moieties, with the nano-sensors being located within pixels. In some cases, the gas is air.

In an aspect, the present disclosure provides a system, comprising a substantially planar nano-sensor array where the array can comprise electrodes proximate to electrically sensitive charged protein structures for controlling the movement of moieties, with the nano-sensors being located within pixels.

In some embodiments, a sample of interest, such as DNA or another nucleic acid molecule, can be associated with a plurality of magnetic carriers. For example, sample DNA can be fixed to magnetic beads. The combined nano-magnetic-electronic platform can include an array of magnetic features such that beads are held in place by a localized magnetic field in each of a plurality of regions. In some embodiments, the beads can be held by electrostatic force due to the charge of the bead or nucleic acid associated with the bead. In some cases, the beads can be held in physical trenches or wells.

Described herein are modifications to the aforementioned systems and various methods and systems for capturing and controlling beads or other particles. Electrodes can be used to generate a gas bubble, generate an electric field, and detect a reaction of interest.

In some embodiments, electrodes can be used to create gas bubbles. The gas bubbles can be formed by electrolysis of water (e.g., to form $O_2$ and $H_2$ gas). The size and duration of the gas bubbles can be controlled by modulating the voltage associated with the electrodes. These gas bubbles can be created in the electrodes of the pixels of the array, next to the magnets also associated with these pixels.

Figure 27A:
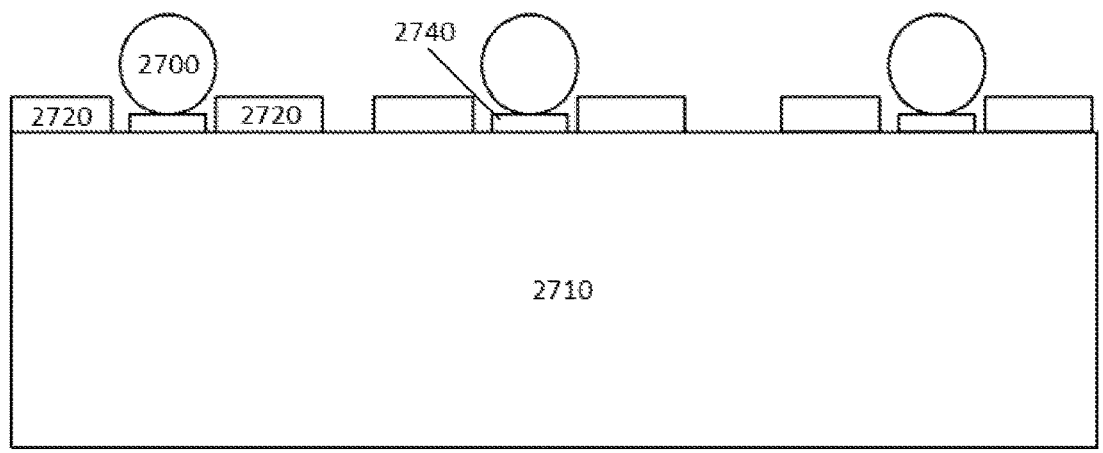
FIG. 27A shows an exemplary embodiment of a substantially planar nano-sensor array where the nano-sensors are electrodes.
Figure 27B:
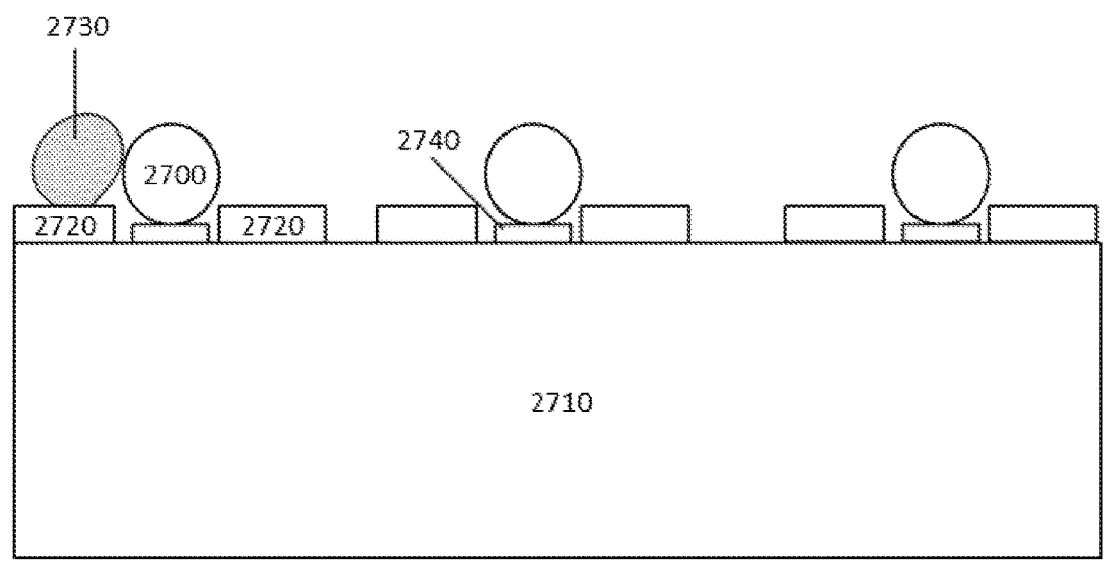
FIG. 27B shows the array of FIG. 27A where the electrodes generate air bubbles due to an applied voltage.
Figure 27C:
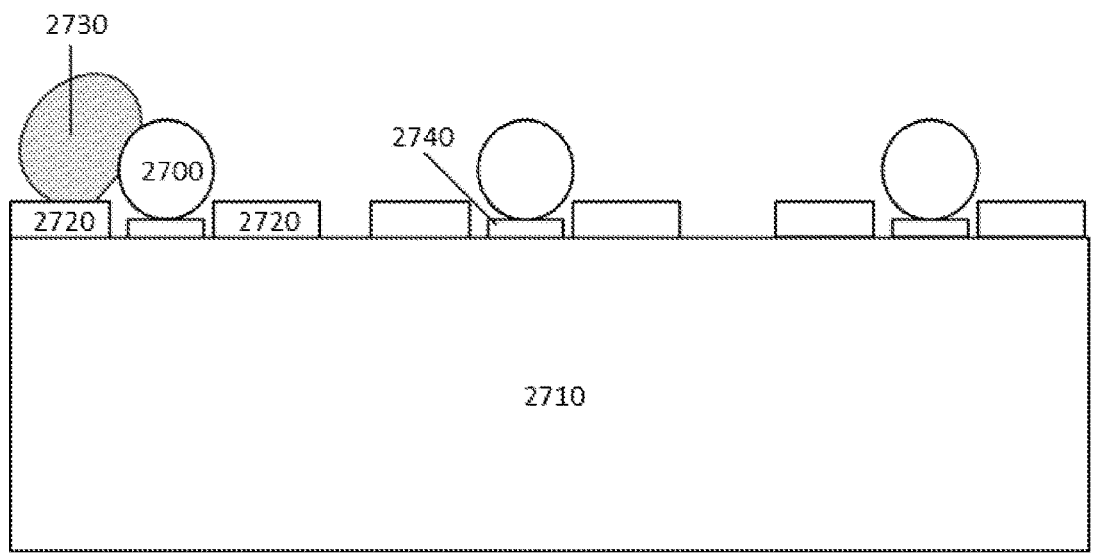
FIG. 27C shows the array of FIG. 27B after some time has passed and the air bubble has grown.
Figure 27D:
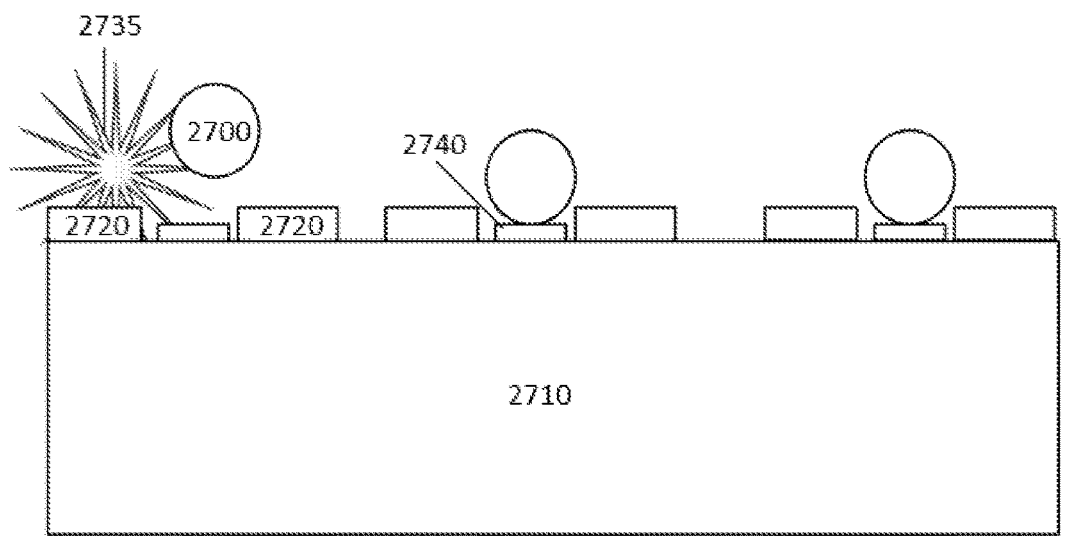
FIG. 27D shows the collapse of the air bubble proximate to a bead, thereby displacing the bead.
Figure 27E:
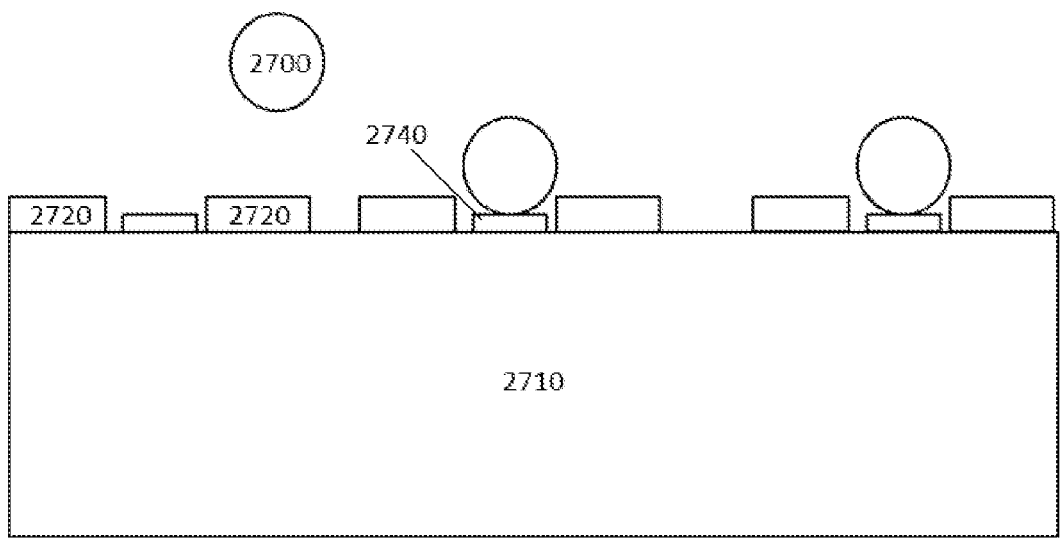
FIG. 27E shows the displaced bead travelling through the microfluidic device as a result of the collapse.

In some embodiments, as shown in FIGS. 27A-27E, the voltage to electrodes 2720 located on a substrate 2710 may be controlled such that the creation of gas bubbles 2730 is timed to achieve a desired function. For example, in order to help remove beads 2700 from a magnet 2740 once a desired reaction is complete, the gas bubble 2730 may be generated on one or more electrodes 2720 near the magnet 2740 and bead 2700. Then, the gas bubble 2730 may be made to collapse 2735 through a variety of methods, including voltage modulation, fluid degassing, and ultrasonic shock. The collapse 2735 of the gas bubble 2730 in close proximity with the bead 2700 may create enough force to dislodge the bead 2700 from the magnet 2740. This can, as shown in FIGS. 27D-27E, thereby release the bead 2700 from the magnet 2740 at a desired time.

In some embodiments, the position of the gas bubble can be controlled via modulation of the voltage associated with the electrodes. The gas bubble may then be used to help direct beads and/or other particles in the system to a desired location.

Figure 28A:
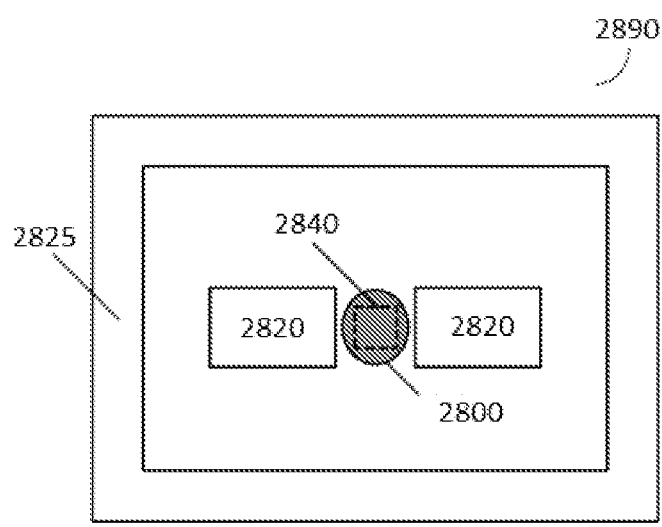
FIG. 28A shows an exemplary pixel in the array and potential components.
Figure 28B:
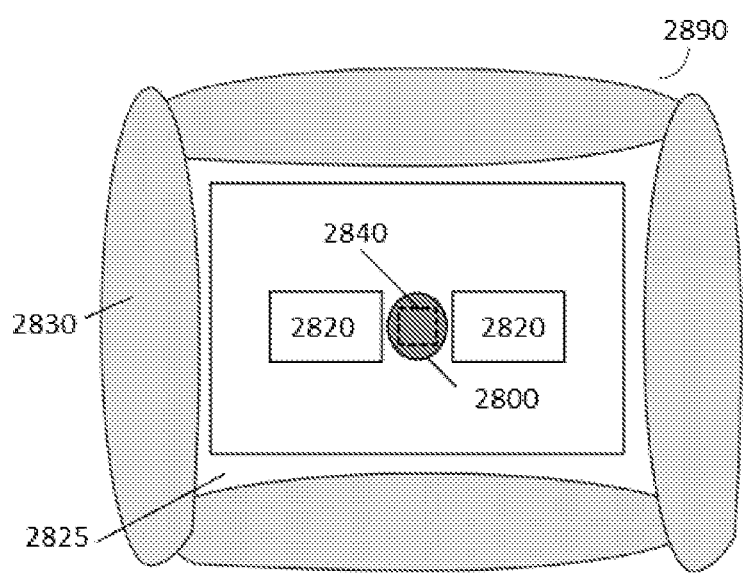
FIG. 28B shows the out electrodes of an exemplary pixel generating air bubbles for pixel isolation and/or confinement of reagents/moieties.

In some embodiments, as shown in a top view in FIG. 28A, a pixel 2890 in an array may include an outer electrode 2825, inner electrodes 2820, a magnet 2840, and a bead 2800. FIG. 28B shows that after a certain voltage is applied, outer electrodes 2825 may generate gas bubbles 2830 around the perimeter of a pixel 2890. This allows for an gas bubble "cage" around the pixel 2890, thereby isolating it from neighboring pixels in an array. This isolation can help to reduce cross-contamination between pixels and help contain reagents and/or moieties within the pixel 2890.

Figure 29A:
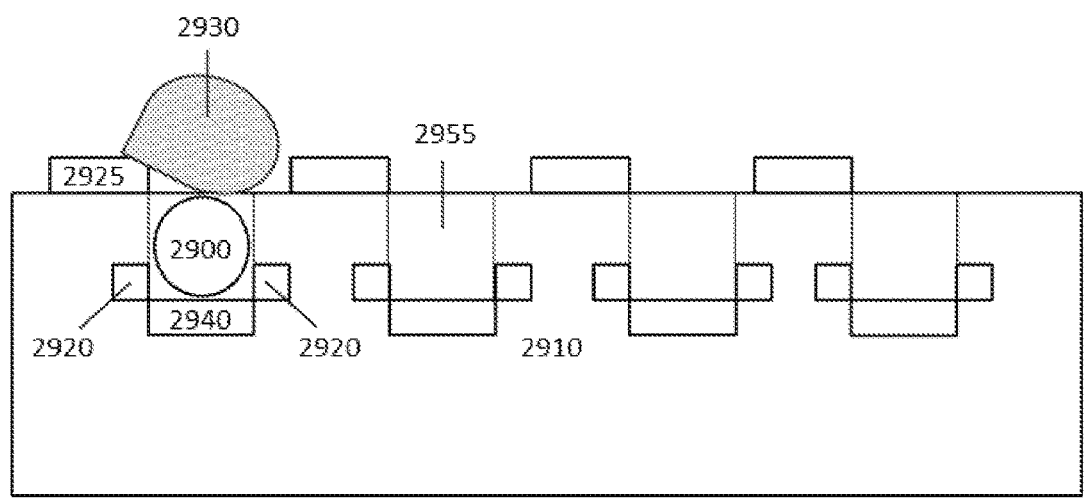
FIG. 29A shows one embodiment of an air bubble generated by an electrode used as a "gate" for an array of wells.

In yet another embodiment, as shown in FIG. 29A, there may be an array of wells 2955 in a substrate 2910 used to capture beads 2900 either in place of or in addition to magnets 2940. The gas bubbles 2930 generated by the upper electrodes 2925 may be used to cover the top of the well 2955 and control which reagents have physical access to the well 2955 and at which time. Thus, the gas bubble 2930 may act as a "gate" for the well 2955 and allow for an additional layer of control of the system. The gas bubble 2930 may be removed by modulating the voltage applied to upper electrodes 2925. There may also be detection electrodes 2920 for the detection of reactions of interest on or proximate to a bead 2900 in a well 2955.

Figure 29B:
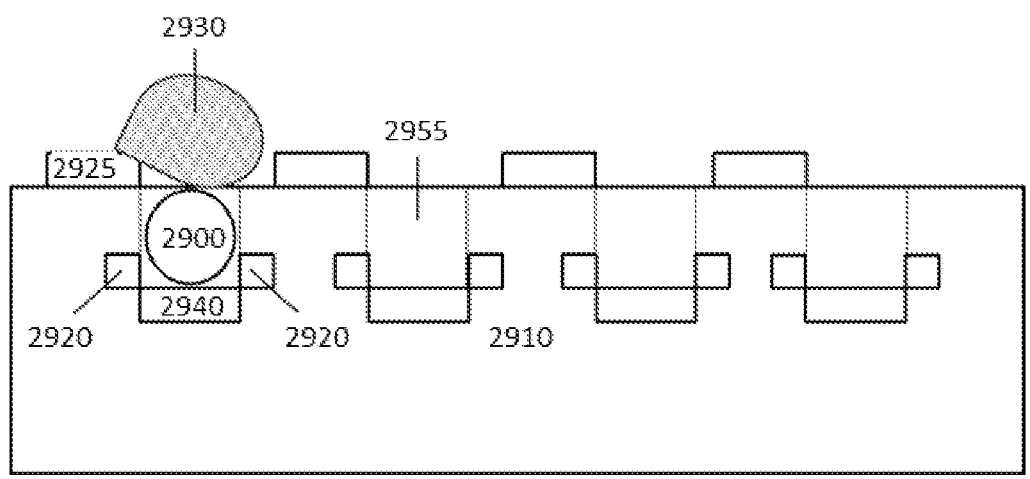
FIG. 29B shows a vertical embodiment of FIG. 29A.

In a further example, as shown in FIG. 29B, the system of FIG. 29A may be placed vertically in a device and the gas bubble 2930 may aid in containing a bead 2900 in the well until a desired release time. In some embodiments, the array and a corresponding chip may be placed vertically instead of horizontally. There may be an array of wells 2955 where there are upper electrodes 2925 and magnets 2940 associated with each well 2955. Gas bubbles 2930 may be generated by the upper electrodes 2925 and can be used to "gate" the wells 2955, thereby helping to control the flow of particles in and out of the wells 2955. For example, the gas bubbles 2930 may be generated to keep beads 2900 inside the wells 2955 and then may be removed when beads 2900 are to be released. Since the array has a vertical orientation, the beads 2900 can fall out of the wells in the absence of the gas bubble "gate" due to gravity overcoming the magnets 2940.

In some cases, in either vertically or horizontally oriented arrays, there may be controllable electromagnets associated with each well, where the modulation of the electromagnets can allow for the capture or for the release of the magnetic beads. In some instances, there may be no magnet and the movement of the beads can be directed by generating and removing gas bubbles.

The disclosure also provides additional methods to control flow into a well. In some cases, a circular electric ring can be placed around the outside of a well. The electric ring can have an electric field associated with it such that charged particles or other charged species are directed into the well. This may enable more efficient reactions as particles of interest reach the well more quickly.

Figure 30A:
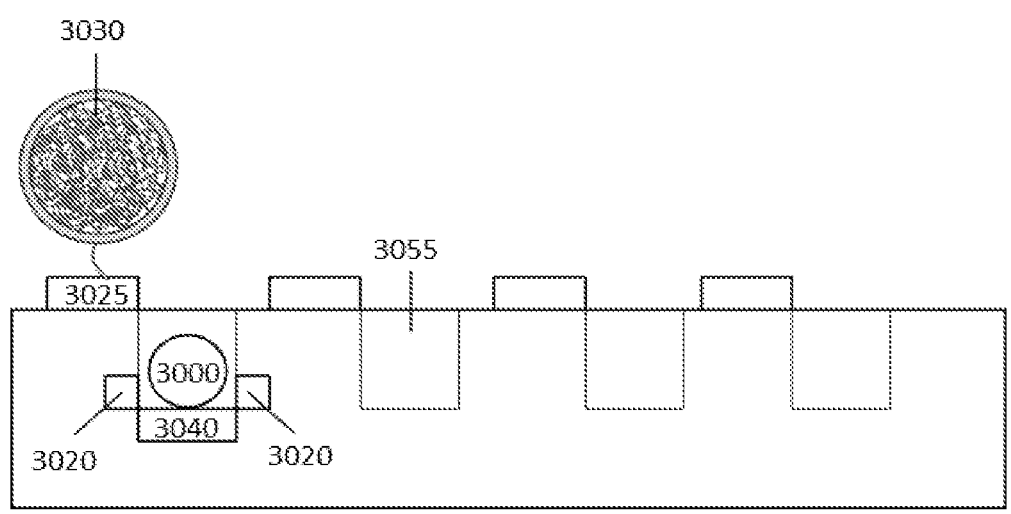
FIG. 30A shows a charged protein structure attached to an upper electrode proximate to an array of wells.
Figure 30B:
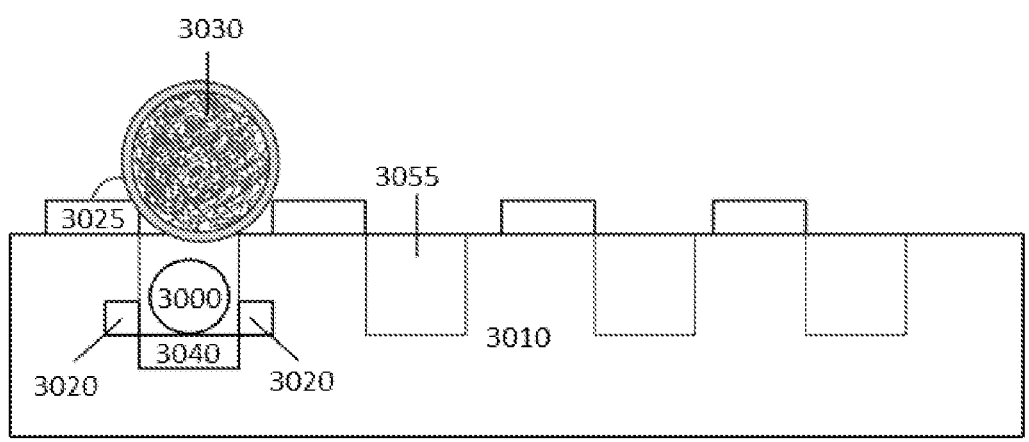
FIG. 30B shows an electrically activated charged protein structure used to "gate" a well.

In some cases, as shown in FIG. 30A, a charged protein structure 3030 may be used to gate an array of wells 3055 located on a substrate 3010. This structure may be attached to upper electrodes 3025 by any suitable method, such as ionic or covalent bonds. The charged protein structure 3030 is shown with an outer casing, but in some cases it may not have an outer casing. As shown in FIG. 30B, the charged protein structure 3030 may be used as a "gate" to cover the well 3055 when electrically activated in order to retain a bead 3000 and any associated moieties or reagents. The structure 3030 may respond to electrical signals by either moving over the well 3055 and/or expanding to cover the well 3055. The well 3055 may also contain magnets 3040 and detection electrodes 3020.

Once the electrical signals are terminated, the charged structure can move to open the entrance to the well. In some embodiments, this structure may also be used with a vertically-configured array.

In another embodiment, a bead may have a hollow channel running through its center. An electrode and/or magnet can be inserted through this channel such that an electrical and/or magnetic gradient is formed. This configuration can create regions on the bead with desired electrical and/or magnetic properties.

Figure 31A:
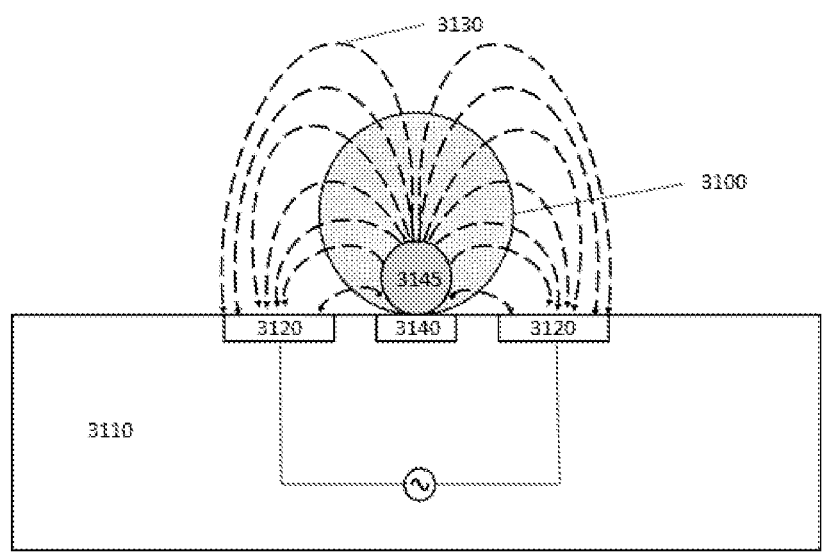
FIG. 31A shows one embodiment of an asymmetric bead and the resulting electric field lines.

In another embodiment, as shown in FIG. 31A, an asymmetric bead 3100 may be configured such that there is an inner magnet 3145 located one side of the bead 3100. In this embodiment, the bead 3100 is "asymmetric" with respect to the placement of the inner magnet 3145. The asymmetric bead 3100 may rest on a magnet 3140 located proximate to a substrate 3110 and can be proximate to detection electrodes 3120. Electric field lines 3130 generated by the detection electrodes 3120 through the bead 3100 are illustrated. The resulting orientation of the electric field lines 3130 throughout bead 3100 may allow for greater sensitivity with respect to the electrodes 3120 detecting electrical changes associated with the bead 3100 when reactions of interest are occurring on or proximate to the bead 3100.

Figure 31B:
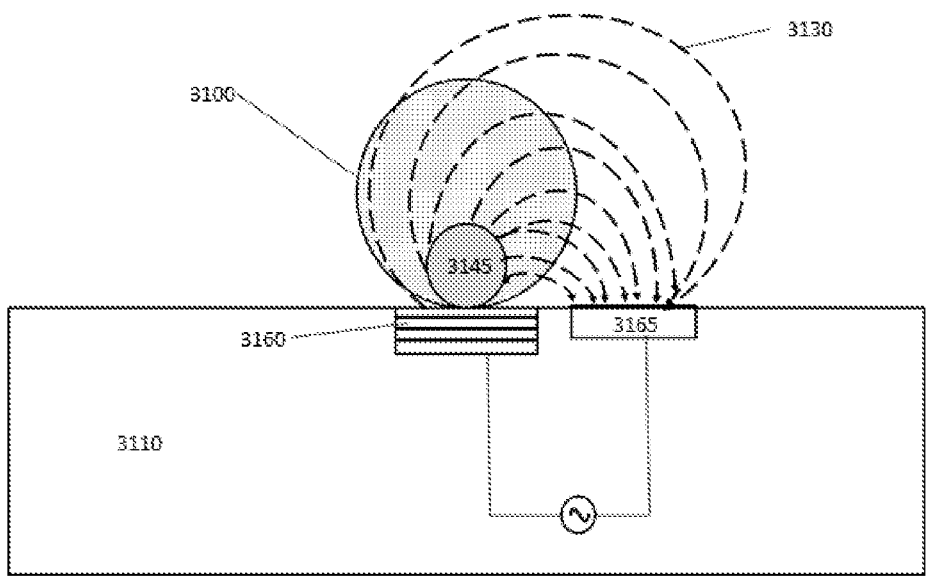
FIG. 31B shows another embodiment of an asymmetric bead and the resulting electric field lines where there is an associated combined electrode-magnet structure.

In a further embodiment, as shown in FIG. 31B, the asymmetric bead 3100 may rest on a combined electrode-magnet 3160 for combined detection and bead retention.

This combined electrode-magnet 3160 may include many alternating layers of various materials, such as for example platinum and magnetized layers. The asymmetric bead 3100 with inner magnet 3145 may act as part of electrode-magnet 3160. The electrode-magnet 3160 may act as a transmitter electrode and an electrode 3165 may act as a receiver electrode. In some embodiments, there may be two receiver electrodes. In other embodiments, the electrode-magnet may consist of a magnet located directly on top of an electrode.

In some embodiments, low-curie temperature magnets may be used in order to control the temperature associated with a given pixel. This may be used in situations where there are a variety of different reactions of interested happening in different pixels in the same array.

Droplet-Based Amplification

Recognized herein is the need for improved methods of amplifying a nucleic acid sample.

The present disclosure provides droplet-based methods and systems for emulsion-free nucleic acid (e.g., DNA) amplification. These methods may be used in conjunction with a high throughput reactor and/or sensor array system that may be used for the detection and analysis of biological and/or chemical reactions of interest. The individual reactor volumes may be, for example in the microliter range, nanoliter range, or picoliter range or at larger or smaller dimensions depending upon the particular application. The reactors and/or sensors may be placed at spatial distances of micrometers or nanometer or at larger or smaller distances depending upon the particular application. The sensor modules may be of a micrometer size or nanometer size or of larger or smaller sizes depending upon the particular application. Systems described herein useful for droplet-based methods and system for emulsion-free nucleic acid amplification can include a sensor array that can be referred to as a 'reactor-sensor array'. The location of each reactor or sensor in the array can also be referred to as a 'pixel'.

In an aspect, the disclosure provides a system comprising a reactor-sensor array where the array comprises hydrophobic and hydrophilic portions, where the reactors and/or sensors are located within the hydrophilic portions and are used for the performance and/or sensing of a biological reaction of interest. In some cases, the system further comprises a magnetic array for binding magnetic particles where at least one magnet is located within, or adjacent to, or corresponds to at least one hydrophilic portion of the array. The pixels can be circular, oval, rectangular, and irregular shape.

An additional aspect the disclosure provides a system comprising a hydrophobic substrate that can comprise an array of hydrophilic regions; a plurality of sensors, with at least one sensor located within or adjacent to each of the hydrophilic regions; and a magnetic array, where at least one magnet of the magnetic array is located within, or adjacent to each of the hydrophilic regions. In some embodiments, the sensors can be used for detecting a chemical reaction (e.g., a nucleic acid amplification reaction, a nucleic acid sequencing reaction). In some embodiments, the system can further comprise a module for generating droplets of reagents for the chemical reaction. The module can for example, generate droplets that comprise particles such as for example beads (e.g., magnetic beads). In some embodiments, the array of hydrophilic regions comprises an array of wells. An individual well of the array can comprise a hydrophilic region.

In some embodiments, the hydrophobic substrate can be created by depositing one or more layers of a suitable hydrophobic material on a substrate (e.g., a chip surface), such as, for example, at least one of alkylsilanes, silicones, teflon, hydrophobic phosphonates, hydrophobic carboxylates and polycarboxylates, hydrophobic polythiols, fluoroalkylsilanes or any combination thereof. The hydrophobic regions can comprise a super-hydrophobic region (e.g., more hydrophobic than other parts of the hydrophobic region), or be functionalized on a chip surface. Moreover, in some embodiments, the hydrophilic regions may comprise any suitable hydrophilic material such as, for example, at least one of silicon oxide, an ozonized surface, silanes, PEGylated silanes, proteins, dextrans, polysaccharides, hydrophilic polymers (e.g., polysulphonic acids), polyacrylic acids, and/or zwitterionic polymers or another hydrophilic modification. In some cases, the hydrophilic regions may be patterned by a photoresist. In some embodiments, the hydrophilic regions can comprise gold or platinum.

The pixels of the system can be any suitable size. In some cases, the pixels are at least about 1 micron, at least about 3 microns, at least about 5 microns, at least about 10 microns, at least about 20 microns, at least about 50 microns or at least about 100 microns in diameter. In some cases, the pixels are at most about 1 micron, at most about 3 micron, at most about 5 microns, at most about 10 microns, at most about 20 microns, at most about 50 microns or at most about 100 microns in diameter.

The reactor-sensor array or another system described herein can have electrodes. In some cases, there is at one or more electrodes per pixel or hydrophilic region. The electrodes can have a square, rectangular, circular, or curved shape.

A module for generating droplets, including droplets with particles may comprise one or more devices that generate the droplets such as, for example, a static spray nozzle, a movable spray nozzle, a static array of spray nozzles, a movable array of spray nozzles, an original printer head, and/or a modified printer head. In some cases, droplets containing reaction materials and/or particles (e.g., beads) can be generated at one location and can be transported close to the reactor-sensor array or hydrophobic array by air and/or an immiscible liquid such as oil, where the droplets deposit on the hydrophilic regions.

In some instances, the droplets containing reaction materials and/or beads are generated at one location of a chip, and are transported to the reactor-sensor array locations through the process of electrowetting (EW) or electrowetting on dielectric (EWOD).

In another aspect, the present disclosure provides a system comprising a reactor-sensor array, where a movable spray nozzle or an array of spray nozzles deposit droplets of reaction material onto locations of the array, and the reactions at these locations are used for the performance and/or sensing of a biological reaction of interest.

In another aspect, the present disclosure provides a system comprising a reactor-sensor array of wells, where the bottom and side walls of the well are hydrophilic and the regions separating the wells are hydrophobic, and the reactor solutions and/or sensors are located within each well, and the reactors and/or sensors are used for the performance and/or sensing of a biological reaction of interest. The droplets within the wells can be created by flowing humid air and/or an immiscible liquid such as oil through the chamber of the system, thereby displacing the reaction materials from the body of the chamber while retaining the reaction materials within the wells.

In another aspect, the present disclosure provides a method for detecting a biological reaction of interest. The method comprises (a) providing an array within a chamber with a plurality of reactors and sensors and magnets where the array comprises hydrophobic and hydrophilic portions, with the reactors and sensors and magnets being located within the hydrophilic portions; (b) flowing in a plurality of magnetic particles such that the particles are immobilized by the magnets; (c) flowing in a solution containing reagents; (d) introducing saturated humid air or an immiscible fluid such as oil into the chamber such that droplets form on the hydrophilic regions; and (e) detecting a reaction of interest in each droplet using the sensors. The method can further comprise using a Peltier device for temperature control. In some cases, the reaction of interest is nucleic acid (e.g., DNA) amplification.

An additional aspect of the disclosure provides a method for generating droplets and, in some cases, detecting species in the droplets. The method can comprise providing a chamber comprising an array of sensors and magnets associated with the sensors, where the array comprises hydrophobic and hydrophilic regions. The sensors and magnets can be located within or adjacent to the hydrophilic regions. The method can further comprise flowing a plurality of magnetic particles over the array, such that the particles are immobilized by the magnets to provide immobilized particles. Additionally, the method can further comprise flowing a solution containing reagents over the immobilized particles and generating droplets of the reagents adjacent to the hydrophilic regions by introducing an immiscible fluid into the chamber. In some embodiments, species (e.g., reagents, products of chemical reactions, detection species, etc.) can be detected in each droplet using the sensors. One or more steps of the method may be repeated, including the flow of the solution over the immobilized particles, the generation of droplets adjacent to hydrophilic regions by introducing an immiscible fluid into the chamber, and the detection of species in the droplets using the sensors. In some embodiments, the immiscible fluid is air (e.g., water-saturated air) or oil. In some embodiments, a Peltier device can be used to control a temperature inside the chamber. In some embodiments, the droplets can be generated by flowing in the solution containing the reagents from a first inlet and flowing in the immiscible fluid from a second inlet.

In some embodiments, volume of a droplet can be at least about 10 picoliters, at least about 50 picoliters, at least about 100 picoliters, at least about 200 picoliters, or at least about 500 picoliters, or at least about 1 nanoliters, at least about 10 nanoliters, at least about 50 nanoliters, at least about 100 nanoliters, or at least about 200 nanoliters. In some embodiments, the volume of a droplet can be at most about 10 picoliters, at most about 50 picoliters, at most about 100 picoliters, at most about 200 picoliters, or at most about 500 picoliters, or at most about 1 nanoliter, at most about 10 nanoliters, at most about 50 nanoliters, at most about 100 nanoliters, or at most about 200 nanoliters.

In some cases, large droplets are placed in corners of the chamber with a heat source underneath. The conditions in the chamber can be controlled in order to isolate pixels and prevent contamination. In some embodiments, droplets may be placed in a corner of the chamber with a heat proximate to one or more of the droplets. In some embodiments, the droplets may be isolated from each other.

In some cases, the droplets can be generated in the chamber by flowing in the solution (e.g., containing aqueous reaction material) from one inlet and flowing in the immiscible fluid (e.g., oil, air) from another inlet. The droplets can be deposited on the hydrophilic regions. In some embodiments, the droplets can be transported via electrowetting (EW) or electrowetting on dielectric (EWOD).

In some cases, sequential flows of template (e.g., such as DNA or another nucleic acid) and an immiscible fluid such as oil are flowed into the device, and an amplification reaction can be performed after each flow of template, in some cases generating a high fraction of array locations that have amplified template. In some instances, sequential flows of nucleotides are used for performing sequencing on nucleic acid (e.g., DNA) templates at each array location. Nucleotide incorporations can be detected by the sensors or other suitable mechanisms such as, for example, fluorescence microscopy. In some embodiments, after droplets are generated, one or more reactions (e.g., nucleic acid amplification reactions, nucleic acid sequencing reactions, etc.) can be performed in the droplets. One of more of the sensors can be used to detect the one or more reactions (e.g., via species generated or consumed in the reaction, etc.).

Figure 32A:
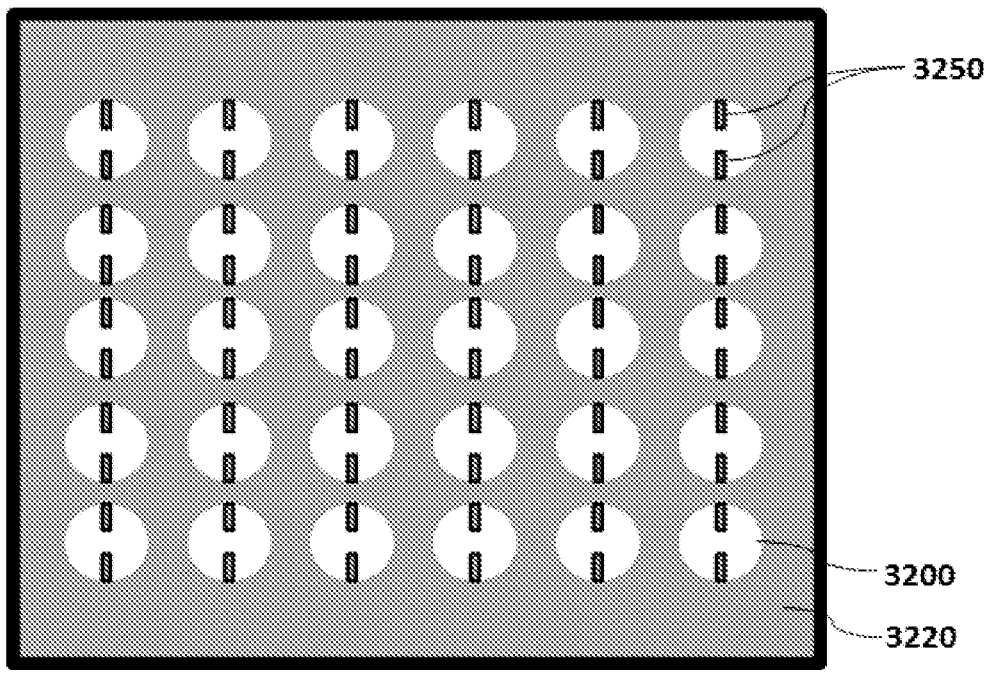
FIG. 32A shows an exemplary embodiment of a top view of a reactor-sensor array according to the systems described herein.

FIG. 32A shows an embodiment having a top view of a nano-array according to the system described herein. The array comprises both hydrophobic portions 3220 and hydrophilic portions 3200. In this embodiment, the hydrophilic portions 3200 are patterned such that they form an array of circular hydrophilic regions separated by hydrophobic portions 3220. Magnets 3250 are located proximate to or within the hydrophilic portions 3200. While the magnets 3250 in FIG. 32A are shown to be such that two magnets are present within the hydrophilic region, there can also be a single magnet located centrally within each hydrophilic region. The magnets may be located in a way that one bead will be held in each droplet. Magnets of different sizes, shapes (rectangular, square, polygonal) and different magnetic strengths may be used to attract and/or hold magnetic beads. In some embodiments, the reactor-sensor array is substantially planar. In another embodiment, the nano-array may be a reactor-sensor array for nucleic acid (e.g., DNA) sequencing.

Figure 32B:
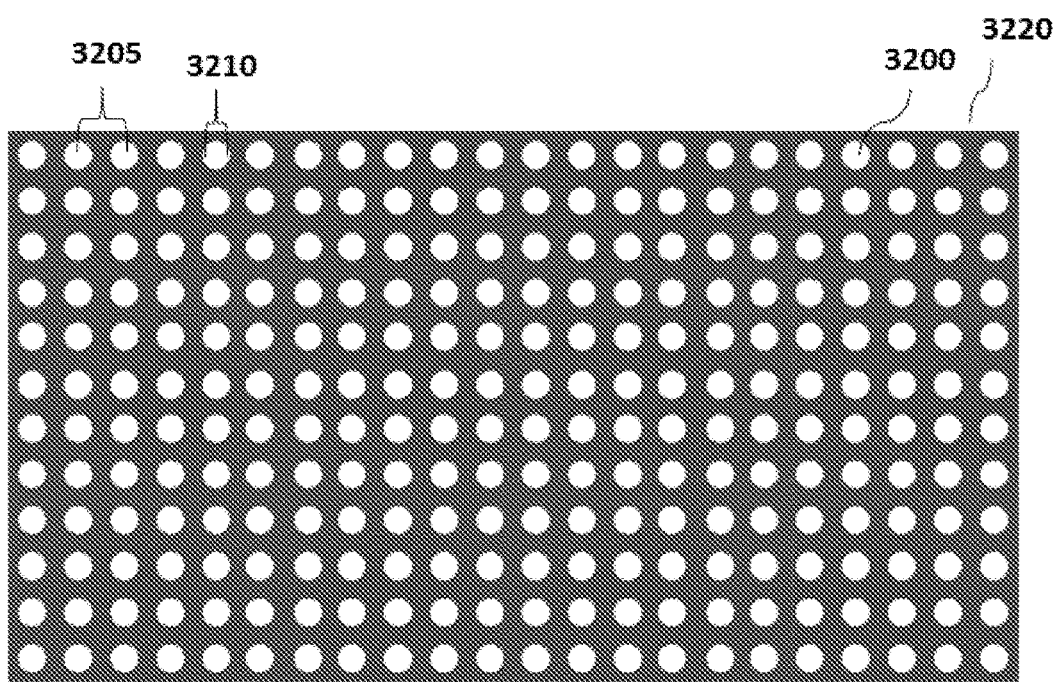
FIG. 32B shows one embodiment of a zoomed out view of a reactor-sensor array.

FIG. 32B is a zoomed out view, in one embodiment, of a reactor-sensor array (magnets 3250 not shown). The pitch size 3205 of the reactor-sensor array may be measured as the distance between the center of each individual hydrophilic region 3210. Droplet-based methods for emulsion free amplification are described herein and the diameter of individual droplets can correspond with the diameter of the pixel 3210.

Although the pixels 3210 that are hydrophilic are shown as having a circular shape, the shape may be rectangular, oval, irregular, or any other shape.

Figure 32C:
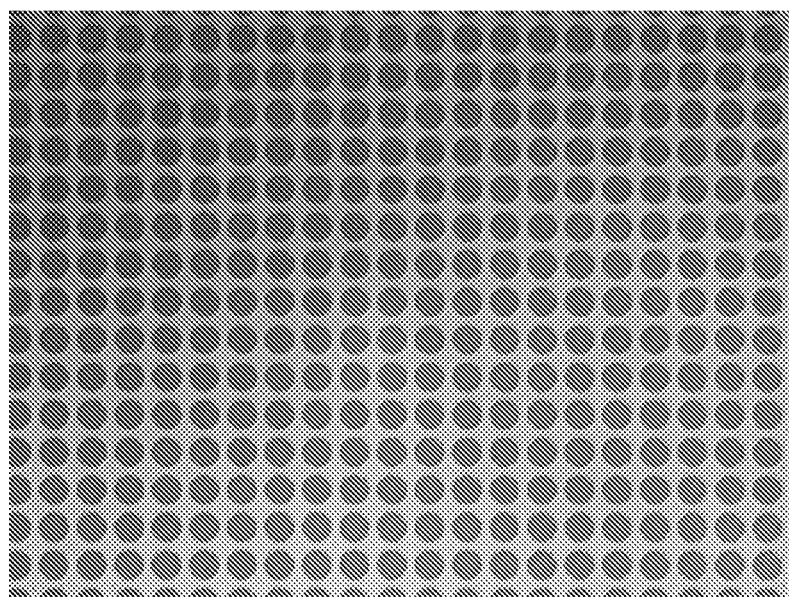
FIG. 32C shows a photograph of the reactor-sensor array shown in FIGS. 32A-32B.
Figure 32D:
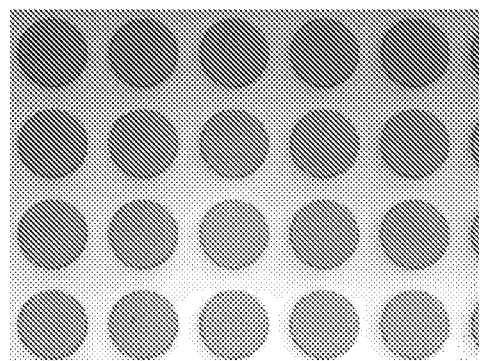
FIG. 32D shows a zoomed in view of the photograph of the reactor-sensor array

FIG. 32C and FIG. 32D are photographs of the reactor-sensor array shown in FIGS. 32A-32B. The hydrophobic regions may be created by depositing one or more layers of any suitable hydrophobic material, such as, for example alkylsilanes, silicones, teflons, hydrophobic phosphonates, hydrophobic carboxylates and polycarboxylates, hydrophobic polythiols and fluoroalkylsilanes. The hydrophilic regions may be comprised of any suitable hydrophilic material such as, for example, one or more layers of silicon oxide, an ozonized surface, silanes, PEGylated silanes, proteins, dextrans, polysaccharides, hydrophilic polymers (e.g., polysulphonic acids), polyacrylic acids, and/or zwitterionic polymers or a hydrophilic material coated on top of the surface. In another embodiment, the hydrophobic region of the chip may comprise a super-hydrophobic surface, (e.g., silica nano-coating, carbon nanotube structures, precipitated calcium carbonate, Manganese Oxide Polystyrene (MnO2/PS) nano-composite or Zinc Oxide Polystyrene (ZnO/PS) nano-composite). In some cases, the surface materials and modifications described here are meant to be only representative, and any modifications that impart hydrophobic or hydrophilic properties to the surfaces can be used. The surface of the substrate may be patterned using any photoresist covering hydrophilic regions. The hydrophobic material can then be applied to the surface. Then, the photoresist may be stripped and surface treatment performed to modify the hydrophilic surface. Alternatively, another embodiment includes substrate patterning where the photoresist initially covers the hydrophobic regions, patterning of hydrophilic regions, removal of the photoresist, followed by patterning of the hydrophobic regions.

In a further embodiment, calculations may be made such that each droplet that surrounds the individual beads contains an appropriate amount of reagents. The hydrophobic regions can serve as a physical barrier between pixels having individual droplets such that there is very little contamination between neighboring pixels. In another embodiment, the temperature of the chamber may be controlled such that the droplets do not evaporate by using, for example, a Peltier device. Once a process such as polymerase chain reaction or isothermal amplification is complete and amplification has occurred, the final step may be a wash step to remove the beads and amplicons.

Figure 33A:
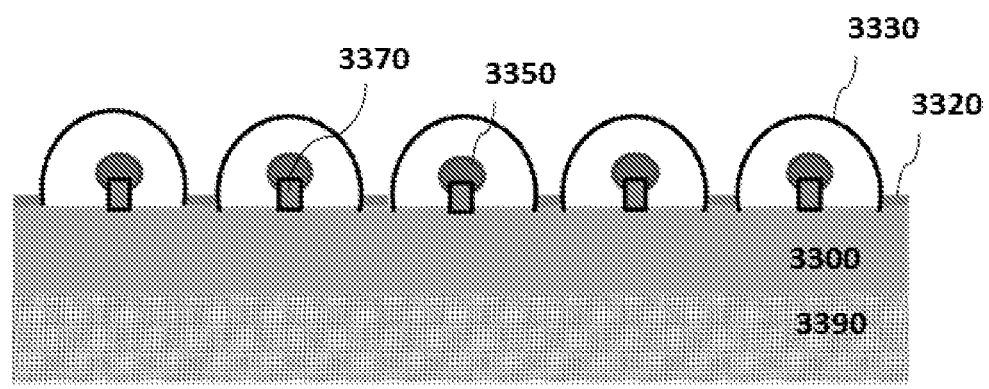
FIG. 33A shows one embodiment of a side view of the beginning of the droplet-based emulsion-free amplification process.

FIG. 33A shows, in one embodiment, a side view of the beginning of an example emulsion free amplification process. Saturated humid air can bebeen injected into the chamber and fluid (including reagents) can condense into droplets 3330 on the hydrophilic areas 3300. The individual pixels are separated by hydrophobic areas 3320 and the entire structure is supported by the substrate 3390. The beads 3350 are immobilized on magnets 3370.

Figure 33B:
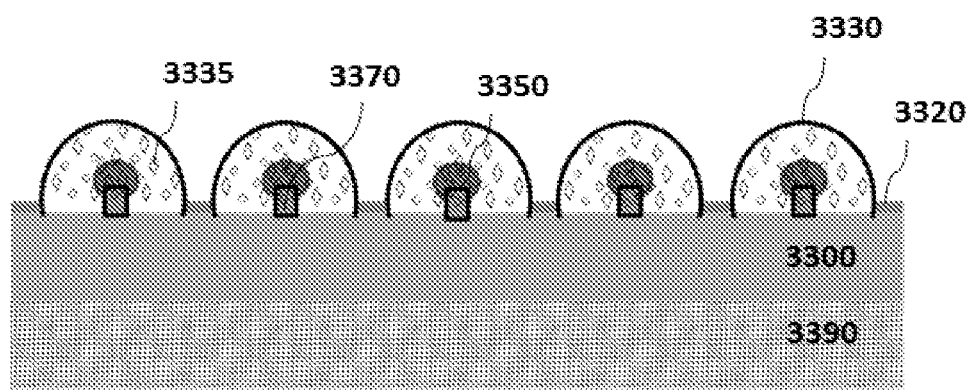
FIG. 33B illustrates in one embodiment the amplicons generated as a result of multiple cycles of a droplet-based emulsion-free amplification process.

FIG. 33B illustrates, in a further embodiment, amplicons 3335 that can be generated as a result of multiple cycles of an amplification process such as polymerase chain reaction (PCR) or an isothermal amplification method. The thermal cycling steps of PCR can cause droplets to shrink and grow according to an increase and decrease in temperature and the resulting cycles of evaporation and condensation of fluid. The droplets can serve as physical barriers that prevent the reagents and amplicons from leaving the individual pixels. This method allows for an emulsion-free type of amplification.

Figure 34:
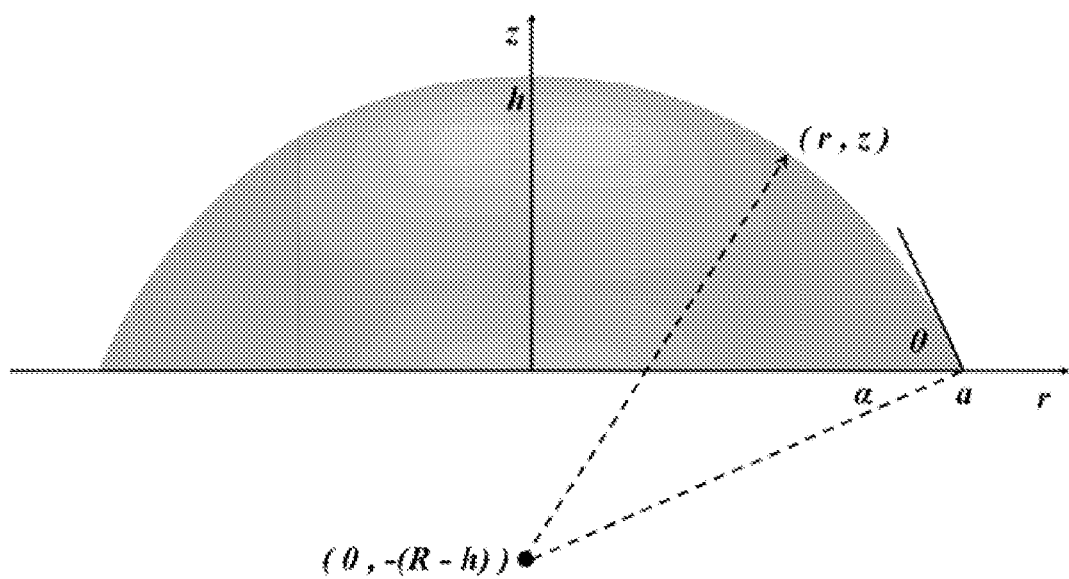
FIG. 34 shows a diagram of the droplet diameter and associated contact angle.
Figure 35:
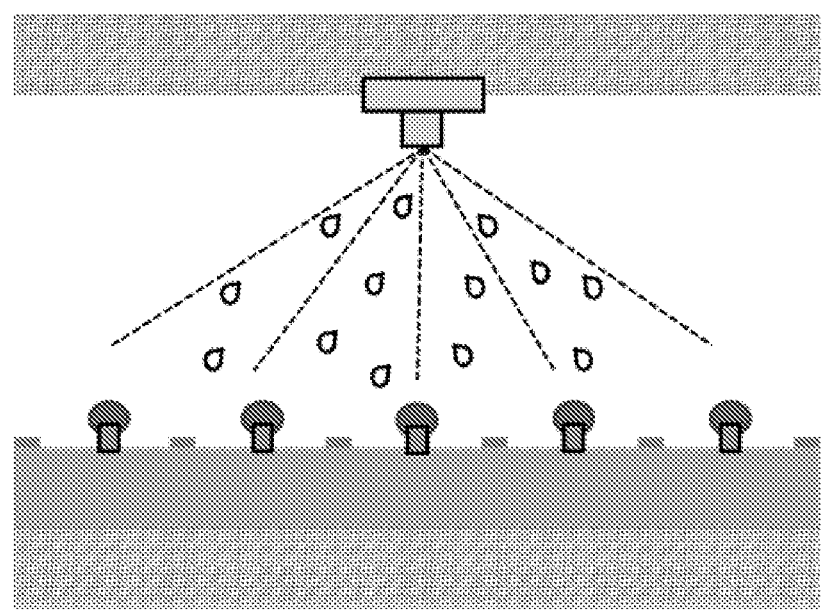
FIG. 35 shows one embodiment of droplet creation using a spray nozzle device where the sprayed fluid accumulates into droplets in the hydrophilic pixels locations.

As shown in FIG. 34, the droplet diameter may be based on the amount of nucleotides and other reagents inside the droplet. Droplet diameter may be calculated according to the volume and the concentration of species inside the droplet. In some embodiments, the contact angle on the surface may be about 65 degrees, 80 degrees, 95 degrees, 100 degrees, 105 degrees, or 115 degrees. In some embodiments the volume of the droplet may be, for example, about 50 nanoliters, 100 nanoliters, or 200 nanoliters. The concentration of nucleotides may be, for example, about 100 micro-molar, 200 micro-molar, or 500 micro-molar. In some embodiments, the pixel size may be about 10 microns, 20 microns, or 50 microns. In some embodiments, the volume of the droplet may be in the picoliter range, the nanoliter range, the microliter range or may be in a larger or smaller range depending upon the particular application In an embodiment, as shown in FIG. 35, a single spray nozzle may spray a number of droplets containing reaction material onto a chip surface that contains beads deposited on magnets situated in hydrophilic pixels. These droplets can then preferentially move to the hydrophilic regions and fuse together.

Figure 36:
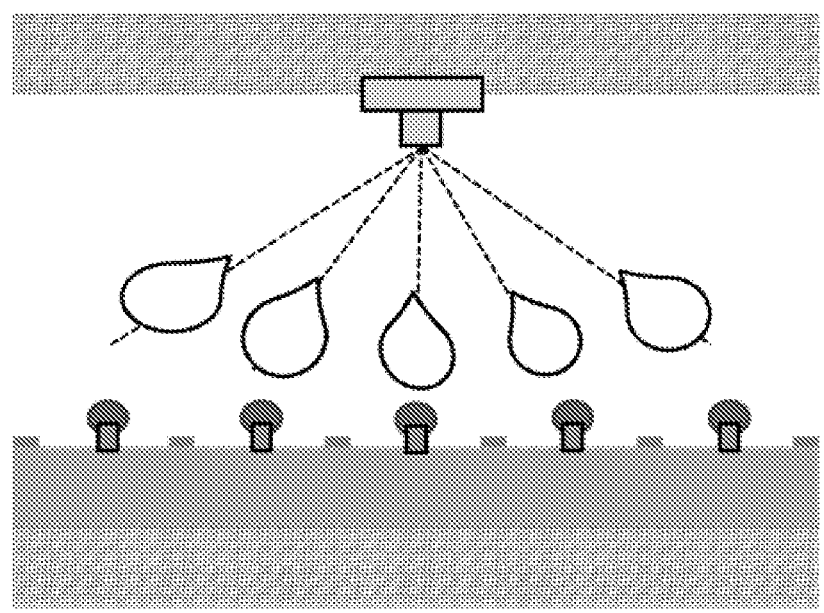
FIG. 36 shows another embodiment of droplet creation using a spray nozzle device where the device sprays uniformly sized droplets onto each hydrophilic pixel location.

In an embodiment, as shown in FIG. 36, a single spray nozzle may spray a number of large droplets containing reaction material onto the chip surface that contains beads deposited on magnets situated in the hydrophilic pixels.

Each individual reaction material droplet may land on the hydrophilic region directly or preferentially move to the closest hydrophilic region due to repulsion by the hydrophobic region.

Figure 37A:
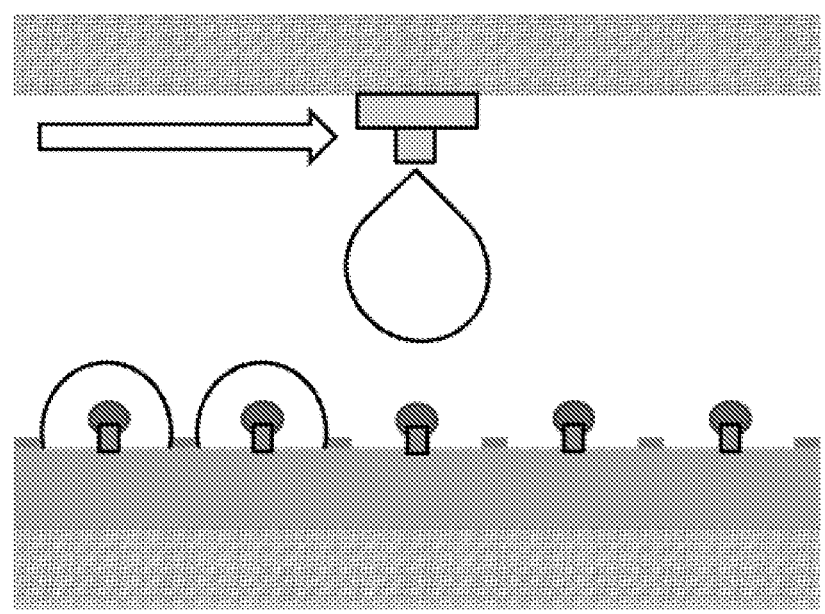
FIG. 37A shows an embodiment of a device for "printing" droplets that moves along the chamber and places one droplet in each pixel.

In an embodiment, as shown in FIG. 37A, a single spray nozzle may move along the whole reactor-sensor array, and deposit appropriately sized droplets containing reaction materials on beads contained within the hydrophilic pixels. Small misalignments in the deposition of these droplets can be corrected by the droplets themselves, due to preferential movement to a hydrophilic region as a result of repulsive interactions with a hydrophobic region. The spray nozzle may be a traditional spray nozzle fitted on a robotic arm, or alternatively, an original or modified printer head, (e.g., an inkjet printer head), which deposits reaction materials.

Figure 37B:
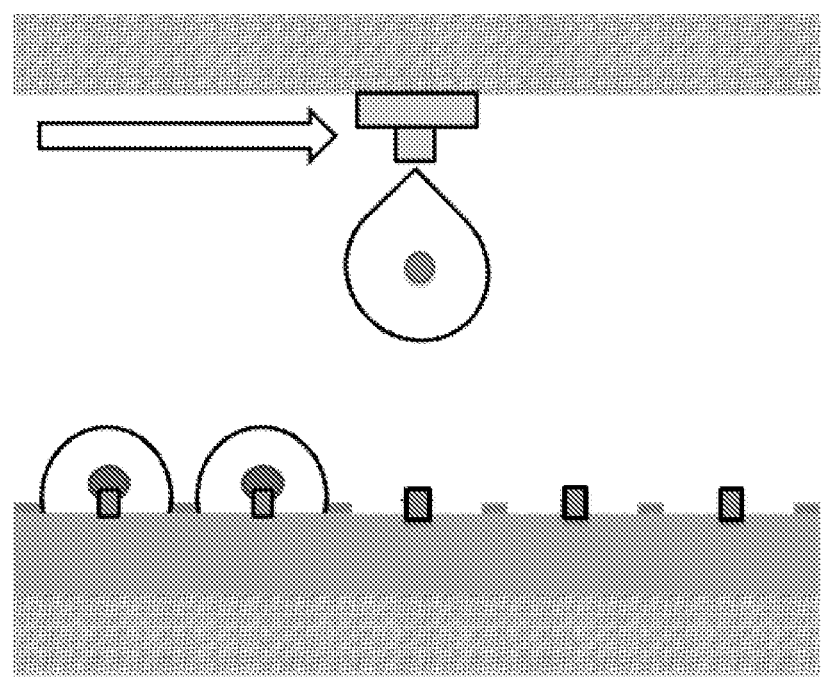
FIG. 37B shows an embodiment of a device for "printing" droplets, each of which contain reaction materials as well as beads, that moves along the chamber and places one droplet (with beads) in each pixel.

In an embodiment, as shown in FIG. 37B, a single spray nozzle may move along a reactor-sensor array, and deposit appropriately sized droplets, which can contain aqueous reaction materials as well as beads, onto the appropriate hydrophilic pixels. The beads can be attracted to the magnet and the aqueous phase can move preferentially to the hydrophilic pixels.

Figure 37C:
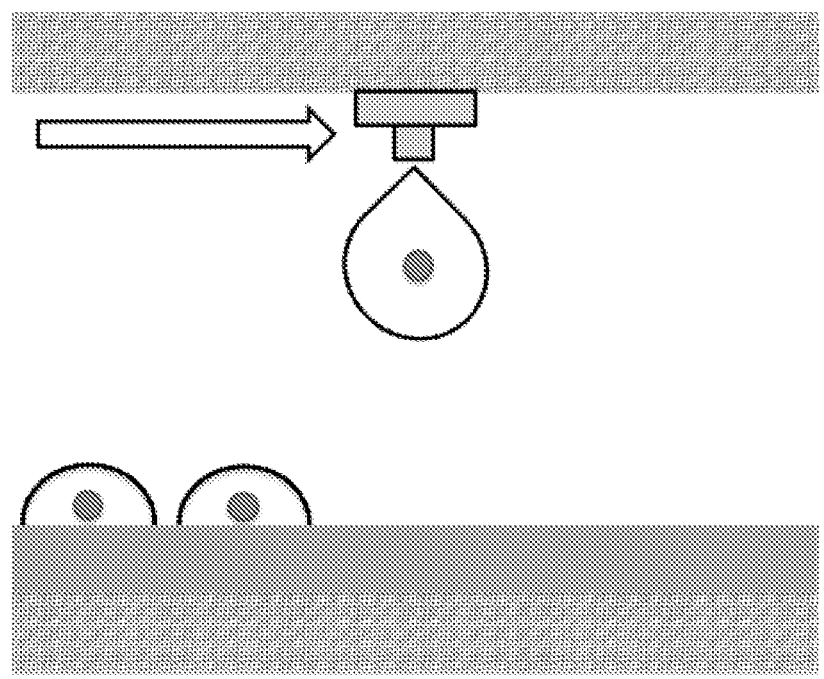
FIG. 37C shows an embodiment of a device for "printing" droplets, each of which contain reaction materials as well as beads, that moves along the chamber and places one droplet in each pixel, where there is no need for patterned hydrophilic pixels.

In another embodiment, as shown in FIG. 37C, the spray nozzle or printer head may deposit individual droplets on a hydrophobic surface (without the need for a patterned hydrophilic pixels array). The hydrophobic nature of the surface can lead to the aqueous droplet beading up and not spreading out and mixing with each other. The array may be placed in a chamber with high humidity, thus preventing evaporation of the droplets.

Figure 38:
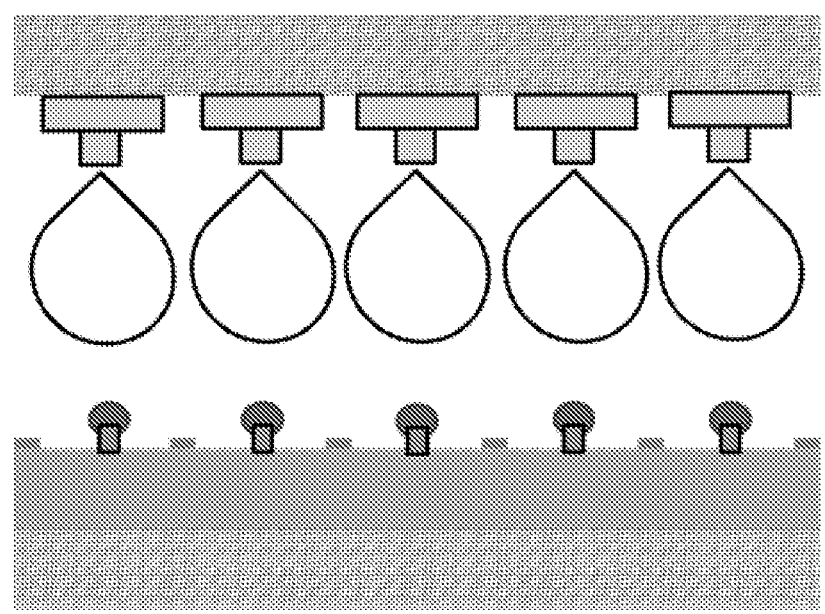
FIG. 38 shows an embodiment where each pixel has a corresponding droplet "printer".
Figure 39:
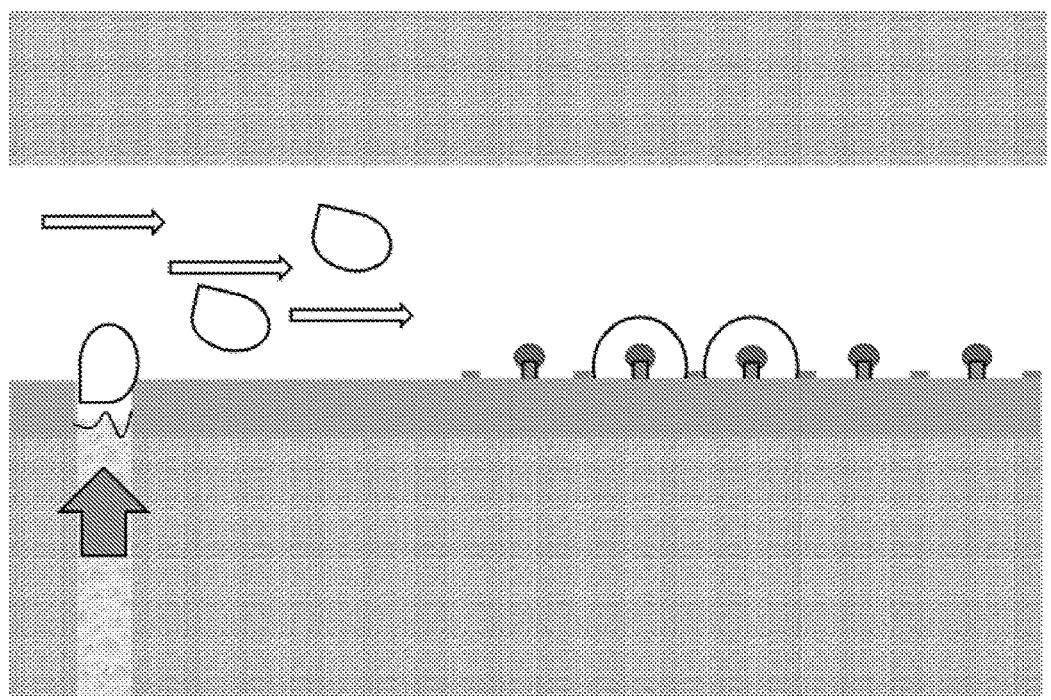
FIG. 39 shows an embodiment where droplets may be created by pushing fluid from a channel perpendicular to the chamber where the chamber has air or oil flowing against the fluid to create droplets, which then get deposited on different pixel locations on the array which have the beads or other amplifying surface.

In an embodiment, as shown in FIG. 38, an array of spray nozzles may deposit reaction materials on top of beads located below the nozzle and within each hydrophilic pixel of the reactor-sensor array. This array of spray nozzles could be static or move around (e.g. with the aid of robotic movement).

In a further embodiment, if the size of the chamber where the nano-array is located is sufficiently small, the injection of saturated air (e.g., water-saturated air) may be optional since the condensation/evaporation cycle of the droplets may be controlled based on the temperature inside the small-volume chamber. If the volume of the chamber is sufficiently small, the "micro-climate" of the chamber may be more easily controlled and the saturated air step may be unnecessary.

In some embodiments, droplets may be placed in the corners of a chamber with a heat source underneath. Such a configuration can control the introduction of saturated air and evaporation/condensation cycles via control of the temperature.

The confinement of nucleic acid (e.g., DNA) or other species in each pixel from neighboring pixels may be achieved by controlling the temperature and relative humidity of a chamber comprising the pixels. Droplets containing a bead (or other type of particle), nucleic acid (e.g., DNA), and reagents may be isolated from neighboring pixels in a chamber via a controlled environment. An evaporation/condensation rate may go to zero or substantially zero by controlling ambient conditions (e.g., temperature and relative humidity) of the air inside of the chamber accurately. In this manner, a droplet may confined a bead, nucleic acid (e.g., DNA), and other reagents and prevent contamination between pixels.

In some embodiments, the droplets may be created by first flowing a layer of fluid into a chamber such that there is sufficient fluid to cover the bottom of the chamber that is patterned with both hydrophilic and hydrophobic areas as shown in FIG. 32A. Then, the chamber may be heated such that a portion of the fluid evaporates into the chamber. This may result in droplets forming on the hydrophilic areas of the chamber and the air in the chamber being saturated with fluid material(s) (e.g.,water). The heating that can induce evaporation of the fluid from the hydrophobic regions may be obtained by selective heating of the hydrophobic surfaces (e.g. by on-chip electronic heaters or laser heating through a mask). Moreover, droplets may grow and diminish in size according to heat cycling that may be used for applications such as PCR amplification in each droplet. In other embodiments, the droplets may stay a relatively constant size for applications where heat cycling is not necessary.

In another embodiment, the droplets may be created by first flowing a layer of fluid into a chamber such that there is sufficient fluid to cover the bottom of the chamber that is patterned with both hydrophilic and hydrophobic areas as shown in FIG. 32A. In this embodiment, there may be electrodes located in each hydrophilic region. The electrodes may each have voltage generating components associated with them such that as the voltage is modulated, bubbles form on or near the electrodes. These bubbles may be used to form "cracks" or divisions in the layer of the fluid. The chamber may or may not be heated. The bubbles may cause the layer of fluid to be displaced such that droplets form on the hydrophilic portions of the chamber. In a further embodiment, there may be one or more electrodes at the top of the chamber for forming bubbles from the top and displacing the layer of fluid onto the hydrophilic portions for forming droplets.

In some embodiments of the systems and methods described above, the droplet size may be large enough to create a "buffer region" such that if evaporation occurs, there is enough fluid left in the droplet to allow for the reaction of interest to occur within the droplet.

Figure 40A:
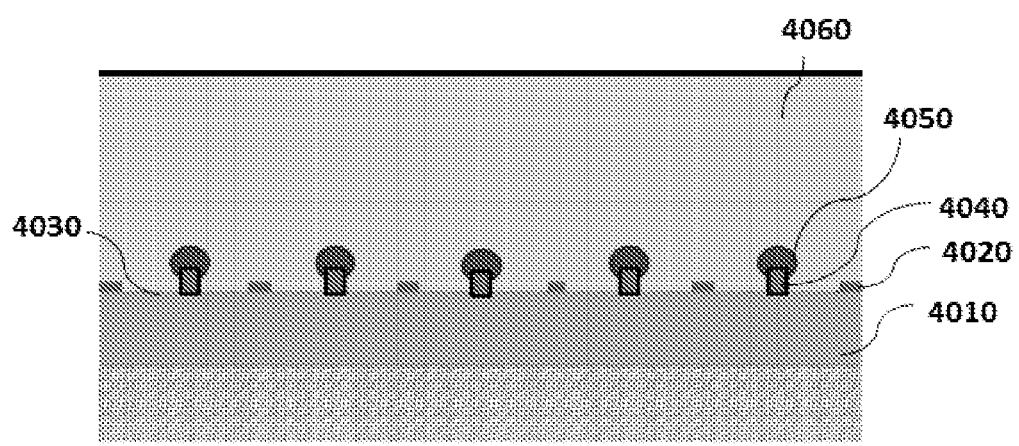
FIG. 40A shows an embodiment where each pixel has a magnet and bead on the hydrophilic region, and the chamber volume is filled with a aqueous solution (e.g., containing reaction material).
Figure 40B:
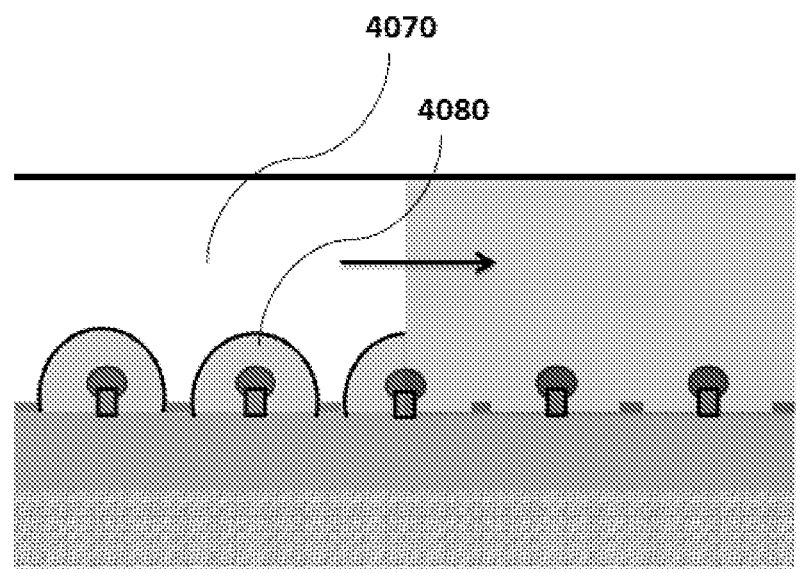
FIG. 40B shows a step following FIG. 40A, where air or an immiscible liquid such as oil is flown through the chamber, leading to droplets of the aqueous solution, (e.g., containing reaction material), to form on the hydrophilic pixels.
Figure 41:
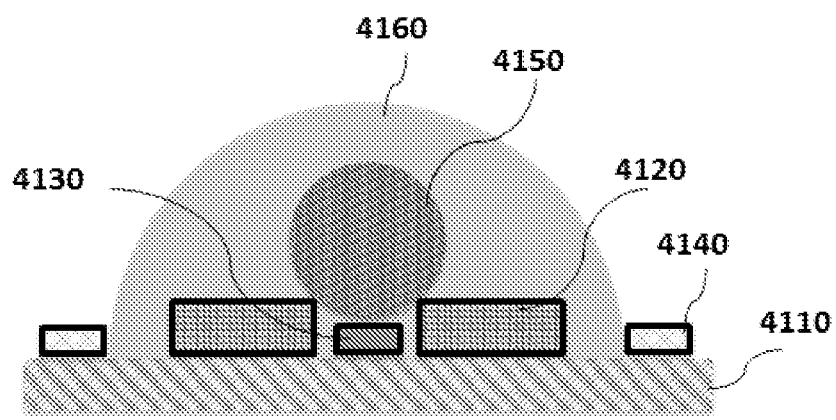
FIG. 41 shows one embodiment of a single pixel of the reactor-sensor array, where there are electronic sensors and/or magnets placed on the chip surface and a bead is deposited on top of the magnet and electrodes.

In some embodiments, such as in FIG. 40A, FIG. 40B, and FIG. 41, droplet-based emulsion-free amplification of nucleic acid (e.g., DNA) may be achieved. Particles, such as for example magnetic beads, may be flowed into the fluidic chamber that houses the reactor-sensor array. The reactor-sensor array may have both hydrophobic regions 4020 and hydrophilic regions 4030. The magnetic beads 4050 may come to rest in individual pixels, immobilized by the magnets 4040 in the pixels. Next, a solution that contains diluted nucleic acid may be flowed into the array such that the single stranded nucleic acid binds to the beads in a one nucleic acid per one bead distribution. Next, a buffer containing amplification reagents 4060 may be injected into the chamber. To finalize the confinement, saturated humid air 4070 may be injected into the chamber such that any remaining fluid or reagents are pushed out except the droplets 4080 formed upon the hydrophilic pixels, leaving the hydrophobic regions dry. As alternatives to saturated humid air, oil or another immiscible liquid may also be used. The liquid in these droplets (or microreactors) can be prevented from evaporation by the air saturated with moisture, by oil or another immiscible liquid, by temperature or some combination of materials. This method of amplification, examples of which are shown in FIG. 40A, FIG. 40B, and FIG. 44 may be referred to as emulsion free, in some cases, because of it does not result in the generation of a traditional emulsion (e.g., by vortexing an aqueous phase in oil (or vice-versa)) despite that the method makes use of aqueous phase droplets on the hydrophilic regions that are surrounded by oil.

Figure 44A:
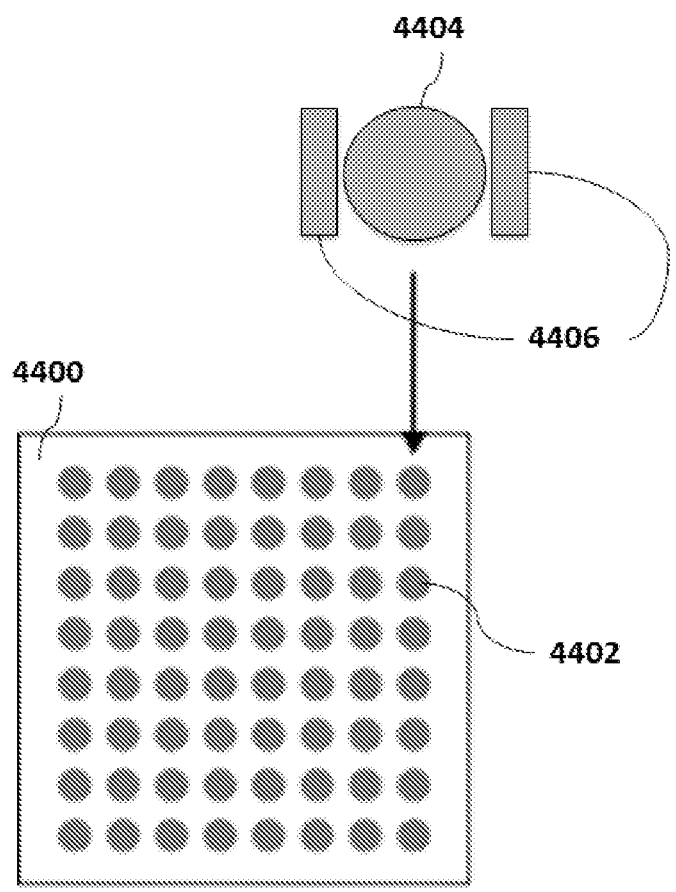
FIG. 44A shows an array of reactors that can be used for amplification of a DNA template as well as sequencing on the same chip.
Figure 44B:
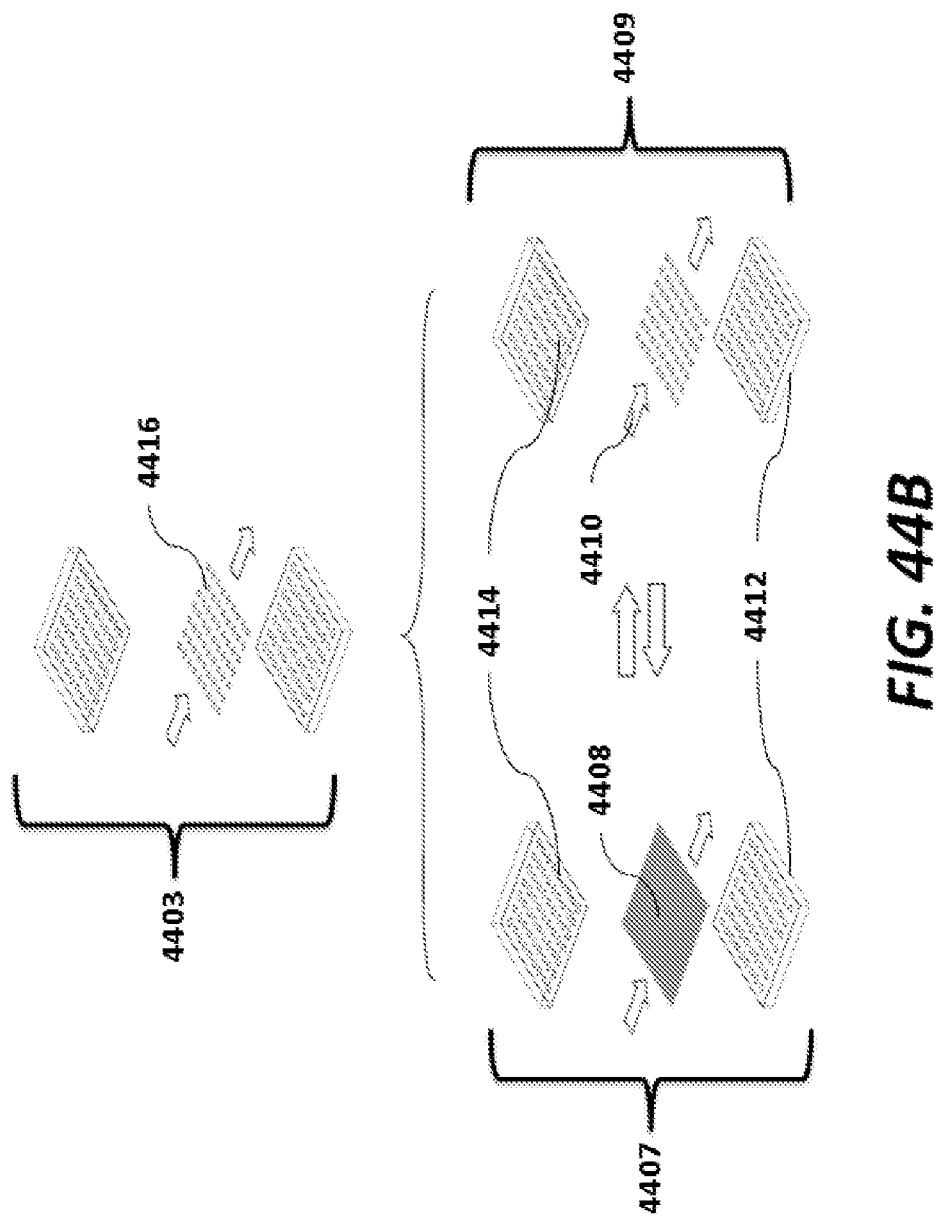
FIG. 44B shows a method for generating clonally amplified templates using the array of FIG. 44A.
Figure 44C:
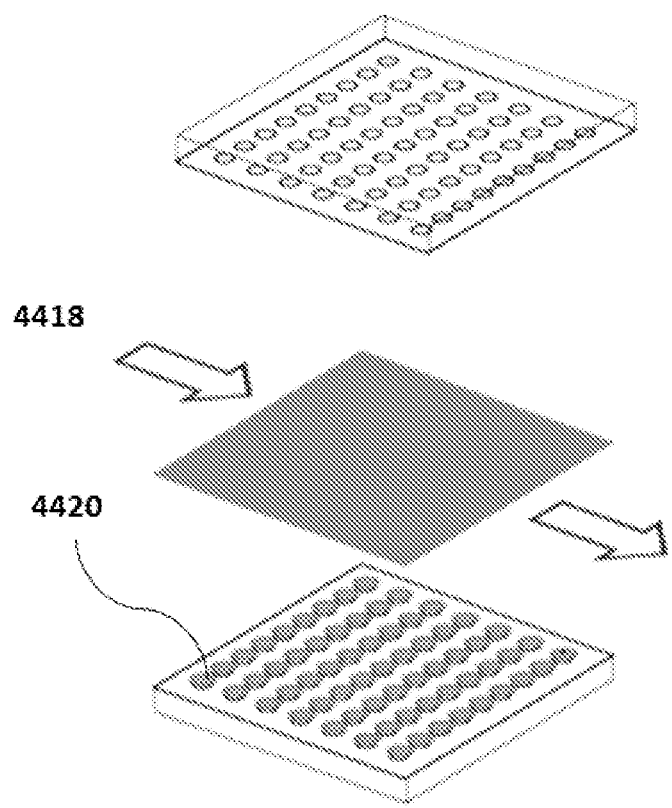
FIG. 44C shows a method for sequencing by synthesis using the array of FIG. 44A.

As shown in FIG. 44A-C, this approach can be used for sequential introduction of nucleic acid (e.g., DNA) templates after every round of amplification, so as to ensure that a high fraction of hydrophilic pixels contain amplified nucleic acid material, such as on a bead contained within that pixel. In particular, during each round of dilute template introduction and amplification, only a fraction of hydrophilic pixels may receive a nucleic acid template and hence undergoes amplification (e.g., on a bead). Such a configuration canmaximize the usage of pixel locations within a chip. Additionally, this approach can also be used for sequencing the amplified material, by flowing in nucleotides in a sequential manner, and detection of incorporation during sequencing, (e.g., by electronic sensors contained within the pixel location or by any other modality (e.g., fluorescence microscopy)).

In an embodiment shown in FIG. 44A, a hydrophobic surface 4400 has an array of aqueous droplets 4402, each arrayed onto a hydrophilic surface adjacent 4404 to a pair of electrodes 4406. FIG. 44B shows the array used for clonal amplification and enrichment 4403. The process includes seeding of single templates at array locations 4407 and then isolating the templates from each other and amplifying the templates 4409. In this step, an aqueous solution containing template 4408 or oil 4410 (immiscible with the template solution) are flowed in an alternating fashion over the array between a first hydrophobic/hydrophilic patterned array 4412 having the electrodes and a second hydrophobic/hydrophilic patterned array 4414 to leave isolated aqueous droplets of amplified template 4416. The amplified template can be sequenced on the array as shown in FIG. 44C. Here, aqueous solutions 4418 containing one or more nucleotides (i.e., A, C, G, and T) are alternately flowed over the array to do sequencing by synthesis at the array positions 4420. Wash solutions can be used between nucleotides to wash away any un-incorporated bases.

In another embodiment, as shown in FIG. 41, the fluidic chip surface 4110 (containing the array of hydrophilic and hydrophobic regions) may also contain a layer of electronic components, including but not limited to metallic electrodes 4120, as well as other electronics (e.g., transistors, amplifiers etc.) below the microreactor (or droplet). There may be one, two, three, four, five, six, seven, eight, nine, ten etc. or more electrodes per pixel. In some embodiments, there may be one or more electrodes in or near the center of each pixel. The electrodes may have any shape, for example, square, rectangular, circular, curved, etc. or any other shape. In a further embodiment, the nano-array may lack electrodes but may have linker molecules deposited on the pixels for immobilizing beads. Electronics could be used to help aid on-chip amplification and/or for sequencing the amplified template (e.g., by detecting the incorporation of nucleotides during sequencing steps in an electronic fashion). Thus, the same chip could be used for both clonal amplification as well as sequencing. Additionally, the fluidic chip could contain magnets 4130 to hold the bead 4150. The fluidic droplet 4160 containing the reagent materials, including but not limited to DNA template, polymerases, enzymes, nucleotides etc., can be contained between the hydrophobic regions 4140. In another embodiment, the reactor-sensor array may not have magnets and the hydrophilic portions may be comprised of a material such as gold or platinum.

Figure 42A:
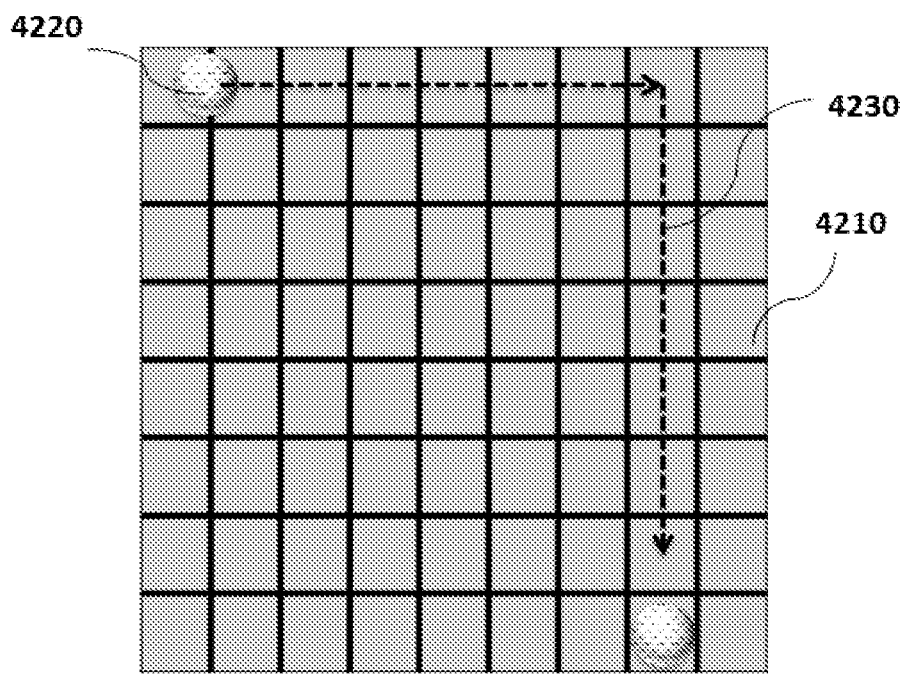
FIG. 42A shows one embodiment where droplets, (e.g., containing reaction material and beads), are generated in one region of the chip and the droplets are moved to a specific location of the chip using an electrowetting mechanism.
Figure 42B:
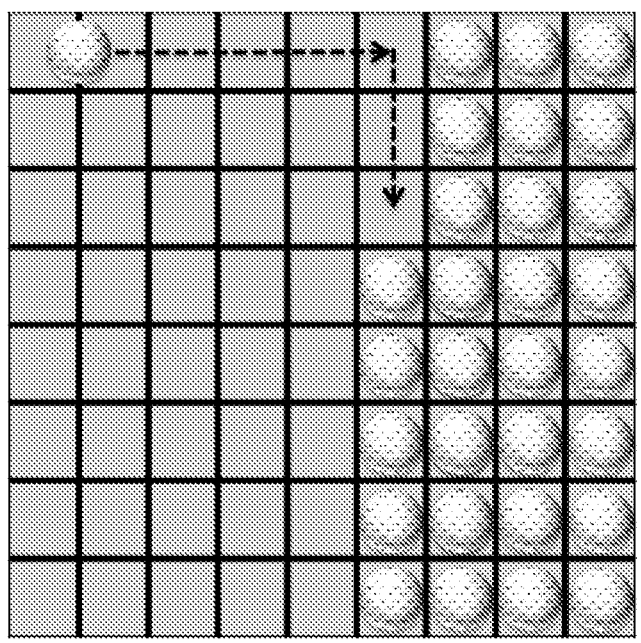
FIG. 42B shows the intermediated state following several rounds of droplet movement as described in FIG. 42A, resulting in the deposition of an array of droplets at the different pixel locations.

In another embodiment, as shown in FIG. 42A and FIG. 42B, the droplets 4220 can be formed and manipulated using electro-wetting (EW) or electrowetting on dielectric (EWOD). The chip surface can be divided into pixels 4210, each of which contains the electronic components needed for electrowetting. Droplets containing the reaction materials, nucleic acid (e.g., DNA) templates and/or beads, can be generated in one location of a chip, (e.g., by a spray mechanism, or any microfluidic droplet generation mechanism), and then moved (4230) to the region corresponding to the desired location on the chip. Such a method is controllable allowing for manipulation of the droplets.

Figure 43A:
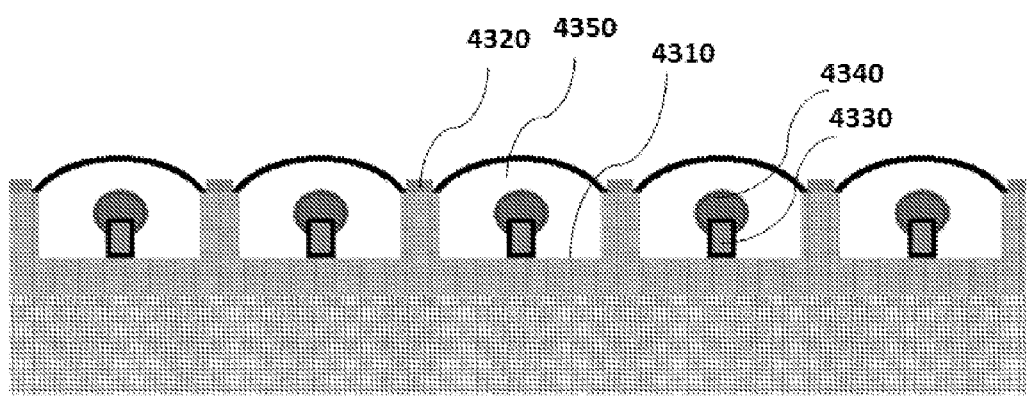
FIG. 43A shows the side view of an embodiment where the chip surface contains a number of wells, with a bead and reaction materials inside each well and reaction materials are flowed into the chip chamber and air (e.g., water-saturated air) or an immiscible fluid like oil is flowed through the chamber to remove all but the materials inside the wells.
Figure 43B:
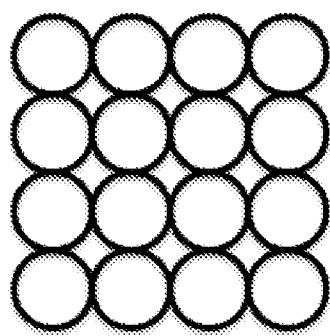
FIG. 43B shows the top view of one embodiment of FIG. 43A, where the wells are circular in cross-section.
Figure 43C:
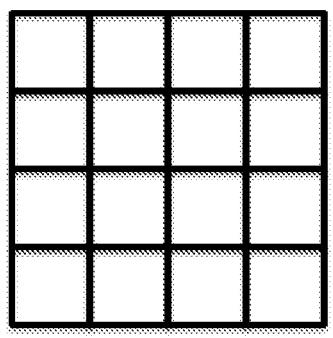
FIG. 43C shows the top view of one embodiment of FIG. 43A, where the wells are square-shaped in cross-section.
Figure 43D:
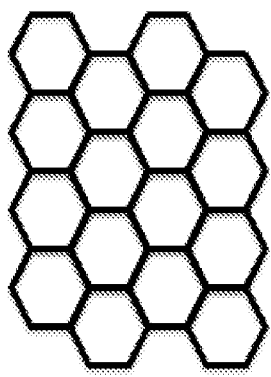
FIG. 43D shows the top view of one embodiment of FIG. 43A, where the wells have a polygonal cross-section, in particular hexagonal in this figure.

In another embodiment, as shown in the cross-sectional view in FIG. 43A, the chip may contain an array of wells (e.g., microwells or nanowells). The chip may be first filled with a fluid which contains reaction materials, nucleic acid (e.g., DNA) templates, and/or beads 4340, and then saturated humid air or oil or another immiscible liquid can be flown through the chip so as to only leave the reaction mixture inside the wells. The walls of each well may provide further physical confinement for amplification. Additionally, the bottom and sides of each well can be coated with a hydrophilic material 4310 and the region separating the wells (e.g. the ceiling of the regions separating the wells) with a hydrophobic material 4320, to further aid attachment of reaction material inside the well, as removal of it outside the well. The embodiment may also contain magnets 4330 inside each well to capture and hold the beads in place inside the well. In some embodiments, such microwells may be present on both the bottom and top surface of a chip. In some embodiments of the system, the wells may be circular in cross-section (FIG. 43B), square in cross-section (FIG. 43C), or polygonal (in particular, hexagonal) in cross-section (FIG. 43D). In some embodiments of the systems and methods described above, the biological assays performed may include nucleic acid (e.g., DNA, or RNA), proteins (e.g., antibodies, enzymes etc.), peptides, carbohydrates, etc. Such biological assays may include detection, amplification, and/or analytical reading of a biological sample of interest.

Fluid Flow

Recognized herein is the need for improved devices for optimizing flow properties in microfluidic devices. The present disclosure provides devices for optimizing flow properties in microfluidic devices, such as rate and uniformity of fluid flow across a microfluidic sensor array.

The size and shape of a microfluidic chamber, or microfluidic cavity, of the device can have an impact on the rate and uniformity of the flow across the sensor array.

An aspect of the disclosure provides a microfluidic device. The microfluidic device can comprise a chamber comprising a first surface having a width (W) and a length (L); a second surface parallel to the first surface; and a space between the first surface and the second surface having a height (H). The space between the first and second surfaces can be configured to direct fluid flow.

Moreover, (H) can have any suitable value. In some embodiments, (H) may be less than about 10 millimeters (mm), less than about 9 mm, less than about 8 mm, less than about 7 mm, less than about 6 mm, less than about 5 mm, less than about 4 mm, less than about 3 mm, less than about 2 mm, less than about 1 mm, less than about 800 (μm) micrometers, less than about 600 μm, less than about 400 μm, less than about 200 μm, less than about 100 μm, less than about 50 μm, less than about 20 μm, less than about 10 μm, less than about 5 μm, less than about 1 μm, less than about 0.1 μm or less than about 0.01 μm or less.

Moreover, (W) can have any suitable value. In some embodiments, (W) may be at least about 1 mm, at least about 2 mm, at least about 3 mm, at least about 4 mm, at least about 5 mm, at least about 6 mm, at least about 7 mm, at least about 8 mm, at least about 9 mm, at least about 10 mm, at least about 15 mm, at least about 20 mm, at least about 25 mm, at least about 30 mm or more. In some embodiments, (W) may be at most about 30 mm, at most about 25 mm, at most about 20 mm, at most about 15 mm, at most about 10 mm, at most about 9 mm, at most about 8 mm, at most about 7 mm, at most about 6 mm, at most about 5 mm, at most about 4 mm, at most about 3 mm, at most about 2 mm, at most about 1 mm or less. In some embodiments, (W) may be about 1 mm, about 2 mm, about 3 mm, about 4 mm, about 5 mm, 6 mm, about 7 mm, about 8 mm, about 9 mm, about 10 mm, about 15 mm, about 20 mm, about 25 mm, about 30 mm or more.

Moreover, (L) can have any suitable value. In some embodiments, (L) may be at least about 1 mm, at least about 2 mm, at least about 3 mm, at least about 4 mm, at least about 5 mm, at least about 6 mm, at least about 7 mm, at least about 8 mm, at least about 9 mm, at least about 10 mm, at least about 15 mm, at least about 20 mm, at least about 25 mm, at least about 30 mm or more. In some embodiments, (L) may be at most about 30 mm, at most about 25 mm, at most about 20 mm, at most about 15 mm, at most about 10 mm, at most about 9 mm, at most about 8 mm, at most about 7 mm, at most about 6 mm, at most about 5 mm, at most about 4 mm, at most about 3 mm, at most about 2 mm, at most about 1 mm or less. In some embodiments, (L) may be about 1 mm, about 2 mm, about 3 mm, about 4 mm, about 5 mm, 6 mm, about 7 mm, about 8 mm, about 9 mm, about 10 mm, about 15 mm, about 20 mm, about 25 mm, about 30 mm or more.

The device can further comprise an input funnel having a wide end in fluid communication with the space between the first surface and the second surface; and a narrow end medial to the wide end and in fluid communication with the wide end. The wide end can have a first thickness ($t_0$) at its mid-point, a second thickness ($t_1$) at its edges, and a height (h) between the wide end to the narrow end. In some cases, ($t_0$) is less than ($t_1$). In some cases, ($t_0$) is substantially the same as or the same as ($t_1$). In some cases, ($t_0$) is greater than ($t_1$). In some cases, the ratio of ($t_0$)/($t_1$) is less than about 0.95, less than about 0.85, less than about 0.80, less than about 0.75, less than about 0.70, less than about 0.65, less than about 0.60, less than about 0.55, less than about 0.50, less than about 0.45, less than about 0.40, less than about 0.35, less than about 0.30, less than about 0.25, less than about 0.20, less than about 0.15, less than about 0.10, less than about 0.05 or less.

Additionally, ($t_0$) can have any suitable value. In some embodiments, ($t_0$) may less than about 1 mm, less than about 900 µm, less than about 800 µm, less than about 700 µm, less than about 600 µm, less than about 500 µm, less than about 400 µm, less than about 300 µm, less than about 200 µm, less than about 100 µm, less than about 50 µm, less than about 20 µm, less than about 10 µm, less than about 5 µm, less than about 1 µm, less than about 0.1 µm or less than about 0.01 µm or less. In some embodiments, ($t_0$) may be about 1 mm, about 900 µm, about 800 µm, about 700 µm, about 600 µm, about 500 µm, about 400 µm, about 300 µm, about 200 µm, about 100 µm, about 50 µm, about 20 µm, about 10 µm, about 5 µm, about 1 µm, about 0.1 µm, about 0.01 µm or less.

Additionally, ($t_1$) can have any suitable value. In some embodiments, ($t_1$) may less than about 1 mm, less than about 900 µm, less than about 800 µm, less than about 700 µm, less than about 600 µm, less than about 500 µm, less than about 400 µm, less than about 300 µm, less than about 200 µm, less than about 100 µm, less than about 50 µm, less than about 20 µm, less than about 10 µm, less than about 5 µm, less than about 1 µm, less than about 0.1 µm or less than about 0.01 µm or less. In some embodiments, ($t_1$) may be about 1 mm, about 900 µm, about 800 µm, about 700 µm, about 600 µm, about 500 µm, about 400 µm, about 300 µm, about 200 µm, about 100 µm, about 50 µm, about 20 µm, about 10 µm, about 5 µm, about 1 µm, about 0.1 µm, about 0.01 µm or less. In some embodiments, H is about 100 µm, ($t_0$) is about 300 µm, ($t_1$) is about 500 µm and h is about 2 millimeters.

Moreover, (h) can have any suitable value. In some embodiments, (h) may be less than about 50 mm, less than about 40 mm, less than about 30 mm, less than about 20 mm, less than about 10 mm, less than about 9 mm, less than about 8 mm, less than about 7 mm, less than about 6 mm, less than about 5 mm, less than about 4 mm, less than about 3 mm, less than about 2 mm, less than about 1 mm, less than about 800 µm, less than about 600 µm, less than about 400 µm, less than about 200 µm, less than about 100 µm, less than about 50 µm, less than about 20 µm, less than about 10 µm, less than about 5 µm, less than about 1 µm, less than about 0.1 µm or less than about 0.01 µm or less. In some embodiments, (h) may be about 50 mm, about 40 mm, about 30 mm, about 20 mm, about 10 mm, about 9 mm, about 8 mm, about 7 mm, about 6 mm, about 5 mm, about 4 mm, about 3 mm, about 2 mm, about 1 mm, about 800 µm, about 600 µm, about 400 µm, about 200 µm, about 100 µm, about 50 µm, about 20 µm, about 10 µm, about 5 µm, about 1 µm, about 0.1 µm, about 0.01 µm or less.

In some embodiments, the device can further comprise an output funnel having a wide end in fluid communication with the space between the first surface and the second surface, and a narrow end in fluid communication with the wide end. The wide end can have a third thickness ($t_2$) at its mid-point and a fourth thickness ($t_3$) at its edges, and a height ($h_2$) between its wide end and narrow end. In some embodiments, the device can be configured to direct fluid flow through the narrow end of the input funnel, through the space between the first surface and the second surface, and out of the narrow end of the output funnel.

In some embodiments, an input funnel and/or an output funnel can be oriented perpendicularly to the first surface and the second surface. In some embodiments, an input funnel and/or an output funnel can be oriented parallel to the first surface and the second surface.

Additionally, ($t_2$) can have any suitable value. In some embodiments, ($t_2$) may less than about 1 mm, less than about 900 µm, less than about 800 µm, less than about 700 µm, less than about 600 µm, less than about 500 µm, less than about 400 µm, less than about 300 µm, less than about 200 µm, less than about 100 µm, less than about 50 µm, less than about 20 µm, less than about 10 µm, less than about 5 µm, less than about 1 µm, less than about 0.1 µm or less than about 0.01 µm or less. In some embodiments, ($t_2$) may be about 1 mm, about 900 µm, about 800 µm, about 700 µm, about 600 µm, about 500 µm, about 400 µm, about 300 µm, about 200 µm, about 100 µm, about 50 µm, about 20 µm, about 10 µm, about 5 µm, about 1 µm, about 0.1 µm, about 0.01 µm or less.

Additionally, ($t_3$) can have any suitable value. In some embodiments, ($t_3$) may less than about 1 mm, less than about 900 µm, less than about 800 µm, less than about 700 µm, less than about 600 µm, less than about 500 µm, less than about 400 µm, less than about 300 µm, less than about 200 µm, less than about 100 µm, less than about 50 µm, less than about 20 µm, less than about 10 µm, less than about 5 µm, less than about 1 µm, less than about 0.1 µm or less than about 0.01 µm or less. In some embodiments, ($t_3$) may be about 1 mm, about 900 µm, about 800 µm, about 700 µm, about 600 µm, about 500 µm, about 400 µm, about 300 µm, about 200 µm, about 100 µm, about 50 µm, about 20 µm, about 10 µm, about 5 µm, about 1 µm, about 0.1 µm, about 0.01 µm or less.

Moreover, ($h_2$) can have any suitable value. In some embodiments, ($h_2$) may be less than about 50 mm, less than about 40 mm, less than about 30 mm, less than about 20 mm, less than about 10 mm, less than about 9 mm, less than about 8 mm, less than about 7 mm, less than about 6 mm, less than about 5 mm, less than about 4 mm, less than about 3 mm, less than about 2 mm, less than about 1 mm, less than about 800 µm, less than about 600 µm, less than about 400 µm, less than about 200 µm, less than about 100 µm, less than about 50 µm, less than about 20 µm, less than about 10 µm, less than about 5 µm, less than about 1 µm, less than about 0.1 µm or less than about 0.01 µm or less. In some embodiments, ($h_2$) may be about 50 mm, about 40 mm, about 30 mm, about 20 mm, about 10 mm, about 9 mm, about 8 mm, about 7 mm, about 6 mm, about 5 mm, about 4 mm, about 3 mm, about 2 mm, about 1 mm, about 800 about 600 about 400 µm, about 200 µm, about 100 µm, about 50 µm, about 20 µm, about 10 µm, about 5 µm, about 1 µm, about 0.1 µm, about 0.01 µm or less.

A device may be configured to direct fluid flow through the space between the first surface and the second surface and/or any input or output funnels of a device such that the directed flow is laminar flow. In some embodiments, a device may be configured to direct fluid flow through the space between the first surface and the second surface and/or any input or output funnels of a device such that the directed flow is turbulent flow or a transition flow in between a laminar flow and a turbulent flow. One measure used to characterize fluid flow is Reynolds number. In general, fluid flow described by a Reynolds number of less than 2100 is considered laminar flow and fluid flow described by a Reynolds number of greater than 4000 is turbulent flow. Reynolds numbers that fall in between 2100 and 4000 are generally considered transition flows.

Accordingly, in some embodiments, a device may be configured to direct fluid flow between the first surface and the second surface an and the second surface and/or any input or output funnel such that the fluid flow has a Reynolds number of less than about 4100, 4000, 3900, 3800, 3700, 3600, 3500, 3400, 3300, 3200, 3100, 3000, 2900, 2800, 2700, 2600, 2500, 2400, 2300, 2200, 2100, 2000, 1900, 1800, 1700, 1600, 1500, 1400, 1300, 1200, 1100, 1000, 900, 800, 700, 600, 500, 400, 300, 200, 100, 50, 25, 10, 1, 0.1, 0.01, 0.001 or less. In some embodiments, a device may be configured to direct fluid flow between the first surface and the second surface an and the second surface and/or any input or output funnel such that the fluid flow has a Reynolds number of greater than about 4100, 4500, 5000, 5500, 6000, 6500, 7000, 7500, 8000, 8500, 9000, 9500, 10000 or higher.

The linear flow rate of a directed fluid flow between any two points within the space between the first surface and second surface may vary and the device may be configured to minimize such variability. For example, the linear flow rate of fluid flow at any two points within the space between the first and second surfaces may vary by at most about 50%, 45%, 40%, 35%, 30%, 25%, 20%, 15%, 10%, 5%, 1% or less. Additionally, the volumetric flow rate of a directed fluid flow between any two points within the space between the first surface and second surface may vary and the device may be configured to minimize such variability. For example, the linear flow rate of fluid flow at any two points within the space between the first and second surfaces may vary by at most about 50%, 45%, 40%, 35%, 30%, 25%, 20%, 15%, 10%, 5%, 1% or less.

In some embodiments, the chamber can comprise walls. The walls may have any suitable shape. For example, the walls may be curved.

In some embodiments, a distance from the first surface to the second surface may be greater near the center of the chamber than at the edges of the chamber. In some embodiments, the distance from the first surface to the second surface may be less near the center of the chamber than at the edges of the chamber. In some embodiments, the distance from the first surface to the second surface may be the same or substantially the same near the center of the chamber than at the edges of the chamber. In some embodiments, the ratio of the distance from the first surface to the second surface at a point near the center of the chamber to a distance from the first surface to the second surface at a point near the edge of the chamber may be less than about 0.95, 0.90, 0.85, 0.80, 0.75, 0.70, 0.65, 0.60, 0.55, 0.50, 0.45, 0.40, 0.35, 0.30, 0.25, 0.20, 0.15, 0.10, 0.05 or less. In some embodiments, the ratio of the distance from the first surface to the second surface near the center of the chamber to ($t_0$) or ($t_1$) is less than about 0.95, 0.90, 0.85, 0.80, 0.75, 0.70, 0.65, 0.60, 0.55, 0.50, 0.45, 0.40, 0.35, 0.30, 0.25, 0.20, 0.15, 0.10, 0.05 or less.

In an aspect, the present disclosure provides a semiconductor microfluidic device comprising a chamber with a floor, walls and a ceiling, where the fluid passing through the chamber is at substantially the same velocity throughout the chamber and there is at least one of an inlet and an outlet. The walls of the chamber can be curved.

The chamber can be shaped such that a height from the floor to the ceiling at the middle of the chamber is less than the height from the floor to the ceiling and the walls of the chamber. In some cases, the chamber has a height of at least 60 µm, 100 µm or 120 µm.

In some embodiments, a connection junction between at least one of the inlets and the outlets as well as the floor is rounded. The chamber can have rounded edges. The chamber can be shaped such that a ratio between a height from the floor to the ceiling at the middle of the chamber versus a height from the floor to the ceiling and the walls of the chamber is about 0.05, 0.1, 0.15, 0.2, 0.25, 0.3, 0.35, 0.4, 0.45 or 0.5.

In some embodiments, at least one of an inlet and an outlet has a funnel shape. The funnel can be oriented horizontally or vertically. The height from the floor to the ceiling at the middle of the chamber can be less than half of the width of the funnel. In some embodiments, the height from the floor to the ceiling at the middle of the chamber is at least 200 µm, 300 µm, 400 µm or 500 µm.

To find the velocity field as well as the pressure drop in a microfluidic cavity, the Navier-Stokes equations for incompressible flow can be solved using steady state conditions. In an example, the working fluid is water at a reference temperature and subject to conditions described by the following equations:

$$(u \cdot \nabla)u = -\frac{1}{\rho} \nabla p + v \nabla^2 u$$

$$\nabla \cdot u = 0$$

The above equations may be solved according to the following boundary conditions:
Walls: no slip boundary condition u=0
Inlets: u=$u_{in}$
Outlet: Reference pressure: p=0

In this embodiment, the above model can describe movement of spherical particles in the fluidic chamber based on the drag force from the fluid flow and the gravity force. The spherical particles, for the above example, can have 1 micron (µm) diameter with a density of 2.2 g/cm$^3$, though it is understood that particles of varying dimensions, shapes and densities may be used. In some embodiments, the spherical particles are magnetic beads.

A uniform flow profile may be desirable for a uniform distribution of beads and reagents within the chamber. It can be preferable to have substantially the same velocity field over the beads in the fluidic chamber in order to have approximately the same sensing condition for all of the beads. In this manner, the fluid passing through the fluidic chamber from the inlet to the outlet can be at substantially the same velocity at all points in the chamber. In some embodiments, there may be more than one inlet and/or outlet.

The chamber can be shaped such that there are no sharp corners. Sharp corners in the walls of the chamber may cause a variety of problems. One issue may be that particles (e.g., beads) may become trapped and/or clump together in the corners of the chamber. Another issue may be that corners in the walls of the chamber may not allow for a uniform flow profile. Sharp corners may also introduce bubbles and/or turbulent flow inside the chamber.

Figure 45:
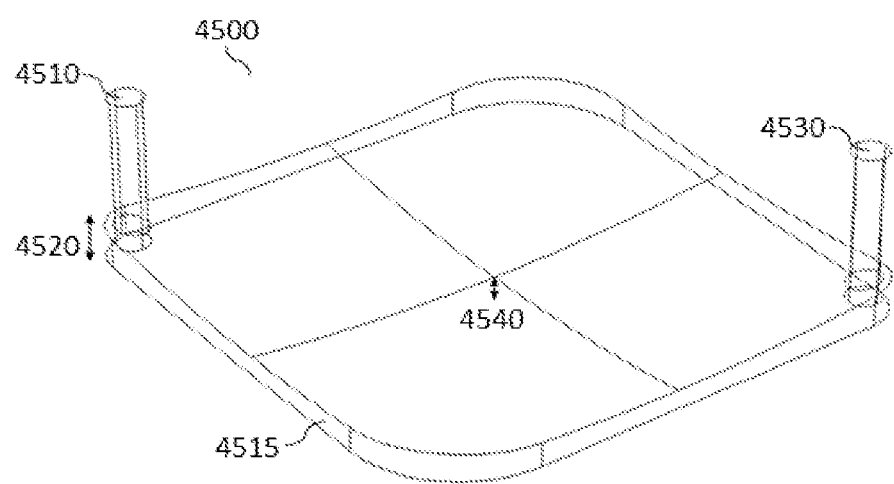
FIG. 45 shows a diagram of an exemplary microfluidic chamber device.

In some embodiments, as shown in FIG. 45, the microfluidic chamber 4500 can be shaped such that there may be an inlet 4510 on one end and the chamber walls 4515 may curve out away from the inlet and then gradually curve back towards the outlet 4530 at the opposite end of the chamber. There may be two "corners" between the inlet and outlet in this configuration, but these corners can be curved such that there is minimal impact on the profile of the flow across the chamber. In some embodiments, there may be more than one inlet and/or more than one outlet, with the chamber having the same or a different shape.

FIG. 45 also shows two other aspects of the microfluidic chamber 4500, namely, the height of the chamber wall 4520 and the height of the chamber ceiling 4520. In some embodiments, the height of the chamber ceiling may be sloped such that the height near the edges of the chamber (the location by the chamber walls) is larger than the height in the middle of the chamber. In some embodiments, chamber ceiling may be sloped.

The ratio between the height near the walls and the height near the center of the chamber may have an impact on the uniformity and rate of the flow across the chamber.

An example of a simulation that can be run using an example chamber includes a chamber with the dimensions as shown in FIG. 45, namely, an inlet 4510 and outlet 4530 diameter (D) of 300 micrometers (μm), a chamber size of 4.5 millimeters (mm) on each side (i.e., an area of 20.25 mm$^2$), a chamber wall height ($H_{wall}$) 4520 of 200 μm, a chamber middle height ($H_m$) 4540 of between about 20 and 200 μm, and an active sensor area of 3.6 mm by 3.6 mm (i.e., 12.96 mm$^2$).

Figure 46A:
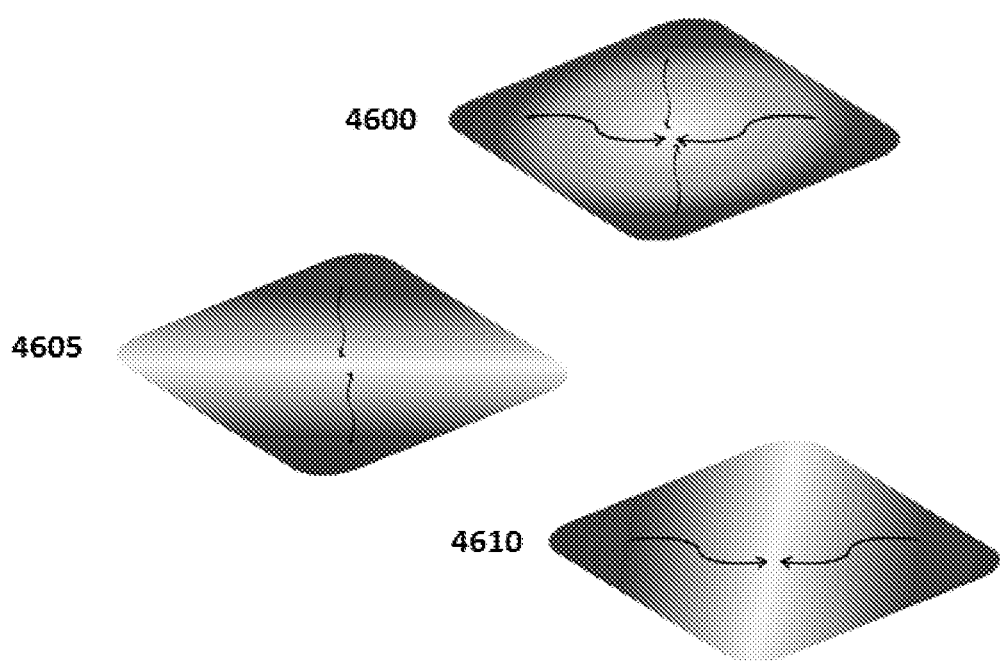
FIG. 46A shows variations on possibilities for sloping the height of the chamber ceiling.

FIG. 46A shows options for sloping the height of the chamber ceiling. In each case, the darker color indicates a larger chamber height and a lighter color indicates a smaller chamber height. In these situations, the transition from a large chamber to a small chamber height may be a gradual, smooth slope. In some embodiments, the chamber height is large on all outside edges of the chamber and slopes downward to a smaller height towards the middle of the chamber (e.g., 4600). In some embodiments, the chamber height is relatively large on only two corners (e.g., the top and bottom corners) and slopes down from those two corners to a smaller height towards the middle of the chamber (e.g., 4605). In some embodiments, the chamber height is relatively large on only two corners (the left and right corners) and slopes down from those two corners to a smaller height towards the middle of the chamber (e.g., 4610).

Figure 46B:
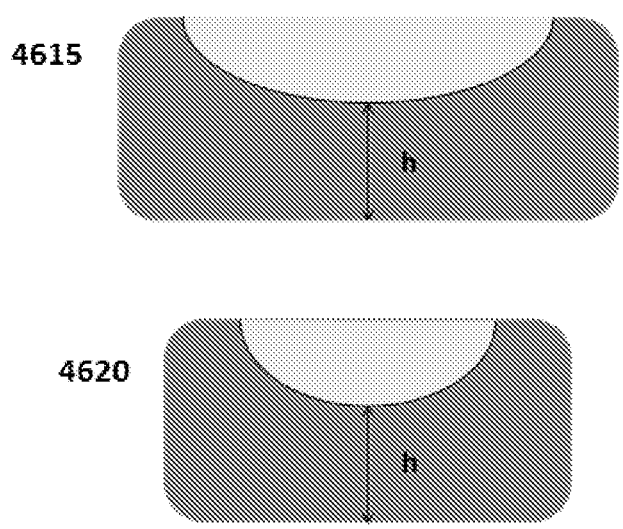
FIG. 46B shows, in one embodiment, two side view of a chamber with a sloping ceiling.

FIG. 46B shows side views of a chamber where the chamber ceiling is sloped from all sides of the chamber towards the middle of the chamber where the ceiling height (h) is less that the height of the chamber walls. Two views 4615 and 4620 show side views from two different sides of the chamber.

Figure 46C:
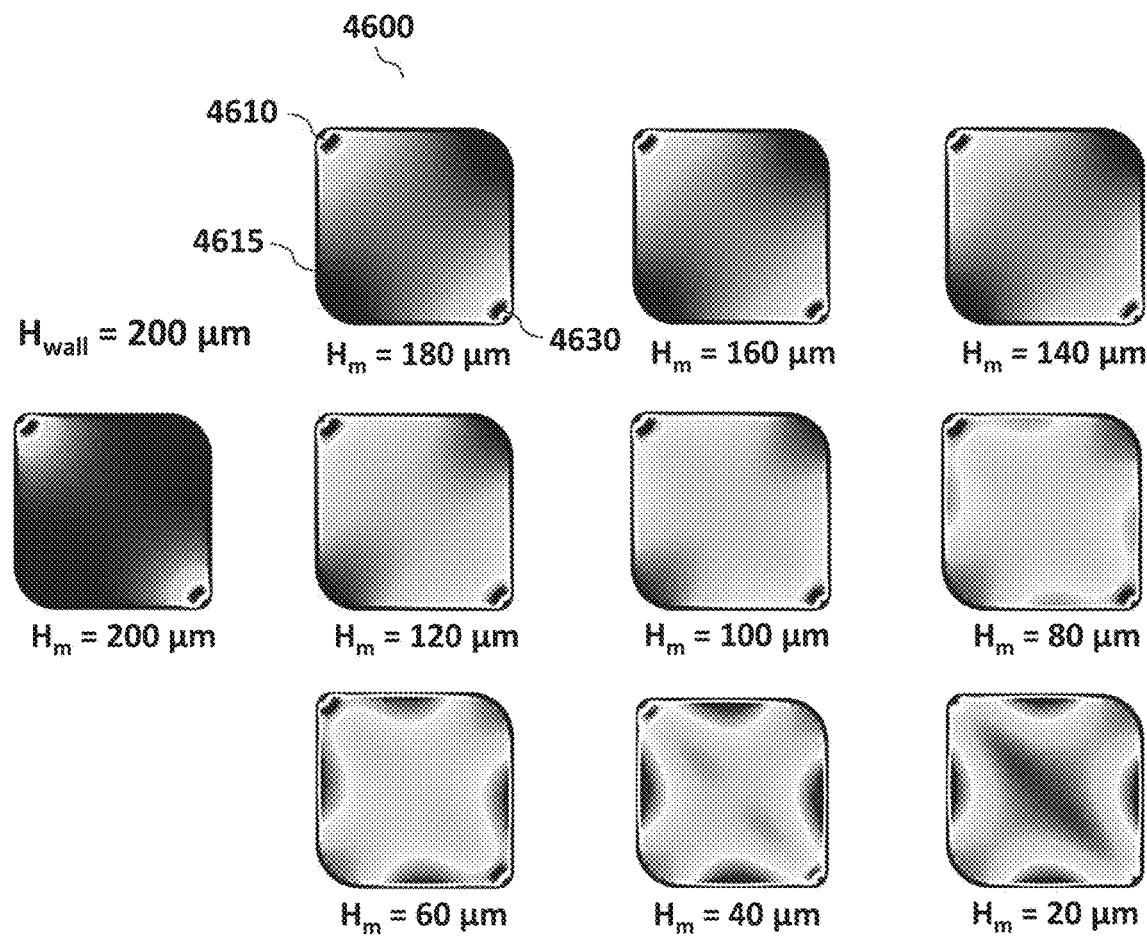
FIG. 46C shows a top view of the flow profile of microfluidic chambers with varying chamber heights near the middle of the chamber.

FIG. 46C shows a top view of the flow profile of microfluidic chambers 4600 with varying chamber heights near the middle of the chamber. The top view of microfluidic chambers 4600 shows the velocity gradients from the inlet 4610 to the outlet 4630. In this example, the height of the chamber walls ($H_{wall}$) is 200 μm. The chamber heights at or around the middle of the chamber ($H_m$) shown here are 20 μm, 40 μm, 60 μm, 80 μm, 100 μm, 120 μm, 140 μm, 160 μm, 180 μm, and 200 μm. In other embodiments, the chamber height may be less than or greater than these values, as these values are shown as an example only. The various flow velocities are illustrated in this figure with the faster flow velocities having a lighter color and the slower flow velocities having a darker color. Thus, the varying degrees of flow uniformity in the chambers are depicted with chambers having uniform flow shown to be more uniform in color and the chambers with non-uniform flow shown to have distinct, different colored regions.

Figure 46D:
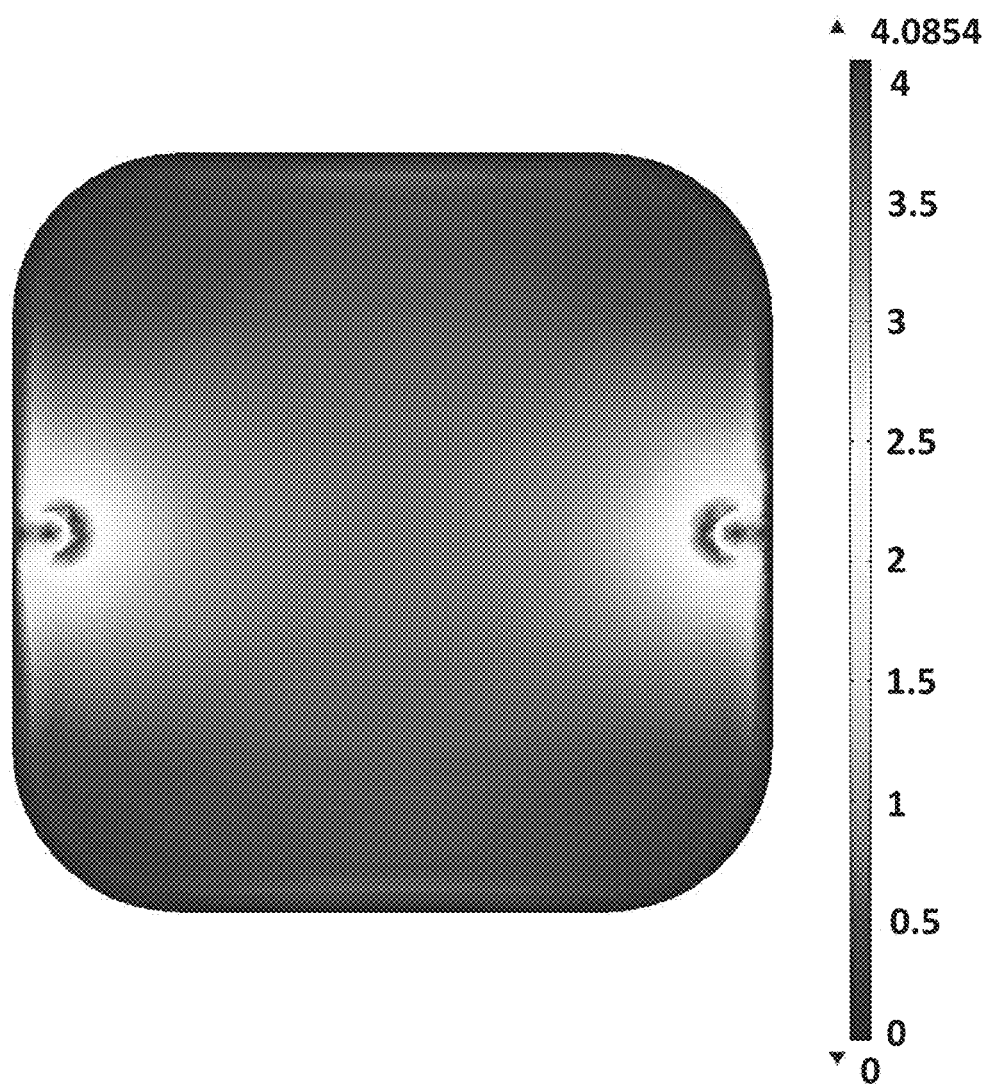
FIG. 46D shows one embodiment where the inlet and outlet are located proximate to the sides of the chamber.

FIG. 46D shows one embodiment of a chamber where the inlet and the outlet is located on the sides of the chamber as opposed to proximate to the "corners" of the chamber (as shown, for example, in FIG. 46C). Varying the location of the inlets and outlets of the chamber may have an impact on both uniformity of flow and smooth injection of beads into the chamber.

Depending on the height at or around the middle of the chamber ($H_m$), the flow can be more or less uniform throughout the chamber and along the chamber walls 4615. For example, the flow in a chamber where the height is 100 μm is more uniform than in a chamber where the height is 20 μm. The height for ideal flow can depend on a variety of factors including the dimensions of the chamber and the type of liquid.

Figure 47:
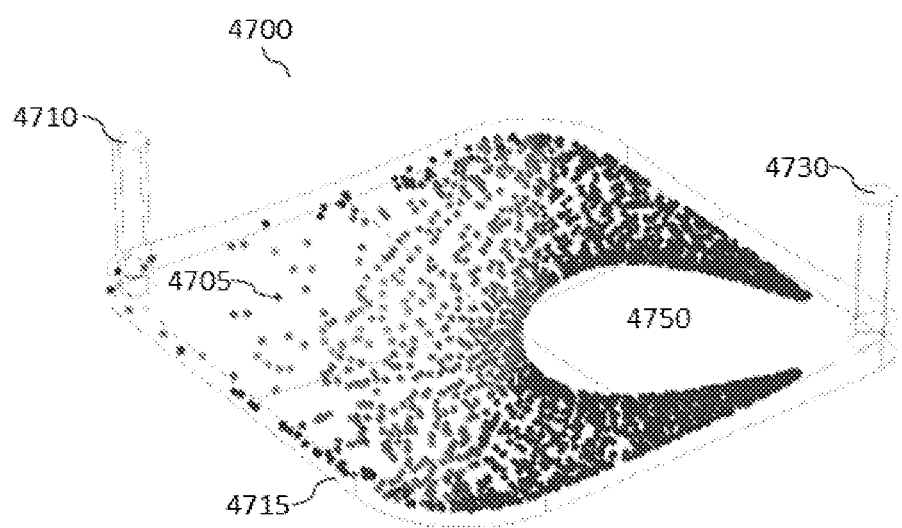
FIG. 47 shows a simulation, after particles are introduced through inlet into the microfluidic chamber, where the height of the chamber at or around the midpoint is 60 microns (um).

FIG. 47 shows an example simulation, after particles 4705 are introduced through inlet 4710 into the microfluidic chamber 4700, where the height of the chamber at or around the midpoint is 60 μm. The darkness of the particle color corresponds with their velocity where the darker color indicates a higher velocity. FIG. 47 illustrates that at this chamber height, the flow near the walls of the chamber 4715 is faster than in the middle, thereby creating a gap 4750 in the flow profile before the particles 4705 exist through the outlet 4730.

Figure 48:
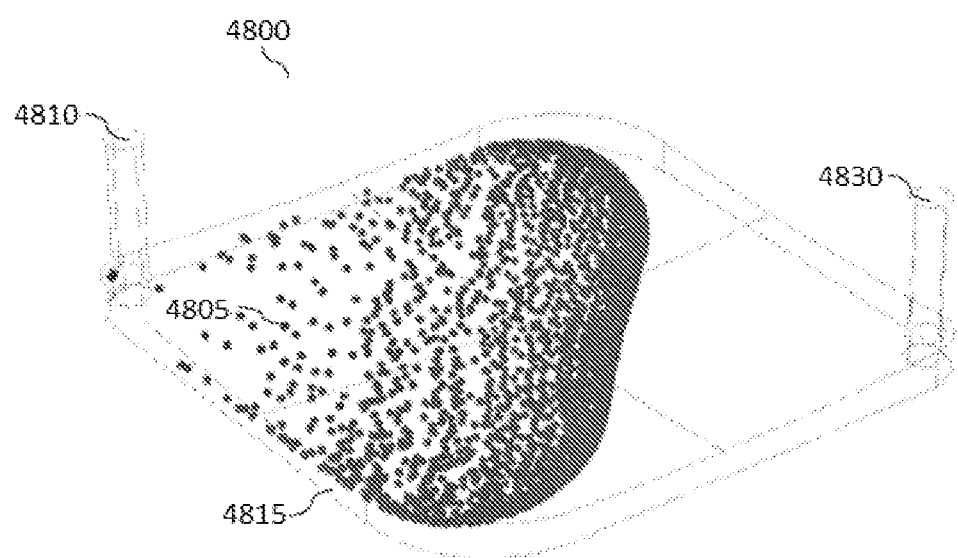
FIG. 48 shows a simulation, after particles are introduced into the microfluidic chamber through an inlet, where the height of the chamber at the midpoint is 120 um.

FIG. 48 shows an example simulation, after particles 4805 are introduced into the microfluidic chamber 4800 through an inlet 4810, where the height of the chamber at the midpoint is 120 μm. In contrast with FIG. 47, this chamber height allows for a more uniform flow throughout the chamber 4800 and along the chamber walls 4815, but with a decrease in velocity as the particles 4805 move towards outlet 4830.

Figure 49A:
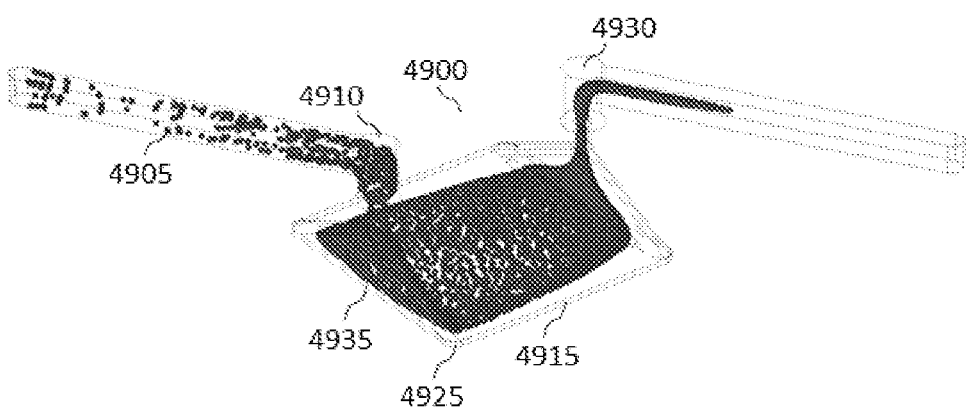
FIG. 49A shows an alternative embodiment of a microfluidic chamber where an inlet and an outlet have a funnel shape.
Figure 49B:
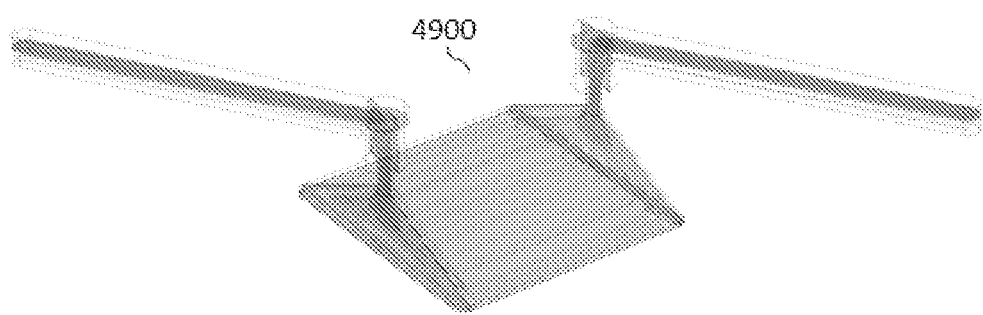
FIG. 49B shows the microfluidic chamber of FIG. 49A with the associated flow lines.

FIG. 49A shows an alternative embodiment of a microfluidic chamber 4900 where an inlet 4910 and an outlet 4930 have a funnel shape to permit a smooth transition of fluid flow from inlet 4910 toward the microfluidic chamber floor. The microfluidic chamber floor may comprise a sensing area for the detection of biological reactions of interest. Such a configuration can give rise to a flow profile of particles 4905 with a laminar flow throughout the microfluidic chamber 4900 and along chamber walls 4915. In some cases, the edges of the microfluidic chamber 4900 shown in FIG. 49A may be rounded both in the corner areas 4925 and the junction 4935 where the inlet/outlet connects with the chamber floor. Having a sloped junction point at these areas may aid in creating a more uniform flow profile. FIG. 49B shows the microfluidic chamber 4900 of FIG. 49A with the associated flow lines.

Figure 49C:
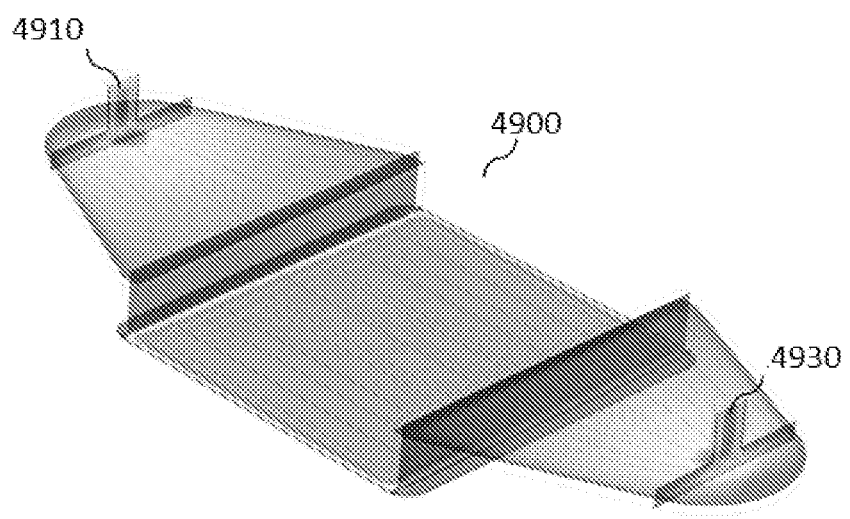
FIG. 49C illustrates, one embodiment of a microfluidic chamber with a funnel shaped inlet and outlet, where the funnel portion is placed horizontally.
Figure 49D:
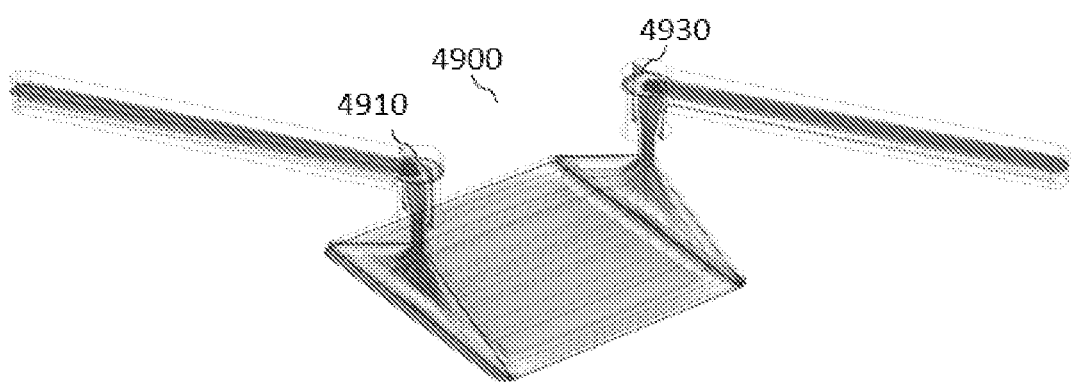
FIG. 49D shows another embodiment of a microfluidic chamber with a funnel shaped inlet and outlet, where the funnel portion is placed vertically.

The funnel can be oriented horizontally or vertically with respect to the microfluidic chamber. FIG. 49C illustrates, in one embodiment of microfluidic chamber 4900, the funnel shaped inlet 4910 and outlet 4930, where the funnel portion is placed horizontally. The funnel part of the channel maybe placed horizontally or vertically based on the available space for an optional fluidic lid (not shown) that may cover microfluidic chamber 4900. FIG. 49D illustrates, in another embodiment of microfluidic chamber 4900, the funnel shaped inlet 4910 and outlet 4930, where the funnel portion is placed vertically.

Figure 50:
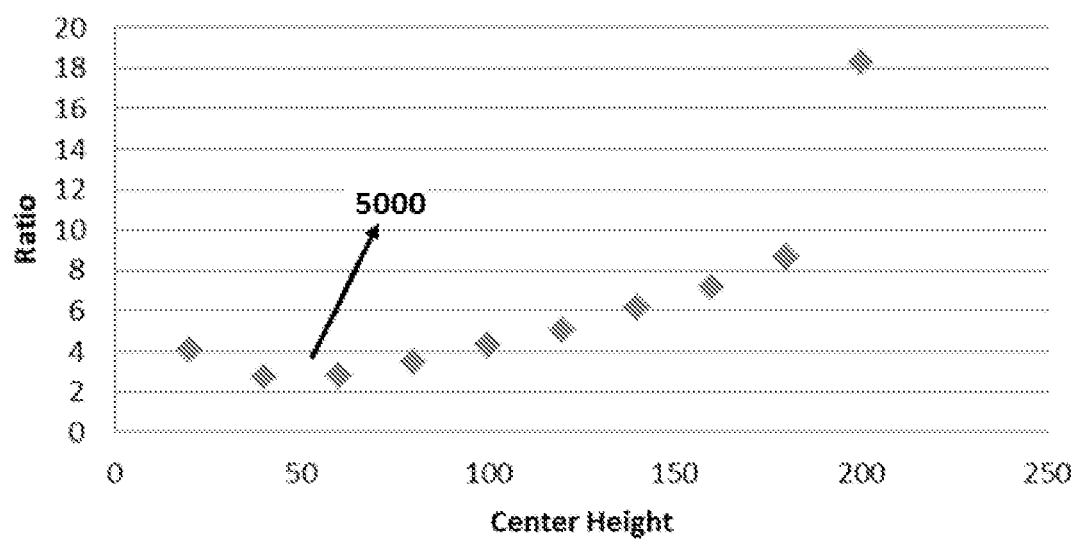
FIG. 50 illustrates the relationship between chamber height at the center and the ratio between the maximum and minimum velocity within the chamber.

FIG. 50 illustrates an example relationship between chamber height at its center and a ratio between the maximum and minimum velocity within an example chamber. FIG. 50 shows that fluid flow can be at its most uniform point 5000, (e.g., with the smallest ratio between maximum and minimum velocity), at around 50 µm for the example chamber. In this embodiment, the following relationship between the height at or around the middle of the chamber ($H_m$) and the height of the chamber walls ($H_{wall}$) can be determined in order to yield a minimum variation in flow velocity (e.g., minimum variation $H_m = 0.25 \times H_{wall}$ for the example chamber described above).

Figure 51:
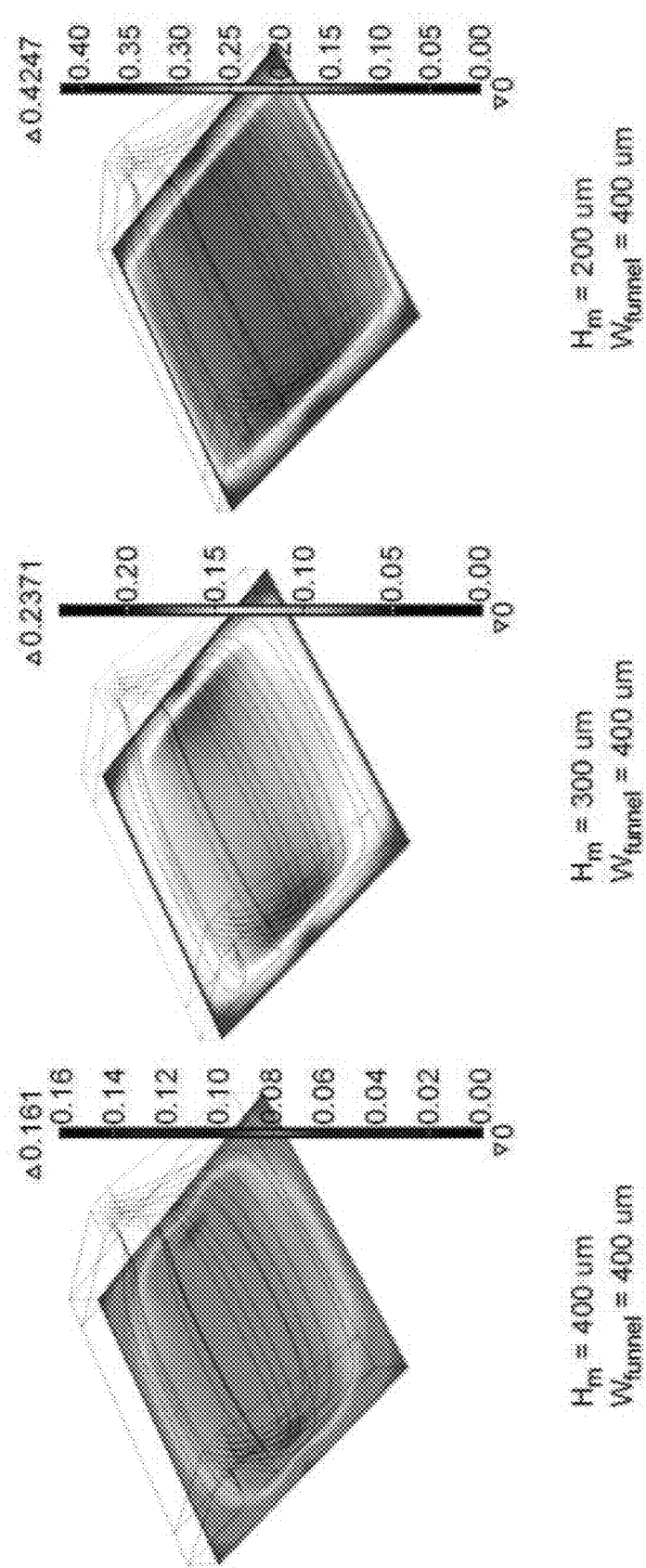
FIG. 51 shows three different exemplary embodiments with chamber of differing heights at or around the middle portion of the chamber.

For the funnel shape chamber of FIGS. 49A-D, the height of the microfluidic chamber at or around the middle may be less than half of the width of the funnel to procure the uniformity of the flow field, as illustrated in FIG. 51. When the height of the chamber at or around the midpoint ($H_m$) is less than the funnel width ($W_{funnel}$), the flow resistance in the chamber can be higher than that of the funnel portions. Therefore, the fluid may fill the funnel first and then flow into the chamber uniformly. In this exemplary embodiment, the following relationship between the height at or around the middle of the chamber ($H_m$) and the funnel width ($W_{funnel}$) can be determined in order to yield a minimum variation in flow velocity (e.g., minimum variation $H_m < 0.5 \times W_{funnel}$ for the funnel shape chamber described above).

FIG. 51 illustrates three different exemplary embodiments where the $H_m$ is 400 µm, 300 µm, and 200 µm from left to right. As in FIGS. 46A-D, the variation in shade illustrates the variation in flow rate with the most uniform flow having the least variation in shade throughout the microfluidic chamber and straighter flow lines.

Figure 52:
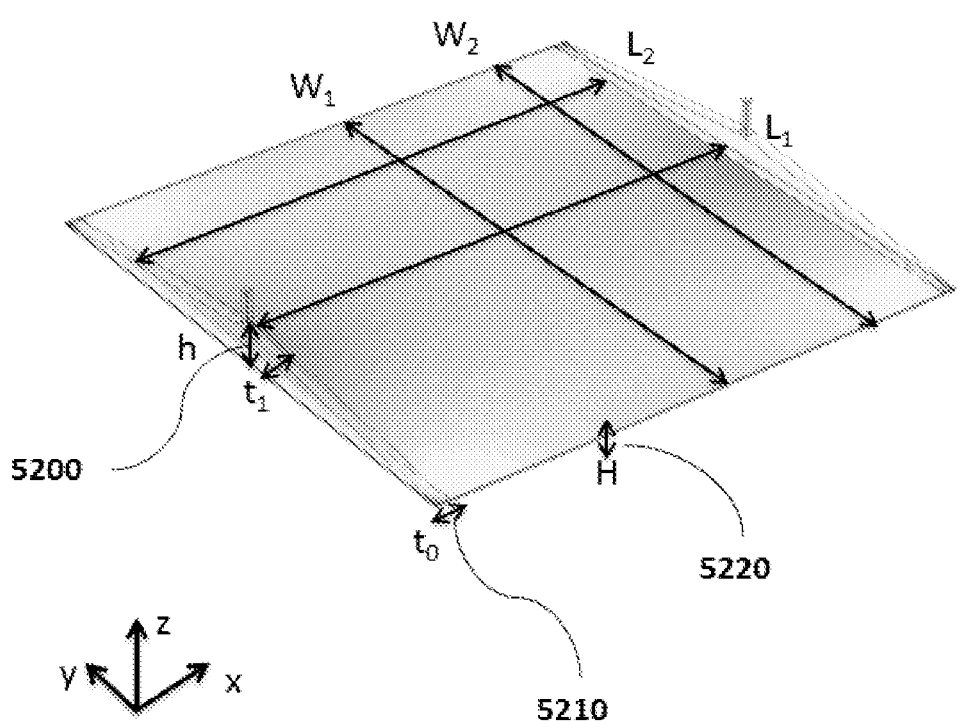
FIG. 52 shows a diagram of a microfluidic chamber device with dimensions.

In some embodiments, a funnel has an inlet medial to a fluidic chamber and an outlet spanning the width of the fluidic chamber, as shown in FIG. 52. The funnel can be oriented vertically (e.g., perpendicularly) to the fluidic chamber. The funnel and chamber can have dimensions that result in a uniform fluid flow over the fluidic chamber. Any dimension can be varied to achieve a uniform flow, however provided herein are examples where the height of the funnel (h) 5200, the thickness of the funnel (t) 5210 and the height of the fluidic channel (H) 5220 are varied to achieve uniform flow.

In some cases, the linear flow rate and/or volumetric flow rate of fluid across the fluidic channel varies by about 25%, about 20%, about 15%, about 10%, about 5%, about 3%, or about 1%. In some instances, the linear flow rate and/or volumetric flow rate of fluid across the fluidic channel varies by at most about 25%, at most about 20%, at most about 15%, at most about 10%, at most about 5%, at most about 3%, or at most about 1%. The flow variation can be calculated between any two points on the fluidic channel, including any point along width of the channel (e.g., $W_1$ or $W_2$ of FIG. 52) or the length of the channel (e.g., $L_1$ or $L_2$ of FIG. 52).

Figure 53A:
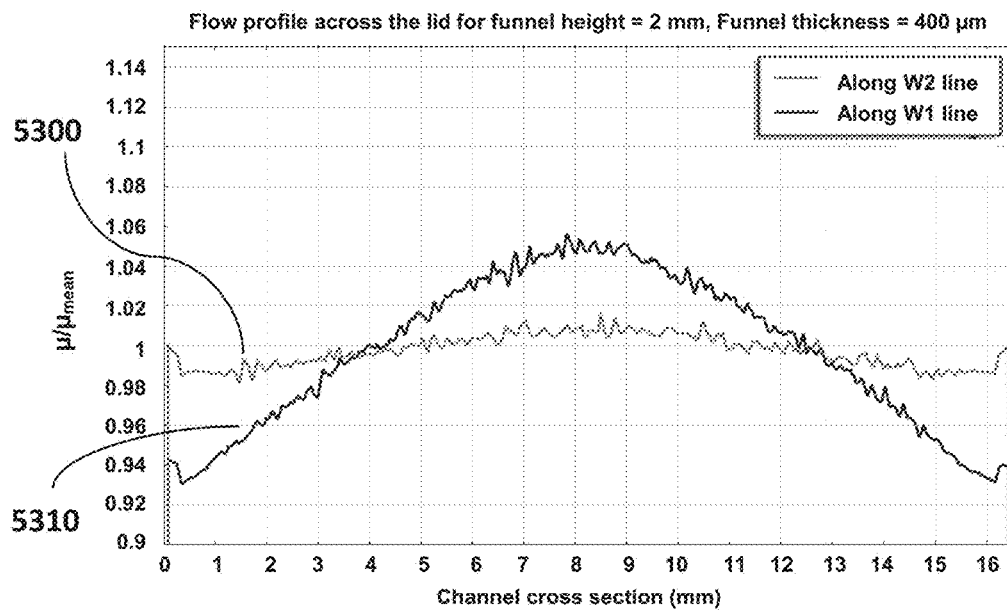
FIG. 53A shows two flow profiles along the channel width for a microfluidic chamber having a funnel of uniform thickness.
Figure 53B:
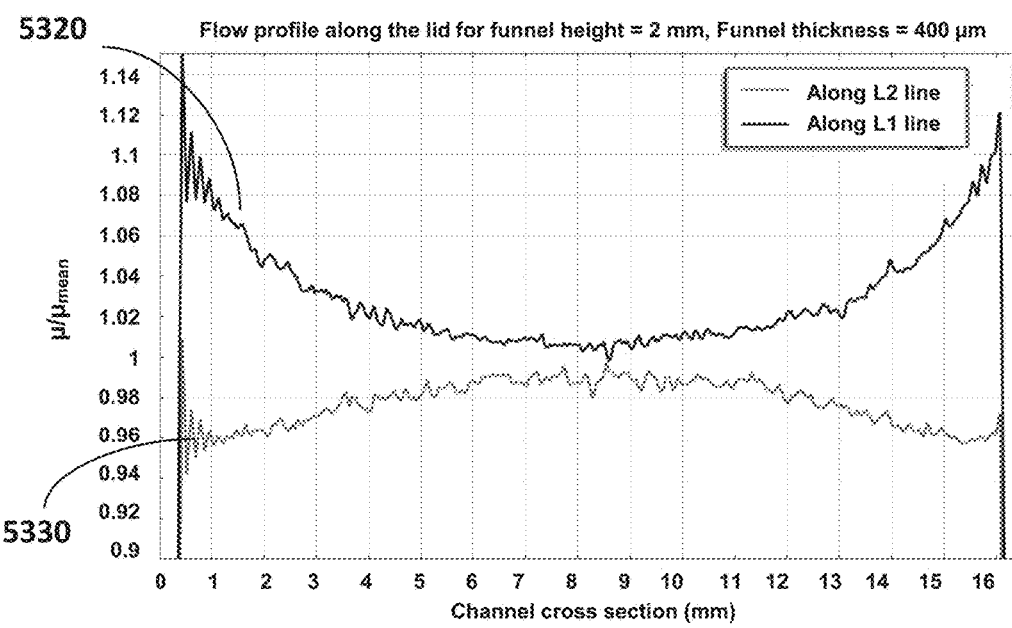
FIG. 53B shows two flow profiles along the channel length for a microfluidic chamber having a funnel of uniform thickness.

The thickness of the funnel (t) can be uniform, or change (e.g., with the thickness being greater at the edges of the funnel 5210 than at the center of the funnel 5200). FIG. 53A shows the flow profile for an example funnel of uniform thickness of 400 um, having a funnel height (h) of 2 mm and a channel height (H) of 100 um. The flow is shown as simulated by computational fluid dynamics across the width of the channel at the center ($W_1$ 5300 and at about 12% of the distance down the length of the channel (i.e., nearer the edge of the channel at $W_2$) 5310. The horizontal axis is distance along the channel cross section measured in millimeters and ranging from 0 to 16.5 mm. The vertical axis is the ratio of flow rate at the position to flow rate at the inlet ranging from 0.05 to 0.065. As seen here, the flow rate is not especially uniform near the edge of the channel 5310. FIG. 53B shows similar results along the length of the channel. Here, the flow profile at the center of the channel ($L_1$) 5320 is contrasted with the flow at the edge of the channel ($L_2$) 5330.

Figure 54A:
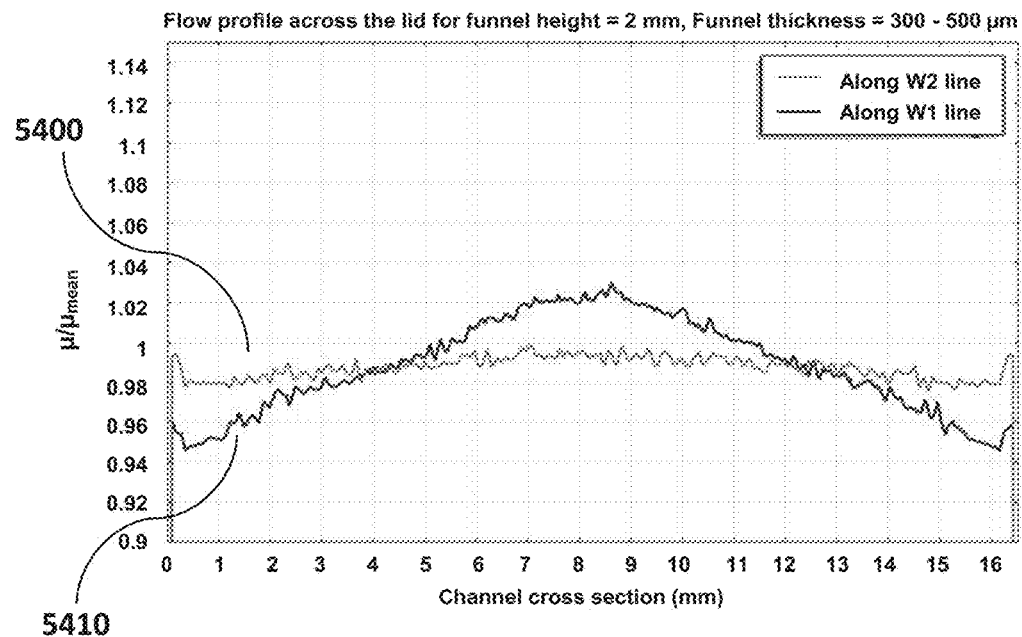
FIG. 54A shows two flow profiles along the channel width for a microfluidic chamber having a funnel of non-uniform thickness.
Figure 54B:
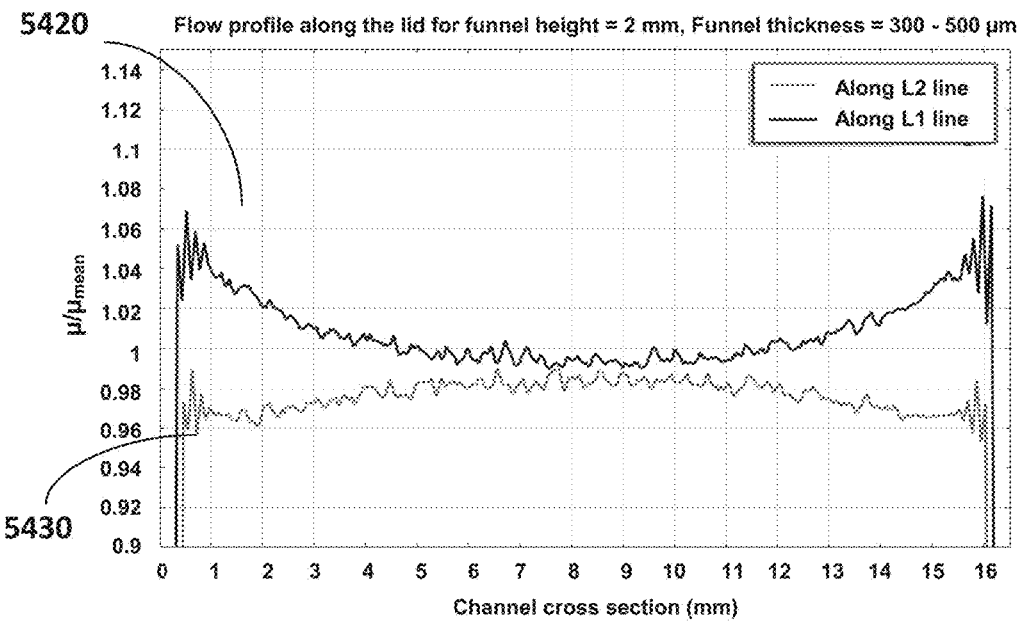
FIG. 54B shows two flow profiles along the channel length for a microfluidic chamber having a funnel of non-uniform thickness.

In contrast, FIG. 54A and FIG. 54B show the enhanced uniformity of flow that can be achieved using an example funnel of varying thickness Like the results shown in FIG. 53A and FIG. 53B, the funnel height (h) is also 2 mm and the channel height (H) is also 100 µm. However, the funnel thickness (t) is varied (e.g., linearly) from 300 µm at the center ($t_0$) to 500 µm at the edges ($t_1$). The results show a uniform flow across the width of the chamber at the center line ($W_1$) 5400 and near the edge ($W_2$) 5410, as well as a uniform flow across the length of the chamber at the center line ($L_1$) 5420 and near the edge ($L_2$) 5430.

Table 2 below shows the flow variation across a cell ($W_1$) and along a cell ($W_2$) for various flow designs having a channel height (H) of 100 µm.

TABLE 2

| Flow cell design | Variation across cell (%) | Variation along cell (%) |
| --- | --- | --- |
| h = 1 mm, t = 400 µm | 12.50 | 29.73 |
| h = 2 mm, t = 400 µm | 10.17 | 14.06 |
| h = 3 mm, t = 400 µm | 5.17 | 8.33 |
| h = 1 mm, t = 300-500 µm | 17.74 | 25.00 |
| h = 2 mm, t = 300-500 µm | 6.78 | 6.67 |

Leak Tester

Recognized herein is the need for improved systems and devices for measuring electrical properties and leakage (the quality of a seal) in microfluidic devices. The present disclosure provides such systems and devices.

Figure 55:
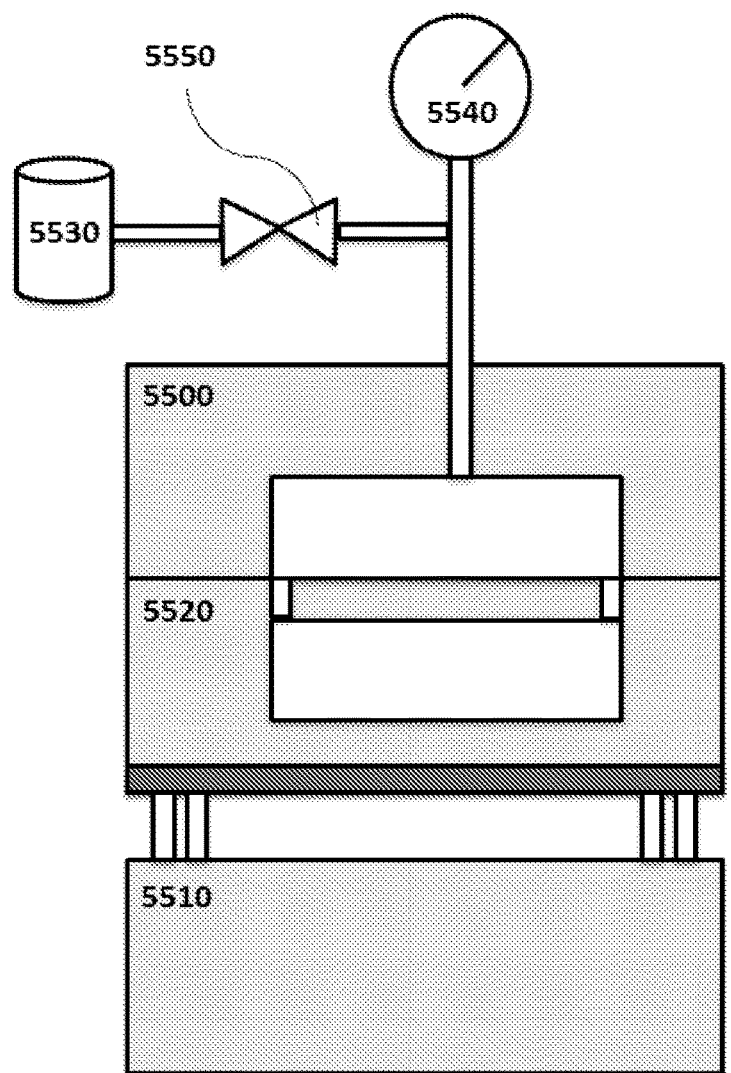
FIG. 55 shows a schematic drawing of a device for testing electrical properties and hermeticity of a microfluidic device.
Figure 56:
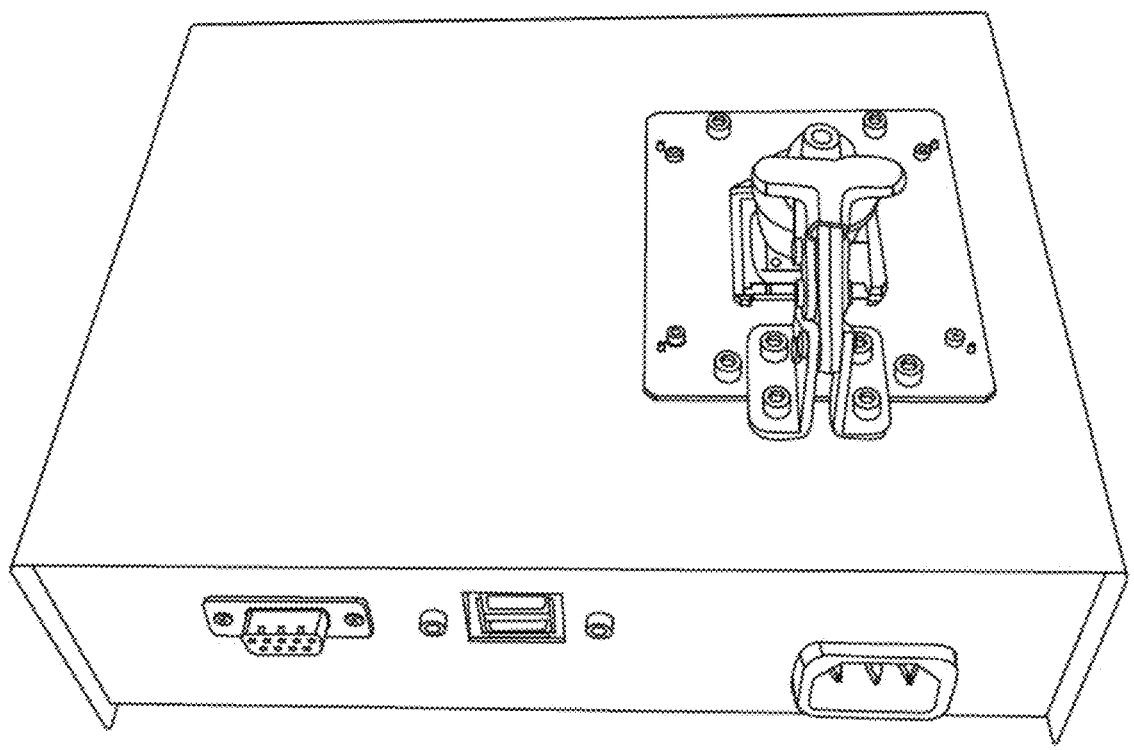
FIG. 56 shows a device for testing electrical properties and hermeticity of a microfluidic device.

As shown in an example system in FIG. 55, the system can comprise a fluid connector 5500 and an electronic tester 5510. The system is shown with a biochip 5520 loaded into the device for testing. The system can have a pump 5530 and a pressure gauge 5540 in fluidic communication with the fluid connector and the microfluidic device for testing for the presence of a fluid leak. A valve 5550 can alternately allow the pump fluidic access to the system or close the pump from the system. A photograph of the system is shown in FIG. 56.

In an aspect, the system can test a hermetic seal between the lid (as described herein) and the die. The degree of hermeticity can be measured or quantified in any suitable way, such as the amount of time that it takes for the pressure of a fluid (e.g., air or water) that is pumped into the system to return to atmospheric pressure (e.g., at least about 1 minute, at least about 1 hour, at least about 1 day, at least about 1 month, or at least about 1 year).

In some cases, a hermetic seal is tested simultaneously with testing of the electrical properties of a chip (e.g., via an electronic tester). The electronic tester can be in contact with pads of a biochip. The fluidic tester can be in contact with inlet/outlet of a biochip lid through a fluidic manifold. The contact between the fluidic manifold and the chip can be free of leaks by using a rubber gasket.

The manifold can be connected to a pressurized air source (e.g. air pump) through a pneumatic valve. In order to test the hermetic seal between die and lid of biochip, the valve of fluidic tester can be opened to pressurize the air inside a flowcell of a biochip, and then closed. Then, the pressure drop of flow cell can be monitored using a pressure gauge. If pressure drop is less than a predefined level, the hermetic seal can be determined to be acceptable.

Simultaneously, the electronic tester can send and receive electrical signals to the chip to test its functionality. The chip can be a complex electronic component that includes one or more functions to collect sensor data (e.g., impedance data). The chip can pass several tests before its functional ability is confirmed. For example, in some cases, a chip may be capable of operating in a sequencing instrument that collects dielectric spectroscopy data (also known as impedance spectroscopy or electrochemical impedance spectroscopy) and measures the dielectric properties of a medium as a function of frequency.

In some cases, the tester may include a heat sink to keep a biochip at appropriate temperature during a test. Also, a fluidic leakage test can be automated by using a computer system, including the computer systems described elsewhere herein.

In some embodiments, a system can be interfaced with an instrument panel architected in user interface software, such as, for example, LABVIEW NI. LABVIEW can make use of computer code (e.g., Python code) adapted for the system.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A microfluidic device, comprising:
   (a) a chamber comprising (i) a first surface having a width (W) and a length (L), (ii) a second surface parallel to the first surface, and (iii) a space between the first surface and the second surface having a height (H), wherein the space between the first surface and second surface is configured to direct fluid flow and H is less than about 3 millimeters (mm); and
   (b) an input funnel having (i) a wide end spanning the width of the first surface and in fluid communication with the space between the first surface and the second surface, and (ii) a narrow end medial to the wide end and in fluid communication with the wide end, wherein the wide end has a first thickness ($t_0$) at its mid-point, a second thickness ($t_1$) at its edges, and a height (h) between the wide end to the narrow end,
   wherein ($t_0$) is less than ($t_1$).

2. The microfluidic device of claim 1, further comprising:
   (c) an output funnel having (i) a wide end in fluid communication with the space between the first surface and the second surface, and (ii) a narrow end in fluid communication with the wide end, wherein the wide end has a third thickness ($t_2$) at its mid-point and a fourth thickness ($t_3$) at its edges, and a height ($h_2$) between the wide end and the narrow end.

3. The microfluidic device of claim 1, wherein the input funnel is oriented perpendicularly to the first surface and the second surface.

4. The microfluidic device of claim 1, wherein the space is configured to direct fluid flow such that the fluid flow has a Reynolds number of less than about 2100.

5. The microfluidic device of claim 1, wherein (H) is less than about 100 micrometers (μm).

6. The microfluidic device of claim 1, wherein a distance from the first surface to the second surface is less proximate to a center of the chamber than at an edge of the chamber.

7. The microfluidic device of claim 1, wherein a ratio of a distance from the first surface to the second surface proximate to a center of the chamber to ($t_0$) or ($t_1$) is less than about 0.8.

8. The microfluidic device of claim 1, wherein at least one of (W) or (L) is at least about 1 mm.

9. The microfluidic device of claim 1, wherein at one or more edges of the chamber, a distance from the first surface to the second surface is the same as a distance from the first surface to the second surface proximate to a center of the chamber.

10. The microfluidic device of claim 1, wherein (H) is less than or equal to 100 μm, ($t_1$) is less than or equal to 500 μm, ($t_0$) is less than or equal to 300 μm, and (h) is less than or equal to 2 mm.

11. The microfluidic device of claim 1, wherein the chamber comprises curved walls.

12. The microfluidic device of claim 1, wherein (h) is less than or equal to about 10 mm.

13. The microfluidic device of claim 1, wherein a ratio of ($t_0$)/($t_1$) is less than about 0.95.

14. The microfluidic device of claim 1, wherein the chamber further comprises a sensor array.

15. The microfluidic device of claim 1, wherein the input funnel further comprises an inlet medial to the chamber, and wherein the inlet is in fluid communication with the narrow end of the input funnel.

16. The microfluidic device of claim 2, wherein the output funnel further comprises an outlet, and wherein the outlet is in fluid communication with the narrow end of the output funnel.

17. The microfluidic device of claim 1, wherein the input funnel comprises a single fluid flow channel.

\* \* \* \* \*

SEQUENCE LISTING

```
<160> NUMBER OF SEQ ID NOS: 1

<210> SEQ ID NO 1
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tcactcatat ttagacccat catttagact catcacgcac agcattta              48
```